US008628927B2

(12) United States Patent
Faham et al.

(10) Patent No.: US 8,628,927 B2
(45) Date of Patent: *Jan. 14, 2014

(54) MONITORING HEALTH AND DISEASE STATUS USING CLONOTYPE PROFILES

(71) Applicants: Malek Faham, Pacifica, CA (US); Thomas Willis, San Francisco, CA (US)

(72) Inventors: Malek Faham, Pacifica, CA (US); Thomas Willis, San Francisco, CA (US)

(73) Assignee: Sequenta, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/763,978

(22) Filed: Feb. 11, 2013

(65) Prior Publication Data
US 2013/0136799 A1    May 30, 2013

Related U.S. Application Data

(63) Continuation of application No. 13/100,365, filed on May 4, 2011, and a continuation-in-part of application No. 12/615,263, filed on Nov. 9, 2009, now Pat. No. 8,236,503.

(60) Provisional application No. 61/332,175, filed on May 6, 2010, provisional application No. 61/455,743, filed on Oct. 25, 2010, provisional application No. 61/446,822, filed on Feb. 25, 2011, provisional application No. 61/112,693, filed on Nov. 7, 2008.

(51) Int. Cl.
*C12P 19/34* (2006.01)
*C12Q 1/68* (2006.01)

(52) U.S. Cl.
USPC ........................................ 435/6.12; 435/91.2

(58) Field of Classification Search
USPC ................................ 435/6.12, 91.2
See application file for complete search history.

(56) References Cited

U.S. PATENT DOCUMENTS

| | | | |
|---|---|---|---|
| 5,296,351 A | 3/1994 | Morley | |
| 5,298,396 A | 3/1994 | Kotzin et al. | |
| 5,336,598 A | 8/1994 | Kotzin et al. | |
| 5,418,134 A | 5/1995 | Morley | |
| 5,635,354 A | 6/1997 | Kourilsky et al. | |
| 5,698,396 A | 12/1997 | Pfreundschuh | |
| 5,776,708 A | 7/1998 | Kotzin et al. | |
| 5,837,447 A | 11/1998 | Gorski | |
| 6,087,096 A | 7/2000 | Dau et al. | |
| 6,090,592 A | 7/2000 | Adams et al. | |
| 6,258,568 B1 | 7/2001 | Nyren | |
| 6,416,948 B1 | 7/2002 | Pilarski et al. | |
| 6,596,492 B2 | 7/2003 | Avery et al. | |
| 6,667,159 B1 | 12/2003 | Walt | |
| 6,964,850 B2 | 11/2005 | Bevilacqua | |
| 7,306,906 B2 | 12/2007 | Maruyama et al. | |
| 7,375,211 B2 | 5/2008 | Kou | |
| 7,691,994 B2 | 4/2010 | Brewer et al. | |
| 7,749,697 B2 | 7/2010 | Oleksiewicz et al. | |
| 8,283,294 B2 | 10/2012 | Kastrup et al. | |
| 2002/0076725 A1 | 6/2002 | Toyosaki-Maeda et al. | |
| 2003/0162197 A1 | 8/2003 | Morley et al. | |
| 2004/0248172 A1 | 12/2004 | Samoszuk et al. | |
| 2005/0064421 A1 | 3/2005 | Gehrmann et al. | |
| 2006/0046258 A1 | 3/2006 | Lapidus et al. | |
| 2006/0085139 A1 | 4/2006 | Collette et al. | |
| 2006/0088876 A1 | 4/2006 | Bauer | |
| 2006/0134125 A1 | 6/2006 | Luxembourg et al. | |
| 2006/0147925 A1 | 7/2006 | Morley et al. | |
| 2006/0234234 A1 | 10/2006 | Van Dongen et al. | |
| 2006/0259248 A1 | 11/2006 | Collette et al. | |
| 2007/0105105 A1 | 5/2007 | Clelland et al. | |
| 2007/0117134 A1 | 5/2007 | Kou | |
| 2007/0160994 A1* | 7/2007 | Lim et al. ........................ 435/6 |
| 2007/0161001 A1 | 7/2007 | Leshkowitz | |
| 2007/0238099 A1 | 10/2007 | Cohen et al. | |
| 2007/0286849 A1 | 12/2007 | Chaturvedi | |
| 2008/0108509 A1 | 5/2008 | Haupl et al. | |
| 2008/0166704 A1 | 7/2008 | Marche et al. | |
| 2008/0166718 A1 | 7/2008 | Lim et al. | |
| 2008/0248484 A1 | 10/2008 | Bauer | |
| 2008/0274904 A1 | 11/2008 | Gormley et al. | |
| 2008/0280774 A1 | 11/2008 | Bureznski | |

(Continued)

FOREIGN PATENT DOCUMENTS

| | | | |
|---|---|---|---|
| EP | 1544308 A1 | 6/2005 | |
| EP | 1549764 B1 | 7/2005 | |

(Continued)

OTHER PUBLICATIONS

U.S. Appl. No. 12/945,678, filed Nov. 12, 2010, Faham et al.
U.S. Appl. No. 13/174,086, filed Jun. 30, 2011, Faham et al.
U.S. Appl. No. 13/196,885, filed Aug. 2, 2011, Moorhead et al.
U.S. Appl. No. 13/369,031, filed Feb. 8, 2012, Faham et al.
U.S. Appl. No. 13/459,701, filed Apr. 30, 2012, Faham et al.
U.S. Appl. No. 13/468,323, filed May 10, 2012, Faham et al.
U.S. Appl. No. 13/487,980, filed Jun. 4, 2012, Faham et al.
U.S. Appl. No. 13/627,497, filed Sep. 26, 2012, Faham et al.
U.S. Appl. No. 61/045,586, filed Apr. 16, 2008, Han et al.
Arstila et al., "A direct estimate of the human αβ T cell receptor diversity," Science 286:958-961 (1999).

(Continued)

*Primary Examiner* — Kenneth R. Horlick
*Assistant Examiner* — Joyce Tung
(74) *Attorney, Agent, or Firm* — Wilson Sonsini Goodrich & Rosati

(57) ABSTRACT

There is a need for improved methods for determining the diagnosis and prognosis of patients with conditions, including autoimmune disease and cancer, especially lymphoid neoplasms, such as lymphomas and leukemias. Provided herein are methods for using DNA sequencing to identify personalized, or patient-specific biomarkers in patients with lymphoid neoplasms, autoimmune disease and other conditions. Identified biomarkers can be used to determine and/or monitor the disease state for a subject with an associated lymphoid disorder or autoimmune disease or other condition. In particular, the invention provides a sensitive method for monitoring lymphoid neoplasms that undergo clonal evolutions without the need to development alternative assays for the evolved or mutated clones serving as patient-specific biomarkers.

29 Claims, 14 Drawing Sheets

(56) References Cited

U.S. PATENT DOCUMENTS

| | | |
|---|---|---|
| 2008/0286777 A1 | 11/2008 | Candeias et al. |
| 2009/0053184 A1 | 2/2009 | Morgan et al. |
| 2009/0181859 A1 | 7/2009 | Muraguchi |
| 2009/0197257 A1 | 8/2009 | Harris |
| 2009/0226975 A1 | 9/2009 | Sabot et al. |
| 2009/0280489 A1 | 11/2009 | Devinder et al. |
| 2009/0298060 A1 | 12/2009 | Lal et al. |
| 2010/0021896 A1 | 1/2010 | Han |
| 2010/0021984 A1 | 1/2010 | Edd |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0151471 A1 | 6/2010 | Faham et al. |
| 2010/0173394 A1 | 7/2010 | Colston, Jr. |
| 2010/0255471 A1 | 10/2010 | Clarke |
| 2010/0285975 A1 | 11/2010 | Mathies |
| 2010/0330571 A1 | 12/2010 | Robins et al. |
| 2011/0003291 A1 | 1/2011 | Pasqual |
| 2011/0207134 A1 | 8/2011 | Faham et al. |
| 2011/0207135 A1 | 8/2011 | Faham et al. |
| 2011/0207617 A1 | 8/2011 | Faham et al. |
| 2012/0135409 A1 | 5/2012 | Faham et al. |
| 2012/0220466 A1 | 8/2012 | Fire et al. |
| 2013/0005584 A1 | 1/2013 | Faham et al. |
| 2013/0017957 A1 | 1/2013 | Faham et al. |

FOREIGN PATENT DOCUMENTS

| | | |
|---|---|---|
| JP | 2007-536939 A | 12/2007 |
| JP | 2008099588 A | 5/2008 |
| WO | WO 93/01838 A1 | 2/1993 |
| WO | WO 2005/059176 A1 | 6/1995 |
| WO | WO 95/28481 A1 | 10/1995 |
| WO | WO 97/18330 A1 | 5/1997 |
| WO | WO 97/46706 A1 | 12/1997 |
| WO | WO 98/01738 A1 | 1/1998 |
| WO | WO 03/044225 A2 | 5/2003 |
| WO | WO 03/059155 A2 | 7/2003 |
| WO | WO 03/044225 A3 | 12/2003 |
| WO | WO 2004/003820 A2 | 1/2004 |
| WO | WO 03/059155 A3 | 3/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/046098 A3 | 8/2004 |
| WO | WO 2004/096985 A2 | 11/2004 |
| WO | WO 2005/005651 A2 | 1/2005 |
| WO | WO 2005/042774 A2 | 5/2005 |
| WO | WO 2005/053603 A2 | 6/2005 |
| WO | WO 2005/084134 A2 | 9/2005 |
| WO | WO 2006/076205 A2 | 7/2006 |
| WO | WO 2006/116155 A2 | 11/2006 |
| WO | WO 2008/026927 A2 | 3/2008 |
| WO | WO 2008/026927 A3 | 4/2008 |
| WO | WO 2008/039694 A2 | 4/2008 |
| WO | WO 2008/108803 A2 | 9/2008 |
| WO | WO 2008/108803 A3 | 12/2008 |
| WO | WO 2008/147879 A1 | 12/2008 |
| WO | WO 2009/015296 A1 | 1/2009 |
| WO | WO 2009/019657 A2 | 2/2009 |
| WO | WO 2009/021215 A1 | 2/2009 |
| WO | WO 2006/076205 A3 | 4/2009 |
| WO | WO 2009/045898 A2 | 4/2009 |
| WO | WO 2009/070767 A2 | 6/2009 |
| WO | WO 2009/019657 A3 | 8/2009 |
| WO | WO 2009/108860 A2 | 9/2009 |
| WO | WO 2009/108866 A2 | 9/2009 |
| WO | WO 2009/070767 A3 | 10/2009 |
| WO | WO 2009/108866 A3 | 10/2009 |
| WO | WO 2009/137255 A2 | 11/2009 |
| WO | WO 2009/137832 A2 | 11/2009 |
| WO | WO 2009/145925 A1 | 12/2009 |
| WO | WO 2009/151628 A2 | 12/2009 |
| WO | WO 2009/158521 A2 | 12/2009 |
| WO | WO 2009/108860 A3 | 1/2010 |
| WO | WO 2009/137255 A3 | 1/2010 |
| WO | WO 2010/011894 A1 | 1/2010 |
| WO | WO 2009/151628 A3 | 2/2010 |
| WO | WO 2010/016352 A1 | 4/2010 |
| WO | WO 2009/158521 A3 | 5/2010 |
| WO | WO 2010/151416 A1 | 12/2010 |
| WO | WO 2011/083296 A1 | 7/2011 |
| WO | WO 2011/106738 A2 | 9/2011 |
| WO | WO 2011/139372 A1 | 11/2011 |
| WO | WO 2011/140433 A2 | 11/2011 |
| WO | WO 2011/106738 A3 | 12/2011 |
| WO | WO 2012/048340 A2 | 4/2012 |
| WO | WO 2012/048340 A3 | 6/2012 |

OTHER PUBLICATIONS

Bagnara, et al. IgV gene intraclonal diversification and clonal evolution in B-cell chronic lymphocytic leukaemia. Br J Haematol. Apr. 2006;133(1):50-8.

Batzoglou. The many faces of sequence alignment. Briefings in Bioinformatics. 2005; 6:6-22.

Beishuizen, et al. Analysis of Ig and T-cell receptor genes in 40 childhood acute lymphoblastic leukemias at diagnosis and subsequent relapse; implications for the detection of minimal residual disease by polymerase chain reaction analysis. Blood, Apr. 15, 1994;83(8):2218-47.

Bene, et al. How and why minimal residual disease studies are necessary in leukemia; a review from WP10 and WP12 of the European LeukaemiaNet, Haematologica. Aug. 2009;94(8):1135-50. Epub Jul. 7, 2009.

Benichou, et al. Rep-Seq: uncovering the immunological repertoire through next-generation sequecing. Immunology. Mar. 2012;135(3):183-91. doi:10.1111/j.1365-2567.2011.03527.x.

Bonarius, et al. Monitoring the T-Cell Receptor Repertoire at Single-Clone Resolution. PLoS One. Dec. 20, 2006;1:e55.

Boria, et al. Primer sets for cloning the human repertoire of T cell receptor variable regions. BMC Immunology, 2008; 9:50.

Boyd et al. Measurement and clinical monitoring of human lymphocyte clonality by massively parallel VDJ pyrosequencing, Sci Transl. Med. 1(12):12ra23 (2009).

Boyd, et al, Individual variation in the germline Ig gene repertoire inferred from variable region gene rearrangements. J Immunol. Jun. 15, 2010;184(12):6986-92. Epub May 21, 2010.

Brehm-Stecher, et al. Single-cell microbiology: tools, technologies, and applications. Microbiology and molecular biology reviews. 2004; 68(3):538-559.

Brisco, et al. Determining the repertoire of IGH gene rearrangements to develop molecular markers for minimal residual disease in B-lineage acute lymphoblastic leukemia. J Mol Diagn. May 2009;11(3):194-200. Epub Mar. 26, 2009.

Bruggemann, et al. Clinical significance of minimal residual disease quantification in adult patients with standard-risk acute lymphoblastic leukemia. Blood. Feb. 1, 2006;107(3):1116-23. Epub Sep. 29, 2005.

Campana, Minimal residual disease in acute lymphoblastic leukemia. Semin Hematol, Jan. 2009;46(1):100-6.

Campbell et al., "Subclonal phylogenetic structures in cancer revealed by ultra-deep sequencing," PNAS 105(35):13081-13086 (2008).

Choi, et al. Clonal evolution in B-lineage acute lymphoblastic leukemia by contemporaneous VH-VH gene replacements and VH-DJH gene rearrangements. Blood. Mar. 15, 1996;87(6):2506-12.

Choi, et al. Relapse in children with acute lymphoblastic leukemia involving selection of a preexisting drug-resistant subclone. Blood. Jul. 15, 2007;110(2);632-9. Epub Mar. 19, 2007.

International Search Report for PCT Application PCT/US2009/006053 dated Jun. 15, 2010.

Costabile, et al. Molecular approaches in the diagnosis of primary immunodeficiency diseases. Hum Mutat. Dec. 2006;27(12):1163-73.

(56) References Cited

OTHER PUBLICATIONS

Cronn et al. Multiplex sequencing of plant chloroplast genomes using Solexa sequencing-by-synthesis technology. Nucleic Acids Res. Nov. 2008:36(19):e122.

Curran et al., "Nucleotide sequencing of psoriatic arthritis tissue before and during methotrexate administration reveals a complex inflammatory T cell infiltrate with very few clones exhibiting features that suggest they drive the inflammatory process by recognizing autoantigens," J Immunol 172:1935-1944 (2004).

Currier, et al. Spectratype/immunoscope analysis of the expressed TCR repertoire. Current Protocols in Immunology. 2000; Supplement 38:10.28.1-10.28.24.

Davi, et al. Lymphocytic progenitor cell origin and clonal evolution of human B-lineage acute lymphoblastic leukemia. Blood. Jul. 15, 1996;88(2):609-21.

Davis, et al. Staining of cell surface human CD4 with2-F-pyrimidine-containing RNA amptamers for flow cytometry. Nucleic Acids Research. 1998; 26(17):3915-3924.

Deng et al., "Gene profiling involved in immature CD4+ T lymphocyte responsible for systemic lupus erythematosus," Molecular Immunology 43:1497-1507 (2006).

Dohm, et al. Substantial biases in ultra-short read data sets from high throughput DNA sequencing. Nucleic Acids Research. 2008; 36:e105.

Dou, et al. Analysis of T cell receptor Vbeta gene usage during the course of disease in patients with chronic hepatitis B. J Biomed Sci. Nov.-Dec. 1998;5(6):428-34.

Du et al., "TCR spectratyping revealed T lymphocytes associated with graft-versus-host disease after allogeneic hematopoietic stem cell transplantation," Leukemia & Lymphoma 48(8):1618-1627 (2007).

Edd, et al. Controlled encapsulation of single cells into monodisperse picoliter drops. Lap Chip. 2008; 8(8):1262-1264.

European office action dated Mar. 28, 2012 for EP Application No. 09764927.1.

Freeman et al., "Profiling the T-cell receptor beta-chain repertoire by massively parallel sequencing," Genome Res. 19(10):1817-1824 (2009).

Fritz et al., "Alterations in the spinal cord T cell repertoire during relapsing experimental autoimmune encephalomyelitis," J Immunol 164:6662-6668 (2000).

Garcia-Castello, et al. Detection of clonal immunoglobulin and T-cell receptor gene recombination in hematological malignancies: monitoring minimal residual disease. Cardiovascular & Haematological Disorders-Drug Targets, 2009; 9:124-135.

Germano: et al. Clonality profile in relapsed precursor-B-ALL children by GeneScan and sequencing analyses. Consequences on minimal residual disease monitoring. Leukemia. Aug. 2003;17(8):1573-82.

Giuggiio, et al. Evolution of the intrahepatic T cell repertoire during chronic hepataitis C virus infection. Viral Immunol. 2005;118(1):179-89.

Golembowski, et al. Clonal evolution in a primary cutaneous follicle center B cell lymphoma revealed by single analysis in sequential biopsies. Immunobiology. Apr. 2000;201(5):631-44.

Gonzalez, et al. Incomplete DJH rearrangements as a novel tumar target for minimal residual disease quantitation in multiple myeloma using real-time PCR. Leukemia. 2003; 17:1051-1057.

Gonzalez, et al. Incomplete DJH rearrangements of the IgH gene are frequent in multiple myelioma patients: immunobioligcal characteristics and clinical applications. Leukemia. 2003; 17:1398-1403.

Gorski, et al. Circulating T cell repertoire complexity in normal individuals and bone marrow recipients analyzed by CDR3 size spectratyping. Correlation with immune status, J Immunol. May 15, 1994;152(10):5109-19.

Green, et al. Clonal diversity of Ig and T-cell-receptor gene rearrangements identifies a subset of childhood B-precursor acute lymphoblastic leukemia with increased risk of relapse. Blood. Aug. 1, 1998;92(3):952-8.

Gurrieri, et al. Chronic lymphocytic leukemia B cells can undergo somatic hypermutation and intraclonal immunoglobulin V(H)DJ(H) gene diversification. J Exp Med. Sep. 2, 2002;196(5):629-39.

Han, et al. Immunorepertoire analysis by multiplex PCR amplification and high throughput sequencing . Abstract. The 96 Annual Meeting of The American Association of Immunologists, Seattle, Washington, May 8-12, 2009. Available at http://jimmunol.org//cgi/content/meeting_abstract/182/1_MeetingAbstracts/42.6?sid=257929fl-97a9-4330-8e96-1750aa240e69. Accessed Nov. 24. 2010.

Heger, M. Studies Highlight Challenges of Immune Repertoire Sequencing's Clinical Applicability. Available at http://www.genomeweb.com/sequencing/studies-highlight-challenges-immune-repertoire-sequencings-clinical-applicabilit?hq_e=el&hq_m=966798&hq_1=10&hq_v=2357e2f0b3. Accessed Apr. 6, 2011.

Holt, "Q &A: BC cancer agency's Robert Holt on sequencing the immune repertoire in immune reconstitution," Genome Web (www.genomeweb.com) Jun. 30, 2009.

Illumina, Data Sheet: Sequencing. Genomic Sequencing, Pub. No. 770.2008-016 Copyright 2010. Reference states: "Current as of Jan. 30, 2009."

International search report and written opinion dated Sep. 22, 2011 for PCT Application No. US11/000791.

International search report and written opinion dated Oct. 19, 2011 for PCT Application No. US11/000792.

Ishii et al., "Isolation and expression profiling of genes upregulated in the peripheral blood cells of systemic lupus erythematosus patients," DNA Research 12:429-439 (2005).

Jacobi et al., "Activated memory B cell subsets correlate with disease activity in systemic lupus erythematosus: delineation by expression of CD27, IgD, and CD95," Arthritis & Rheumatism 58(6):1762-1773 (2008).

Jacobi et al., "Correlation between circulating CD27high plasma cells and disease activity in patients with systemic lupus erythematosus," Arthritis & Rheumatism 48(5):1332-1342 (2003).

Jena, et al. Amplification of genes, single transcripts and cDNA libraries from one cell and direct sequence analysis of amplified products derived from one molecule. J. Immunol. Methods. 1996; 190:199-213.

Kato et al., "Analysis of accumulated T cell clonotypes in patients with systemic lupus erythematosus," Arthritis & Rheumatism 43(12):2712-2721 (2000).

Kim, et al An efficient and reliable DNA extraction method for preimplantation genetic diagnosis: a comparison of allele drop out and amplification rates using different single cell iysis methods. Fertility and Sterility. 2009; 92: 814-818.

Kim, et al. Polony multiplex analysis of gene expression (PMAGE) in mouse hypertrophic cardiomyopathy. Science. Jun. 8, 2007;316(5830):1481-4.

Kneba, et al. Analysis of rearranged T-cell receptor beta-chain genes by polymerase chain reaction (PCR0 DNA sequencing and automated high resolution PCR fragment analysis. Blood. 1995; 86:3930-3937.

Kobari, et al. T cells accumulating in the inflamed joints of a spontaneous murine model of rheumatoid arthritis become restricted to common clonotypes during disease progression. Int Immunol. Jan. 2004;16(1):131-8.

Langerak, et al. Immunoglobulin/T-cell receptor clonality diagnostics. Exoert Opin. Med. Diagn. 2007; 1(3):451-461.

Langerak, et al. Polymerase chain reaction-based clonality testing in tissue samples with reactive lymphoproliferations: usefulness and pitfalls. A report of the BIOMED-2 Concerted Action BMH4-CT98-3936. Leukemia. Feb. 2007;21(2):222-9. Epub Dec. 14, 2006.

Laplaud et al., "Blood T-cell receptor β chain transcriptome in multiple sclerosis. Characterization of the T cells with altered CDR3 length distribution," Brain 127:981-995 (2004).

Laplaud et al., "Serial blood T cell repertoire alterations in multiple sclerosis patients; correlation with clinical and MRI parameters," J Neroimmunol 177:151-160 (2006).

Li, et al. An improved one-tube RT-PCR protocol for analyzing single-cell gene expression in individual mammalian cells, Anal. Bioanal. Chem. 2010; 397: 1853-1859.

(56) References Cited

OTHER PUBLICATIONS

Li, et al, Clonal rearrangements in childhood and adult precursor B acute lymphoblastic leukemia: a comparative polymerase chain reaction study using multiple sets of primers. Eur J Haematol. Oct. 1999;63(4):211-8.

Li, et al. Detailed clonality analysis of relapsing precursor B acute lymphoblastic leukemia: implications for minimal residual disease detection. Leukemia Research. 2001; 25:1033-1045.

Li, et al. Sequence analysisn of clonal immunoglobulin and T-cell receptor gene rearrangements in children with acute lymphoblastic leukemia at diagnosis and at relapse: implications for pathogenesis and for the clinical utility of PCR-based methods of minimal residual disease detection. Blood. 2003; 102:4520-4526.

Li, et al. Utilization of Ig heavy chain variable, diversity, and joining gene segments in children with B-lineage acute lymphoblastic leukemia: implications for the mechanisms of VDJ recombination and for pathogenesis. Blood. Jun. 15, 2004;103(12):4602-9. Epub Mar. 9, 2004.

Logan, et al. High-throughput VDJ sequencing for quantification of minimal residual disease in chronic lymphocytic leukemia and immune reconstitution assessment. Proc Natl Acad Sci U S A. Dec. 27, 2011;108(52):21194-9. Epub Dec. 12, 2011.

Lovisa, et al. IgH and IgK gene rearrangements as PCR targets for pediatric Burkitt's lymphoma and mature B-ALL MRD analysis. Lab Invest. Oct. 2009;89(10):1182-6. Epub Aug. 10, 2009.

Luo et al., "Analysis of the interindividual conservation of T cell receptor α- and β-chain variable regions gene in the peripheral blood of patients with systemic lupus erythematosus," Clin Exp Immunol 154:316-324 (2008).

Margulies, et al. Genome sequencing in microfabricated high-density picolitre reactors. Nature. Sep. 15, 2005;437(7057):376-80. Epub Jul. 31, 2005.

Mato et al., "Correlation of clonal T cell expansion with disease activity in systemic lupus etythematosus," Int Immunol 9(4):547-554 (1997).

Matolcsy, et al. Clonal evolution of B cells in transformation from low- to high-grade lymphoma. Eur J Immunol. Apr. 1999;29(4):1253-64.

Matsumoto et al., "CDR3 spectratyping analysis of the TCR repertoire in myasthenia gravis," J Immunol 176;5100-5107 (2006).

Matsumoto et al., "Complementarity-determining region 3 spectratyping analysis of the TCR repertoire in multiple sclerosis," J Immunol 170;4840-4853 (2003).

Meleshko, et al. Rearrangements of IgH, TCRD and TCRG genes as clonality marker of childhood acute lymphoblastic leukemia. Exp Oncol. Dec. 2005;27(4):319-24.

Menezes et al., "A public T cell clonotype within a heterogeneous autoreactive repertoire is dominant in driving EAE," J Clin Invest 117(8):2176-2185 (2007).

Michalek, et al. Detection and long-term in vivo monitoring of individual tumor-specific T cell clones in patients with metastatic melanoma. J Immunol. Jun. 1, 2007;178(11):6789-95.

Moss, et al. The human T cell reeptor in health and disease. Annu. Rev. Immunol. 1992; 10:71-96.

Muraro et al., "Molecular tracking of antigen-specific T cell clones in neurological immune-mediated disorders," Brain 126:20-31 (2003).

Nardi, et al. Quantitative monitoring by polymerase colony assay of known mutations resistant to ABL kinase inhibitors. Oncogene. Jan. 31, 2008;27(6):775-82. Epub Aug. 6, 2007, 1-8.

Neale, et al. Comparative analysis of flow cytometry and polymerase chain reaction for the detection of minimal residual disease in childhood acute lymphoblastic leukemia. Leukemia. May 2004;18(5):934-8.

Nguyen, et al. Identification of errors introduced during high throughput sequencing of the T cell receptor repertoire. BMC Genomics. Feb. 11, 2011;12:106.

Notification of Grant dated Jul. 26, 2011 for patent serial No. GB 2467704.

Novak, et al. Single-cell multiplex gene detection and sequencing With microfluidically generated agarose emulsions. Angewandte Chemie. 2011;50: 390-395, with supplemental material.

Office action dated May 9, 2012 for U.S. Appl. No. 13/00,395.

Office action dated Sep. 15, 2011 for U.S. Appl. No. 12/615,263.

Ogle, et al. Direst measurement of lymphocyte receptor diversity. Nucleic Acids Research. 2003; 31(22):e139.

Okajima et al., "Analysis of T cell receptor Vβ diversity in peripheral CD4+ and CD8+ T lymphocytes in patients with autoimmune thyroid diseases," Clin Exp Immunol 155:166-172 (2008).

Packer et al, "Optimized clonotypic analysis of T-cell receptor repertoire in immune reconstitution," Exp. Hematol 35(3):516-521 (2007).

Panzer-Grumayer, et al. Immunogenotype changes prevail in relapses of young children with TEL-AML1-positive acute lymphoblastic leukemia and derive mainly from clonal selection. Clin Cancer Res. Nov. 1, 2005;11(21):7720-7.

Pels, et al. Clonal evolution as pathogenetic machanism in relapse of primary CNS lymphoma. Neurology. Jul. 13, 2004;63(1):167-9.

Pira, et al. Human naive CD4 T-cell clones specific for HIV envelope persist for years in vivo in the absence of antigenic challenge. J Acquir Immune Defic Syndr. Oct. 1, 2005;40(2):132-9.

Pop, et al, Bioinformatics challenges of new sequencing technology. Trends Genet. Mar. 2008;24(3):142-9.

Ray, et al. Single cell multiplex PCR amplification of five dystrophin gene exons combined with gender determination. Molecular Human Reproduction. 2001; 7(5): 489-494.

Reddy, et al. Systems analysis of adaptive immunity by utilization of high-throughput technologies. Curr Opin Biotechnol. Aug. 2011;22(4):584-9. Epub May 12, 2011.

Reinartz, et al. Massively parallel signature sequencing (MPSS) as a tool for in-depth quantitative gene expression profiling in all organisms. Brief Funct Genomic Proteamic. Feb. 2002;1(1):95-104.

Ria, et al. Collagen-specific T-cell repertoire in blood and synovial fluid varies with disease activity in early rheumatoid arthritis, Arthritis Res Ther. 2008;10(6):R135. Epub Nov. 17, 2008.

Rickison, et al. Human cytotoxic T lymphocyte responses to Epstein-Barr virus infection. Annu Rev Immunol. 1997;15:405-31.

Risitano et al., "In-vivo dominant immune responses in aplastic anaemia: molecular tracking of putatively pathogenetic T-cell clones by TCR β-CDR3 sequencing," Lancet 364:355-364 (2004).

Robins et al., "Comprehensive assessment of T-cell receptor beta-chain diversity in alphabeta T cells," Blood 114(19):4099-4107 (2009).

Robins, et al. Ultra-sensitive detection of rare T cell clones. Immunol Methods. Jan. 31, 2012;375(1-2):14-9, Epub Sep. 10, 2011.

Rosenquist, et al. Clonal evolution as judged by immunoglobulin heavy chain gene rearrangements in relapsing precursor-B acute lymphoblastic leukemia. Eur J Haematol. Sep. 1999;63(3):171-9.

Rougemont, et al. Probabilistic base calling of Solexa sequencing data. BMC Bioinformatics. 2008; 9:431.

Ryan, et al. Clonal evolution of lymphoblastoid cell lines. Lab Invest. Nov. 2006;86(11):1193-200. Epub Oct. 2, 2006.

Schaufelberger, et al. An uneven expression of T cell receptor V genes in the arterial wall and peripheral blood in giant cell arteritis. Inflammation. Dec. 2008;31(6):372-83.

Scholler, et al. Analysis of T cell receptor alpha beta variability in lymphocytes infiltrating melanoma primary tumours and metastatic lesions, Cancer Immunol Immunother. Oct. 1994;39(4):239-48.

Schwab et al, "CD8+ T-cell clones dominate brain infiltrates in Rasmussen encephalitis and persist in the periphery," Brain 132:1236-1246 (2009).

Shen, et al. Comparing platforms for *C. elegans* mutant identification using high-throughput whole-genome sequencing. PLoS One. 2008;3(12):e4012.

Skulina et al., "Multiple sclerosis: brain-infiltrating CD8+ T cells persist as clonal expansions in the cerebrospinal fluid and blood," PNAS 101(8):2428-2433 (2004).

Sramkova, et al. Detectable minimal residual disease befor allogeneic hematopoietic stem cell transplantation predicts extremely poor prognosis in children with acute lymphoblastic leukemia. Pediatr Blood Cancer. Jan. 2007;48(1):93-100.

(56) References Cited

OTHER PUBLICATIONS

Steenbergen, et al. Distinct ongoing Ig heavy chain rearrangement processes in childhood B-precursor acute lymphoblastic leukemia. Blood, Jul. 15, 1993;82(2):581-9.
Steward, et al. A polymerase chain reaction study of the stability of Ig heavy-chain and T-cell receptor delta gene rearrangements between presentation and relapse of childhood B-lineage acute lymphoblastic leukemia. Blood, Mar. 1, 1994;83(5):1355-62.
Struyk, et al. T cell receptors in rheumatoid arthritis. Arthritis Rheum, May 1995;38(3):577-89.
Sumida et al., "T cell receptor repertoire of infiltrating T cells in lips of Sjögren's syndrome patients," J Clin Invest 89;611-685 (1992).
Sumida et al., "T cell receptor Vα repertoire of infiltrating T cells in labial salivary glands from patients with Sjögren's syndrome," J Rheumatol 21: 1655-1661 (1994).
Tackenberg et al. "Clonal expansions of CD4+ β helper T cells in autoimmune myasthenia gravis," Eur J Immunol 37;849-803 (2007).
Tajiri, et al. Cell-microarray analysis of antigen-specifie B-cells: single cell analysis of antigen receptor expression and specificity. Cytometry Part A. 2007; 71A: 961-967.
Thornhill et al. A comparison of different lysis buffers to assess allele dropout from single cells for preimplantation genetic diagnosis. Prenatal Diagnosis, 2001; 21: 490-497.
Tokimitsu, et al, Single lymphocyte analysis with a microwell array chip. Cytometry. 2007; Part A, 71A: 1003-1010.
UK Combined Search Report and Office action dated Jun. 29, 2012 for UK application No. GB1209668.1.
UK Combined Search Report and Office action dated May 26, 2011 for UK application No. GB1105068.9.
UK office action dated May 25, 2011 for UK application No. GB1009641.0.
UK office action dated Oct. 20, 2010 for UK application No. GB1009641.0.
UK Search Report and office action dated Jan. 12, 2012 for UK application No. GB1120209.0.
UK Search Report and office action dated Jul. 7, 2010 for UK application No. GB1009641.0.
Umibe et al., "Clonal expansion of T cells infiltrating in the airways of non-atopic asthmatics," Clin Exp Immunol 119:390-397 (2000).
Van Dongen, et al. Design and standardization of PCR primers and protocols for detection of clonal immunoglobulin and T-cell receptor gene recombinations in suspect lymphoproliferations: report of the BIOMED-2 Concerted Action BMH4-CT98-3936, Leukemia. Dec. 2003;17(12):2257-317.
Wang, et al. High throughput sequencing reveals a complex pattern of dynamic interrelationships among human T cell subsets. Proc Natl Acad Sci U S A. Jan. 26, 2010; 107(4): 1518-1523.
Wang, et al. Quantitative measurement of pathogen-specific human memory T cell repertoire diversity using a CDR3 beta-specific microarray. BMC Genomics, Sep. 19, 2007;8:329.
Warren et al., "Profiling model T-cell metagenomes with short reads," Bioinformatics 25(4):458-464 (2009).
Warren, et al. Exhaustive T-cell repertoire sequencing of human peripheral blood samples reveals signatures of antigen selection and is directly measured repertoire size of at least 1 million clonotypes. Genome Res. Feb. 24, 2011. [Epub ahead of print].
Weinstein et al., "High-throughput sequencing of the zebrafish antibody repertoire," Science 324:807-810 (2009).
Wells, et al. Strategies for preimplantation genetic diagnosis of single gene disorders by DNA amplification. Prenatal Diagnosis. 1998; 18: 1389-1401.
Wetmur, et al. An emulsion polymerase chain reaction-based method for molecular haplotyping. Methods in Molecular Biology. 1996; 410: 351-361.
Wetmur, et al. Linking emulsion PCR haplotype analysis. chapter 11, in Park (editor), PCR Protocols, Methods En Molecular Biology. 2011; 687: 165-175.
Wetmur, et al. Molecular haplotyping by linking emulsion PCR: analysis of paraoxonase 1 haplotypes and phenotypes. Nucleic Acids Research. 2005; 33(8):2615-2619.
Wlodarski, et al. Molecular strategies for detection and quantitation of the clonal cytotoxic T-cell responses in aplastic anemia and myelodysplastic syndrome. Blood. 2006; 108:202-2641.
Wlodarski, et al. Pathologic clonal cytotoxic T-cell responses: nonrandom nature of the T-cell-receptor restriction in large granular lymphocyte leukemia. Blood. 2005; 106:2769-2779.
Yin et al., "Antiretroviral therapy restores diversity in the T-cell receptor Vβ repertoire of CD4 T-cell subpopulations among human immunodeficiency virus type 1-infected children and adolescents," Clin Vac Immunol 16(9):1293-1301 (2009).
Yon, et al, Precise gene fusion by PCR. Nucleic Acids Research. 1989; 17(12):4895.
Zaliova, et al. Quantification of fusion transcript reveals a subgroup with distinct biological properties and predicts relapse in BCR/ABL-positive ALL; implications for residual disease monitoring. Leukemia. May 2009;23(5):944-51. Epub Jan. 22, 2009.
Zeng, et al. High-performance single cell genetic analysis using microfluidic emulsion generator arrays. Anal. Chem. 2010;82:3183-3190.
Zhou, et al. High throughput analysis of TCR-beta rearrangement and gene expression in single cells. 2006; 86:314-321.
Bruggemann et al, "Standardized MRD quantification in European ALL trials: Proceedings of the Second International Symposium on MRD assessment in Kiel, Germany, Sep. 18-20, 2008," Leukemia, 24: 521-535 (2010).
Gerlinger et al, "How Darwinian models inform therapeutic failure initiated by clonal heterogeneity in cancer medicine," British Journal of Cancer, 103: 1139-1143 (2010).
Szczepanski et al, "Comparative analysis of Ig and TCR gene rearrangements at diagnosis and at relapse of childhood precursor-B-ALL provides improved strategies for selection of stable PCR targets for monitoring of minimal residual disease," Blood, 99(7): 2315-2323 (2002).
Szczepanski, "Why and how to quantify minimal residual disease in acute lymphoblastic leukemia?," Leukemia, 21: 622-626 (2007).
van der Velden et al, "Detection of minimal residual disease in hematologic malignancies by real-time quantitative PCR: principles, approaches, and laboratory aspects," Leukemia, 17: 1013-1034 (2003).
van der Velden et al, "Analysis of minimal residual disease by Ig/TCR gene rearrangements: guidelines for interpretation of real-time quantitative PCR data," Leukemia, 21: 604-611 (2007).
Alatrakchi, et al. T-cell clonal in patients with B-cell lymphoproliferative disorders. J Immunother. Sep. 1998;21(5):363-70.
Guo, et al. Sequence changes at the V-D junction of the VH1 heavy chain of anti-phosphocholine antibodies alter binding to and protection against *Streptococcus pneumoniae*. Int Immunol May 1997;9(5):665-77.
Howe, et al. T cell receptor clonotype analysis of T cell responses: Diagnostic application of a clonotypic database. Blood. 2003; 102:Abstract 3918.
Office action dated Mar. 20, 2013 for U.S. Appl. No. 13/487,980.
Office action dated Apr. 22, 2013 for U.S. Appl. No. 13/214,111.
Office action dated Dec. 6, 2012 for U.S. Appl. No. 13/100,395.
Sfanos, et al. Phenotypic analysis of prostate-infiltrating lymphocytes reveals TH17 and Treg skewing. Clin Cancer Res. Jun. 1, 2008;14(11):3254-61. doi: 10.1158/1078-0432.CCR-07-5164.
Sing, et al. A molecular comparison of T lymphocyte populations infiltrating the liver and circulating in the blood of patients with chronic hepatitis B: evidence for antigen-driven selection of a public complementarity-determining region 3 (CDR3) motif. Hepatology. May 2001;33(5):1288-98.
UK combined search and examination report dated Mar. 20, 2013 for GB 1300533.5.
U.S. Appl. No. 13/861,941, filed Apr. 12, 2013, Pepin et al.
Wu, et al. High-throughput sequencing detects minimal residual disease in acute T lymphoblastic leukemia. Sci Transl Med. May 16, 2012;4(134):134ra63. doi: 10 .1126/scitranslmed.3003656.
U.S. Appl. No. 13/905,406, filed May 30, 2013, Faham et al.
U.S. Appl. No. 13/908,813, filed Jun. 3, 2013, Faham et al.

(56) References Cited

OTHER PUBLICATIONS

Chen, A novel approach for the analysis of T-cell reconstitution by using a T-cell receptor beta-based oligonucleotide microarray in hematopoietic stem cell transplantation, Exp Hematol. May 2007;35(5):831-41.
Office action dated Jun. 6, 2013 for U.S. Appl. No. 13/100,365.
Office action dated Jun. 6, 2013 for U.S. Appl. No. 13/100,389.
Office action dated Jun. 20, 2013 for U.S. Appl. No. 13/214,111.
Office Action dated Nov. 6, 2013 for U.S. Appl. No. 13/468,323.
Office action dated Nov. 27, 2013 for U.S. Appl. No. 13/196,885.
Office action dated Oct. 16, 2013 for U.S. Appl. No. 13/487,980.
Office action dated Oct. 7, 2013 for U.S. Appl. No. 13/459,701.

* cited by examiner

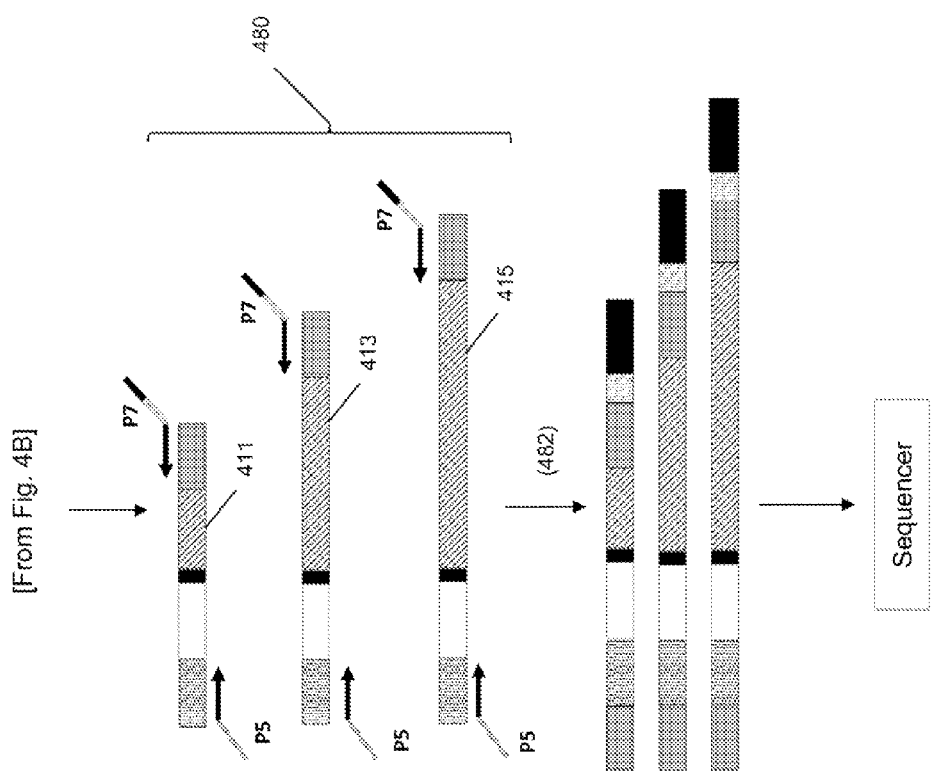

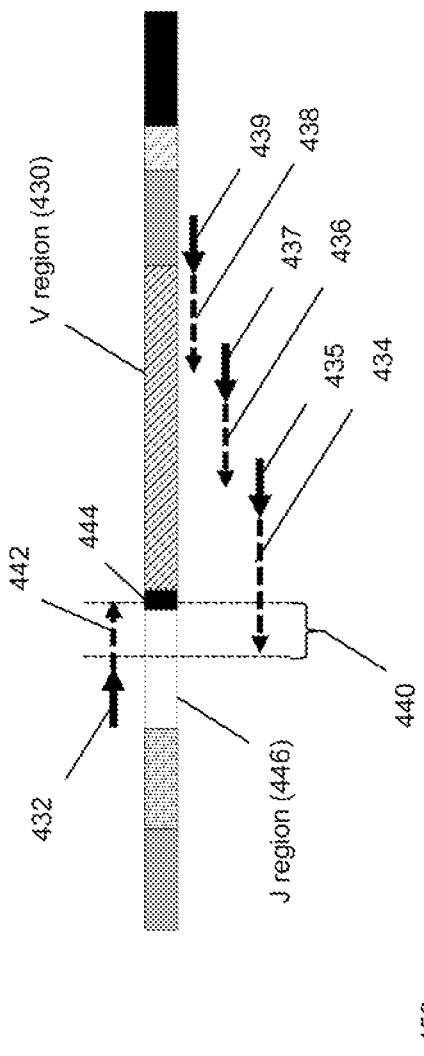
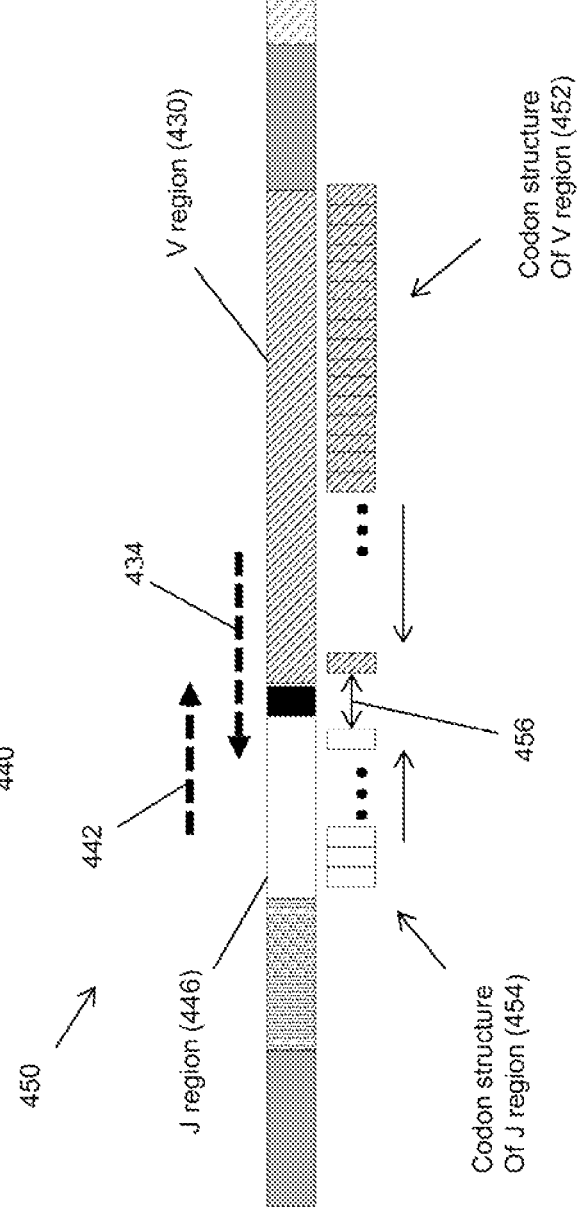
Fig. 4D
Fig. 4E

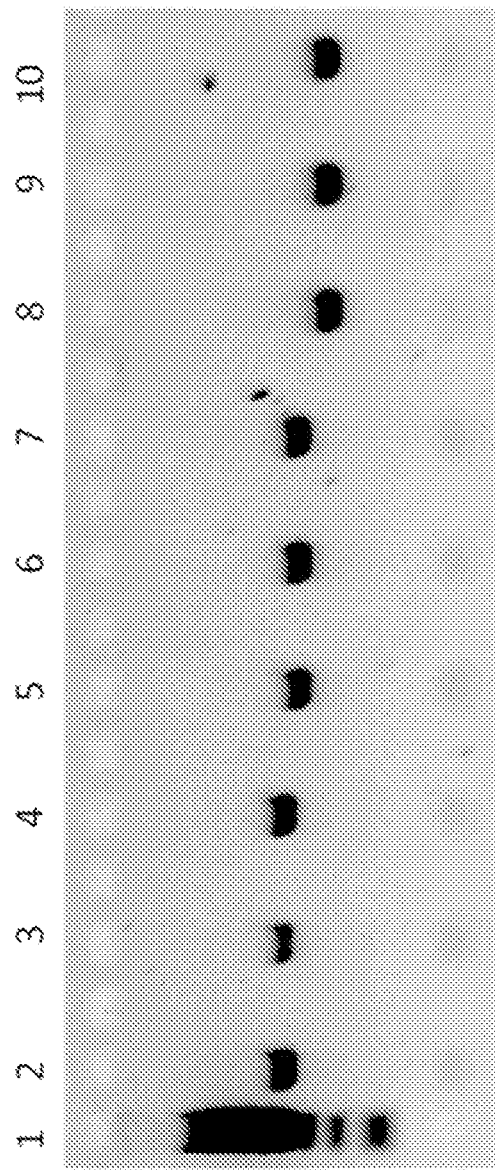

Amplification products after 2 stage PCRs with the 3 sets of V segment primers in stage 1 are shown. All use the J primers in the first stage. Lane 1 is the 100 bp size ladder (NEB), 2-4 amplification with primer set A, 5-7 with primer set B, and 8-10 with primer set C. The 3 different lanes for each primer set is for 3 different V segment primer concentrations. Since the second stage PCR primers are the same for all three pools, we have also shown that three products of the first stage PCR can be pooled to be amplified in the second stage PCR.

Fig. 8A

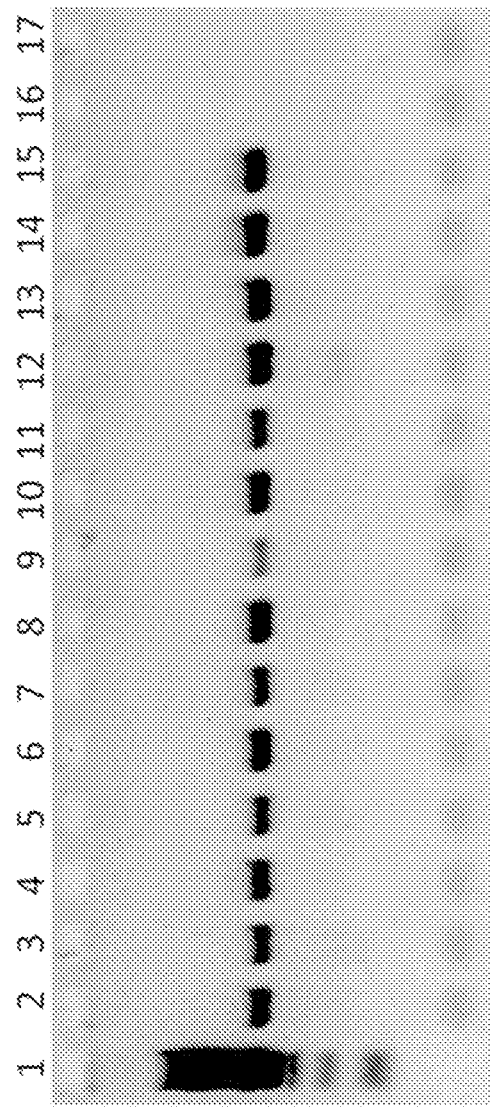

Amplification products after 2 stage PCRs with the J primers and the A set of V segment primers in stage 1 are shown. Lane 1 is the 100 bp size ladder (NEB), 2-9 use different amount of input blood genomic DNA (lane2-3: 250 ng, 4-5 and 10-11: 500 ng, 6-7: 1μg, and 8-9: 2.5 μg). Lanes 12-13 use 250 ng of spleen genomic DNA. Lanes 14-15 use 250 ng of the Raji B cell line (positive control), and lane 16-17 use 250 ng of Jurkat T cell line (negative control). The two reactions for each genomic DNA concentration use different primer concentrations.

Fig. 8B

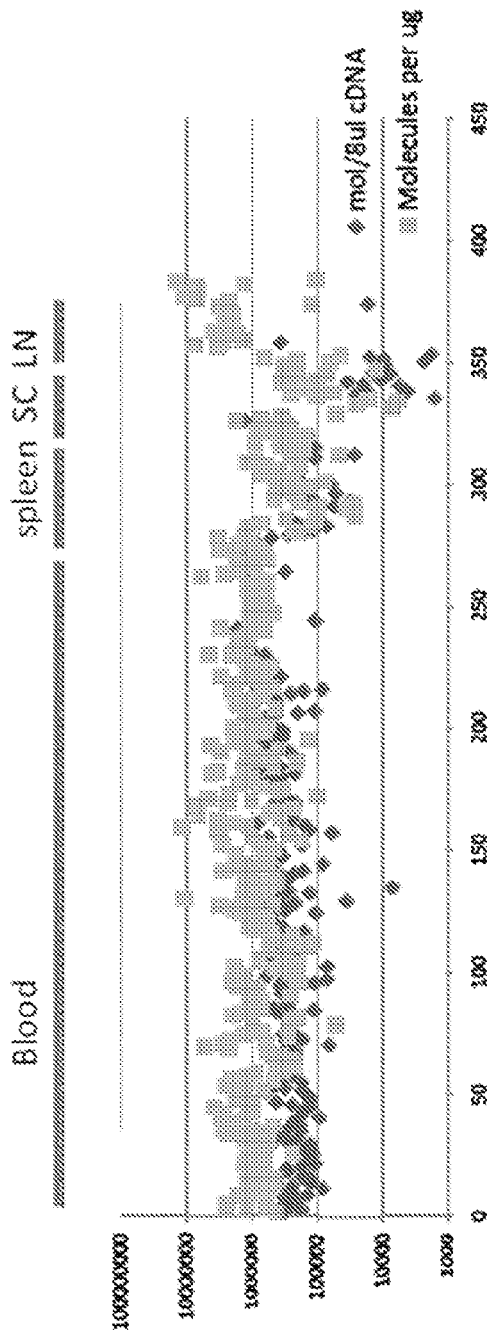

Real time PCR using standards with known numbers of molecules were used to determine the number of TCRβ molecules in the input DNA. The dark colored dots depict the number of molecules that were ultimately amplified in the multiplex PCR, and the light colored dots show the number of molecules per μg RNA assuming a perfect 1:1 relationship between RNA and cDNA. (SC is spinal cord and LN is lymph node).

Fig. 9

SEQUENCE LISTING

<160> NUMBER OF SEQ ID NOS: 197

<210> SEQ ID NO 1
<211> LENGTH: 20
<212> TYPE: DNA
<213> ORGANISM: Homo sapiens

<400> SEQUENCE: 1

```
agcgacctcg ggtgggaaca                                              20

<210> SEQ ID NO 2
<211> LENGTH: 23
<212> TYPE: DNA
<213> ORGANISM: Homo sapiens

<400> SEQUENCE: 2
aactatgttt tggtatcgtc agt                                          23

<210> SEQ ID NO 3
<211> LENGTH: 23
<212> TYPE: DNA
<213> ORGANISM: Homo sapiens

<400> SEQUENCE: 3
aactatgttt tggtatcgtc agt                                          23

<210> SEQ ID NO 4
<211> LENGTH: 21
<212> TYPE: DNA
<213> ORGANISM: Homo sapiens

<400> SEQUENCE: 4
agtgtatcct ggtaccaaca g                                            21

<210> SEQ ID NO 5
<211> LENGTH: 21
<212> TYPE: DNA
<213> ORGANISM: Homo sapiens

<400> SEQUENCE: 5
agtgtgtact ggtaccaaca g                                            21

<210> SEQ ID NO 6
<211> LENGTH: 21
<212> TYPE: DNA
<213> ORGANISM: Homo sapiens

<400> SEQUENCE: 6
actgtgtcct ggtaccaaca g                                            21

<210> SEQ ID NO 7
<211> LENGTH: 21
<212> TYPE: DNA
<213> ORGANISM: Homo sapiens

<400> SEQUENCE: 7
agtgtgtcct ggtaccaaca g                                            21

<210> SEQ ID NO 8
<211> LENGTH: 21
<212> TYPE: DNA
<213> ORGANISM: Homo sapiens

<400> SEQUENCE: 8
tctgtgtact ggtaccaaca g                                            21

<210> SEQ ID NO 9
<211> LENGTH: 20
<212> TYPE: DNA
<213> ORGANISM: Homo sapiens

<400> SEQUENCE: 9
```

-continued

```
cccctttactg gtaccgacag                                              20

<210> SEQ ID NO 10
<211> LENGTH: 20
<212> TYPE: DNA
<213> ORGANISM: Homo sapiens

<400> SEQUENCE: 10
gcctttactg gtaccgacag                                               20

<210> SEQ ID NO 11
<211> LENGTH: 21
<212> TYPE: DNA
<213> ORGANISM: Homo sapiens

<400> SEQUENCE: 11 cccctttactg gtaccgacaa a                                            21

<210> SEQ ID NO 12
<211> LENGTH: 19
<212> TYPE: DNA
<213> ORGANISM: Homo sapiens

<400> SEQUENCE: 12
ttttggtacc aacaggtcc                                                19

<210> SEQ ID NO 13
<211> LENGTH: 19
<212> TYPE: DNA
<213> ORGANISM: Homo sapiens

<400> SEQUENCE: 13
ttttggtacc aacaggccc                                                19

<210> SEQ ID NO 14
<211> LENGTH: 22
<212> TYPE: DNA
<213> ORGANISM: Homo sapiens

<400> SEQUENCE: 14 aacccttttat tggtatcaac ag                                           22

<210> SEQ ID NO 15
<211> LENGTH: 21
<212> TYPE: DNA
<213> ORGANISM: Homo sapiens

<400> SEQUENCE: 15
cgctatgtat tggtacaagc a                                             21

<210> SEQ ID NO 16
<211> LENGTH: 21
<212> TYPE: DNA
<213> ORGANISM: Homo sapiens

<400> SEQUENCE: 16
cgctatgtat tggtacaagc a                                             21

<210> SEQ ID NO 17
<211> LENGTH: 23
<212> TYPE: DNA
<213> ORGANISM: Homo sapiens

<400> SEQUENCE: 17
```

```
tttctggtac agacagacca tga                                            23

<210> SEQ ID NO 18
<211> LENGTH: 27
<212> TYPE: DNA
<213> ORGANISM: Homo sapiens

<400> SEQUENCE: 18
tactatgtat tggtataaac aggactc                                        27

<210> SEQ ID NO 19
<211> LENGTH: 22
<212> TYPE: DNA
<213> ORGANISM: Homo sapiens

<400> SEQUENCE: 19
caaaatgtac tggtatcaac aa                                             22

<210> SEQ ID NO 20
<211> LENGTH: 22
<212> TYPE: DNA
<213> ORGANISM: Homo sapiens

<400> SEQUENCE: 20
caaaatgtac tggtatcaac aa                                             22

<210> SEQ ID NO 21
<211> LENGTH: 22
<212> TYPE: DNA
<213> ORGANISM: Homo sapiens

<400> SEQUENCE: 21
atgtactggt atcgacaaga cc                                             22

<210> SEQ ID NO 22
<211> LENGTH: 23
<212> TYPE: DNA
<213> ORGANISM: Homo sapiens

<400> SEQUENCE: 22
tgccatgtac tggtatagac aag                                            23

<210> SEQ ID NO 23
<211> LENGTH: 23
<212> TYPE: DNA
<213> ORGANISM: Homo sapiens

<400> SEQUENCE: 23
atacttgtcc tggtatcgac aag                                            23

<210> SEQ ID NO 24
<211> LENGTH: 22
<212> TYPE: DNA
<213> ORGANISM: Homo sapiens

<400> SEQUENCE: 24
atatgttctg gtatcgacaa ga                                             22

<210> SEQ ID NO 25
<211> LENGTH: 22
<212> TYPE: DNA
<213> ORGANISM: Homo sapiens

<400> SEQUENCE: 25
```

```
atatgtcctg gtatcgacaa ga                                       22

<210> SEQ ID NO 26
<211> LENGTH: 22
<212> TYPE: DNA
<213> ORGANISM: Homo sapiens

<400> SEQUENCE: 26
acatgtcctg gtatcgacaa ga                                       22

<210> SEQ ID NO 27
<211> LENGTH: 24
<212> TYPE: DNA
<213> ORGANISM: Homo sapiens

<400> SEQUENCE: 27
taatctttat tggtatcgac gtgt                                     24

<210> SEQ ID NO 28
<211> LENGTH: 20
<212> TYPE: DNA
<213> ORGANISM: Homo sapiens

<400> SEQUENCE: 28
gccatgtact ggtaccgaca                                          20

<210> SEQ ID NO 29
<211> LENGTH: 22
<212> TYPE: DNA
<213> ORGANISM: Homo sapiens

<400> SEQUENCE: 29
tcatgtttac tggtatcggc ag                                       22

<210> SEQ ID NO 30
<211> LENGTH: 21
<212> TYPE: DNA
<213> ORGANISM: Homo sapiens

<400> SEQUENCE: 30
caacctatac tggtaccgac a                                        21

<210> SEQ ID NO 31
<211> LENGTH: 22
<212> TYPE: DNA
<213> ORGANISM: Homo sapiens

<400> SEQUENCE: 31
catgctaccc tttactggta cc                                       22

<210> SEQ ID NO 32
<211> LENGTH: 22
<212> TYPE: DNA
<213> ORGANISM: Homo sapiens

<400> SEQUENCE: 32
cacaataccc tttactggta cc                                       22

<210> SEQ ID NO 33
<211> LENGTH: 26
<212> TYPE: DNA
<213> ORGANISM: Homo sapiens

<400> SEQUENCE: 33
```

```
atacttctat tggtacagac aaatct                                          26

<210> SEQ ID NO 34
<211> LENGTH: 21
<212> TYPE: DNA
<213> ORGANISM: Homo sapiens

<400> SEQUENCE: 34
cactgtctac tggtaccagc a                                               21

<210> SEQ ID NO 35
<211> LENGTH: 21
<212> TYPE: DNA
<213> ORGANISM: Homo sapiens

<400> SEQUENCE: 35
cgtcatgtac tggtaccagc a                                               21

<210> SEQ ID NO 36
<211> LENGTH: 21
<212> TYPE: DNA
<213> ORGANISM: unknown
<220> FEATURE:
<223> OTHER INFORMATION: primer

<400> SEQUENCE: 36
aatgatacgg cgaccaccga g                                               21

<210> SEQ ID NO 37
<211> LENGTH: 24
<212> TYPE: DNA
<213> ORGANISM: Unknown
<220> FEATURE:
<223> OTHER INFORMATION: primer

<400> SEQUENCE: 37
caagcagaag acggcatacg agat                                            24

<210> SEQ ID NO 38
<211> LENGTH: 34
<212> TYPE: DNA
<213> ORGANISM: Unknown
<220> FEATURE:
<223> OTHER INFORMATION: primer

<400> SEQUENCE: 38
agatcggaag agcacacgtc tgaactccag tcac                                 34

<210> SEQ ID NO 39
<211> LENGTH: 34
<212> TYPE: DNA
<213> ORGANISM: Unknown
<220> FEATURE:
<223> OTHER INFORMATION: primer

<400> SEQUENCE: 39
gtgactggag ttcagacgtg tgctcttccg atct                                 34

<210> SEQ ID NO 40
<211> LENGTH: 24
<212> TYPE: DNA
<213> ORGANISM: Homo sapiens

<400> SEQUENCE: 40
cctcagtgaa ggtctcctgc aagg                                            24
```

<210> SEQ ID NO 41
<211> LENGTH: 24
<212> TYPE: DNA
<213> ORGANISM: Homo sapiens

<400> SEQUENCE: 41
cctcggtgaa ggtctcctgc aagg                                    24

<210> SEQ ID NO 42
<211> LENGTH: 24
<212> TYPE: DNA
<213> ORGANISM: Homo sapiens

<400> SEQUENCE: 42
cctcagtgaa ggtttcctgc aagg                                    24

<210> SEQ ID NO 43
<211> LENGTH: 27
<212> TYPE: DNA
<213> ORGANISM: Homo sapiens

<400> SEQUENCE: 43
gggctacagt gaaaatctcc tgcaagg                                 27

<210> SEQ ID NO 44
<211> LENGTH: 26
<212> TYPE: DNA
<213> ORGANISM: Homo sapiens

<400> SEQUENCE: 44
aaacccacac agaccctcac gctgac                                  26

<210> SEQ ID NO 45
<211> LENGTH: 26
<212> TYPE: DNA
<213> ORGANISM: Homo sapiens

<400> SEQUENCE: 45
aaacccacag agaccctcac gctgac                                  26

<210> SEQ ID NO 46
<211> LENGTH: 26
<212> TYPE: DNA
<213> ORGANISM: Homo sapiens

<400> SEQUENCE: 46
aaacccacac agaccctcac actgac                                  26

<210> SEQ ID NO 47
<211> LENGTH: 25
<212> TYPE: DNA
<213> ORGANISM: Homo sapiens

<400> SEQUENCE: 47 ctgggggtc cctgagactc tcctg                                    25

<210> SEQ ID NO 48
<211> LENGTH: 25
<212> TYPE: DNA
<213> ORGANISM: Homo sapiens

<400> SEQUENCE: 48 ctgggggtc ccttagactc tcctg                                    25

```
<210> SEQ ID NO 49
<211> LENGTH: 25
<212> TYPE: DNA
<213> ORGANISM: Homo sapiens

<400> SEQUENCE: 49
cagggcggtc cctgagactc tcctg                                          25

<210> SEQ ID NO 50
<211> LENGTH: 25
<212> TYPE: DNA
<213> ORGANISM: Homo sapiens

<400> SEQUENCE: 50
cagggccgtc cctgagactc tcctg                                          25

<210> SEQ ID NO 51
<211> LENGTH: 25
<212> TYPE: DNA
<213> ORGANISM: Homo sapiens

<400> SEQUENCE: 51 ctgggggtc cctgaaactc tcctg                                           25

<210> SEQ ID NO 52
<211> LENGTH: 25
<212> TYPE: DNA
<213> ORGANISM: Homo sapiens

<400> SEQUENCE: 52
ctggcaggtc cctgagactc tcctg                                          25

<210> SEQ ID NO 53
<211> LENGTH: 25
<212> TYPE: DNA
<213> ORGANISM: Homo sapiens

<400> SEQUENCE: 53
ctggagggtc cctgagactc tcctg                                          25

<210> SEQ ID NO 54
<211> LENGTH: 25
<212> TYPE: DNA
<213> ORGANISM: Homo sapiens

<400> SEQUENCE: 54
ctgggaggtc cctgagactc tcctg                                          25

<210> SEQ ID NO 55
<211> LENGTH: 23
<212> TYPE: DNA
<213> ORGANISM: Homo sapiens

<400> SEQUENCE: 55
tgggggggcc ctgagactct cct                                            23

<210> SEQ ID NO 56
<211> LENGTH: 25
<212> TYPE: DNA
<213> ORGANISM: Homo sapiens

<400> SEQUENCE: 56
cttcggagac cctgtccctc acctg                                          25
```

```
<210> SEQ ID NO 57
<211> LENGTH: 25
<212> TYPE: DNA
<213> ORGANISM: Homo sapiens

<400> SEQUENCE: 57
cttcggacac cctgtccctc acctg                                          25

<210> SEQ ID NO 58
<211> LENGTH: 25
<212> TYPE: DNA
<213> ORGANISM: Homo sapiens

<400> SEQUENCE: 58
cttcacagac cctgtccctc acctg                                          25

<210> SEQ ID NO 59
<211> LENGTH: 25
<212> TYPE: DNA
<213> ORGANISM: Homo sapiens

<400> SEQUENCE: 59
cttcggagac cccgtccctc acctg                                          25

<210> SEQ ID NO 60
<211> LENGTH: 22
<212> TYPE: DNA
<213> ORGANISM: Homo sapiens

<400> SEQUENCE: 60
cggggaccct gtccctcacc tg                                             22

<210> SEQ ID NO 61
<211> LENGTH: 29
<212> TYPE: DNA
<213> ORGANISM: Homo sapiens

<400> SEQUENCE: 61
gatctcctgt aagggttctg gatacagct                                      29

<210> SEQ ID NO 62
<211> LENGTH: 25
<212> TYPE: DNA
<213> ORGANISM: Homo sapiens

<400> SEQUENCE: 62
tcgcagaccc tctcactcac ctgtg                                          25

<210> SEQ ID NO 63
<211> LENGTH: 25
<212> TYPE: DNA
<213> ORGANISM: Homo sapiens

<400> SEQUENCE: 63
tggatcaggc agtccccatc gagag                                          25

<210> SEQ ID NO 64
<211> LENGTH: 20
<212> TYPE: DNA
<213> ORGANISM: Homo sapiens

<400> SEQUENCE: 64
gctgggtgcg ccagatgccc                                                20
```

-continued

```
<210> SEQ ID NO 65
<211> LENGTH: 20
<212> TYPE: DNA
<213> ORGANISM: Homo sapiens

<400> SEQUENCE: 65
tggatccgtc agcccccagg                                                   20

<210> SEQ ID NO 66
<211> LENGTH: 20
<212> TYPE: DNA
<213> ORGANISM: Homo sapiens

<400> SEQUENCE: 66
tggatccgtc agcccccggg                                                   20

<210> SEQ ID NO 67
<211> LENGTH: 21
<212> TYPE: DNA
<213> ORGANISM: Homo sapiens

<400> SEQUENCE: 67
gtgcgacagg cccctggaca a                                                 21

<210> SEQ ID NO 68
<211> LENGTH: 23
<212> TYPE: DNA
<213> ORGANISM: Homo sapiens

<400> SEQUENCE: 68
gggtgcgaca ggccactgga caa                                               23

<210> SEQ ID NO 69
<211> LENGTH: 21
<212> TYPE: DNA
<213> ORGANISM: Homo sapiens

<400> SEQUENCE: 69
gtgcgccagg cccccggaca a                                                 21

<210> SEQ ID NO 70
<211> LENGTH: 23
<212> TYPE: DNA
<213> ORGANISM: Homo sapiens

<400> SEQUENCE: 70
gggtgcgaca ggctcgtgga caa                                               23

<210> SEQ ID NO 71
<211> LENGTH: 23
<212> TYPE: DNA
<213> ORGANISM: Homo sapiens

<400> SEQUENCE: 71
gggtgcaaca ggcccctgga aaa                                               23

<210> SEQ ID NO 72
<211> LENGTH: 23
<212> TYPE: DNA
<213> ORGANISM: Homo sapiens

<400> SEQUENCE: 72
gggtgcgaca ggctcctgga aaa                                               23
```

```
<210> SEQ ID NO 73
<211> LENGTH: 21
<212> TYPE: DNA
<213> ORGANISM: Homo sapiens

<400> SEQUENCE: 73
gtgcgacagg cccccggaca a                                              21

<210> SEQ ID NO 74
<211> LENGTH: 21
<212> TYPE: DNA
<213> ORGANISM: Homo sapiens

<400> SEQUENCE: 74
gtgcgacagg cccccagaca a                                              21

<210> SEQ ID NO 75
<211> LENGTH: 21
<212> TYPE: DNA
<213> ORGANISM: Homo sapiens

<400> SEQUENCE: 75
tccgccagcc cccagggaag g                                              21

<210> SEQ ID NO 76
<211> LENGTH: 21
<212> TYPE: DNA
<213> ORGANISM: Homo sapiens

<400> SEQUENCE: 76
tccggcagcc cccagggaag g                                              21

<210> SEQ ID NO 77
<211> LENGTH: 21
<212> TYPE: DNA
<213> ORGANISM: Homo sapiens

<400> SEQUENCE: 77
tccggcagcc accagggaag g                                              21

<210> SEQ ID NO 78
<211> LENGTH: 21
<212> TYPE: DNA
<213> ORGANISM: Homo sapiens

<400> SEQUENCE: 78
tccgccagca cccagggaag g                                              21

<210> SEQ ID NO 79
<211> LENGTH: 19
<212> TYPE: DNA
<213> ORGANISM: Homo sapiens

<400> SEQUENCE: 79
tccggcagcc cgccgggaa                                                 19

<210> SEQ ID NO 80
<211> LENGTH: 19
<212> TYPE: DNA
<213> ORGANISM: Homo sapiens

<400> SEQUENCE: 80
tccggcagcc gccgggaa                                                  19
```

```
<210> SEQ ID NO 81
<211> LENGTH: 21
<212> TYPE: DNA
<213> ORGANISM: Homo sapiens

<400> SEQUENCE: 81
tccggcagcc cgctgggaag g                                              21

<210> SEQ ID NO 82
<211> LENGTH: 21
<212> TYPE: DNA
<213> ORGANISM: Homo sapiens

<400> SEQUENCE: 82
tccgccagcc cctagggaag g                                              21

<210> SEQ ID NO 83
<211> LENGTH: 21
<212> TYPE: DNA
<213> ORGANISM: Homo sapiens

<400> SEQUENCE: 83
ggtccgccag gctccaggga a                                              21

<210> SEQ ID NO 84
<211> LENGTH: 21
<212> TYPE: DNA
<213> ORGANISM: Homo sapiens

<400> SEQUENCE: 84
gttccgccag gctccaggga a                                              21

<210> SEQ ID NO 85
<211> LENGTH: 21
<212> TYPE: DNA
<213> ORGANISM: Homo sapiens

<400> SEQUENCE: 85
ggtccgccag gcttccggga a                                              21

<210> SEQ ID NO 86
<211> LENGTH: 21
<212> TYPE: DNA
<213> ORGANISM: Homo sapiens

<400> SEQUENCE: 86
ggtccgtcaa gctccgggga a                                              21

<210> SEQ ID NO 87
<211> LENGTH: 21
<212> TYPE: DNA
<213> ORGANISM: Homo sapiens

<400> SEQUENCE: 87
gatccgccag gctccaggga a                                              21

<210> SEQ ID NO 88
<211> LENGTH: 21
<212> TYPE: DNA
<213> ORGANISM: Homo sapiens

<400> SEQUENCE: 88
ggtccgccaa gctccaggga a                                              21
```

<210> SEQ ID NO 89
<211> LENGTH: 21
<212> TYPE: DNA
<213> ORGANISM: Homo sapiens

<400> SEQUENCE: 89
ggtccgccag gctccaggca a                                        21

<210> SEQ ID NO 90
<211> LENGTH: 21
<212> TYPE: DNA
<213> ORGANISM: Homo sapiens

<400> SEQUENCE: 90
ggtccgccag gctccaggca a                                        21

<210> SEQ ID NO 91
<211> LENGTH: 21
<212> TYPE: DNA
<213> ORGANISM: Homo sapiens

<400> SEQUENCE: 91
ggtccgccag gctccgggca a                                        21

<210> SEQ ID NO 92
<211> LENGTH: 24
<212> TYPE: DNA
<213> ORGANISM: Homo sapiens

<400> SEQUENCE: 92
gggtccgtca agctccaggg aagg                                     24

<210> SEQ ID NO 93
<211> LENGTH: 24
<212> TYPE: DNA
<213> ORGANISM: Homo sapiens

<400> SEQUENCE: 93
ctgggtccgc caagctacag gaaa                                     24

<210> SEQ ID NO 94
<211> LENGTH: 21
<212> TYPE: DNA
<213> ORGANISM: Homo sapiens

<400> SEQUENCE: 94
ggtccgccag cctccaggga a                                        21

<210> SEQ ID NO 95
<211> LENGTH: 21
<212> TYPE: DNA
<213> ORGANISM: Homo sapiens

<400> SEQUENCE: 95
ggtccggcaa gctccaggga a                                        21

<210> SEQ ID NO 96
<211> LENGTH: 25
<212> TYPE: DNA
<213> ORGANISM: Homo sapiens

<400> SEQUENCE: 96
ctaaaggctg aggacactgc cgtgt                                    25

```
<210> SEQ ID NO 97
<211> LENGTH: 25
<212> TYPE: DNA
<213> ORGANISM: Homo sapiens

<400> SEQUENCE: 97
ctctgtgact cccgaggaca cggct                                    25

<210> SEQ ID NO 98
<211> LENGTH: 22
<212> TYPE: DNA
<213> ORGANISM: Homo sapiens

<400> SEQUENCE: 98
agtggagcag cctgaaggcc tc                                       22

<210> SEQ ID NO 99
<211> LENGTH: 25
<212> TYPE: DNA
<213> ORGANISM: Homo sapiens

<400> SEQUENCE: 99
tgaccaacat ggaccctgtg gacac                                    25

<210> SEQ ID NO 100
<211> LENGTH: 25
<212> TYPE: DNA
<213> ORGANISM: Homo sapiens

<400> SEQUENCE: 100
acatggagct gagcagcctg agatc                                    25

<210> SEQ ID NO 101
<211> LENGTH: 25
<212> TYPE: DNA
<213> ORGANISM: Homo sapiens

<400> SEQUENCE: 101
acatggagct gagcaggctg agatc                                    25

<210> SEQ ID NO 102
<211> LENGTH: 25
<212> TYPE: DNA
<213> ORGANISM: Homo sapiens

<400> SEQUENCE: 102
acatggagct gaggagcctg agatc                                    25

<210> SEQ ID NO 103
<211> LENGTH: 28
<212> TYPE: DNA
<213> ORGANISM: Homo sapiens

<400> SEQUENCE: 103
acatggagct gaggagccta agatctga                                 28

<210> SEQ ID NO 104
<211> LENGTH: 22
<212> TYPE: DNA
<213> ORGANISM: Homo sapiens

<400> SEQUENCE: 104
gagctctgtg accgccgcgg ac                                       22
```

```
<210> SEQ ID NO 105
<211> LENGTH: 23
<212> TYPE: DNA
<213> ORGANISM: Homo sapiens

<400> SEQUENCE: 105
gagctctgtg accgccgtgg aca                                           23

<210> SEQ ID NO 106
<211> LENGTH: 25
<212> TYPE: DNA
<213> ORGANISM: Homo sapiens

<400> SEQUENCE: 106
gagctctgtg accgctgcag acacg                                         25

<210> SEQ ID NO 107
<211> LENGTH: 23
<212> TYPE: DNA
<213> ORGANISM: Homo sapiens

<400> SEQUENCE: 107
gagctctgtg accgctgcgg aca                                           23

<210> SEQ ID NO 108
<211> LENGTH: 25
<212> TYPE: DNA
<213> ORGANISM: Homo sapiens

<400> SEQUENCE: 108
gagctctgtg actgccgcag acacg                                         25

<210> SEQ ID NO 109
<211> LENGTH: 25
<212> TYPE: DNA
<213> ORGANISM: Homo sapiens

<400> SEQUENCE: 109
gagctctgtg actgcagcag acacg                                         25

<210> SEQ ID NO 110
<211> LENGTH: 23
<212> TYPE: DNA
<213> ORGANISM: Homo sapiens

<400> SEQUENCE: 110
gagctctgtg actgccgcgg aca                                           23

<210> SEQ ID NO 111
<211> LENGTH: 22
<212> TYPE: DNA
<213> ORGANISM: Homo sapiens

<400> SEQUENCE: 111
gagctctgtg accgcggacg cg                                            22

<210> SEQ ID NO 112
<211> LENGTH: 21
<212> TYPE: DNA
<213> ORGANISM: Homo sapiens

<400> SEQUENCE: 112
ggctctgtga ccgccgcgga c                                             21
```

```
<210> SEQ ID NO 113
<211> LENGTH: 23
<212> TYPE: DNA
<213> ORGANISM: Homo sapiens

<400> SEQUENCE: 113
gagctctgtg accgccgcag aca                                              23

<210> SEQ ID NO 114
<211> LENGTH: 23
<212> TYPE: DNA
<213> ORGANISM: Homo sapiens

<400> SEQUENCE: 114
gagctctgtg accgctgaca cgg                                              23

<210> SEQ ID NO 115
<211> LENGTH: 28
<212> TYPE: DNA
<213> ORGANISM: Homo sapiens

<400> SEQUENCE: 115
caaatgaaca gcctgagagc cgaggaca                                         28

<210> SEQ ID NO 116
<211> LENGTH: 28
<212> TYPE: DNA
<213> ORGANISM: Homo sapiens

<400> SEQUENCE: 116
caaatgaaca gcctgaaaac cgaggaca                                         28

<210> SEQ ID NO 117
<211> LENGTH: 28
<212> TYPE: DNA
<213> ORGANISM: Homo sapiens

<400> SEQUENCE: 117
caaatgaaca gtctgaaaac cgaggaca                                         28

<210> SEQ ID NO 118
<211> LENGTH: 28
<212> TYPE: DNA
<213> ORGANISM: Homo sapiens

<400> SEQUENCE: 118
caaatgatca gcctgaaaac cgaggaca                                         28

<210> SEQ ID NO 119
<211> LENGTH: 30
<212> TYPE: DNA
<213> ORGANISM: Homo sapiens

<400> SEQUENCE: 119
caaatgaaca gtctgagaac tgaggacacc                                       30

<210> SEQ ID NO 120
<211> LENGTH: 28
<212> TYPE: DNA
<213> ORGANISM: Homo sapiens

<400> SEQUENCE: 120
caaatgaaca gtctgagagc cgaggaca                                         28
```

```
<210> SEQ ID NO 121
<211> LENGTH: 28
<212> TYPE: DNA
<213> ORGANISM: Homo sapiens

<400> SEQUENCE: 121
caaatgaaca gcctgagagc tgaggaca                                          28

<210> SEQ ID NO 122
<211> LENGTH: 28
<212> TYPE: DNA
<213> ORGANISM: Homo sapiens

<400> SEQUENCE: 122
caaatgagca gcctgagagc tgaggaca                                          28

<210> SEQ ID NO 123
<211> LENGTH: 28
<212> TYPE: DNA
<213> ORGANISM: Homo sapiens

<400> SEQUENCE: 123
caaatgaaca gcctgagaga cgaggaca                                          28

<210> SEQ ID NO 124
<211> LENGTH: 28
<212> TYPE: DNA
<213> ORGANISM: Homo sapiens

<400> SEQUENCE: 124
caaatgggca gcctgagagc tgaggaca                                          28

<210> SEQ ID NO 125
<211> LENGTH: 26
<212> TYPE: DNA
<213> ORGANISM: Homo sapiens

<400> SEQUENCE: 125
caaatgaaca gcctgagagc cgggga                                            26

<210> SEQ ID NO 126
<211> LENGTH: 28
<212> TYPE: DNA
<213> ORGANISM: Homo sapiens

<400> SEQUENCE: 126
caaatgaaca gtctgagagc tgaggaca                                          28

<210> SEQ ID NO 127
<211> LENGTH: 28
<212> TYPE: DNA
<213> ORGANISM: Homo sapiens

<400> SEQUENCE: 127
caaatgagca gtctgagagc tgaggaca                                          28

<210> SEQ ID NO 128
<211> LENGTH: 20
<212> TYPE: DNA
<213> ORGANISM: Homo sapiens

<400> SEQUENCE: 128
gccaggggga agaccgatgg                                                   20
```

```
<210> SEQ ID NO 129
<211> LENGTH: 20
<212> TYPE: DNA
<213> ORGANISM: Homo sapiens

<400> SEQUENCE: 129
gccaggggga agacggatgg                                                 20

<210> SEQ ID NO 130
<211> LENGTH: 50
<212> TYPE: DNA
<213> ORGANISM: Homo sapiens

<400> SEQUENCE: 130
aatgatacgg cgaccaccga gatctgggaa gacgatgggc ccttggtgga                 50

<210> SEQ ID NO 131
<211> LENGTH: 22
<212> TYPE: DNA
<213> ORGANISM: Homo sapiens

<400> SEQUENCE: 131
gtgtgagctg gatccgtcag cc                                              22

<210> SEQ ID NO 132
<211> LENGTH: 22
<212> TYPE: DNA
<213> ORGANISM: Homo sapiens

<400> SEQUENCE: 132
gtgtgggctg gatccgtcag cc                                              22

<210> SEQ ID NO 133
<211> LENGTH: 22
<212> TYPE: DNA
<213> ORGANISM: Homo sapiens

<400> SEQUENCE: 133
gtgcgagctg gatccgtcag cc                                              22

<210> SEQ ID NO 134
<211> LENGTH: 24
<212> TYPE: DNA
<213> ORGANISM: Homo sapiens

<400> SEQUENCE: 134
gcagcctaaa ggctgaggac actg                                            24

<210> SEQ ID NO 135
<211> LENGTH: 24
<212> TYPE: DNA
<213> ORGANISM: Homo sapiens

<400> SEQUENCE: 135
gcacgctaaa ggctgaggac actg                                            24

<210> SEQ ID NO 136
<211> LENGTH: 41
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a, c, g, or t
```

```
<400> SEQUENCE: 136
acgagcctca tgcgtaganc tcacctgagg agacggtgac c                 41

<210> SEQ ID NO 137
<211> LENGTH: 41
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a, c, g, or t

<400> SEQUENCE: 137
acgagcctca tgcgtaganc tcacctgagg agacagtgac c                 41

<210> SEQ ID NO 138
<211> LENGTH: 41
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a, c, g, or t

<400> SEQUENCE: 138
acgagcctca tgcgtaganc ttacctgaag agacggtgac c                 41

<210> SEQ ID NO 139
<211> LENGTH: 41
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a, c, g, or t

<400> SEQUENCE: 139
acgagcctca tgcgtaganc ttacctgagg agacggtgac c                 41

<210> SEQ ID NO 140
<211> LENGTH: 25
<212> TYPE: DNA
<213> ORGANISM: Homo sapiens

<400> SEQUENCE: 140
aatgatacgg cgaccaccga gatct                                   25

<210> SEQ ID NO 141
<211> LENGTH: 64
<212> TYPE: DNA
<213> ORGANISM: Unknown
<220> FEATURE:
<223> OTHER INFORMATION: primer
<220> FEATURE:
<221> NAME/KEY: misc_feature
<222> LOCATION: (25)..(30)
<223> OTHER INFORMATION: n is a, c, g, or t

<400> SEQUENCE: 141
caagcagaag acggcatacg agatnnnnnn gtgactggag ttcagacgtg tgctcttccg  60
atct                                                          64

<210> SEQ ID NO 142
<211> LENGTH: 23
<212> TYPE: DNA
<213> ORGANISM: mouse
```

```
<400> SEQUENCE: 142
tgatggctca aacaaggaga cct                                          23

<210> SEQ ID NO 143
<211> LENGTH: 57
<212> TYPE: DNA
<213> ORGANISM: mouse

<400> SEQUENCE: 143
aatgatacgg cgaccaccga gatctgacct tgggtggagt cacatttctc agatcct     57

<210> SEQ ID NO 144
<211> LENGTH: 58
<212> TYPE: DNA
<213> ORGANISM: Homo sapiens

<400> SEQUENCE: 144
aatgatacgg cgaccaccga gatctacact ctttccctac acgagcctca tgcgtaga    58

<210> SEQ ID NO 145
<211> LENGTH: 23
<212> TYPE: DNA
<213> ORGANISM: mouse

<400> SEQUENCE: 145
caaagaggtc aaatctcttc ccg                                          23

<210> SEQ ID NO 146
<211> LENGTH: 24
<212> TYPE: DNA
<213> ORGANISM: mouse

<400> SEQUENCE: 146
cttatggaca atcagactgc ctca                                         24

<210> SEQ ID NO 147
<211> LENGTH: 28
<212> TYPE: DNA
<213> ORGANISM: mouse

<400> SEQUENCE: 147
gtcatggaga agtctaaact gtttaagg                                     28

<210> SEQ ID NO 148
<211> LENGTH: 23
<212> TYPE: DNA
<213> ORGANISM: mouse

<400> SEQUENCE: 148
gtaaacgaaa cagttccaag gcg                                          23

<210> SEQ ID NO 149
<211> LENGTH: 26
<212> TYPE: DNA
<213> ORGANISM: mouse

<400> SEQUENCE: 149
ggtgcccagt cgttttatac ctgaat                                       26

<210> SEQ ID NO 150
<211> LENGTH: 25
<212> TYPE: DNA
<213> ORGANISM: mouse
```

-continued

```
<400> SEQUENCE: 150
cccagcagat tctcagtcca acagt                                          25

<210> SEQ ID NO 151
<211> LENGTH: 24
<212> TYPE: DNA
<213> ORGANISM: mouse

<400> SEQUENCE: 151
agatatccct gatggataca aggc                                           24

<210> SEQ ID NO 152
<211> LENGTH: 24
<212> TYPE: DNA
<213> ORGANISM: mouse

<400> SEQUENCE: 152
agatatccct gatgggtaca aggc                                           24

<210> SEQ ID NO 153
<211> LENGTH: 24
<212> TYPE: DNA
<213> ORGANISM: mouse

<400> SEQUENCE: 153
agatgtccct gatgggtaca aggc                                           24

<210> SEQ ID NO 154
<211> LENGTH: 24
<212> TYPE: DNA
<213> ORGANISM: mouse

<400> SEQUENCE: 154
gataattcac agttgccctc ggat                                           24

<210> SEQ ID NO 155
<211> LENGTH: 22
<212> TYPE: DNA
<213> ORGANISM: mouse

<400> SEQUENCE: 155
gatggtgggg ctttcaagga tc                                             22

<210> SEQ ID NO 156
<211> LENGTH: 24
<212> TYPE: DNA
<213> ORGANISM: mouse

<400> SEQUENCE: 156
caagctccta tagatgattc aggg                                           24

<210> SEQ ID NO 157
<211> LENGTH: 27
<212> TYPE: DNA
<213> ORGANISM: mouse

<400> SEQUENCE: 157
ctatgataag attttgaaca gggaagc                                        27

<210> SEQ ID NO 158
<211> LENGTH: 32
<212> TYPE: DNA
<213> ORGANISM: mouse
```

-continued

```
<210> SEQ ID NO 159
<211> LENGTH: 24
<212> TYPE: DNA
<213> ORGANISM: mouse

<400> SEQUENCE: 159
gcactttcta ctgtgaactc agca                                            24

<210> SEQ ID NO 160
<211> LENGTH: 25
<212> TYPE: DNA
<213> ORGANISM: mouse

<400> SEQUENCE: 160
cttgatcaaa tagacatggt caagg                                           25

<210> SEQ ID NO 161
<211> LENGTH: 26
<212> TYPE: DNA
<213> ORGANISM: mouse

<400> SEQUENCE: 161
agagattctc agctaagtgt tcctcg                                          26

<210> SEQ ID NO 162
<211> LENGTH: 25
<212> TYPE: DNA
<213> ORGANISM: mouse

<400> SEQUENCE: 162
gttcttcagc aaatagacat gactg                                           25

<210> SEQ ID NO 163
<211> LENGTH: 25
<212> TYPE: DNA
<213> ORGANISM: mouse

<400> SEQUENCE: 163
agcgaaggag acatccctaa aggat                                           25

<210> SEQ ID NO 164
<211> LENGTH: 25
<212> TYPE: DNA
<213> ORGANISM: mouse

<400> SEQUENCE: 164
cgagagtgga ttcaccaagg acaag                                           25

<210> SEQ ID NO 165
<211> LENGTH: 14
<212> TYPE: DNA
<213> ORGANISM: Homo sapiens

<400> SEQUENCE: 165
agatcggaag agca                                                       14

<210> SEQ ID NO 166
<211> LENGTH: 20
<212> TYPE: DNA
<213> ORGANISM: Homo sapiens
```

<400> SEQUENCE: 158
gatctactat tcaataactg aaaacgatct tc                                   32

```
<400> SEQUENCE: 166
gcctttattg gtaccgacag                                              20

<210> SEQ ID NO 167
<211> LENGTH: 20
<212> TYPE: DNA
<213> ORGANISM: Homo sapiens

<400> SEQUENCE: 167
ccctttattg gtaccgacag                                              20

<210> SEQ ID NO 168
<211> LENGTH: 21
<212> TYPE: DNA
<213> ORGANISM: Homo sapiens

<400> SEQUENCE: 168
ggctatgtat tggtacaagc a                                            21

<210> SEQ ID NO 169
<211> LENGTH: 20
<212> TYPE: DNA
<213> ORGANISM: Homo sapiens

<400> SEQUENCE: 169
gtatcgacaa gacccaggca                                              20

<210> SEQ ID NO 170
<211> LENGTH: 22
<212> TYPE: DNA
<213> ORGANISM: Homo sapiens

<400> SEQUENCE: 170
atgtcctggt atcgacaaga cc                                           22

<210> SEQ ID NO 171
<211> LENGTH: 53
<212> TYPE: DNA
<213> ORGANISM: mouse

<400> SEQUENCE: 171
caaaatacag cgtttctgca ctaccccaag ctatactgct ggcacagaga aaa         53

<210> SEQ ID NO 172
<211> LENGTH: 53
<212> TYPE: DNA
<213> ORGANISM: mouse

<400> SEQUENCE: 172
caaaatacag cgtttctgca ctcccccagg ctatactgct ggcacagaga aaa         53

<210> SEQ ID NO 173
<211> LENGTH: 53
<212> TYPE: DNA
<213> ORGANISM: mouse

<400> SEQUENCE: 173
caaaatacag cgtttctgca ctaccccagg ctatactgct ggcacagaga aaa         53

<210> SEQ ID NO 174
<211> LENGTH: 53
<212> TYPE: DNA
<213> ORGANISM: mouse
```

<400> SEQUENCE: 174
caaaatacag cgtttctgca ctcccccaag ctatactgct ggcacagaga aaa          53

<210> SEQ ID NO 175
<211> LENGTH: 53
<212> TYPE: DNA
<213> ORGANISM: mouse

<400> SEQUENCE: 175
caaaatacag cgtttctgca cttccccagg ctatactgct ggcacagaga aaa          53

<210> SEQ ID NO 176
<211> LENGTH: 53
<212> TYPE: DNA
<213> ORGANISM: mouse

<400> SEQUENCE: 176
caaaatacag cgtttctgca ctaccccagg caatactgct ggcacagaga aaa          53

<210> SEQ ID NO 177
<211> LENGTH: 53
<212> TYPE: DNA
<213> ORGANISM: mouse

<400> SEQUENCE: 177
caaaatacag cgtttctgca ctcccccagg caatactgct ggcacagaga aaa          53

<210> SEQ ID NO 178
<211> LENGTH: 53
<212> TYPE: DNA
<213> ORGANISM: mouse

<400> SEQUENCE: 178
caaaatacag cgtttctgca ctgccccaag ctatactgct ggcacagaga aaa          53

<210> SEQ ID NO 179
<211> LENGTH: 53
<212> TYPE: DNA
<213> ORGANISM: mouse

<400> SEQUENCE: 179
caaaatacag cgtttctgca ctgccccagg ctatactgct ggcacagaga aaa          53

<210> SEQ ID NO 180
<211> LENGTH: 53
<212> TYPE: DNA
<213> ORGANISM: mouse

<400> SEQUENCE: 180
caaaatacag cgtttctgcg ctcccccatg ctatactgct ggcacagaga aaa          53

<210> SEQ ID NO 181
<211> LENGTH: 53
<212> TYPE: DNA
<213> ORGANISM: Homo sapiens

<400> SEQUENCE: 181
ctggccccaa ttccatctgc ctgtaaagca tgtacagtaa tacacagccg tgt          53

<210> SEQ ID NO 182
<211> LENGTH: 53
<212> TYPE: DNA
<213> ORGANISM: Homo sapiens -continued

<400> SEQUENCE: 182
ctggccccag ttccatttgg tagtaaaaca tgtacagtaa tacacagccg tgt    53

<210> SEQ ID NO 183
<211> LENGTH: 53
<212> TYPE: DNA
<213> ORGANISM: Homo sapiens

<400> SEQUENCE: 183
ctggccccaa ttccacttgg tagtaaaaca tgtacagtaa tacacagccg tgt    53

<210> SEQ ID NO 184
<211> LENGTH: 53
<212> TYPE: DNA
<213> ORGANISM: Homo sapiens

<400> SEQUENCE: 184
ctggccccaa ttccacttgg tggtaaaaca tgtacaataa tagacagccg tgt    53

<210> SEQ ID NO 185
<211> LENGTH: 53
<212> TYPE: DNA
<213> ORGANISM: Homo sapiens

<400> SEQUENCE: 185
ctggccccag ttccatttgg tagtaaaaca tgtacagtaa tatacagcag tgt    53

<210> SEQ ID NO 186
<211> LENGTH: 53
<212> TYPE: DNA
<213> ORGANISM: Homo sapiens

<400> SEQUENCE: 186
ctggccccag ttccatttgg tagtaaaaca tgtacagtaa tatacagctg tgt    53

<210> SEQ ID NO 187
<211> LENGTH: 53
<212> TYPE: DNA
<213> ORGANISM: Homo sapiens

<400> SEQUENCE: 187
ctggccccag ttccatttgg tagtaaaaca tgtacagtaa tatacagcgg tgt    53

<210> SEQ ID NO 188
<211> LENGTH: 53
<212> TYPE: DNA
<213> ORGANISM: Homo sapiens

<400> SEQUENCE: 188
ctggccccaa ttccacttgg tagtaaaaca tgtacagtaa tagacagcag tgt    53

<210> SEQ ID NO 189
<211> LENGTH: 53
<212> TYPE: DNA
<213> ORGANISM: Homo sapiens

<400> SEQUENCE: 189
ctggccccag ttccatttgg tagtaaaaca tgtacagtaa tatacggccg tgt    53

<210> SEQ ID NO 190
<211> LENGTH: 53
<212> TYPE: DNA
<213> ORGANISM: Homo sapiens -continued

<400> SEQUENCE: 190
ctggccccag ttccatttgg tagtaaaaca tgtacagtaa tatacagccg ttg          53

<210> SEQ ID NO 191
<211> LENGTH: 53
<212> TYPE: DNA
<213> ORGANISM: Homo sapiens

<400> SEQUENCE: 191
ctggccccag ttccatctcg tagtaaaaca tgtacaataa tacacagccg tgt          53

<210> SEQ ID NO 192
<211> LENGTH: 53
<212> TYPE: DNA
<213> ORGANISM: Homo sapiens

<400> SEQUENCE: 192
ctggccccag ttccatctgg tagtaaaaca cgtacaataa tacacagccg tgt          53

<210> SEQ ID NO 193
<211> LENGTH: 17
<212> TYPE: PRT
<213> ORGANISM: mouse

<400> SEQUENCE: 193

Phe Leu Cys Ala Ser Ser Ile Ala Trp Gly Ser Ala Glu Thr Leu Tyr
1               5                   10                  15

Phe

<210> SEQ ID NO 194
<211> LENGTH: 17
<212> TYPE: PRT
<213> ORGANISM: mouse

<400> SEQUENCE: 194

Leu Tyr Cys Thr Cys Ser Ala Leu Gly Gly Ser Ser Tyr Glu Gln Tyr
1               5                   10                  15

Phe

<210> SEQ ID NO 195
<211> LENGTH: 17
<212> TYPE: PRT
<213> ORGANISM: Homo sapiens

<400> SEQUENCE: 195

Thr Ala Val Tyr Tyr Cys Thr Cys Phe Thr Gly Arg Trp Asn Trp Gly
1               5                   10                  15

Gln

<210> SEQ ID NO 196
<211> LENGTH: 17
<212> TYPE: PRT
<213> ORGANISM: Homo sapiens

<400> SEQUENCE: 196

Thr Ala Val Tyr Tyr Cys Thr Cys Phe Thr Thr Lys Trp Asn Trp Gly
1               5                   10                  15

Gln

<210> SEQ ID NO 197
<211> LENGTH: 17
<212> TYPE: PRT

```
<213> ORGANISM: Homo sapiens

<400> SEQUENCE: 197

Thr Ala Val Tyr Tyr Cys Thr Cys Phe Thr Thr Arg Trp Asn Trp Gly
1               5                   10                  15
Gln
```

MONITORING HEALTH AND DISEASE STATUS USING CLONOTYPE PROFILES

This application is a continuation of co-pending U.S. application Ser. No. 13/100,365 filed 4 May 2011, which claims priority from U.S. provisional application Ser. No. 60/332,175 filed 6 May 2010, Ser. No. 61/455,743 filed 25 Oct. 2010, and Ser. No. 61/446,822 filed 25 Feb. 2011, and which is a continuation-in-part of U.S. application Ser. No. 12/615,263 filed 9 Nov. 2009 (now U.S. Pat. No. 8,236,503), which claims priority from U.S. provisional application Ser. No. 61/112,693 filed 7 Nov. 2008, all of the foregoing applications being incorporated herein by reference in their entireties.

TECHNICAL FIELD

The invention relates generally to monitoring health and disease conditions of an individual by molecular measurements, and more particularly, to monitoring health and disease conditions of an individual by measuring profiles immune system molecules using high throughput DNA sequencing.

BACKGROUND OF THE INVENTION

The adaptive immune system, comprising humoral (or B cell mediated) and cytotoxic (or T cell-mediated) responses, has evolved to attack specific molecular features on their respective targets. The occurrence of one response to a specific target provides a host with "memory" of it, giving it a capability to mount a stronger response if the same target were to appear another time. Usually any protein or polysaccharide can serve as the target for some subset of the adaptive immune response cells or their products that recognize specific molecular features, or epitopes, on the target.

Since autoimmune disease involves the recognition by some component of the adaptive immune system to self targets, aspects of the adaptive immune system have been examined to aid in diagnosis and prognosis of such diseases. Using standard immunological techniques, the humoral immune system has been investigated by looking for circulating autoantibodies. Autoantibodies, like antinuclear, anti-dsDNA, and rheumatoid factor, have been identified for several diseases. These antibodies may not themselves be pathological, nor is the target they recognize in the body necessarily the same as that tested for in vitro; however, measurement of their levels aids in the diagnosis and in some cases has some prognostic and treatment implications.

Another methodology to study the adaptive immune system in autoimmune and lymphoid diseases is based on the analysis of the diversity of the adaptive immune cells. Activation of the adaptive immune cells leads to their clonal expansion. Evidence of this clonal expansion is usually obtained by amplification from the blood RNA or DNA of part of the nucleic acid sequence coding for the antigen recognition region. For example. PCR primers to amplify sequences that have a specific V segment of the β chain in T-cell receptor (analogous to antibody heavy chain) are used to amplify the J segments or J and D segments connected to the specific V segment. When a diverse cell population is present it is expected to amplify fragments with a distribution of slightly different size amplicons, but clonal expansion causes specific sizes to become enriched and thus more intense as visualized as bands on a gel. In the technique called "spectratyping" each of the V segments is amplified with the J and D segments to assess whether any of these amplicons shows a clonal expansion.

One problem of the spectratyping approach is that many distinct sequences can have the same length and hence are indistinguishable. Therefore only dramatic clonal expansion can be discerned by spectratyping. There is need to improve methods of diagnosing and aiding prognosis of autoimmune disease and autoimmune disease states as well as other diseases for which the immune system plays a central role.

While additional specificity in profiling the immune system would be of great utility in allowing its impact on human health to be better predicted, still greater utility would be delivered if methods were developed that would allow the specific T and B cells involved in disease processes to be identified even if those particular sequences had never before been observed. The vast diversity of the immune system provides it with an immense reserve of potentially useful cells but also presents a challenge to the researcher trying to use this repertoire for predictive purposes. Any single sequence targeting an antigen is one of a vast number that could be involved with and/or correlated to the disease process in a given individual. Methods that would identify which of the many cells in a given individual are involved with disease processes would be of great value to human health.

Immune cells profiling also has utility in the diagnosis and management of cancers. Treatment of cancers frequently involves the evaluation of response to treatment as well as monitoring for the recurrence of disease. Most common methodologies to monitor response and cancer recurrence are radiographic evaluations as well as blood biomarkers. For example, CT scans are frequently used to monitor cancer recurrence in multiple diseases including colon cancer. Similarly, protein biomarkers, like PSA and CEA, are blood biomarkers used to follow prostate and colon cancers. Specific genomic rearrangements generate another attractive target to use for following cancer cells. For example, the BCR-ABL translocation present in the vast majority of Chronic Myelogenous Leukemia (CML) patients has emerged as an analyte to assess the state of the disease. The specificity of the translocation to the leukemic cells and its amenability to be assayed by PCR technology allowed for the generation of a highly specific and sensitive test that is now used routinely to monitor CML patients.

Immune cell (or clonotype) profiling can be used to generate markers for lymphoid neoplasms. Cancer in the lymphoid cell lineage is a heterogeneous set of clinical diseases often reflecting the developmental stage of the cell that have undergone the transformation to a cancerous cell. Acute Lymphoblastic Leukemia (ALL) most often arises in immature lymphocytes. On the other hand, Multiple Myeloma (MM) occurs in plasma cells that have differentiated to produce antibodies. Similarly the different types of lymphomas often reflect different cell developmental stages. These diseases occur in different age groups, have different prognosis and mortality, and can be treated with distinct regimens.

These diseases are frequently treated with chemotherapy, radiotherapy, and/or bone marrow transplant. The disease recurrence is then monitored by different methods depending on the particular clinical situation. These methods include the assessment of blood and/or bone marrow using standard blood counts and morphology, flow cytometry (FCM) using cell surface markers, protein electrophoresis, as well as molecular techniques like PCR and FISH. In addition, radiographic studies like CT and PET scanning are frequently utilized for monitoring the recurrence of some of the lymphoid cancers. These methods suffer from invasiveness (bone marrow), cost and radiation risk, and/or lack of sensitivity.

Some molecular markers specific to a cancer cell detectable by PCR in a sensitive manner are present in a fraction of the lymphoid neoplasms. For example BCR-ABL is present in a fraction of ALL patients and it can serve as a marker to monitor for the relapse of the tumor. Unfortunately, for the majority of patients there are no such markers that can be used for sensitive and specific detection of relapse. FCM can be used to detect Minimum Residual Disease (MRD) which is useful for prognostic purposes. In this technique using multicolor Flow Activated Cell Sorting (FACS), a cancer cell can be identified by the virtue of the particular cell surface markers that it has. The sensitivity of this technique in the hands of experts is limited to $<10^{-4}$, (1 cancer cell in 10,000 normal cells) and markers present at one time point may disappear later. Therefore FCM is generally not useful in detecting early relapse in blood samples.

PCR provides a sensitive methodology for detection of specific sequences and it has been used to detect the particular rearrangement in B cell receptor (BCRs) or T cell receptors (TCRs) of the cancer cell. This technique capitalizes on the fact that B or T cell receptors in a lymphocyte are created after imperfect recombination events that generate unique sequences for the different lymphocytes. For example, a TCR is comprised of TCRα and TCRβ chains. TCRα is created through the recombination that links one of several different V regions to one of several J regions. Similarly TCRβ is created through recombination that creates one V. D, and J segment in tandem. In both cases the recombination is often not perfect and some bases can be deleted from the germ line segment sequences and other bases (called the N and P bases) may be added. The sequence between the V and J segments is referred to as the NDN region.

These sequences can then serve as a tag for these lymphocytes and their progeny. Since these recombination events also occur in the cells that ultimately become malignant, unique sequences of the B and T cell receptors can serve as tags to detect the cancer cells. The tag sequence is patient specific, and in fact it may change in the same patient because of clonal evolution. To define the sequence of the T or B cell receptor from the leukemic cells for a patient the diagnostic leukemia sample that is usually highly enriched for the leukemic clone is used. For example. T and/or B cell receptor DNA is amplified from a diagnostic sample, and the product is run on a gel which can separate DNA based on size (sometime referred to as "spectratyping"); or alternatively heteroduplex analysis can be done. A large degree of skewing of the observed size distribution indicates monoclonal expansion, which may then be confirmed by sequencing a sample from the skewed separation peak. Without such subsequent sequencing, it is often difficult to determine whether such skewing has monoclonal or polyclonal origins, e.g. Van Dongen et al, U.S. patent publication 2006/0234234.

Once the sequence tag is identified, real time PCR using Taqman probes can be used to monitor the level of that sequence. The NDN region is usually not long enough to encompass the PCR primers and the detection oligonucleotide. Therefore typically PCR primers complementary to the V and J regions and a Taqman probe that include some of the NDN bases of the leukemic clone are used. The primers provide some of the specificity, as they amplify only a fraction of the entire repertoire. The specificity to the particular clonotype is provided by the hybridization of Taqman probe. Therefore the assay sensitivity is usually not as good as in a typical PCR (e.g., BCR-ABL) where the primer pair (with or without the Taqman probe) provides the specificity. It was shown that the sensitivity can be as high as $10^{-5}$ for some sequences but can be significantly worse depending on the hybridization specificity provided by the Taqman probe whose sequence is complementary to at least part of the NDN region. Given the low sensitivity for some probes the assay may not work for any of the rearrangements in a particular patient. The issue of clone evolution has also been raised previously further reducing the likelihood of detecting low level leukemia. In addition this technique is cumbersome requiring the generation of patient-specific Taqman probes as well as template to be used as standards. These patient-specific standards need to be used at each time the patient sample is to be tested. The inconsistency of the sensitivity among patients, the cumbersome nature, and the logistical issues of getting appropriate controls for the assay has greatly limited its use. Therefore there is a need to generate markers that can be used for relapse monitoring in patients with lymphoid neoplasms. In some embodiments the invention disclosed herein enables a very general, sensitive, and specific set of markers to be developed to manage patients with lymphoid cancers using immune cell sequencing.

It would be advantageous for many fields, including particularly the autoimmune and lymphoid cancer fields, if there were available assays for assessing clonotype profiles of individuals that were more sensitive and comprehensive than current techniques and that were generally applicable without the need of manufacturing individualized reagents

SUMMARY OF THE INVENTION

The present invention is directed to methods for using sequence-based profiles of immune repertoires, or clonotype profiles, to detect and monitor disease or non-disease conditions. The invention is exemplified in a number of implementations and applications, some of which are summarized below and throughout the specification.

In one aspect the invention is directed to a method of monitoring a disease comprising the steps of (a) identifying one or more patient-specific clonotypes correlated with a disease by determining a clonotype profile from a sample of lymphocytes in a disease-related tissue, the sample comprising a repertoire of clonotypes from the disease-related tissue; (b) determining a clonotype profile from a sample of peripheral blood cells to identify a presence, absence and/or level of the one or more patient-specific clonotypes correlated with the disease, such peripheral blood sample comprising a repertoire of clonotypes; and (c) repeating step (b) to monitor the disease or condition in the patient. In one embodiment, the step of identifying further includes determining a clonotype profile from a sample of lymphocytes in a non-disease-related tissue in the same patient and comparing such clonotype profile with that from said disease-related tissue to identify said one or more patient-specific clonotypes. Diseases that can be monitored include, but are not limited to, lymphoid proliferative disorders, solid tumors, infectious diseases, and autoimmune diseases. The size of repertoire may vary widely depending on particular applications, but in one embodiment, a repertoire includes every clonotype in a sample from an individual present at a frequency of 0.01 percent or greater with a probability of ninety-nine percent. In other embodiments, a repertoire includes every clonotype in a sample from an individual present at a frequency of 0.001 percent or greater with a probability of ninety-nine percent.

In another aspect the invention is directed to a method for monitoring a disease comprising the steps of A method of monitoring a disease in a patient, the method comprising the steps of: (a) determining a clonotype profile from a sample of lymphocytes of an individual afflicted with a disease and a clonotype profile from the same individual from a sample of lymphocytes enriched on the basis of cell surface markers associated with the disease to identify one or more patient-specific clonotypes correlated with the disease, wherein each of the samples comprises a repertoire of clonotypes of the enriched and non-enriched lymphocyte populations; (b) determining a level of each of the one or more patient-specific clonotypes in a clonotype profile from a sample of peripheral blood cells, such sample having a defined volume and comprising a repertoire of clonotypes thereof; and (c) repeating step (b) to monitor the disease or condition in the patient.

In further embodiments of the above methods, the respective steps of determining a repertoire from a sample of peripheral blood cells further comprises including as one or more patient-specific clonotypes any previously unrecorded clonotypes that are phylogenic clonotypes of the one or more patient-specific clonotypes. Whenever the disease is a lymphoid proliferative disorder, the one or more patient-specific clonotypes of such embodiments may further include additional cancer-related mutations and genetic rearrangements, such as V region replacements (described more fully below) readily identified by methods of the invention.

In another aspect, the invention further provides a method of simultaneously measuring lymphocyte numbers and clonotype expression levels in a sample comprising the steps of: (i) obtaining from an individual a sample comprising T cells and/or B cells; (ii) sequencing spatially isolated individual molecules derived from genomic DNA of said cells, such spatially isolated individual molecules comprising a number of clonotypes corresponding to a number of lymphocytes in the sample; (iii) sequencing spatially isolated individual molecules derived from RNA of said cells, such spatially isolated individual molecules comprising numbers of clonotypes corresponding to expression levels thereof in the lymphocytes of the sample; and (iv) determining clonotype expression levels in lymphocytes of the sample by comparing for each clonotype the number determined from isolated individual molecules derived from genomic DNA of said cells and the number determined from isolated individual molecules derived from RNA of said cells.

The invention overcomes several deficiencies in the prior art by providing, among other advantages, sequence-based methods for measuring with much greater sensitivity clonotypes correlated with disease or health conditions. The invention further provides such assays in a general format applicable to any patient without the need for manufacturing individualized or patent-specific reagents. Such advances have particularly useful applications in the areas of autoimmunity and lymphoid cancers. In the latter area, the invention further provides assay and monitoring methods that are capable of detecting and tracking not only very low levels of disease-correlated clonotypes but also such clonotypes that have undergone modifications that would escape detection by prior methodologies. This latter feature is of tremendous value, for example, in monitoring minimal residual disease in lymphoid cancers.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the invention.

BRIEF DESCRIPTION OF THE DRAWINGS

The novel features of the invention are set forth with particularity in the appended claims. A better understanding of the features and advantages of the present invention is obtained by reference to the following detailed description that sets forth illustrative embodiments, in which the principles of the invention are utilized, and the accompanying drawings of which:

FIGS. 4B-4C illustrates a PCR scheme for generating three sequencing templates from an IgH chain in three separate reactions after which the resulting amplicons are combined for a secondary PCR to add P5 and P7 primer binding sites. FIG. 4D illustrates the locations of sequence reads generated for an IgH chain. FIG. 4E illustrates the use of the codon structure of V and J regions to improve base calls in the NDN region.

FIG. 8 the number of TCRβ molecules from samples. 8A and 8B show data from IgH amplification from genomic DNA FIG. 9 shows data indicating that multiplex amplifications in accordance with the invention have minimal amplification bias.

DETAILED DESCRIPTION OF THE INVENTION

Figure 1A:
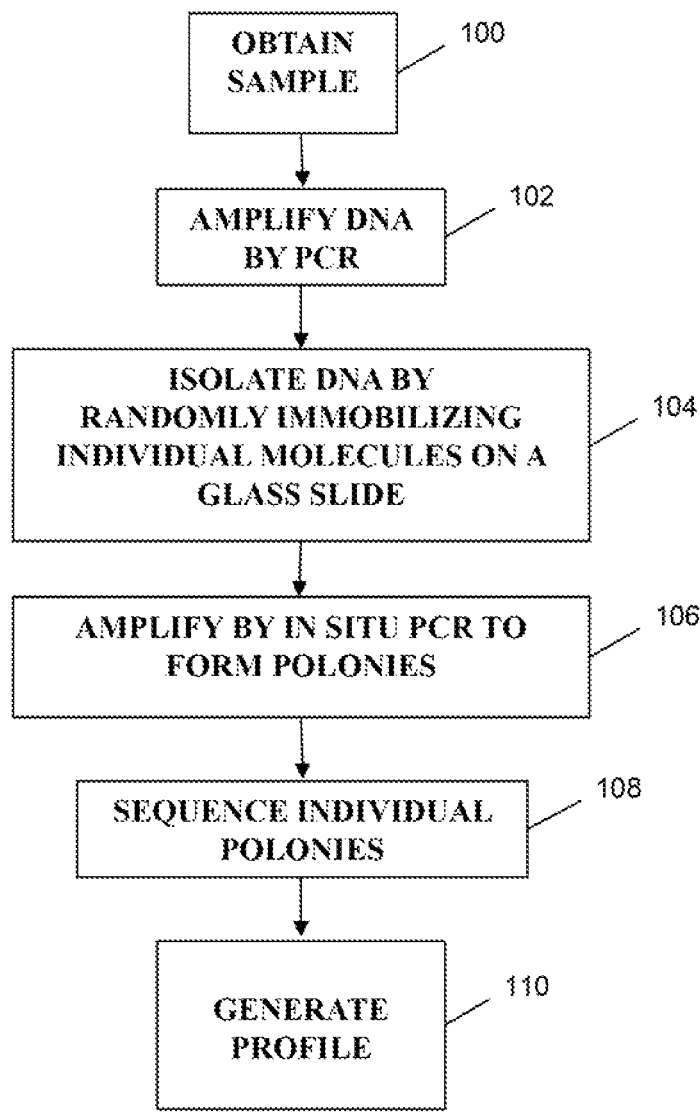
FIG. 1A is a flow diagram of an embodiment of a method of the provided invention for determining clonotype profiles.
Figure 1B:
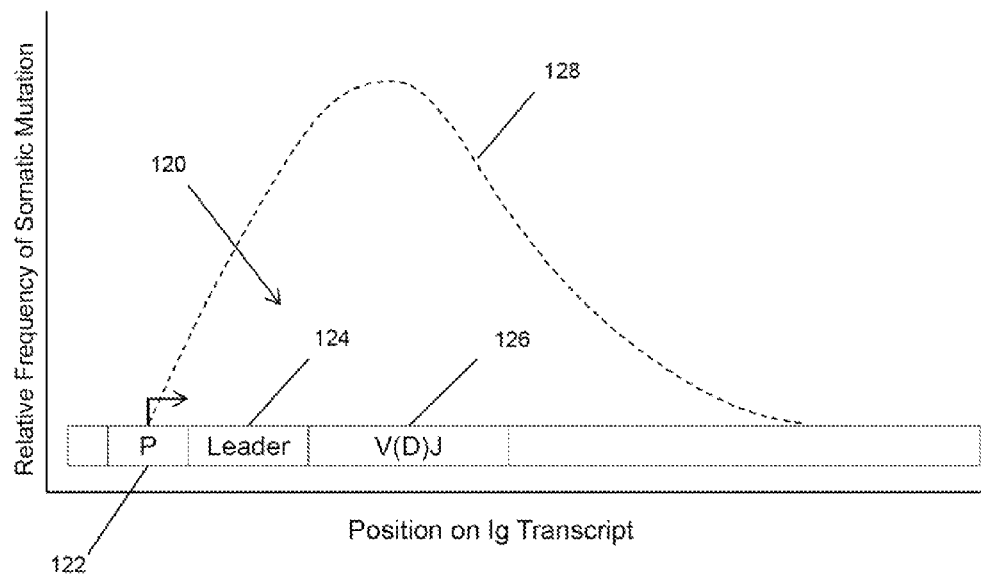
FIG. 1B illustrates the relative distribution of somatic mutations that occurs in immunoglobulins produced by B cells.

One aspect of this invention utilizes next generation sequencing technologies to evaluate the levels of TCR or BCR rearrangements in a population of lymphocytes. These sequencing technologies can obtain 1 million or more reads from a sample at a reasonable cost. A clonotype present at a frequency of 1/1,000,000 or lower can still be detected in a specific manner using these technologies. Multiplex amplification to amplify all the different types of sequences of a specific portion of gene or transcript can be accomplished from a sample from blood or bone marrow DNA. For example, to amplify IgH sequences, several primers complementary to all the known V segments and alleles can be used along with several primers complementary to all the J segments and alleles. FIG. 1A illustrates steps of such a method for an embodiment employing one class of DNA sequencers (e.g. Solexa sequencing-by-synthesis, as described below) for profiling clonotypes of a sample. A sample containing B cells or T cells is obtained (100) after which DNA or RNA is extracted and amplified (102) in a reaction that preferentially amplifies clonotypes and attaches terminal sequences for subsequent amplification and sequencing. Individual molecules of the amplified clonotypes are randomly distributed on a solid surface (104), such as, a glass surface, which has been configured to permit a second in situ amplification to produce clonal populations (or polonies) of each individual molecule (106). The molecules of each polony are then sequenced (108), for example, using a sequencing-by-synthesis technique, after which the types and abundances of the sequences are tabulated to form a clonotype profile (110), or equivalently a repertoire profile. The method can be performed with little amplification bias among the different sequences. RNA from the TCRβ and IgH genes can be amplified with only small differences in the efficiencies of the different V primers, thereby validating the possibility of doing the same from DNA. This scheme can ameliorate problems for the real time readout for detection of low level TCR and/or BCR rearrangements.

Sensitivity is determined by counting statistics (that is, sensitivity is increased by increasing cell and sequencing sample sizes) and equivalent amplification (that is, clonotypes having varied sequences may be amplified without significant bias in a multiplex amplification reaction, such as a PCR, as illustrated below). Since sensitivity is ultimately limited by counting statistics, to obtain more sensitivity one can simply obtain more cells (i.e. larger samples) and more sequencing reads. With sufficient sequencing reads the sensitivity is limited by the number of lymphocytes in the sample. In contrast, sensitivity for the real time PCR assay is limited by background. Moreover a patient's specific clones can be determined by sequencing a diagnostic leukemia or lymphoma sample. Once the clonotype is determined, its level can be determined in samples at subsequent time points. In some preferred embodiments there is no requirement for a patient-specific probes or primers or the utilization of patient-specific templates to be run as standards. Instead patient-specific clones are followed by storing the data regarding the relevant sequences for each patient, and the same assay works for all patients.

In general, some embodiments of the invention include methods for applying nucleic acid sequencing techniques to the task of monitoring the repertoire of adaptive immunity cells for profiling the immune system. The profiles of the immune system generated can be used for diagnosis of diseases and disorders, and for diagnosis of states of diseases and disorders. The methods of immune profiling of the provided invention can be used in monitoring diseases and disorders and assessing treatment of diseases and disorders. The diseases and disorders that the methods of the provided invention can be applied to include autoimmune disease, including systemic lupus erythematosus (SLE), multiple sclerosis (MS), rheumatoid arthritis (RA), and ankylosing spondylitis (AS). The methods of the provided invention can be applied to the diagnosis, monitoring, and treatment of transplant rejection and immune aging. Furthermore, the methods of immune profiling of the provided invention can be used for diagnosing, monitoring, and treating other diseases related to the immune system, including cancer and infectious disease.

Sequencing individual amplified molecules can distinguish different sequences and hence has the sensitivity to detect quantitative changes in clonal expansion. In general, in one embodiment of the provided invention, a method for determining a profile of recombined DNA sequences in T-cells and/or B-cells is provided. The method can comprise steps including isolating samples from a subject, one or more rounds of nucleic acid amplification, spatially isolating individual nucleic acids, and sequencing nucleic acids. The nucleic acids can be DNA or RNA. The recombined DNA sequences in T-cells and/or B-cells can be termed clonotypes.

In one aspect, a method for determining one or more correlating clonotypes in a subject or individual is provided. In another aspect, a method for developing an algorithm that can predict one or more correlating clonotypes in any sample from a subject with a disease is provided. In another aspect, a method for discovering one or more correlating clonotypes for an individual using an algorithm that can predict one or more correlating clonotypes in any sample from a subject is provided. In another aspect, a method for generating an algorithm that calculates a disease activity score is provided. In another aspect, a method for monitoring the disease state of an individual is provided.

T and B cell repertoire profiling can be of value for diseases with inflammatory aspects. This inflammation is often due to autoimmune and/or hypersensitivity reaction. These diseases include cardiovascular disease, Alzheimer disease, and pre-eclampsia. Inflammation has also been associated with abnormal metabolic states including obesity and diabetes. Other inflammation related diseases exist. In one aspect of the invention, a segment of recombined B cell nucleic acid is amplified by a PCR with a plurality of forward primers or a plurality of reverse primers to generate a nested set of templates (see FIGS. 4A and 4B and their descriptions below). Templates from such a set may be further amplified on a surface to form separate amplicons (e.g. by bridge PCR using a cBot instrument, Illumina, San Diego, Calif.). Templates from the same nested set may be associated with one another by sequence reads generated at their common ends. Nested sets of templates allow a sequencing chemistry with relative high error rates to be used to analyze longer sequences than otherwise would be possible, while at the same time maintaining high average quality scores over the entire length of the sequence. The nested sets also ensure that at least one sequence read is obtained from a V region even if it has been subjected to somatic hypermutation. In one embodiment, sequencing chemistries may be used for analyzing highly variable nucleic acids, such as IgH molecules, that have error rates no better than the following: 0.2 percent of sequence reads contain at least one error in positions 1-50; 0.2-1.0 percent of sequence reads contain at least one error in positions 51-75; 0.5-1.5 percent of sequence reads contain at least one error in positions 76-100; and 1-5 percent of sequence reads contain at least one error in positions 101-125. In another embodiment, sequencing primer binding sites are positioned so that when extended they produce a series of sequence reads where each sequence read except the last overlaps its immediately adjacent downstream primer binding site and/or sequence read, thereby providing continuous sequence coverage with higher quality scores than would be possible if a single long template were used to generate a single long sequence read.

I. Further Aspects and Embodiments

Further aspects and embodiments of the invention include the following: A method for determining a profile of recombined DNA sequences in T-cells and/or B-cells is provided comprising: obtaining a sample from a subject comprising T-cells and/or B-cells, spatially isolating individual molecules of genomic DNA from said cells; sequencing said spatially isolated individual molecules of genomic DNA, and determining the levels of different sequences from said sample to generate said profile of recombined DNA sequences. A method for determining a profile of recombined DNA sequences in T-cells and/or B-cells is provided comprising: obtaining a sample from a subject comprising T-cells and/or B-cells, spatially isolating individual molecules of genomic DNA from said cells, amplifying said individual molecules of genomic DNA, sequencing said amplified DNA, and determining the levels of different sequences from said sample to generate said profile of recombined DNA sequences. A method for determining a profile of recombined DNA sequences in T-cells and/or B-cells is provided comprising: obtaining a sample from a subject comprising T-cells and/or B-cells, amplifying genomic DNA from said cells, spatially isolating individual molecules of said amplified DNA, sequencing said spatially isolated individual molecules of amplified DNA; and determining the levels of different sequences from said sample to generate said profile of recombined DNA sequences. A method for determining a profile of recombined DNA sequences in T-cells and/or B-cells is provided comprising: obtaining a sample front a subject comprising T-cells and/or B-cells, amplifying genomic DNA from said cells, spatially isolating individual molecules of said amplified DNA, re-amplifying said amplified DNA molecules, sequencing said re-amplified DNA molecules, and determining the levels of different sequences from said sample to generate said profile of recombined DNA sequences. A method for determining a profile of sequences of recombined DNA in T-cells and/or B-cells is provided comprising: obtaining a sample from a subject comprising T-cells and/or B-cells, reverse transcribing RNA from said cells to form cDNA, spatially isolating individual molecules of said cDNA, optionally re-amplifying said spatially isolated individual molecules of cDNA, sequencing said cDNA and/or re-amplified cDNA; and determining the levels of different sequences from said sample to generate said profile of recombined DNA sequences. A method for determining a profile of recombined DNA sequences in T-cells and/or B-cells is provided comprising: obtaining a sample from a subject comprising T-cells and/or B-cells; spatially isolating individual cells in said sample, sequencing individual molecules of nucleic from said cells; and determining the levels of different sequences from said sample to generate said profile of recombined DNA sequences. In one embodiment, said amplifying and/or re-amplifying comprises PCR, multiplex PCR, TMA, NASBA, or LAMP. In another embodiment, said spatially isolating comprises separating said DNA or cDNA in two dimensions on a solid support, separating said DNA or cDNA in three dimensions in a solution with micelles, or separating molecules using micro-reaction chambers. In another embodiment, said amplifying and/or re-amplifying is by growth of bacteria harboring subcloned DNA or cDNA, amplification of DNA or cDNA on a slide, or amplification of DNA or cDNA on a bead. In another embodiment, said sequencing comprises dideoxy sequencing. In another embodiment, said sequencing comprises sequencing by synthesis using reversibly terminated labeled nucleotides. In another embodiment, said sequencing comprises detection of pyrophosphate release on nucleotide incorporation. In another embodiment, said sequencing comprises allele specific hybridization to a library of labeled oligonucleotide probes. In another embodiment, said sequencing comprises sequencing by synthesis using allele specific hybridization to a library of labeled oligonucleotide probes followed by ligation of said probes. In another embodiment, said sequencing comprises real time monitoring of the incorporation of labeled nucleotides during a polymerization step. In another embodiment, said recombined DNA sequences comprise T-cell receptor genes and/or immunoglobulin genes. In another embodiment, said sequencing comprises sequencing a subset of the full clonal sequences of immunoglobulin and/or T-cell receptor genes. In another embodiment, said subset of the full clonal sequence comprises the V-D junction, D-J junction of an immunoglobulin or T-cell receptor gene, the full variable region of an immunoglobulin or T-cell receptor gene, the antigen recognition region, or the complementarity determining region 3 (CDR3). In another embodiment, said T-cell receptor genes comprise T-cell receptor β genes. In another embodiment, said immunoglobulin genes comprise immunoglobulin heavy genes. In another embodiment, said amplifying or re-amplifying comprises a plurality of primers complementary to V segments and one primer complementary to a C segment. In another embodiment, said amplifying or re-amplifying comprises a plurality of primers complementary to V segments and a plurality of primers complementary to C segments. In another embodiment, said plurality of primers complementary to V segments comprises at least three different primers for each V segment and the plurality of primers complementary to C segments comprises at least 1, at least 2, at least 3, at least 4, at least 5, or at least 6 primers. In another embodiment, said T- or B-cells are subsets of the total T and B cells. In another embodiment, said subset of T-cells are CD4+, CD8+ cells, or CD27 high cells. In another embodiment, said sample comprises at least 100,000, at least 500,000, at least 750,000, of at least 1,000,000 T-cells. In another embodiment, said sequencing comprises at least 1000 reads per run, at least 10,000 reads per run, at least 100,000 reads per nm, or at least 1,000,000 reads per run. In another embodiment, said sequencing comprises generating about 30 bp, about 40 bp, about 50 bp, about 60 bp, about 70 bp, about 80 bp, about 90 bp, about 100 bp, about 110, or about 120 bp per read. In another embodiment, said sample is taken when the subject is at a flare state of an autoimmune disease. In another embodiment, said sample is taken from a subject having or suspected of having systemic lupus erythematosus. In another aspect, a method for determining one or more correlating clonotypes in a subject is provided comprising: generating one or more clonotype profiles by nucleic acid sequencing individual, spatially isolated molecules from at least one sample from the subject, wherein the at least one sample is related to a first state of the disease, and determining one or more correlating clonotypes in the subject based on the one or more clonotype profiles. In one embodiment, said at least one sample is from a tissue affected by the disease. In another embodiment, said determination of one or more correlating clonotypes comprises comparing clonotype profiles from at least two samples. In another embodiment, the first state of the disease is a peak state of the disease. In another embodiment, said one or more correlating clonotypes are present in the peak state of the disease. In another embodiment, said one or more correlating clonotypes are absent in the peak state of the disease. In another embodiment, said one or more correlating clonotypes are high in the peak state of the disease. In another embodiment, said one or more correlating clonotypes are low in the peak state of the disease. In another embodiment, said sample comprises T-cells and/or B-cells. In another embodiment, said T-cells and/or B-cells comprise a subset of T-cells and/or B-cells. In another embodiment, said subset of T-cells and/or B-cells are enriched by interaction with a marker. In another embodiment, said marker is a cell surface marker on the subset of T-cells and/or B-cells. In another embodiment, said subset of T-cells and/or B-cells interact with an antigen specifically present in the disease. In another embodiment, the disease is systemic lupus erythematosus or multiple sclerosis. In another aspect, a method for developing an algorithm that can predict one or more correlating clonotypes in any sample from a subject with a disease is provided comprising: a) generating a plurality of clonotype profiles from a set of samples, wherein the samples are relevant to the disease, b) identifying one or more correlating clonotypes from the set of samples, c) using sequence parameters and/or functional data from one or more correlating clonotypes identified in b) to develop the algorithm that can predict correlating clonotypes in any sample from a subject with the disease. In one embodiment, the set of samples are taken from one or more tissues affected by the disease. In another embodiment, said identification of one or more correlating clonotypes comprises comparing clonotype profiles from at least two samples. In another embodiment, said functional data include binding ability of markers on T-cell and/or B-cell surface or interaction with antigen by a T-cell or B-cell. In another embodiment, said sequence parameters comprise nucleic acid sequence and predicted amino acid sequence. In another embodiment, the samples are from one or more individuals at a peak stage of the disease. In another embodiment, said one or more correlating clonotypes are present in the peak state of the disease. In another embodiment, said one or more correlating clonotypes are at a high level in the peak state of the disease. In another embodiment, said one or more correlating clonotypes are at a low level in the peak state of the disease. In another embodiment, the one or more correlating clonotypes are absent at the peak state of the disease. In another embodiment, the disease is systemic lupus erythematosus or multiple sclerosis. In another embodiment, a method for discovering one or more correlating clonotypes for an individual is provided, comprising inputting a clonotype profile from a sample from the individual into an algorithm, and using the algorithm to determine one or more correlating clonotypes for the individual. In one embodiment, the algorithm is an algorithm that can predict one or more correlating clonotypes in any sample from a subject with a disease is provided comprising, said algorithm being developed by: a) generating a plurality of clonotype profiles from a set of samples, wherein the samples are relevant to the disease, b) identifying one or more correlating clonotypes from the set of samples, c) using sequence parameters and/or functional data from one or more correlating clonotypes identified in b) to develop an algorithm that can predict correlating clonotypes in any sample from a subject with the disease. In one embodiment, said sample is at taken at a peak state of disease. In another embodiment, the sample is taken from disease affected tissue. In another aspect, a method for generating an algorithm that calculates a disease activity score is provided comprising: developing an algorithm that uses a set of factors to combine levels of correlating clonotypes into a disease activity score, comparing the disease activity score to clinical data regarding the disease state, and optimizing the factors in order to maximize the correlation between clinical data and the disease activity score. In one embodiment, method for monitoring the disease state of an individual is provided comprising: a) determining a clonotype profile from a sample from the individual, b) inputting the clonotype profile information from a) into an algorithm that calculates a disease activity score, wherein is algorithm is generated by developing an algorithm that uses a set of factors to combine levels of correlating clonotypes into a disease activity score, comparing the disease activity score to clinical data regarding the disease state, and optimizing the factors in order to maximize the correlation between clinical data and the disease activity score, and c) using the algorithm that calculates a disease activity score to generate a score predictive of the disease state of the individual. In another embodiment, the method for monitoring the disease state of an individual further comprises determining one or more correlating clonotypes in the individual, and inputting information the one or more correlating clonotypes into the algorithm. In another embodiment, said determining one or more correlating clonotypes in the individual comprises a) generating one or more clonotype profiles by nucleic acid sequencing individual, spatially isolated molecules from at least one sample from the subject, wherein the at least one sample is related to a first state of the disease, and b) determining one or more correlating clonotypes in the subject based on the one or more clonotype profiles. In another embodiment, said determining one or more correlating clonotypes in the individual comprises a) inputting a clonotype profile from a sample from the individual into an algorithm that can predict one or more correlating clonotypes, wherein said algorithm that can predict one or more correlating clonotypes is developed by i) generating a plurality of clonotype profiles from a set of samples, wherein the samples are relevant to the disease, ii) identifying one or more correlating clonotypes from the set of samples, iii) using sequence parameters and/or functional data from one or more correlating clonotypes identified in ii) to develop the algorithm that can predict correlating clonotypes in any sample from a subject with the disease, and c) using the algorithm that can predict one or more correlating clonotypes to determine one or more correlating clonotypes for the individual. In another embodiment, the disease is systemic lupus erythematosus or multiple sclerosis. In another aspect, a method of determining one or more correlating T or B cell clonotypes is provided comprising: a) dividing a sample of cells from a subject into at least two samples, b) generating one or more clonotype profiles by nucleic acid sequencing individually spatially isolated molecules from one of the samples of cells from the subject, c) enriching another sample of cells from this subject based on at least one molecular parameter of the cells, d) generating a one of more clonotype profiles by nucleic acid sequencing individually spatially isolated molecules from the enriched sample of the subject, and e) identifying at least one clonotype based on clonotypes whose abundance within the sample has been altered between the enriched sample and the unenriched sample. In another embodiment, the molecular parameter is a cell surface marker. In another embodiment, the enrichment is done by capturing cells using a solid phase immobilized affinity marker. In another embodiment, the solid surface is a set of beads. In another embodiment, the solid surface is a column. In another embodiment, the marker is labeled using a fluorescent moiety. In another embodiment, the enrichment is accomplished by flow cytometry using the fluorescent label. In another embodiment, the cells are B lymphocytes and the enrichment is done using antigens that bind the B cell receptor. In another embodiment, the enrichment is done through capture a solid surface on which antigens are immobilized. In another embodiment, the antigen is used to label the B lymphocytes and the enrichment is accomplished using flow cytometry using this label. In another embodiment, the cells are T lymphocytes and the enrichment is done using a method that allows the T cells that react to a specific antigen to be labeled and enriched using flow cytometry. In another embodiment, the T cells are labeled using the intracellular cytokine staining method. In another embodiment, the T cells are labeled using the cytokine capture method. In another embodiment, the molecular parameter the B cell receptor that is capable of binding at least one antigen that is specific to a pathogen. In another embodiment, the molecular parameter is the T cell receptor that is capable of binding at least on antigen that is specific to a pathogen. In another embodiment, the sample is taken from a patient that has been exposed to a pathogen at a first time point. In another aspect a method for determining a set of clonotypes in an individual that correlate with an immune reaction to a pathogen is provided comprising: a) dividing a sample of cells from a subject into at least two samples b) generating one or more clonotype profiles by nucleic acid sequencing individually spatially isolated molecules from one sample of cells from the subject, c) enriching another sample of cells from this subject based on the cells ability to bind at least one antigen from the pathogen d) generating a one of more clonotype profiles by nucleic acid sequencing individually spatially isolated molecules from the enriched sample of the subject and, e) identifying at least one correlating clonotype based on clonotypes whose abundance within the sample has been altered between the enriched sample and the unenriched sample. In another aspect a method for determining a set of clonotypes in an individual that correlate with an immune reaction to a tumor is provided comprising: a) dividing a sample of cells from a subject into at least two samples b) generating one or more clonotype profiles by nucleic acid sequencing individually spatially isolated molecules from one sample of cells from the subject c) enriching another sample of cells from this subject based on the cells ability to bind at least one autoantigen present in the tumor d) generating a one of more clonotype profiles by nucleic acid sequencing individually spatially isolated molecules from the enriched sample of the subject e) identifying at least one correlating clonotype based on clonotypes whose abundance within the sample has been altered between the enriched sample and the unenriched sample. In another embodiment, the levels of correlating clonotypes are used to assess the risk that the individual has a tumor. In another embodiment, the antigens are known to be present in a tumor that has already occurred in that individual and the correlating clonotypes are used to assess the risk of tumor recurrence. In another embodiment, the antigens are known to be present in tumors in other individuals and the clonotypes are used to assess the risk of cancer in a patient who has not had a tumor detected previously. In another aspect a method for determining a set of clonotypes in an individual that correlate with an immune reaction to a materials released in the bloodstream by damage to an organ is provided comprising: a) dividing a sample of cells from a subject into at least two samples b) generating one or more clonotype profiles by nucleic acid sequencing individually spatially isolated molecules from one sample of cells front the subject c) enriching another sample of cells from this subject based on the cells ability to bind at least one autoantigen present in the damaged organs d) generating a one of more clonotype profiles by nucleic acid sequencing individually spatially isolated molecules from the enriched sample of the subject and e) identifying at least one correlating clonotype based on clonotypes whose abundance within the sample has been altered between the enriched sample and the unenriched sample. In another embodiment, the levels of correlating clonotypes are used to assess the risk that the individual has organ damage. In another aspect a method for determining a set of clonotypes in an individual that correlate with an immune reaction to a therapeutic agent is provided comprising: a) dividing a sample of cells from a subject into at least two samples b) generating one or more clonotype profiles by nucleic acid sequencing individually spatially isolated molecules from one sample of cells from the subject c) enriching another sample of cells from this subject based on the cells ability to bind at least one antigen contained in the therapeutic agent d) generating a one of more clonotype profiles by nucleic acid sequencing individually spatially isolated molecules from the enriched sample of the subject and e) identifying at least one correlating clonotype based on clonotypes whose abundance within the sample has been altered between the enriched sample and the unenriched sample. In another embodiment, the levels of correlating clonotypes are used to assess the risk that the individual is exhibiting hypersensitivity to a therapeutic agent. In another aspect a method for determining a set of clonotypes in an individual that correlate with an immune reaction to a arterial plaque is provided comprising: a) dividing a sample of cells from a subject into at least two samples b) generating one or more clonotype profiles by nucleic acid sequencing individually spatially isolated molecules from one sample of cells from the subject c) enriching another sample of cells from this subject based on the cells ability to bind at least one antigen present in arterial plaque d) generating a one of more clonotype profiles by nucleic acid sequencing individually spatially isolated molecules from the enriched sample of the subject and e) identifying at least one correlating clonotype based on clonotypes whose abundance within the sample has been altered between the enriched sample and the unenriched sample. In another embodiment, the levels of correlating clonotypes are used to assess the risk that the individual has a cardiovascular disease. In another embodiment, the levels of correlating clonotypes are used to assess the risk that arterial plaque is unstable. In another aspect a method for determining a sequence identifier found in cells involved in a lymphoid neoplasm is described comprising: a) obtaining a sample of cells from the affected individual in which the cancerous cells are known to exist b) generating one or more clonotype profiles related to at least one immune cell genomic rearrangement by nucleic acid sequencing individually spatially isolated molecules from the cells in the sample c) identifying the sequence identifier as the sequence of the clonotype associated with the tumor. In another embodiment, the sample is from the bone marrow of the patient. In another embodiment, the sample is from the blood of the patient. In another embodiment, the sample is from a biopsy of a solid lymphoid tumor. In another embodiment, the immune cell genomic rearrangement is a VDJ rearrangement of IgH in a B cell. In another embodiment, the immune cell genomic rearrangement is a DJ rearrangement of IgH in a B cell. In another embodiment, the immune cell genomic rearrangement is a VJ rearrangement of IgK in a B cell. In another embodiment, the immune cell genomic rearrangement is a VJ rearrangement of IgL in a B cell. In another embodiment, the immune cell genomic rearrangement is a VDJ rearrangement of TCR β in a T cell. In another embodiment, the immune cell genomic rearrangement is a DJ rearrangement of TCR β in a T cell. In another embodiment, the immune cell genomic rearrangement is a VJ rearrangement of TCR α in a T cell. In another embodiment, the immune cell genomic rearrangement is a VJ rearrangement of TCR λ in a T cell. In another embodiment, the immune cell genomic rearrangement is a VDJ rearrangement of TCR δ in a T cell. In another embodiment, the immune cell genomic rearrangement is a VD rearrangement of TCR δ in a T cell. In another embodiment, the immune cell genomic rearrangement is a translocation of a J segment of IgH to another region of the genome. In another embodiment, the immune cell genomic rearrangement is a translocation of any J segment to another region of the genome. In another embodiment, the identification of the tumor associated clonotype is done by clonotype frequency. In another embodiment, the identification of the tumor associated clonotype is done by clonotype frequency. In another embodiment, the identification of the tumor associated clonotype is done by the detection of cross lineage rearrangement. In another embodiment, the identification of the tumor associated clonotype is done by identifying nonfunctional rearrangements\In another embodiment, the identification of the tumor associated clonotype is done by associating cell clonotypes with at least one molecular marker associated with the tumor. In another aspect a method of determining the levels of circulating lymphoid tumor cells within an individual whose tumor has been associated with a unique sequence identifier at a first time point involving is described comprising: a) obtaining a sample of cells from the patient b) generating one or more clonotype profiles related to at least one immune cell genomic rearrangement by nucleic acid sequencing individually spatially isolated molecules from the cells in the sample c) determining the levels of tumor cells from the level of the clonotypes associated with the sequence identifier. In another aspect a method of determining the levels of circulating lymphoid tumor cells within an individual whose tumor has been associated with a unique sequence identifier at a first time point involving is described comprising: a) obtaining a sample of cells from the patient b) enriching the cells based on at least one molecular marker c) generating one or more clonotype profiles related to at least one immune cell genomic rearrangement by nucleic acid sequencing individually spatially isolated molecules from the cells in the sample d) determining the levels of tumor cells from the level of the clonotypes associated with the sequence identifier. In another embodiment, the sample is a blood sample. In another embodiment, the sample is a bone marrow sample. In another embodiment, the sample is a lymph sample. In another embodiment, the sample is a tissue sample. In another embodiment, the cells are labeled fluorescently and enriched using flow cytometry. In another embodiment, the cells are enriched through binding to a solid support. In another embodiment, the clonotype is defined to be the clonotype that contains the unique sequence identifier. In another embodiment, the clonotypes are determined to be those clonotypes that are likely to have resulted from mutations and rearrangements to the sequence identifier. In another embodiment, the levels of circulating tumor cells and/or the change in the levels of the circulating tumor cells are used in an algorithm to produce a score that correlates with the risk of having a clinical tumor recurrence. In another embodiment, the levels of circulating tumor cells and/or the change in the levels of the circulating tumor cells are used to make a treatment decision.

II. Methods of Determining Clonotype Profiles

The methods of the invention can be used to generate profiles of recombined DNA sequences, or clonotypes, in a sample from a subject. In one embodiment, a method for determining a profile of recombined DNA sequences in T-cells and/or B-cells is provided including obtaining a sample from a subject comprising T-cells and/or B-cells, isolating individual molecules of genomic DNA from said cells, sequencing the isolated individual molecules of genomic DNA, and determining the levels of different sequences from the sample to generate said profile of recombined DNA sequences.

In another embodiment, a method for determining a profile of recombined DNA sequences in T-cells and/or B-cells is provided including obtaining a sample from a subject comprising T-cells and/or B-cells, isolating individual molecules of genomic DNA from the cells, amplifying the individual molecules of genomic DNA, sequencing the amplified DNA, and determining the levels of different sequences from the sample to generate said profile of recombined DNA sequences.

In another embodiment, a method for determining a profile of recombined DNA sequences in T-cells and/or B-cells is provided including obtaining a sample from a subject comprising T-cells and/or B-cells, amplifying genomic DNA from the cells, isolating individual molecules of the amplified DNA, sequencing the isolated individual molecules of amplified DNA, and determining the levels of different sequences from the sample to generate the profile of recombined DNA sequences.

In another embodiment, a method for determining a profile of recombined DNA sequences in T-cells and/or B-cells is provided including obtaining a sample from a subject including T-cells and/or B-cells, amplifying genomic DNA from the cells, isolating individual molecules of the amplified DNA, re-amplifying the amplified DNA molecules, sequencing the re-amplified DNA molecules, and determining the levels of different sequences from the sample to generate the profile of recombined DNA sequences.

In another embodiment, a method for determining a profile of sequences of recombined DNA in T-cells and/or B-cells is provided including obtaining a sample from a subject comprising T-cells and/or B-cells, isolating RNA from said sample, reverse transcribing the RNA from said cells to form cDNA, isolating individual molecules of said cDNA, optionally re-amplifying said cDNA, sequencing said isolated individual molecules of said cDNA or re-amplified DNA, and determining the levels of different sequences from said sample to generate said profile of recombined DNA sequences.

In another embodiment, a method for determining a profile of sequences of recombined DNA in T-cells and/or B-cells is provided including obtaining a sample from a subject including T-cells and/or B-cells, isolating individual molecules of RNA from said sample, sequencing the individual molecules of RNA, and determining the levels of different sequences from said sample to generate the profile of recombined DNA sequences.

Subjects and Samples

The methods of the provided invention can use samples from subjects or individuals (e.g., patients). The subject can be a patient, for example, a patient with an autoimmune disease. The subject can be a patient with an infectious disease or cancer, such as a leukemia or a lymphoma. The subject can be a mammal, for example, a human. The subject can be male or female. The subject can be an infant, a child, or an adult. In some embodiments the subject is no longer living. In some embodiments the subject is alive. The subject can be an individual who was exposed to a biologic weapon.

The subject could also be a non-human animal. The non-human animal could be a domestic pet or a farm animal. The non-human animal could be a dog, cat, cow, horse, goat, or pig. The non-human animal could be a cloned animal. The non-human animal could be involved in the production of pharmaceuticals.

Samples used in the methods of the provided invention can include, for example, a bodily fluid from a subject, including amniotic fluid surrounding a fetus, aqueous humor, bile, blood and blood plasma, cerumen (earwax). Cowper's fluid or pre-ejaculatory fluid, chyle, chyme, female ejaculate, interstitial fluid, lymph, menses, breast milk, mucus (including snot and phlegm), pleural fluid, pus, saliva, sebum (skin oil), semen, serum, sweat, tears, urine, vaginal lubrication, vomit, water, feces, internal body fluids, including cerebrospinal fluid surrounding the brain and the spinal cord, synovial fluid surrounding bone joints, intracellular fluid is the fluid inside cells, and vitreous humour the fluids in the eyeball. In one embodiment, the sample is a blood sample. The blood sample can be about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 mL. The sample can be Cerebral Spinal Fluid (CSF) when the subject has multiple sclerosis, synovial fluid when the subject has rheumatoid arthritis, and skin (or other organ) biopsy when the subject has systemic lupus. In one embodiment, the clonotype can be identified from the available body fluid/tissue most likely to reflect pathology followed by later monitoring the levels of the clonotypes form a different body fluid, for example, blood. Samples can also include solvents in which biologic material has been dissolved. Samples can be analyzed at a time when a disease is inactive. Samples can be analyzed at a time when a disease is active. Samples can be obtained at a time when a disease is inactive. Samples can be obtained at a time when a disease is active. The sample can be obtained by a health care provider, for example, a physician, physician assistant, nurse, veterinarian, dermatologist, rheumatologist, dentist, paramedic, or surgeon. The sample can be obtained by a research technician. The sample can be provided by the subject. The sample can be provided anonymously. The sample can be provided through the mail. The sample can be provided by a law enforcement agency or by an investigator. More than one sample from a subject can be obtained.

The sample can be a biopsy, e.g., a skin biopsy. The biopsy can be from, for example, brain, liver, lung, heart, colon, kidney, or bone marrow. Any biopsy technique used by those skilled in the art can be used for isolating a sample from a subject. For example, a biopsy can be an open biopsy, in which general anesthesia is used. The biopsy can be a closed biopsy, in which a smaller cut is made than in an open biopsy. The biopsy can be a core or incisional biopsy, in which part of the tissue is removed. The biopsy can be an excisional biopsy, in which attempts to remove an entire lesion are made. The biopsy can be a fine needle aspiration biopsy, in which a sample of tissue or fluid is removed with a needle.

The sample can be obtained from bodily material which is left behind by a subject. Such discarded material can include human waste. Discarded material could also include shed skin cells, blood, teeth or hair.

The sample can include immune cells, for example, the immune cells can include T-cells and/or B-cells. T-cells (T lymphocytes) include, for example, cells that express T cell receptors. T-cells include Helper T cells (effector T cells or Th cells), cytotoxic T cells (CTLs), memory T cells, and regulatory T cells. The sample can include a single cell in some applications (e.g., a calibration test to define relevant T cells) or more generally at least 1,000, at least 10,000, at least 100,000, at least 250,000, at least 500,000, at least 750,000, or at least 1,000,000 T-cells.

B-cells include, for example, plasma B cells, memory B cells, B1 cells, B2 cells, marginal-zone B cells, and follicular B cells. B-cells can express immunoglobulins (antibodies, B cell receptor). The sample can include a single cell in some applications (e.g., a calibration test to define relevant B cells) or more generally at least 1,000, at least 10,000, at least 100,000, at least 250,000, at least 500,000, at least 750,000, or at least 1,000,000 B-cells.

The sample can include nucleic acid, for example. DNA (e.g., genomic DNA or mitochondrial DNA) or RNA (e.g., messenger RNA or microRNA). The nucleic acid can be cell-free DNA or RNA. e.g. extracted from the circulatory system, Vlassov et al., Curr. Mol. Med., 10: 142-165 (2010); Swamp et al, FEBS Lett., 581: 795-799 (2007). In the methods of the provided invention, the amount of RNA or DNA from a subject that can be analyzed includes, for example, as low as a single cell in some applications (e.g., a calibration test) and as many as 10 million of cells or more translating to a range of DNA of 6 pg-60 ug, and RNA of approximately 1 pg-10 ug.

As discussed more fully below (Definitions), a sample of lymphocytes is sufficiently large so that substantially every T cell or B cell with a distinct clonotype is represented therein, thereby forming a repertoire (as the term is used herein). In one embodiment, a sample is taken that contains with a probability of ninety-nine percent every clonotype of a population present at a frequency of 0.001 percent or greater. In another embodiment, a sample is taken that contains with a probability of ninety-nine percent every clonotype of a population present at a frequency of 0.0001 percent or greater. In one embodiment, a sample of B cells or T cells includes at least a half million cells, and in another embodiment such sample includes at least one million cells.

Whenever a source of material from which a sample is taken is scarce, such as, clinical study samples, or the like, DNA from the material may be amplified by a non-biasing technique, such as whole genome amplification (WGA), multiple displacement amplification (MDA); or like technique, e.g. Hawkins et al, Curr. Opin. Biotech., 13: 65-67 (2002); Dean et al, Genome Research, 11: 1095-1099 (2001); Wang et al, Nucleic Acids Research, 32: e76 (2004); Hosono et al, Genome Research, 13: 954-964 (2003); and the like.

Blood samples are of particular interest, especially in monitoring lymphoid neoplasms, such as lymphomas, leukemias, or the like, and may be obtained using conventional techniques, e.g. Innis et al, editors, PCR Protocols (Academic Press, 1990); or the like. For example, white blood cells may be separated from blood samples using convention techniques, e.g. RosetteSep kit (Stem Cell Technologies. Vancouver, Canada). Blood samples may range in volume from 100 μL to 10 mL; in one aspect, blood sample volumes are in the range of from 200 100 μL to 2 mL. DNA and/or RNA may then be extracted from such blood sample using conventional techniques for use in methods of the invention, e.g. DNeasy Blood & Tissue Kit (Qiagen. Valencia, Calif.). Optionally, subsets of white blood cells, e.g. lymphocytes, may be further isolated using conventional techniques, e.g. fluorescently activated cell sorting (FACS)(Becton Dickinson, San Jose, Calif.), magnetically activated cell sorting (MACS)(Miltenyi Biotec, Auburn, Calif.), or the like.

In other embodiments, nucleic acids are analyzed from a sample of a subset of cells. A method to separate cells, for example by using a cell surface marker, can be employed. For example, cells can be isolated by cell sorting flow-cytometry, flow-sorting, fluorescent activated cell sorting (FACS), bead based separation such as magnetic cell sorting (MACS; e.g., using antibody coated magnetic particles), size-based separation (e.g., a sieve, an array of obstacles, or a filter), sorting in a microfluidics device, antibody-based separation, sedimentation, affinity adsorption, affinity extraction, or density gradient centrifugation. Cells can be purified by laser capture microdissection. Sorting can be based on cell size, morphology, or intracellular or extracellular markers. Methods for isolating or sorting tumor cells are described, for example, in Nagrath S. et al. (2007) Nature 450:1235-1239; U.S. Pat. Nos. 6,008,002, 7,232,653, and 7,332,288; PCT Publication No. WO2008157220A1; and US Patent Application Nos.

US20080138805A1 and US20090186065; and Rosenberg R. et al. (2002) Cytometry 49:150-158, each of which is herein incorporated by reference in their entireties.

The subset of cells can be a subset of T-cells and/or B-cells. The subset of T cells can be CD4+, CD8+, or CD27high cells. Cocktails of antibodies for labeling and/or separating a large variety of T-cell and B-cell subsets are commercially available from vendors such as Quest Diagnostic (San Juan Capistrano, Calif.); Dako (Denmark); and the like. The following are examples of kits available for disease related subsets (where the antigen specificity of the antibodies are listed: precursor B-lymphoblastic leukemia/lymphoma (CD19, CD79a (cytoplasmic), CD20, CD10, TDt, HLADR, CD34, IgM (cytoplasmic)); diffuse large B cell lymphoma (CD20, CD19, CD22, CD79a, CD30); follicular lymphoma (CD20, CD10, CD10, BCL2, BCL6); mantle cell leukemia (CD19, CD20, CD5, CD23-, BCL1); and the like.

Fluorescence-activated cell sorting (FACS) uses light scattering and fluorescent characteristics to sort cells. A fluorescent property can be imparted on a cell using, e.g., nucleic acid probes or antibodies conjugated to a fluorescent dye. A cell suspension can form a stream of flowing liquid. The stream of cells forms drops that contain approximately one cell per drop. Before the stream forms drops, a fluorescent characteristic of each cell is measured. A charge is placed on an electrical charging ring prior to fluorescence intensity measurement and the opposite charge is carried on the drop as it breaks from the stream. The charged drops pass through two high voltage deflection plates that divert drops into different containers based upon their charge. The charge can be directly applied to the stream and the drop breaking off retains the charge of the same sign as the stream. The stream is then returned to neutral after the drop breaks off.

Direct or indirect immunofluorescence can be used in FACS. In direct immunofluorescence, an antibody is directly conjugated to a fluorescent dye. In indirect immunofluorescence, the primary antibody is not labeled, and a secondary antibody is conjugated to a fluorescent dye.

Since the identifying recombinations are present in the DNA of each individual's adaptive immunity cell as well as their associated RNA transcripts, either RNA or DNA can be sequenced in the methods of the provided invention. A recombined sequence from a T-cell or B-cell encoding a T cell receptor or immunoglobulin molecule, or a portion thereof, is referred to as a clonotype. The DNA or RNA can correspond to sequences from T-cell receptor (TCR) genes or immunoglobulin (Ig) genes that encode antibodies. For example, the DNA and RNA can correspond to sequences encoding $\alpha$, $\beta$, $\gamma$, or $\delta$ chains of a TCR. In a majority of T-cells, the TCR is a heterodimer consisting of an $\alpha$-chain and $\beta$-chain. The TCR$\alpha$ chain is generated by VJ recombination, and the $\beta$ chain receptor is generated by V(D)J recombination. For the TCR$\beta$ chain, in humans there are 48 V segments, 2 D segments, and 13 J segments. Several bases may be deleted and others added (called N and P nucleotides) at each of the two junctions. In a minority of T-cells, the TCRs consist of $\gamma$ and $\delta$ delta chains. The TCR $\gamma$ chain is generated by VJ recombination, and the TCR $\delta$ chain is generated by V(D)J recombination (Kenneth Murphy, Paul Travers, and Mark Walport, *Janeway's Immunology* 7th edition, Garland Science, 2007, which is herein incorporated by reference in its entirety).

The DNA and RNA analyzed in the methods of the invention can correspond to sequences encoding heavy chain immunoglobulins (IgH) with constant regions ($\alpha$, $\delta$, $\epsilon$, $\gamma$, or $\mu$) or light chain immunoglobulins (IgK or IgL) with constant regions $\lambda$ or $\kappa$. Each antibody has two identical light chains and two identical heavy chains. Each chain is composed of a constant (C) and a variable region. For the heavy chain, the variable region is composed of a variable (V), diversity (D), and joining (J) segments. Several distinct sequences coding for each type of these segments are present in the genome. A specific VDJ recombination event occurs during the development of a B-cell, marking that cell to generate a specific heavy chain. Diversity in the light chain is generated in a similar fashion except that there is no D region so there is only VJ recombination. Somatic mutation often occurs close to the site of the recombination, causing the addition or deletion of several nucleotides, further increasing the diversity of heavy and light chains generated by B-cells. The possible diversity of the antibodies generated by a B-cell is then the product of the different heavy and light chains. The variable regions of the heavy and light chains contribute to form the antigen recognition (or binding) region or site. Added to this diversity is a process of somatic hypermutation which can occur after a specific response is mounted against some epitope.

As mentioned above, in accordance with the invention, primers may be selected to generate amplicons of subsets of recombined nucleic acids extracted from lymphocytes. Such subsets may be referred to herein as "somatically rearranged regions." Somatically rearranged regions may comprise nucleic acids from developing or from fully developed lymphocytes, where developing lymphocytes are cells in which rearrangement of immune genes has not been completed to form molecules having full V(D)J regions. Exemplary incomplete somatically rearranged regions include incomplete IgH molecules (such as, molecules containing only D-J regions), incomplete TCR$\delta$ molecules (such as, molecules containing only D-J regions), and inactive IgK (for example, comprising Kde-V regions). Incomplete rearrangements are also found in fully developed immune cells associated with the second chromosome in a cell in which the first chromosome formed a productive rearrangement.

Controlling for Sample Amounts and Estimating Cell Numbers

Adequate sampling of the cells is an important aspect of interpreting the repertoire data, as described further below in the definitions of "clonotype" and "repertoire." For example, starting with 1,000 cells creates a minimum frequency that the assay is sensitive to regardless of how many sequencing reads are obtained. Therefore one aspect of this invention is the development of methods to quantitate the number of input immune receptor molecules. This has been implemented for TCR$\beta$ and IgH sequences. In either case a set of primers are used that are capable of amplifying all the different sequences. In order to obtain an absolute number of copies, a real time PCR with the multiplex of primers is performed along with a standard with a known number of immune receptor copies. An example of real time PCR data associated with the mouse vaccination example is shown in FIG. 9. This real time PCR measurement can be made from the amplification reaction that will subsequently be sequenced or can be done on a separate aliquot of the same sample. In the case of DNA, the absolute number of rearranged immune receptor molecules can be readily converted to number of cells (within 2 fold as some cells will have 2 rearranged copies of the specific immune receptor assessed and others will have one). In the case of cDNA the measured total number of rearranged molecules in the real time sample can be extrapolated to define the total number of these molecules used in another amplification reaction of the same sample. In addition, this method can be combined with a method to determine the total amount of RNA to define the number of rearranged immune receptor molecules in a unit amount (say 1 µg) of RNA assuming a specific efficiency of cDNA synthesis. If the total amount of cDNA is measured then the efficiency of cDNA synthesis need not be considered. If the number of cells is also known then the rearranged immune receptor copies per cell can be computed. If the number of cells is not known, one can estimate it from the total RNA as cells of specific type usually generate comparable amount of RNA. Therefore from the copies of rearranged immune receptor molecules per 1 µg one can estimate the number of these molecules per cell.

One disadvantage of doing a separate real time PCR from the reaction that would be processed for sequencing is that there might be inhibitory effects that are different in the real time PCR from the other reaction as different enzymes, input DNA, and other conditions may be utilized. Processing the products of the real time PCR for sequencing would ameliorate this problem. However low copy number using real time PCR can be due to either low number of copies or to inhibitory effects, or other suboptimal conditions in the reaction.

Another approach that can be utilized is to add a known amount of unique immune receptor rearranged molecules with a known sequence, i.e. known amounts of one or more internal standards, to the cDNA or genomic DNA from a sample of unknown quantity. By counting the relative number of molecules that are obtained for the known added sequence compared to the rest of the sequences of the same sample, one can estimate the number of rearranged immune receptor molecules in the initial cDNA sample. (Such techniques for molecular counting are well-known, e.g. Brenner et al, U.S. Pat. No. 7,537,897, which is incorporated herein by reference). Data from sequencing the added unique sequence can be used to distinguish the different possibilities if a real time PCR calibration is being used as well. Low copy number of rearranged immune receptor in the DNA (or cDNA) would create a high ratio between the number of molecules for the spiked sequence compared to the rest of the sample sequences. On the other hand, if the measured low copy number by real time PCR is due to inefficiency in the reaction, the ratio would not be high.

In one aspect, the invention provides methods for measuring clonotype expression at a cellular level. That is, as noted above, clonotypes may be used to count lymphocytes; therefore, by measuring clonotypes derived from genomic DNA and the same clonotypes derived from RNA, cell-based expression of clonotypes may be determined. A method for simultaneously measuring lymphocyte numbers and clonotype expression levels in a sample may comprise the steps of: (a) obtaining from an individual a sample comprising T cells and/or B cells; (b) sequencing spatially isolated individual molecules derived from genomic DNA of said cells, such spatially isolated individual molecules comprising a number of clonotypes corresponding to a number of lymphocytes in the sample; (c) sequencing spatially isolated individual molecules derived from RNA of said cells, such spatially isolated individual molecules comprising numbers of clonotypes corresponding to expression levels thereof in the lymphocytes of the sample; and (d) determining clonotype expression levels in lymphocytes of the sample by comparing for each clonotype the number determined from isolated individual molecules derived from genomic DNA of said cells and the number determined from isolated individual molecules derived from RNA of said cells. Genomic DNA and RNA are readily extracted from the same sample using commercially available kits, such as the AllPrep DNA/RNA Mini Kit (Qiagen GmbH, Germany). As mentioned above, in one embodiment, the step of determining further includes determining said number of lymphocytes in said sample by adding a known quantity of an internal standard to said genomic DNA. In another embodiment, where for example the sample is peripheral blood, the sample has a defined volume which permits a concentration of said lymphocytes to be determined in said sample. Typically, such a defined volume is in the range of from 1 mL to 50 mL, and more usually, in the range of from 1 mL to 10 mL. In another embodiment, numbers of the same clonotype derived from genomic DNA and RNA are compared by simply dividing the number of clonotypes determined from the isolated individual molecules derived from the RNA by the number of clonotypes determined from the isolated individual molecules derived from said genomic DNA. Such two sets of clonotypes are readily distinguished in the same sequencing run by the use of labels, particularly oligonucleotide tags that are attached during the sample preparation process. For Solexa-based sequencing, such labels may be incorporated with the tags used to identify different samples by (for example) adding a single nucleotide to the tag to indicate DNA or RNA, or simply using an additional tag so that each patient sample is labeled with two tags, one for the genomic DNA fraction and one for the RNA fraction. Thus, said step of sequencing said spatially isolation individual molecules derived from said RNA may include labeling each of said spatially isolated individual molecules with a first label indicating its RNA origin and said step of sequencing said spatially isolation individual molecules derived from said genomic DNA may include labeling each of said spatially isolated individual molecules with a second label indicating its genomic DNA origin such that the first label is distinguishable from the second label. In one embodiment, such labels are distinct oligonucleotide tags that are identified by sequencing.

Likewise, the invention may be used to provide simultaneously (that is, based on measurements on a single sample) lymphocyte number and clonality. Such embodiment may be implemented with the following steps: (a) obtaining from an individual a sample comprising T cells and/or B cells; (b) sequencing spatially isolated individual molecules derived from nucleic acid of said cells, such spatially isolated individual molecules comprising a number of clonotypes corresponding to a number of lymphocytes in the sample; (c) determining the number of lymphocytes from the number of spatially isolated individual molecules; (d) determining abundances of different sequences of the spatially isolated individual molecules to generate a clonotype profile and a measure of clonality based thereon. The nucleic acid from the lymphocytes may be genomic DNA and/or RNA; however, preferably the nucleic acid is genomic DNA. Similarly as above, in one embodiment, the step of determining said number further includes determining said number of lymphocytes in said sample by adding a known quantity of an internal standard to said genomic DNA. And similarly, when the sample is a peripheral blood sample it has a defined volume so that a concentration of said lymphocytes in said sample is determined. In some embodiments of the above, only B cells are employed and in other embodiments only T cells are employed.

Amplification of Nucleic Acid Populations

As noted below, amplicons of target populations of nucleic acids may be generated by a variety of amplification techniques. In one aspect of the invention, multiplex PCR is used to amplify members of a mixture of nucleic acids, particularly mixtures comprising recombined immune molecules such as T cell receptors, B cell receptors, or portions thereof. Guidance for carrying out multiplex PCRs of such immune molecules is found in the following references, which are incorporated by reference: Morley, U.S. Pat. No. 5,296,351; Gorski, U.S. Pat. No. 5,837,447; Dau, U.S. Pat. No. 6,087,096; Von Dongen et al, U.S. patent publication 2006/0234234; European patent publication EP 1544308B1; and the like. The foregoing references describe the technique referred to as "spectratyping," where a population of immune molecules are amplified by multiplex PCR after which the sequences of the resulting amplicon are physically separated, e.g. by electrophoresis, in order to determine whether there is a predominant size class. Such a class would indicate a predominant clonal population of lymphocytes which, in turn, would be indicative of disease state. In spectratyping, it is important to select primers that display little or no cross-reactivity (i.e. that do not anneal to binding sites of other primers); otherwise there may be a false representation of size classes in the amplicon. In the present invention, so long as the nucleic acids of a population are uniformly amplified, cross-reactivity of primers is permissible because the sequences of the amplified nucleic acids are analyzed in the present invention, not merely their sizes. As described more fully below, in one aspect, the step of spatially isolating individual nucleic acid molecules is achieved by carrying out a primary multiplex amplification of a preselected somatically rearranged region or portion thereof (i.e. target sequences) using forward and reverse primers that each have tails non-complementary to the target sequences to produce a first amplicon whose member sequences have common sequences at each end that allow further manipulation. For example, such common ends may include primer binding sites for continued amplification using just a single forward primer and a single reverse primer instead of multiples of each, or for bridge amplification of individual molecules on a solid surface, or the like. Such common ends may be added in a single amplification as described above, or they may be added in a two-step procedure to avoid difficulties associated with manufacturing and exercising quality control over mixtures of long primers (e.g. 50-70 bases or more). In such a two-step process (described more fully below and illustrated in FIGS. 4A-4B), the primary amplification is carried out as described above, except that the primer tails are limited in length to provide only forward and reverse primer binding sites at the ends of the sequences of the first amplicon. A secondary amplification is then carried out using secondary amplification primers specific to these primer binding sites to add further sequences to the ends of a second amplicon. The secondary amplification printers have tails non-complementary to the target sequences, which form the ends of the second amplicon and which may be used in connection with sequencing the clonotypes of the second amplicon. In one embodiment, such added sequences may include primer binding sites for generating sequence reads and primer binding sites for carrying out bridge PCR on a solid surface to generate clonal populations of spatially isolated individual molecules, for example, when Solexa-based sequencing is used. In this latter approach, a sample of sequences from the second amplicon are disposed on a solid surface that has attached complementary oligonucleotides capable of annealing to sequences of the sample, after which cycles of primer extension, denaturation, annealing are implemented until clonal populations of templates are formed. Preferably, the size of the sample is selected so that (i) it includes an effective representation of clonotypes in the original sample, and (ii) the density of clonal populations on the solid surface is in a range that permits unambiguous sequence determination of clonotypes.

In addition to ensuring that the sample contains sufficient cells to be representative of the original sample, it is important that the amplicons generated by the multiplex PCR reaction be representative of the cells in the reaction. In order to achieve this, primer conditions should be selected such that amplification from every cell in the reaction occurs.

TCR or BCR sequences or portions thereof can be amplified from nucleic acid in a multiplex reaction using at least one primer that anneals to the C region and one or more primers that can anneal to one or more V segments (as illustrated in FIGS. 2A-2B and FIGS. 4A-4B and discussed more fully below). The number of primers that anneal to V segments in a multiplex reaction can be, for example, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80. The number of primers that anneal to V segments in a multiplex reaction can be, for example, 10-60, 20-50, 30-50, 40-50, 20-40, 30-40, or 35-40. The primers can anneal to different V segments. For IgH genes, because of the possibility of somatic mutations in the V segments, multiple primers that anneal to each V segment can be used; for example, 1, 2, 3, 4, or 5 primers per V segment. The number of primers that anneal to C segments in a multiplex reaction can include, for example, at least 1, 2, 3, 4, 5, 6, 7, 8, 9, 10, 11, 12, 13, 14, or 15. The number of primers that anneal to C segments in a multiplex reaction can be 1-10, 2-9, 3-8, 4-7, 3-8, or 3-6. Amplification of TCR or immunoglobulin genes can occur as described in Example 3 and/or Example 4.

The region to be amplified can include the full clonal sequence or a subset of the clonal sequence, including the V-D junction. D-J junction of an immunoglobulin or T-cell receptor gene, the full variable region of an immunoglobulin or T-cell receptor gene, the antigen recognition region, or a CDR, e.g., complementarity determining region 3 (CDR3).

Figure 3A:
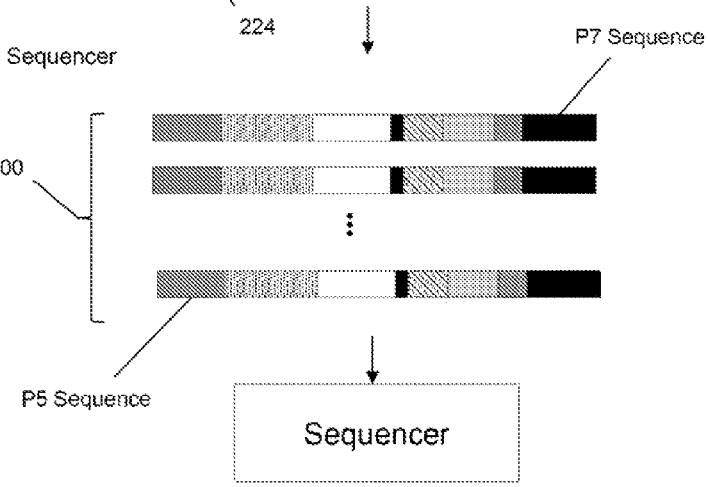
FIG. 3A illustrates a PCR product that was amplified using the scheme of FIGS. 2A-2B, which is going to undergo a secondary PCR to add bridge amplification and sequencing primer binding sites for Solexa-based sequencing.
Figure 3B:
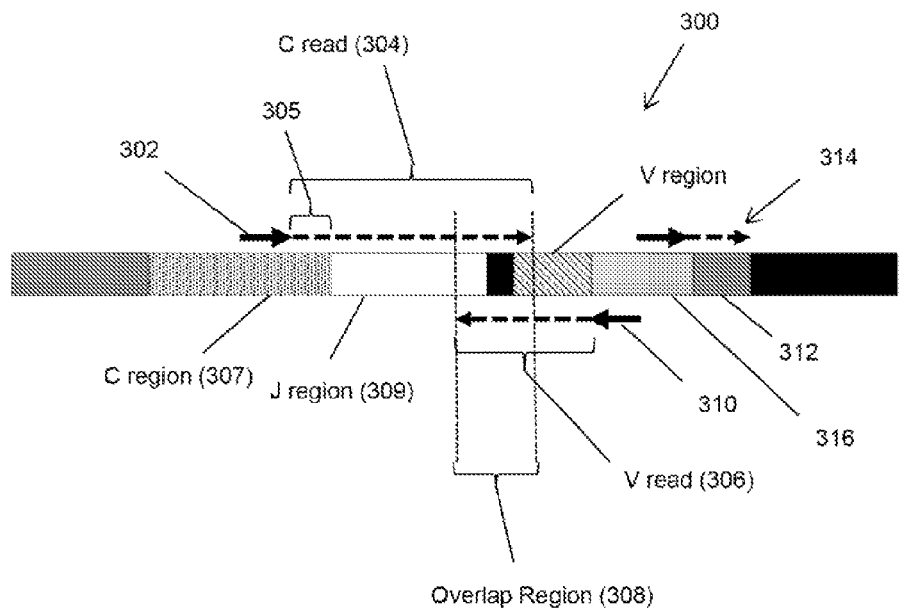
FIG. 3B illustrates details of one embodiment of determining a nucleotide sequence of the PCR product of FIG. 3A.
Figure 3C:
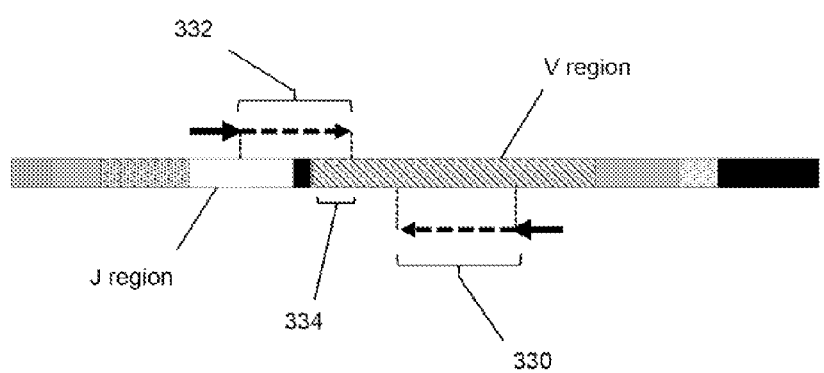
FIG. 3C illustrates details of another embodiment of determining a nucleotide sequence of the PCR product of FIG. 3A.

The TCR or immunoglobulin sequence can amplified using a primary and a secondary amplification step. Each of the different amplification steps can comprise different primers. The different primers can introduce sequence not originally present in the immune gene sequence. For example, the amplification procedure can add new primer binding sites to the ends of the target sequences to convert a multiplex amplification to a singleplex amplification or the amplification procedure can add one or more tags to the 5' and/or 3' end of amplified TCR or immunoglobulin sequence (as illustrated in FIGS. 3A-3C). The tag can be sequence that facilitates subsequent sequencing of the amplified DNA. The tag can be sequence that facilitates binding the amplified sequence to a solid support.

Other methods for amplification may not employ any primers in the V region. Instead, a specific primer can be used from the C segment and a generic primer can be put in the other side (5'). The generic primer can be appended in the cDNA synthesis through different methods including the well described methods of strand switching. Similarly, the generic primer can be appended after cDNA making through different methods including ligation.

Other means of amplifying nucleic acid that can be used in the methods of the provided invention include, for example, reverse transcription-PCR, real-time PCR, quantitative real-time PCR, digital PCR (dPCR), digital emulsion PCR (dePCR), clonal PCR, amplified fragment length polymorphism PCR (AFLP PCR), allele specific PCR, assembly PCR, asymmetric PCR (in which a great excess of primers for a chosen strand is used), colony PCR, helicase-dependent amplification (HDA), Hot Start PCR, inverse PCR (IPCR), in situ PCR long PCR (extension of DNA greater than about 5 kilobases), multiplex PCR, nested PCR (uses more than one pair of primers), single-cell PCR, touchdown PCR, loop-mediated isothermal PCR (LAMP), and nucleic acid sequence based amplification (NASBA). Other amplification schemes include: Ligase Chain Reaction, Branch DNA Amplification, Rolling Circle Amplification. Circle to Circle Amplification, SPIA amplification, Target Amplification by Capture and Ligation (TACL) amplification, and RACE amplification.

The information in RNA in a sample can be converted to cDNA by using reverse transcription. PolyA primers, random primers, and/or gene specific primers can be used in reverse transcription reactions in accordance with conventional protocols.

After amplification of DNA from the genome (or amplification of nucleic acid in the form of cDNA by reverse transcribing RNA), the individual nucleic acid molecules can be isolated, optionally re-amplified, and then sequenced individually. Exemplary amplification protocols may be found in van Dongen et al. Leukemia, 17: 2257-2317 (2003) or van Dongen et al, U.S. patent publication 2006/0234234, which is incorporated by reference. Briefly, an exemplary protocol is as follows: Reaction buffer: ABI Buffer II or ABI Gold Buffer (Life Technologies. San Diego, Calif.); 50 µL final reaction volume; 100 ng sample DNA; 10 pmol of each primer (subject to adjustments to balance amplification as described below); dNTPs at 200 µM final concentration; $MgCl_2$ at 1.5 mM final concentration (subject to optimization depending on target sequences and polymerase); Taq polymerase (1-2 U/tube); cycling conditions: preactivation 7 min at 95° C.; annealing at 60° C.; cycling times: 30 s denaturation; 30 s annealing; 30 s extension.

Polymerases that can be used for amplification in the methods of the invention are commercially available and include, for example. Taq polymerase, AccuPrime polymerase, or Pfu. The choice of polymerase to use can be based on whether fidelity or efficiency is preferred.

Methods for isolation of nucleic acids from a pool include spatial separation of the molecules in two dimensions on a solid substrate (e.g., glass slide), spatial separation of the molecules in three dimensions in a solution within micelles (such as can be achieved using oil emulsions with or without immobilizing the molecules on a solid surface such as heads), or using microreaction chambers in, for example, microfluidic or nano-fluidic chips. Dilution can be used to ensure that on average a single molecule is present in a given volume, spatial region, bead, or reaction chamber. Guidance for such methods of isolating individual nucleic acid molecules is found in the following references: Sambrook, Molecular Cloning: A Laboratory Manual (Cold Spring Harbor Laboratory Press, 2001s); Shendure et al. Science, 309: 1728-1732 (including supplemental material) (2005); U.S. Pat. No. 6,300,070; Bentley et al. Nature, 456: 53-59 (including supplemental material) (2008); U.S. Pat. No. 7,323,305; Matsubara et al. Biosensors & Bioelectronics, 20: 1482-1490 (2005); U.S. Pat. No. 6,753,147; and the like.

Real time PCR, picogreen staining, nanofluidic electrophoresis (e.g. LabChip) or UV absorption measurements can be used in an initial step to judge the functional amount of amplifiable material.

Methods for re-amplification of nucleic acids include bacterial growth of isolated colonies transformed with nucleic acid, amplification on a slide (e.g. PCR colonies (polonies)), and amplification on a bead (e.g. in an emulsion PCR). The same method can be used to amplify and re-amplify the nucleic acid or a different method can be used to amplify and reamplify the nucleic acid.

In certain embodiments the subcloning steps include a step in which a common primer is attached to the DNA or RNA through an amplification or ligation step. This primer is then used to amplify the clones and as a recognition sequence for hybridization of a primer for sequencing (e.g. as illustrated in FIGS. 2A-2B and 4A-4B, and discussed more fully below).

In one aspect, multiplex amplifications are carried out so that relative amounts of sequences in a starting population are substantially the same as those in the amplified population, or amplicon. That is, multiplex amplifications are carried out with minimal amplification bias among member sequences of a sample population. In one embodiment, such relative amounts are substantially the same if each relative amount in an amplicon is within five fold of its value in the starting sample. In another embodiment, such relative amounts are substantially the same if each relative amount in an amplicon is within two fold of its value in the starting sample. As discussed more fully below, amplification bias in PCR may be detected and corrected using conventional techniques so that a set of PCR primers may be selected for a predetermined repertoire that provide unbiased amplification of any sample.

In regard to many repertoires based on TCR or BCR sequences, a multiplex amplification optionally uses all the V segments. The reaction is optimized to attempt to get amplification that maintains the relative abundance of the sequences amplified by different V segment primers. Some of the primers are related, and hence many of the primers may "cross talk," amplifying templates that are not perfectly matched with it. The conditions are optimized so that each template can be amplified in a similar fashion irrespective of which primer amplified it. In other words if there are two templates, then after 1,000 fold amplification both templates can be amplified approximately 1,000 fold, and it does not matter that for one of the templates half of the amplified products carried a different primer because of the cross talk. In subsequent analysis of the sequencing data the primer sequence is eliminated from the analysis, and hence it does not matter what primer is used in the amplification as long as the templates are amplified equally.

Since the amount of each template is not known in a cDNA population generated from mRNA, a set of standards may be generated using singleplex PCRs of a cDNA population of clonotypes. This was carried out for a repertoire of TCRβ clonotypes. The product in each of 34 such PCRs (using in the separate reactions primers of Example 3) comprised a plurality of sequences with one V primer. The different products were carefully quantitated to create a set of standards at the same concentration. A pool of all 34 primers was used and 34 real time PCRs were performed using the pool of primers and each of the standard sequences as a template. Ideally without bias all the 34 standards will show equal efficiency of amplification by real time PCR. That suggests that each sequence is amplified equally even though the presence of cross talk makes it unclear what primers are carrying out the amplification. This optimization is consistent with the goal of having equal amplification irrespective of the actual primers that is incorporated in the amplification product. Increasing the total primer pool concentration significantly reduced the dynamic range as expected from increasing the efficiency of the amplification. Furthermore for templates that seemed to amplify more efficiently than the average, the concentration of their perfectly matched primer in the pool was decreased. Conversely for templates that were inefficiently amplified the concentration of their perfectly matched primer was increased. This optimization demonstrated that all the templates are amplified within two fold of the average amplification.

Figure 2A:
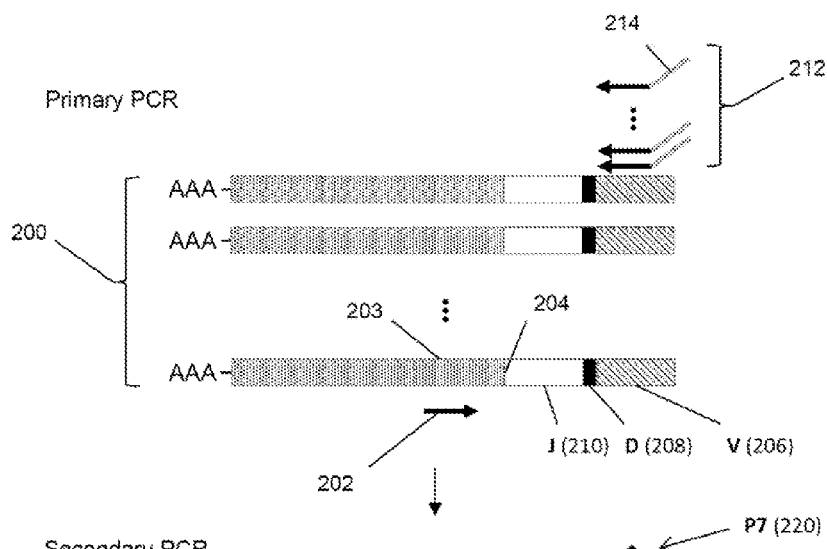
FIGS. 2A-2B show a two-staged PCR scheme for amplifying TCRβ genes.
Figure 2B:
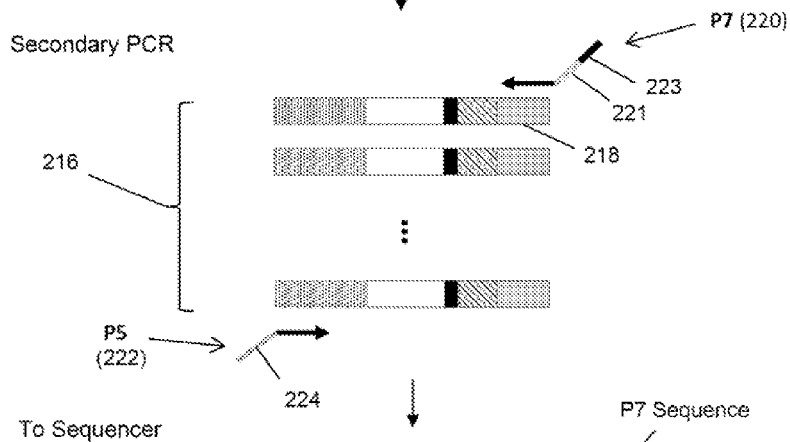

Amplification bias may also be avoided by carrying out a two-stage amplification (as illustrated in FIGS. 2A-2B) wherein a small number of amplification cycles are implemented in a first, or primary, stage using primers having tails non-complementary with the target sequences. The tails include primer binding sites that are added to the ends of the sequences of the primary amplicon so that such sites are used in a second stage amplification using only a single forward primer and a single reverse primer, thereby eliminating a primary cause of amplification bias. Preferably, the primary PCR will have a small enough number of cycles (e.g. 5-10) to minimize the differential amplification by the different primers. The secondary amplification is done with one pair of primers and hence the issue of differential amplification is minimal. One percent of the primary PCR is taken directly to the secondary PCR. Thirty-five cycles (equivalent to ~28 cycles without the 100 fold dilution step) used between the two amplifications were sufficient to show a robust amplification irrespective of whether the breakdown of cycles were: one cycle primary and 34 secondary or 25 primary and 10 secondary. Even though ideally doing only 1 cycle in the primary PCR may decrease the amplification bias, there are other considerations. One aspect of this is representation. This plays a role when the starting input amount is not in excess to the number of reads ultimately obtained. For example, if 1,000,000 reads are obtained and starting with 1,000,000 input molecules then taking only representation from 100,000 molecules to the secondary amplification would degrade the precision of estimating the relative abundance of the different species in the original sample. The 100 fold dilution between the 2 steps means that the representation is reduced unless the primary PCR amplification generated significantly more than 100 molecules. This indicates that a minimum 8 cycles (256 fold), but more comfortably 10 cycle (~1,000 fold), may be used. The alternative to that is to take more than 1% of the primary PCR into the secondary but because of the high concentration of primer used in the primary PCR, a big dilution factor is can be used to ensure these primers do not interfere in the amplification and worsen the amplification bias between sequences. Another alternative is to add a purification or enzymatic step to eliminate the primers from the primary PCR to allow a smaller dilution of it. In this example, the primary PCR was 10 cycles and the second 25 cycles.

Figure 5:
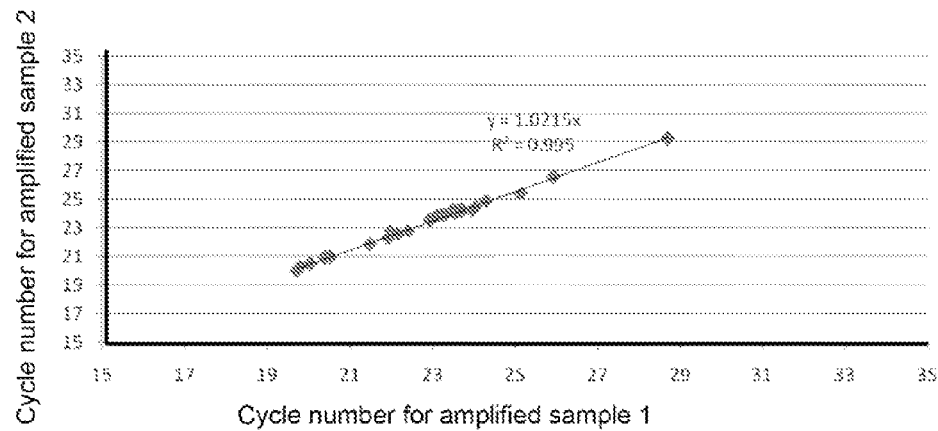
FIG. 5 shows data evidencing the reproducibility of multiplex PCRs of the invention.

The reproducibility of a multiplex PCR may be assessed as follows, as exemplified with the test set of primers from Example 2. Two primary PCR reactions are performed using the test set of primers, e.g. the pooled TCRβ primers and the C primer (of Example 2) and one cDNA sample as a template. The relative abundance in each amplified template is assessed using real time PCR. Using each of the two amplified products as a template, thirty four different real time PCR reactions were performed using the C primer and one of the V primers in each reaction. The data shown in FIG. 5 demonstrate that the relative abundance determined by real time PCR was highly reproducible using all the V primers for two samples, indicating that the multiplexed amplification is highly reproducible. The cycle number (Ct value) for each of the real time PCR amplifications using the one multiplexed amplification product as a template is shown on the X axis and using the second multiplexed amplification product as a template is depicted on the Y axis.

Figure 6:
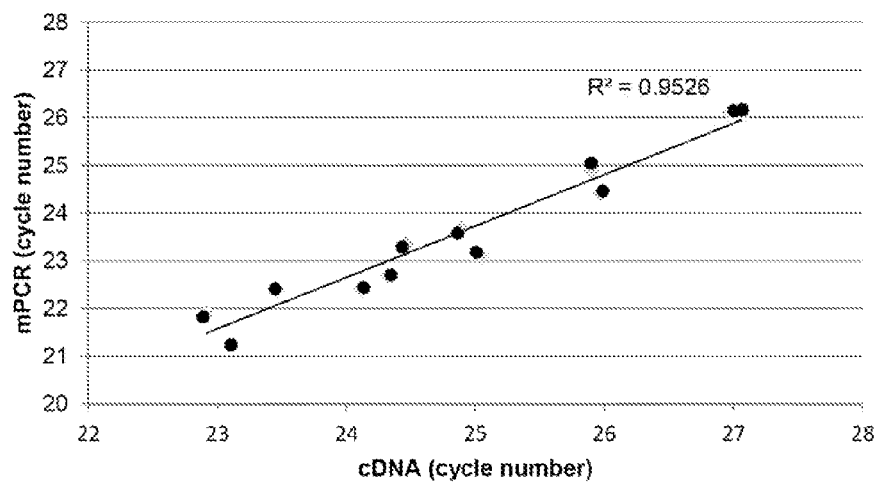
FIG. 6 shows data that demonstrate that multiplex PCRs of the invention introduce minimal amplification bias.

The amount of amplification bias of a set of primers may be assessed using the following procedure, which is exemplified using the primer set of Example 2. The test primer set (as above) is used to amplify a cDNA as a template (e.g. obtained from mRNA extracted from lymphocytes). The amount of template amplified by each of the 34 different primers (along with C segment primer) is determined using real time PCR and that amount is compared with the amount amplified using the same primers with the cDNA. Since there may be cross talk even if the relative abundance among the internal sequences in the amplified product and the cDNA were the same, only significant differences in amplification may be detected using this readout. This possibility may be tested by synthesizing collection of primers to amplify internal segments of a number of the starting cDNA sequences. For example, 12 oligos were designed that can, when used with C segment primer, amplify sequences internal to the above V segment primers. If there is minimal amplification bias, then the concentration of these internal sequences should change little between the starting cDNA and the amplified products. Data from this example is shown in FIG. 6. There, a cDNA sample was used as a template for a multiplexed amplification using the pooled TCRβ primers and the C primer (from Example 2). The C primer and the downstream internal primers were used for the initial amplification of template material from the multiplex amplification. Similarly real time PCR was used to assess the relative abundance of these same sequences in the cDNA. If the multiplexed amplification had any significant biases, the relative abundance in the amplified material would be very different from that in the cDNA. As can be seen in FIG. 6, high correlation was seen demonstrating minimal amplification bias in the multiplexed amplification. The cycle number (Ct value) for each of the real time PCR amplification using internal primers, and cDNA and the multiplexed amplification product as template is shown on X and Y axis, respectively.

The initial amplification can be done from DNA or RNA (e.g., after conversion to cDNA).

Sequencing Nucleic Acid Populations

Any high-throughput technique for sequencing nucleic acids can be used in the method of the invention. DNA sequencing techniques include dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of the separated molecules has more recently been demonstrated by sequential or single extension reactions using polymerases or ligases as well as by single or sequential differential hybridizations with libraries of probes. These reactions have been performed on many clonal sequences in parallel including demonstrations in current commercial applications of over 100 million sequences in parallel. These sequencing approaches can thus be used to study the repertoire of T-cell receptor (TCR) and/or B-cell receptor (BCR). In one aspect of the invention, high-throughput methods of sequencing are employed that comprise a step of spatially isolating individual molecules on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing. U.S. patent publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)). In another aspect, such methods comprise amplifying the isolated molecules either before or after they are spatially isolated on a solid surface. Prior amplification may comprise emulsion-based amplification, such as emulsion PCR, or rolling circle amplification. Of particular interest is Solexa-based sequencing where individual template molecules are spatially isolated on a solid surface, after which they are amplified in parallel by bridge PCR to form separate clonal populations, or clusters, and then sequenced, as described in Bentley et al (cited above) and in manufacturer's instructions (e.g. TruSeq™ Sample Preparation Kit and Data Sheet, Illumnina, Inc., San Diego, Calif., 2010); and further in the following references: U.S. Pat. Nos. 6,090,592; 6,300,070; 7,115,400; and EP0972081B1, which are incorporated by reference. In one embodiment, individual molecules disposed and amplified on a solid surface form clusters in a density of at least $10^5$ clusters per $cm^2$; or in a density of at least $5 \times 10^5$ per $cm^2$; or in a density of at least $10^6$ clusters per $cm^2$. In one embodiment, sequencing chemistries are employed having relatively high error rates. In such embodiments, the average quality scores produced by such chemistries are monotonically declining functions of sequence read lengths. In one embodiment, such decline corresponds to 0.5 percent of sequence reads have at least one error in positions 1-75; 1 percent of sequence reads have at least one error in positions 76-100; and 2 percent of sequence reads have at least one error in positions 101-125.

In one aspect, for each sample from an individual, the sequencing technique used in the methods of the invention generates sequences of least 1000 clonotypes per run; in another aspect, such technique generates sequences of at least 10,000 clonotypes per run; in another aspect, such technique generates sequences of at least 1000,000 clonotypes per run; in another aspect, such technique generates sequences of at least 500,000 clonotypes per run; and in another aspect, such technique generates sequences of at least 1,000,000 clonotypes per run. In still another aspect, such technique generates sequences of between 100,000 to 1,000,000 clonotypes per run per individual sample.

The sequencing technique used in the methods of the provided invention can generate about 30 bp, about 40 bp, about 50 bp, about 60 bp, about 70 bp, about 80 bp, about 90 bp, about 100 bp, about 110, about 120 bp per read, about 150 bp, about 200 bp, about 250 bp, about 300 bp, about 350 bp, about 400 bp, about 450 bp, about 500 bp, about 550 bp, or about 600 bp per read.

The sequencing technique used in the methods of the provided invention can generate at least 30, 40, 50, 60, 70, 80, 90, 100, 110, 120, 150, 200, 250, 300, 350, 400, 450, 500, 550, or 600 bp per read. In one aspect, a sequence-based clonotype profile of an individual is obtained using the following steps: (a) obtaining a nucleic acid sample from T-cells and/or B-cells of the individual; (b) spatially isolating individual molecules derived from such nucleic acid sample, the individual molecules comprising nested sets of templates each generated from a nucleic acid in the sample and each containing a somatically rearranged region or a portion thereof, each nested set being capable of producing a plurality of sequence reads each extending in the same direction and each starting from a different position on the nucleic acid from which the nested set was generated, (c) sequencing said spatially isolated individual molecules; and (d) determining abundances of different sequences of the nucleic acid molecules from the nucleic acid sample to generate the clonotype profile. In one embodiment, the step of sequencing includes producing a plurality of sequence reads for each of the nested sets. In another embodiment, each of the somatically rearranged regions comprise a V region and a J region, and each of the plurality of sequence reads starts from a different position in the V region and extends in the direction of its associated J region. In another embodiment, the step of sequencing comprises bidirectionally sequencing each of the spatially isolated individual molecules to produce at least one forward sequence read and at least one reverse sequence read. Further to the latter embodiment, at least one of the forward sequence reads and at least one of the reverse sequence reads have an overlap region such that bases of such overlap region are determined by a reverse complementary relationship between such sequence reads. In still another embodiment, each of the somatically rearranged regions comprise a V region and a J region and the step of sequencing further includes determining a sequence of each of the individual nucleic acid molecules from one or more of its forward sequence reads and at least one reverse sequence read starting from a position in a J region and extending in the direction of its associated V region. In another embodiment, individual molecules comprise nucleic acids selected from the group consisting of complete IgH molecules, incomplete IgH molecules, complete IgK complete, IgK inactive molecules, TCRβ molecules, TCRγ molecules, complete TCRδ molecules, and incomplete TCRδ molecules. In another embodiment, the step of sequencing comprises generating the sequence reads having monotonically decreasing quality scores. Further to the latter embodiment, monotonically decreasing quality scores are such that the sequence reads have error rates no better than the following: 0.2 percent of sequence reads contain at least one error in base positions 1 to 50, 0.2 to 1.0 percent of sequence reads contain at least one error in positions 51-75, 0.5 to 1.5 percent of sequence reads contain at least one error in positions 76-100.

As noted below in the definition of repertoire, different predetermined regions of immunoglobulin or T cell receptor genes can be sequenced. In some embodiments, the full sequence of the variable regions can be sequenced to identify and quantify a clonotype.

A unique subset of the full clonal sequences can be sequenced. In some embodiments, nucleotides comprising the VD and the DJ junctions are sequenced to uniquely identify and quantify a clonotype. In other embodiments, the fragment that can be sequenced is the full variable region. In yet another embodiment, the antigen recognition region or the complementarity determining region 3 (CDR3) is sequenced. A fragment containing the full CDR3 or the full variable region can be amplified to allow the sequencing of the CDR3 comprising parts of the V, D, and J segments.

In one embodiment, only the CDR3 is amplified and sequenced. Amplification and sequencing of the CDR3 can be accomplished by using primers specific to one or more V segment sequences (as well as one or more primer(s) on the other side of the amplicon in the C segment). Primers for each of the V segments can be utilized in one or more amplification reactions leading to the amplification of the full repertoire of sequences. This repertoire of sequences can then be mixed and subjected to separation, with or without amplification, and sequenced using any of the sequencing techniques described. When the amplification with the various V primers is done in separate tubes, the number of molecules carrying the different V segments can be "normalized" due to PCR saturation. For example, if one particular V segment had one or several clonal expansions leading to its representation more than other segments this information may be erased or decreased since the PCR reaction for each segment can be driven to saturation or close to it. Real time PCR can be used to quantify how much of each V segment is present. The full CDR3 can be sequenced, or a subset of the sequence CDR3 can be sequenced.

In one embodiment, only a subset of clonotypes is analyzed. This can be accomplished by amplifying with a primer specific to the subset of clonotypes, for example, a primer that is specific to the V segment. Unique clonotypes can be identified by sequencing with long contiguous reads that provide full connectivity. In some embodiments, when several sequences of interest are present, a short read length across only one of the junctions can generate degenerate tags that are not unique to a specific clonotype but are shared among multiple clonotypes. For example sequencing across die V/J junction can lump all the sequences with the same V/J irrespective of the D segment as one clonotype. Information on the full connectivity of all segments allows sequences to be distinguished that may share the same V and J segments but are connected to different D segments, for example.

Clonotype Determination from Sequence Data

Figure 4A:
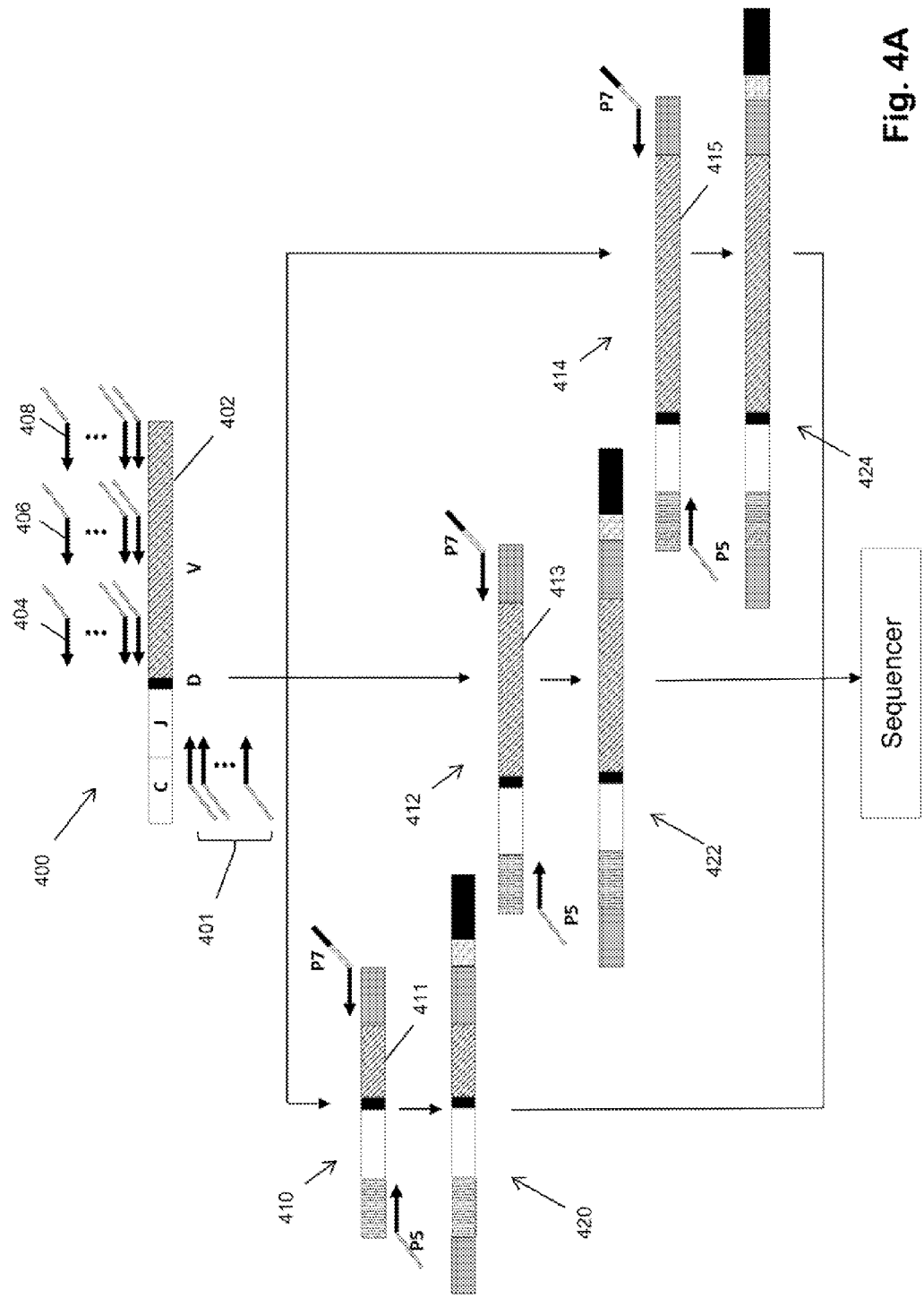
FIG. 4A illustrates a PCR scheme for generating three sequencing templates from an IgH chain in a single reaction.
Figure 4B:
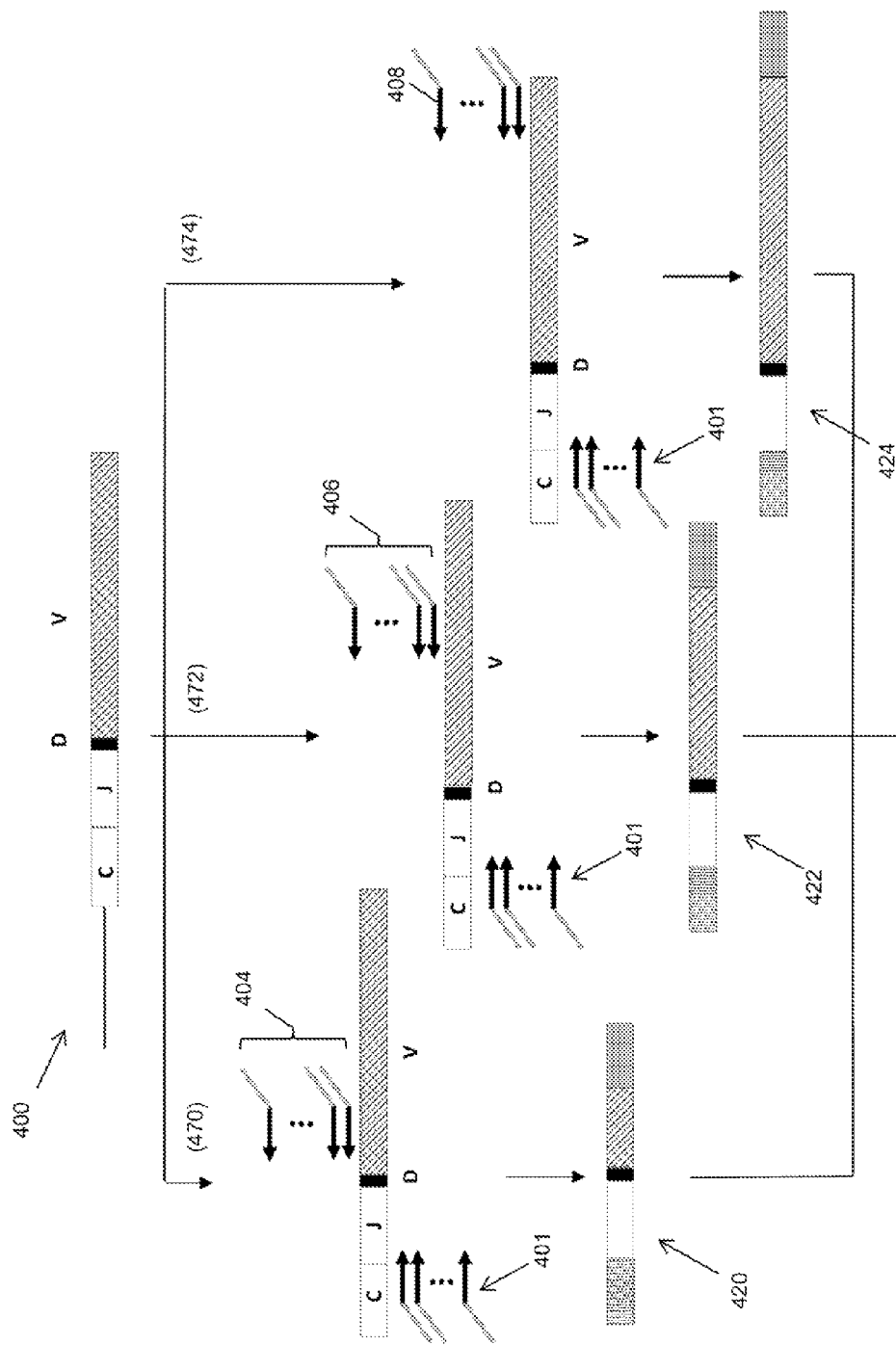

In one aspect of the invention, sequences of clonotypes (including but not limited to those derived from IgH, TCRα, TCRβ, TCRγ, TCRδ, and/or IgLκ (IgK)) may be determined by combining information from one or more sequence reads, for example, along the V(D)J regions of the selected chains. In another aspect, sequences of clonotypes are determined by combining information from a plurality of sequence reads. (As used herein, a "sequence read" is a sequence of data generated by a sequencing technique from which a sequence of nucleotides is determined. Typically, sequence reads are made by extending a primer along a template nucleic acid, e.g. with a DNA polymerase or a DNA ligase. Data is generated by recording signals, such as optical, chemical (e.g. pH change), or electrical signals, associated with such extension.) Such pluralities of sequence reads may include one or more sequence reads along a sense strand (i.e. "forward" sequence reads) and one or more sequence reads along its complementary strand (i.e. "reverse" sequence reads). When multiple sequence reads are generated along the same strand, separate templates are first generated by amplifying sample molecules with primers selected for the different positions of the sequence reads. This concept is illustrated in FIG. 4A where primers (404, 406 and 408) are employed to generate amplicons (410, 412, and 414, respectively) in a single reaction. Such amplifications may be carried out in the same reaction or in separate reactions. In one aspect, whenever PCR is employed, separate amplification reactions are used for generating the separate templates which, in turn, are combined and used to generate multiple sequence reads along the same strand. This latter approach is preferable for avoiding the need to balance primer concentrations (and/or other reaction parameters) to ensure equal amplification of the multiple templates (sometimes referred to herein as "balanced amplification" or "unbiased amplification"). The generation of templates in separate reactions is illustrated in FIGS. 4B-4C. There a sample containing IgH (400) is divided into three portions (472, 474, and 476) which are added to separate PCRs using J region primers (401) and V region primers (404, 406, and 408, respectively) to produce amplicons (420, 422 and 424, respectively). The latter amplicons are then combined (478) in secondary PCR (480) using P5 and P7 primers to prepare the templates (482) for bridge PCR and sequencing on an Illumnina GA sequencer, or like instrument.

Sequence reads of the invention may have a wide variety of lengths, depending in pan on the sequencing technique being employed. For example, for some techniques, several trade-offs may arise in its implementation, for example, (i) the number and lengths of sequence reads per template and (ii) the cost and duration of a sequencing operation. In one embodiment, sequence reads are in the range of from 20 to 400 nucleotides; in another embodiment, sequence reads are in a range of from 30 to 200 nucleotides; in still another embodiment, sequence reads are in the range of from 30 to 120 nucleotides. In one embodiment, 1 to 4 sequence reads are generated for determining the sequence of each clonotype; in another embodiment, 2 to 4 sequence reads are generated for determining the sequence of each clonotype; and in another embodiment, 2 to 3 sequence reads are generated for determining the sequence of each clonotype. In the foregoing embodiments, the numbers given are exclusive of sequence reads used to identify samples from different individuals. The lengths of the various sequence reads used in the embodiments described below may also vary based on the information that is sought to be captured by the read, for example, the starting location and length of a sequence read may be designed to provide the length of an NDN region as well as its nucleotide sequence; thus, sequence reads spanning the entire NDN region are selected. In other aspects, one or more sequence reads encompasses the D and/or NDN regions.

In another aspect of the invention, sequences of clonotypes are determined in pan by aligning sequence reads to one or more V region reference sequences and one or more J region reference sequences, and in part by base determination without alignment to reference sequences, such as in the highly variable NDN region. A variety of alignment algorithms may be applied to the sequence reads and reference sequences. For example, guidance for selecting alignment methods is available in Batzoglou, Briefings in Bioinformatics, 6: 6-22 (2005), which is incorporated by reference. In one aspect, whenever V reads or C reads (described more fully below) are aligned to V and J region reference sequences, a tree search algorithm is employed, e.g. Connen et al, Introduction to Algorithms. Third Edition (The MIT Press, 2009). The codon structures of V and J reference sequences may be used in an alignment process to remove sequencing errors and/or to determine a confidence level in the resulting alignment, as described more fully below. In another aspect, an end of at least one forward read and an end of at least one reverse read overlap in an overlap region (e.g. 308 in FIG. 3B), so that the bases of the reads are in a reverse complementary relationship with one another. Thus, for example, if a forward read in the overlap region is "5'-acgttgc", then a reverse read in a reverse complementary relationship is "5'-gcaacgt" within the same overlap region. In one aspect, bases within such an overlap region are determined, at least in part, from such a reverse complementary relationship. That is, a likelihood of a base call (or a related quality score) in a prospective overlap region is increased if it preserves, or is consistent with, a reverse complementary relationship between the two sequence reads. In one aspect, clonotypes of TCR β and IgH chains (illustrated in FIG. 3B) are determined by at least one sequence read starting in its J region and extending in the direction of its associated V region (referred to herein as a "C read" (304)) and at least one sequence read starting in its V region and extending in the direction of its associated J region (referred to herein as a "V read" (306)). Overlap region (308) may or may not encompass the NDN region (315) as shown in FIG.

3B. Overlap region (308) may be entirely in the J region, entirely in the NDN region, entirely in the V region, or it may encompass a J region-NDN region boundary or a V region-NDN region boundary, or both such boundaries (as illustrated in FIG. 3B). Typically, such sequence reads are generated by extending sequencing primers, e.g. (302) and (310) in FIG. 3B, with a polymerase in a sequencing-by-synthesis reaction, e.g. Metzger, Nature Reviews Genetics, 11: 31-46 (2010); Fuller et al, Nature Biotechnology, 27: 1013-1023 (2009). The binding sites for primers (302) and (310) are predetermined, so that they can provide a starting point or anchoring point for initial alignment and analysis of the sequence reads. In one embodiment, a C read is positioned so that it encompasses the D and/or NDN region of the TCR β or IgH chain and includes a portion of the adjacent V region, e.g. as illustrated in FIGS. 3B and 3C. In one aspect, the overlap of the V read and the C read in the V region is used to align the reads with one another. In other embodiments, such alignment of sequence reads is not necessary, e.g. with TCRβ chains, so that a V read may only be long enough to identify the particular V region of a clonotype. This latter aspect is illustrated in FIG. 3C. Sequence read (330) is used to identify a V region, with or without overlapping another sequence read, and another sequence read (332) traverses the NDN region and is used to determine the sequence thereof. Portion (334) of sequence read (332) that extends into the V region is used to associate the sequence information of sequence read (332) with that of sequence read (330) to determine a clonotype. For some sequencing methods, such as base-by-base approaches like the Solexa sequencing method, sequencing nm time and reagent costs are reduced by minimizing the number of sequencing cycles in an analysis. Optionally, as illustrated in FIG. 3B, amplicon (300) is produced with sample tag (312) to distinguish between clonotypes originating from different biological samples, e.g. different patients. Sample tag (312) may be identified by annealing a primer to primer binding region (316) and extending it (314) to produce a sequence read across tag (312), from which sample tag (312) is decoded.

The IgH chain is more challenging to analyze than TCRβ chain because of at least two factors: i) the presence of somatic mutations makes the mapping or alignment more difficult, and ii) the NDN region is larger so that it is often not possible to map a portion of the V segment to the C read. In one aspect of the invention, this problem is overcome by using a plurality of primer sets for generating V reads, which are located at different locations along the V region, preferably so that the primer binding sites are nonoverlapping and spaced apart, and with at least one primer binding site adjacent to the NDN region, e.g. in one embodiment from 5 to 50 bases from the V-NDN junction, or in another embodiment from 10 to 50 bases from the V-NDN junction. The redundancy of a plurality of primer sets minimizes the risk of failing to detect a clonotype due to a failure of one or two primers having binding sites affected by somatic mutations. In addition, the presence of at least one primer binding site adjacent to the NDN region makes it more likely that a V read will overlap with the C read and hence effectively extend the length of the C read. This allows for the generation of a continuous sequence that spans all sizes of NDN regions and that can also map substantially the entire V and J regions on both sides of the NDN region. Embodiments for carrying out such a scheme are illustrated in FIGS. 4A and 4D. In FIG. 4A, a sample comprising IgH chains (400) are sequenced by generating a plurality amplicons for each chain by amplifying the chains with a single set of J region primers (401) and a plurality (three shown) of sets of V region (402) primers (404, 406, 408) to produce a plurality of nested amplicons (e.g., 410, 412, 416) all comprising the same NDN region and having different lengths encompassing successively larger portions (411, 413, 415) of V region (402). Members of a nested set may be grouped together after sequencing by noting the identify (or substantial identity) of their respective NDN, J and/or C regions, thereby allowing reconstruction of a longer V(D)J segment than would be the case otherwise for a sequencing platform with limited read length and/or sequence quality. In one embodiment, the plurality of primer sets may be a number in the range of from 2 to 5. In another embodiment the plurality is 2-3; and still another embodiment the plurality is 3. The concentrations and positions of the primers in a plurality may vary widely. Concentrations of the V region primers may or may not be the same. In one embodiment, the primer closest to the NDN region has a higher concentration than the other primers of the plurality, e.g. to insure that amplicons containing the NDN region are represented in the resulting amplicon. One or more primers (e.g. 435 and 437 in FIG. 4B) adjacent to the NDN region (444) may be used to generate one or more sequence reads (e.g. 434 and 436) that overlap the sequence read (442) generated by J region primer (432), thereby improving the quality of base calls in overlap region (440). Sequence reads from the plurality of primers may or may not overlap the adjacent downstream primer binding site and/or adjacent downstream sequence read. In one embodiment, sequence reads proximal to the NDN region (e.g. 436 and 438) may be used to identify the particular V region associated with the clonotype. Such a plurality of primers reduces the likelihood of incomplete or failed amplification in case one of the primer binding sites is hypermutated during immunoglobulin development. It also increases the likelihood that diversity introduced by hypermutation of the V region will be capture in a clonotype sequence. A secondary PCR may be performed to prepare the nested amplicons for sequencing, e.g. by amplifying with the P5 (401) and P7 (404, 406, 408) primers as illustrated to produce amplicons (420, 422, and 424), which may be distributed as single molecules on a solid surface, where they are further amplified by bridge PCR, or like technique.

Base calling in NDN regions (particularly of IgH chains) can be improved by using the codon structure of the flanking J and V regions, as illustrated in FIG. 4C. (As used herein, "codon structure" means the codons of the natural reading frame of segments of TCR or BCR transcripts or genes outside of the NDN regions, e.g. the V region, J region, or the like.) There amplicon (450), which is an enlarged view of the amplicon of FIG. 48, is shown along with the relative positions of C read (442) and adjacent V read (434) above and the codon structures (452 and 454) of V region (430) and J region (446), respectively, below. In accordance with this aspect of the invention, after the codon structures (452 and 454) are identified by conventional alignment to the V and J reference sequences, bases in NDN region (456) are called (or identified) one base at a time moving from J region (446) toward V region (430) and in the opposite direction from V region (430) toward J region (446) using sequence reads (434) and (442). Under normal biological conditions, only the recombined TCR or IgH sequences that have in frame codons from the V region through the NDN region and to the J region are expressed as proteins. That is, of the variants generated somatically the only ones expressed are those whose J region and V region codon frames are in-frame with one another and remain in-frame through the NDN region. (Here the correct frames of the V and J regions are determined from reference sequences). If an out-of-frame sequence is identified based one or more low quality base calls, the corresponding clonotype is flagged for re-evaluation or as a potential disease-related anomaly. If the sequence identified is in-frame and based on high quality base calls, then there is greater confidence that the corresponding clonotype has been correctly called. Accordingly, in one aspect, the invention includes a method of determining V(D)J-based clonotypes from bidirectional sequence reads comprising the steps of: (a) generating at least one J region sequence read that begins in a J region and extends into an NDN region and at least one V region sequence read that begins in the V regions and extends toward the NDN region such that the J region sequence read and the V region sequence read are overlapping in an overlap region, and the J region and the V region each have a codon structure; (b) determining whether the codon structure of the J region extended into the NDN region is in frame with the codon structure of the V region extended toward the NDN region. In a further embodiment, the step of generating includes generating at least one V region sequence read that begins in the V region and extends through the NDN region to the J region, such that the J region sequence read and the V region sequence read are overlapping in an overlap region.

Analyzing Sequence Reads. Coalescing sequence reads into clonotypes. Constructing clonotypes from sequence read data depends in part on the sequencing method used to generate such data, as the different methods have different expected read lengths and data quality. In one approach, a Solexa sequencer is employed to generate sequence read data for analysis. In one embodiment, a sample is obtained that provides at least $0.5$-$1.0 \times 10^6$ lymphocytes to produce at least 1 million template molecules, which after optional amplification may produce a corresponding one million or more clonal populations of template molecules (or clusters). For most high throughput sequencing approaches, including the Solexa approach, such over sampling at the cluster level is desirable so that each template sequence is determined with a large degree of redundancy to increase the accuracy of sequence determination. For Solexa-based implementations, preferably the sequence of each independent template is determined 10 times or more. For other sequencing approaches with different expected read lengths and data quality, different levels of redundancy may be used for comparable accuracy of sequence determination. Those of ordinary skill in the art recognize that the above parameters, e.g. sample size, redundancy, and the like, are design choices related to particular applications.

Reducing a set of reads for a given sample into its distinct clonotypes and recording the number of reads for each clonotype would be a trivial computational problem if sequencing technology was error free. However, in the presence of sequencing errors, each clonotype is surrounded by a 'cloud' of reads with varying numbers of errors with respect to the true clonotype sequence. The higher the number of such errors the smaller the density if the surrounding cloud, i.e. the cloud drops off in density as we move away from the clonotype in sequence space. A variety of algorithms are available for converting sequence reads into clonotypes. In one aspect, coalescing of sequence reads depends on three factors: the number of sequences obtained for each of the two clonotypes of interest; the number of bases at which they differ, and the sequencing quality at the positions at which they are discordant. A likelihood ratio is assessed that is based on the expected error rates and binomial distribution of errors. For example two clonotypes, one with 150 reads and the other with 2 reads with one difference between them in an area of poor sequencing quality will likely be coalesced as they are likely to be generated by sequencing error. On the other hand two clonotypes, one with 100 reads and the other with 50 reads with two differences between them are not coalesced as they are considered to be unlikely to be generated by sequencing error. In one embodiment of the invention, the algorithm described below may be used for determining clonotypes from sequence reads.

This cloud of reads surrounding each clonotype can be modeled using the binomial distribution and a simple model for the probability of a single base error. This latter error model can be inferred from mapping V and J segments or from the clonotype finding algorithm itself, via self-consistency and convergence. A model is constructed for the probability of a given 'cloud' sequence Y with read count C2 and E errors (with respect to sequence X) being part of a true clonotype sequence X with perfect read count C1 under the null model that X is the only true clonotype in this region of sequence space. A decision is made whether or not to coalesce sequence Y into the clonotype X according the parameters C1, C2, and E. For any given C1 and E a max value C2 is pre-calculated for deciding to coalesce the sequence Y. The max values for C2 are chosen so that the probability of failing to coalesce Y under the null hypothesis that Y is part of clonotype X is less than some value P after integrating over all possible sequences Y with error E in the neighborhood of sequence X. The value P is controls the behavior of the algorithm and makes the coalescing more or less permissive.

If a sequence Y is not coalesced into clonotype X because its read count is above the threshold C2 for coalescing into clonotype X then it becomes a candidate for seeding separate clonotypes. The algorithm also makes sure than any other sequences Y2, Y3, etc. which are 'nearer' to this sequence Y (that had been deemed independent of X) are not aggregated into X. This concept of 'nearness' includes both error counts with respect to Y and X and the absolute read count of X and Y. i.e. it is modeled in the same fashion as the above model for the cloud of error sequences around clonotype X. In this way 'cloud' sequences can be properly attributed to their correct clonotype if they happen to be 'near' more than one clonotype.

The algorithm proceeds in a top down fashion by starting with the sequence X with the highest read count. This sequence seeds the first clonotype. Neighboring sequences are either coalesced into this clonotype if their counts are below the precalculated thresholds (see above), or left alone if they are above the threshold or 'closer' to another sequence that was not coalesced. After searching all neighboring sequences within a maximum error count, the process of coalescing reads into clonotype X is finished. Its reads and all reads that have been coalesced into it are accounted for and removed from the list of reads available for making other clonotypes. The next sequence is then moved on to with the highest read count. Neighboring reads are coalesced into this clonotype as above and this process is continued until there are no more sequences with read counts above a given threshold, e.g. until all sequences with more than 1 count have been used as seeds for clonotypes.

In another embodiment of the above algorithm, a further test may be added for determining whether to coalesce a candidate sequence Y into an existing clonotype X, which takes into account quality score of the relevant sequence reads. The average quality score(s) are determined for sequence(s) Y (averaged across all reads with sequence Y) were sequences Y and X differ. If the average score is above a predetermined value then it is more likely that the difference indicates a truly different clonotype that should not be coalesced and if the average score is below such predetermined value then it is more likely that sequence Y is caused by sequencing errors and therefore should be coalesced into X.

Sequence Tree. The above algorithm of coalescing reads into clonotypes is dependent upon having an efficient way of finding all sequences with less than E errors from some input sequence X. This problem is solved using a sequence tree. The implementation of this tree has some unusual features in that the nodes of the tree are not restricted to being single letters of DNA. The nodes can have arbitrarily long sequences. This allows for a more efficient use of computer memory.

All of the reads of a given sample are placed into the sequence tree. Each leaf nodes holds pointers to its associated reads. It corresponds to a unique sequence given by traversing backwards in the tree from the leaf to the root node. The first sequence is placed into a simple tree with one root node and one leaf node that contains the full sequence of the read. Sequences are next added one by one. For each added sequence either a new branch is formed at the last point of common sequence between the read and the existing tree or add the read to an existing leaf node if the tree already contains the sequence.

Having placed all the reads into the tree it is easy to use the tree for the following purposes: 1. Highest read count: Sorting leaf nodes by read count allows us to find the leaf node (i.e. sequence) with the most reads. 2. Finding neighboring leafs: for any sequence all paths through the tree which have less than X errors with respect to this sequence are searchable. A path is started at the root and branch this path into separate paths proceeding along the tree. The current error count of each path as proceeding along the tree is noted. When the error count exceeds the max allowed errors the given path is terminated. In this way large parts of the tree are pruned as early as possible. This is an efficient way of finding all paths (i.e. all leafs) within X errors from any given sequence.

Somatic Hypermutations. In one embodiment. IgH-based clonotypes that have undergone somatic hypermutation are determined as follows. A somatic mutation is defined as a sequenced base that is different from the corresponding base of a reference sequence (of the relevant segment, usually V, J or C) and that is present in a statistically significant number of reads. In one embodiment, C reads may be used to find somatic mutations with respect to the mapped J segment and likewise V reads for the V segment. Only pieces of the C and V reads are used that were either directly mapped to J or V segments or that were inside the clonotype extension up to the NDN boundary. In this way, the NDN region is avoided and the same 'sequence information' is not used for mutation finding that was previously used for clonotype determination (to avoid erroneously classifying as mutations nucleotides that are really just different recombed NDN regions). For each segment type, the mapped segment (major allele) is used as a scaffold and all reads are considered which have mapped to this allele during the read mapping phase. Each position of the reference sequences where at least one read has mapped is analyzed for somatic mutations. In one embodiment, the criteria for accepting a non-reference base as a valid mutation include the following: 1) at least N reads with the given mutation base, 2) at least a given fraction N/M reads (where M is the total number of mapped reads at this base position) and 3) a statistical cut based on the binomial distribution, the average Q score of the N reads at the mutation base as well as the number (M-N) of reads with a non-mutation base. Preferably, the above parameters are selected so that the false discovery rate of mutations per clonotype is less than 1 in 1000, and more preferably, less than 1 in 10000.

Phylogenic Clonotypes (Clans). In some diseases, such as cancers, including lymphoid proliferative disorders, a single lymphocyte progenitor may give rise to many related lymphocyte progeny, each possessing and/or expressing a slightly different TCR or BCR, and therefore a different clonotype, due to on-going somatic hypermutation or to disease-related somatic mutation(s), such as base substitutions, aberrant rearrangements, or the like. Cells producing such clonotypes are referred to herein as phylogenic clones, and a set of such related clones are referred to herein as a "clan." Likewise, clonotypes of phylogenic clones are referred to as phylogenic clonotypes and a set of phylogenic clonotypes may be referred to as a clan of clonotypes. In one aspect, methods of the invention comprise monitoring the frequency of a clan of clonotypes (i.e., the sum of frequencies of the constituent phylogenic clonotypes of the clan), rather than a frequency of an individual clonotype. (The expression "one or more patient-specific clonotypes" encompasses the concept of clans). Phylogenic clonotypes may be identified by one or more measures of relatedness to a parent clonotype. In one embodiment, phylogenic clonotypes may be grouped into the same clan by percent homology, as described more fully below. In another embodiment, phylogenic clonotypes are identified by common usage of V regions. J regions, and/or NDN regions. For example, a clan may be defined by clonotypes having common J and ND regions but different V regions (sometimes referred to as "VH replacement"); or it may be defined by clonotypes having the same V and J regions (identically mutated by base substitutions from their respective reference sequences) but with different NDN regions or it may be defined by a clonotype that has undergone one or more insertions and/or deletions of from 1-10 bases, or from 1-5 bases, or from 1-3 bases, to generate clan members. In another embodiment, clonotypes are assigned to the same clan if they satisfy the following criteria: i) they are mapped to the same V and J reference segments, with the mappings occurring at the same relative positions in the clonotype sequence, and ii) their NDN regions are substantially identical. "Substantial" in reference to clan membership means that some small differences in the NDN region are allowed because somatic mutations may have occurred in this region. Preferably, in one embodiment, to avoid falsely calling a mutation in the NDN region, whether a base substitution is accepted as a cancer-related mutation depends directly on the size of the NDN region of the clan. For example, a method may accept a clonotype as a clan member if it has a one-base difference from clan NDN sequence(s) as a cancer-related mutation if the length of the clan NDN sequence(s) is m nucleotides or greater. e.g. 9 nucleotides or greater, otherwise it is not accepted, or if it has a two-base difference from clan NDN sequence(s) as cancer-related mutations if the length of the clan NDN sequence(s) is n nucleotides or greater, e.g. 20 nucleotides or greater, otherwise it is not accepted, In another embodiment, members of a clan are determined using the following criteria: (a) V read maps to the same V region, (b) C read maps to the same J region, (c) NDN region substantially identical (as described above), and (d) position of NDN region between V-NDN boundary and J-NDN boundary is the same (or equivalently, the number of downstream base additions to D and the number of upstream base additions to D are the same). As used herein, the term "C read" may refer to a read generated from a sequencing primer that anneals either to a C region (in the case of using an RNA sample) or to a J region (in the case of using a DNA sample). As explained elsewhere, this is because a C region is joined with a J region in a post-transcriptional splicing process.

Phylogenic clonotypes of a single sample may be grouped into clans and clans from successive samples acquired at different times may be compared with one another. In particular, in one aspect of the invention, clans containing clonotypes correlated with a disease, such as a lymphoid neoplasm, are identified among clonotypes determined from each samples at each time point. The set (or clan) of correlating clonotypes from each time point is compared with that of the immediately previous sample to determine disease status by, for example, determining in successive clans whether a frequency of a particular clonotype increases or decreases, whether a new correlating clonotype appears that is known from population studies or databases to be correlating, or the like. A determined status could be continued remission, incipient relapse, evidence of further clonal evolution, or the like.

Isotype usage. In a further aspect, the invention provides clonotype profiles that include isotype usage information. Whenever IgH- or TCRβ-based clonotypes are determined from RNA, post-transcriptional splicing joins C regions to J regions, as illustrated in FIG. 3B. In one aspect, sequencing primers used to generate C reads (e.g. 304) are anneal to a predetermined primer binding site (302) in C region (307) at the junction with J region (309). If primer binding site (302) is selected so that C read (304) includes a portion (305) of C region (307), then the identity of C region (307) may be determined which, in turn, permits the isotype of the synthesized BCR to be determined. In one embodiment, primer binding site (302) is selected so that C read (304) includes at least six nucleotides of C region (307); in another embodiment, primer binding site (302) is selected so that C read (304) includes at least 8 nucleotides of C region (307). Each clonotype determined in accordance with this embodiment includes sequence information from portion (305) of its corresponding C region and from such sequence information its corresponding isotype is determined. In one aspect of the invention, correlating clonotypes may have a first isotype at the time they are initially determined, but may switch to another type of isotype during the time they are being monitored. This embodiment is capable of detecting such switches by noting previously unrecorded clonotypes that have identical sequences to the correlating clonotypes, except for the sequence of portion (305) which corresponds to a different isotype.

It is expected that PCR error is concentrated in some bases that were mutated in the early cycles of PCR. Sequencing error is expected to be distributed in many bases even though it is totally random as the error is likely to have some systematic biases. It is assumed that some bases will have sequencing error at a higher rate, say 5% (5 fold the average). Given these assumptions, sequencing error becomes the dominant type of error. Distinguish PCR errors from the occurrence of highly related clonotypes will play a role in analysis. Given the biological significance to determining that there are two or more highly related clonotypes, a conservative approach to making such calls is taken. The detection of enough of the minor clonotypes so as to be sure with high confidence (say 99.9%) that there are more than one clonotype is considered. For example of clonotypes that are present at 100 copies/1,000,000, the minor variant is detected 14 or more times for it to be designated as an independent clonotype. Similarly, for clonotypes present at 1,000 copies/1,000,000 the minor variant can be detected 74 or more times to be designated as an independent clonotype. This algorithm can be enhanced by using the base quality score that is obtained with each sequenced base. If the relationship between quality score and error rate is validated above, then instead of employing the conservative 5% error rate for all bases, the quality score can be used to decide the number of reads that need to be present to call an independent clonotype. The median quality score of the specific base in all the reads can be used, or more rigorously, the likelihood of being an error can be computed given the quality score of the specific base in each read, and then the probabilities can be combined (assuming independence) to estimate the likely number of sequencing error for that base. As a result, there are different thresholds of rejecting the sequencing error hypothesis for different bases with different quality scores. For example for a clonotype present at 1,000 copies per 1,000,000 the minor variant is designated independent when it is detected 22 and 74 times if the probability of error were 0.01 and 0.05, respectively.

III. Correlating Clonotypes and Medical Algorithms

The invention provides methods for identifying clonotypes whose presence, absence and/or level is correlated to a disease state and for using such information to make diagnostic or prognostic decisions. In one aspect, information from clonotype profiles, which may be coupled with other medical information, such as expression levels of non-TCR or non-BCR genes, physiological condition, or the like, is presented to patients or healthcare providers in the context of an algorithm; that is, a set of one or more steps in which results of tests and/or examinations are assessed and (i) either a course of action is determined or a decision as to health or disease status is made or (ii) a series of decisions are made in accordance with a flow chart, or like decision-making structure, that leads to a course of action, or a decision as to health or disease status. Algorithms of the invention may vary widely in format. For example, an algorithm may simply suggest that a patient should be treated with a drug, if a certain clonotype, or subset of clonotypes, exceeds a predetermined ratio in a clonotype profile, or increases in proportion at more than a predetermined rate between monitoring measurements. Even more simply, an algorithm may merely indicate that a positive correlation exist between a disease status and a level of one or more clonotypes and/or a function of TCRs or BCRs encoded by one or more clonotypes. More complex algorithms may include patient physiological information in addition to information from one or more clonotype profiles. For example, in complex disorders, such as some autoimmune disorders, clonotype profile information may be combined in an algorithm with other patient data such as prior course of treatment, presence, absence or intensity of symptoms, e.g. rash, joint inflammation, expression of particular genes, or the like. In one aspect of the invention, an algorithm for use with monitoring lymphoid disorders provides a predetermined fractional value above which the proportion of a clonotype (and/or evolutionarily related clonotypes) in a clonotype profile of a sample (such as a blood sample) indicates a relapse of disease or a resistance to a treatment. Such algorithms may consist of or include conventional measures of TCR or BCR clonality. In another aspect, an algorithm for use with monitoring autoimmune disorders provides one or more predetermined fractional values above which a proportion of clonotypes in a clonotype profile encoding TCRs or BCRs specific for one or more predetermined antigens, respectively, indicates the onset of an autoimmune flare-up.

A. Correlating Versus Non-correlating Clonotypes

The methods of the present invention provide means for distinguishing a) correlating clonotypes (which can be those clonotypes whose level correlate with disease) from b) non-correlating clonotypes (which can be those clonotypes whose levels do not correlate with disease). In one embodiment, a correlating clonotype can display either positive or negative correlation with disease. In another embodiment, a clonotype present at a peak state of a disease but not present at a non-peak state of a disease can be a correlating clonotype (positive correlation with disease). In another embodiment, a clonotype that is more abundant (i.e. is present at a higher level of molecules) in a peak state (or stage) of a disease than at a non-peak state of the disease can be a correlating clonotype (positive correlation with the disease). In another embodiment, a clonotype absent at a peak state of a disease but present during a non-peak state of the disease can be a correlating clonotype (negative correlation with disease). In another embodiment, a clonotype that is less abundant at a peak state of a disease than at a non-peak state of a disease can be a correlating clonotype (negative correlation with disease). In another embodiment, a correlating clonotype for an individual is determined by an algorithm.

B. Discovering Correlating and Non-correlating Clonotypes Using a Calibration Test without a Population Study.

In one embodiment of the invention, correlating clonotypes are identified by looking at the clonotypes present in some sample that has relevance to a disease state. This sample could be blood from a sample at a peak state of disease (e.g. a blood sample from an MS or lupus patient during an acute flare), or it could be from a disease-affected, or disease-related, tissue, that is enriched for T and B cells involved in the disease for that individual, such as an inflammation or tumor. Examples of these tissues could be kidney biopsies of lupus patients with kidney inflammations, cerebral spinal fluid (CSF) in MS patients during a flare, synovial fluid for rheumatoid arthritis patients, or tumor samples from cancer patients. In all of these examples, it is likely that the tissues will contain relevant T and B cells that are related to the disease (though not necessarily the causative agents). It is notable that if this method is used to identify the clonotypes that are relevant to disease, they will only be relevant to the individual in whose sample they were detected. As a result, a specific calibration test is needed in order to use this method to identify correlating clonotypes in any given individual with a disease. That is, in one aspect, correlating clonotypes are discovered or determined by generating a clonotype profile from a sample taken from a tissue directly affected by, or relevant to, a disease (sometimes referred to herein as a "disease-related tissue"). In a further aspect, such determination further includes generating a clonotype profile from a sample taken from a tissue not affected by, or relevant to, a disease (sometimes referred to herein as a "non-disease-related tissue"), then comparing the former and latter clonotype profiles to identify correlating clonotypes as those that are at a high level, low level or that are functionally distinct, e.g. encode TCRs or BCRs specific for a particular antigen. In one aspect, such determination is made by identifying clonotypes present in a clonotype profile from an affected, or disease-related, tissue at a higher frequency than the same clonotypes in a clonotype profile of non-affected, or non-disease-related, tissue.

In one embodiment, a method for determining one or more correlating clonotypes in a subject is provided. The method can include steps for a) generating one or more clonotype profiles by nucleic acid sequencing individual, spatially isolated molecules from at least one sample from the subject, wherein the at least one sample is related to a first state of the disease, and b) determining one or more correlating clonotypes in the subject based on the one or more clonotype profiles.

In one embodiment, at least one sample is from a tissue affected by the disease. In another embodiment, said determination of one or more correlating clonotypes comprises comparing clonotype profiles from at least two samples. In another embodiment, the first state of the disease is a peak state of the disease. In another embodiment, one or more correlating clonotypes are present in the peak state of the disease. In another embodiment, the one or more correlating clonotypes are absent in the peak state of the disease. In another embodiment, one or more correlating clonotypes are high in the peak state of the disease. In another embodiment, one or more correlating clonotypes are low in the peak state of the disease. In another embodiment, the sample comprises T-cells and/or B-cells. In another embodiment, the T-cells and/or B-cells comprise a subset of T-cells and/or B-cells. In another embodiment, the subset of T-cells and/or B-cells are enriched by interaction with a marker. In another embodiment, the marker is a cell surface marker on the subset of T-cells and/or B-cells. In another embodiment, the subset of T-cells and/or B-cells interacts with an antigen specifically present in the disease. For example, in the case of lymphoproliferative disorders, such as lymphomas, a calibrating sample may be obtained from lymphoid tissues, from lesions caused by the disorder. e.g. metastatic lesions, or from tissues indirectly affected by the disorder by enrichment as suggested above. For lymphoid neoplasms there is widely available guidance and commercially available kits for immunophenotyping and enriching disease-related lymphocytes, e.g. "U.S.-Canadian consensus recommendations on the immunophenotypic analysis of haematologic neoplasia by flow cytometry," Cytometry, 30: 214-263 (1997); Multi-Mix™ Antibody Panels for Immunophenotyping Leukemia and Lymphoma by Flow Cytometry (Dako. Denmark); and the like. Lymphoid tissues include lymph nodes, spleen, tonsils, adenoids, thymus, and the like.

In one embodiment, the disease is an autoimmune disease. In another embodiment, the autoimmune disease is systemic lupus erythematosus, multiple sclerosis, rheumatoid arthritis, or Ankylosing Spondylitis.

In some embodiments, the correlating clonotypes are identified by looking at the clonotypes present in some sample that has relevance to a state other than a disease state. These states could include exposure to non-disease causing antigens, such as sub-symptomatic allergic reactions to local pollens. Such an embodiment could be used to identify whether an individual had recently returned to a geography which contained the antigen. The states could include exposure to an antigen related to an industrial process or the manufacture or production of bioterrorism agents.

C. Discovering Correlating and Non-correlating Clonotypes Using a Population Study.

In one embodiment, a method is provided for identifying correlating clonotypes using a population study. The utility of the population study is that it allows the specific information about correlating clonotypes that have been ascertained in individuals with known disease state outcomes to be generalized to allow such correlating clonotypes to be identified in all future subjects without the need for a calibration test. Knowledge of a specific set of correlating clonotypes can be used to extract rules about the likely attributes (parameters) of clonotypes that will correlate in future subjects. Such embodiment is implemented with the following steps: (a) generating clonotype profiles for each of a set of samples from tissues affected by, or relevant to, a disease; (b) determining clonotypes that are at a high level or low level relative to the same clonotypes in samples from non-affected tissues or that are functionally distinct from clonotypes in samples from non-affected tissues. As used herein, in one aspect, "functionally distinct" in reference to clonotypes means that TCRs or BCRs encoded by one are specific for a different antigen, protein or complex than the other. Optionally, the above embodiment may further include a step of developing an algorithm for predicting correlating clonotypes in any sample from the sequence information of the clonotypes determined in above steps (a) and/or (b) or from the functional data, i.e. a determination that the newly measured clonotypes encode TCRs or BCRs specific for an antigen, protein or complex specific for the disease under observation.

In connection with the above, one or more patient-specific clonotypes may be identified by matching clonotypes determined in one or more initial measurements ("determined clonotypes") with clonotypes known to be correlated with said disease, which may be available through a population study, database, or the like. In one aspect, matching such clonotypes comprises finding identity between an amino acid sequence encoded by the determined clonotype and that of an amino acid sequence encoded by a clonotype known to be correlated to the disease, or a substantially identical variant the latter clonotype. As used herein, "substantially identical variant", in one aspect, means the sequences being compared or matched are at least 80 percent identical, or at least 90 percent identical, whether nucleic acid sequence or amino acid sequence. In another aspect, substantially identical variant means differing by 5 or less base or amino acid additions, deletions and/or substitutions. In another aspect, matching such clonotypes comprises finding identity between the determined clonotype and a nucleic acid sequence of a clonotype known to be correlated to the disease, or a substantially identical variant of the latter clonotype. In still another aspect, matching such clonotypes comprises finding identity between the determined clonotype and a nucleic acid sequence of a clonotype known to be correlated to the disease, or a substantially identical variant of the latter clonotype.

In one embodiment, the provided invention encompasses methods that include identifying correlating and non-correlating clonotypes by sequencing the immune cell repertoire in a study of samples from patients with disease(s) and optionally healthy controls at different times and, in the case of the patients with a disease, at different (and known) states of the disease course characterized by clinical data. The disease can be, for example, an autoimmune disease. The clonotypes whose level is correlated with measures of disease in these different states can be used to develop an algorithm that predicts the identity of a larger set of sequences that will correlate with disease as distinct from those that will not correlate with disease in all individuals. Unlike the case of the calibration test, correlating sequences need not have been present in the discovery study but can be predicted based on these sequences. For example, a correlating sequence can be TCR gene DNA sequence that encodes the same amino acid sequence as the DNA sequence of a clonotype identified in the discovery study. Furthermore, the algorithm that can predict one or more correlating clonotypes can be used to identify clonotypes in a sample from any individual and is in no way unique to a given individual, thus allowing the correlating clonotypes to be predicted in a novel sample without prior knowledge of the clonotypes present in that individual.

In one aspect, a method for developing an algorithm that predicts one or more correlating clonotypes in any sample from a subject with a disease is provided comprising: a) generating a plurality of clonotype profiles from a set of samples, wherein the samples are relevant to the disease, b) identifying one or more correlating clonotypes from the set of samples, c) using sequence parameters and/or functional data from one or more correlating clonotypes identified in b) to develop an algorithm that can predict correlating clonotypes in any sample from a subject with the disease.

In one embodiment, the set of samples are taken from one or more tissues affected by the disease.

In another embodiment, the identifying one or more correlating clonotypes comprises comparing clonotype profiles from at least two samples. In another embodiment, the functional data include binding ability of markers in T-cell and/or B-cells or interaction with antigen by a T-cell or B cell. In another embodiment, said sequence parameters comprise nucleic acid sequence and predicted amino acid sequence. In another embodiment, the samples are from one or more individuals at a peak stage of the disease. In another embodiment, said one or more correlating clonotypes are present in the peak state of the disease. In another embodiment, said one or more correlating clonotypes are at a high level in the peak state of the disease. In another embodiment, one or more correlating clonotypes are at a low level in the peak state of the disease. In another embodiment one or more correlating clonotypes are absent at the peak state of the disease.

In one embodiment, the disease is an autoimmune disease. In another embodiment, the autoimmune disease is systemic hupus erythematosus, multiple sclerosis, rheumatoid arthritis, or Ankylosing Spondylitis.

In another aspect, a method for discovering one or more correlating clonotypes for an individual is provided, comprising a) inputting a clonotype profile from a sample from the individual into an algorithm, and b) using the algorithm to determine one or more correlating clonotypes for the individual. The algorithm can be an algorithm developed by: a) generating a plurality of clonotype profiles from a set of samples, wherein the samples are relevant to the disease, b) identifying one or more correlating clonotypes from the set of samples, and c) using sequence parameters and/or functional data from one or more correlating clonotypes identified in b) to develop the algorithm that can predict correlating clonotypes in any sample from a subject with the disease.

In some embodiments, the correlating clonotypes are identified clonotypes present in populations that have been exposed to an antigen which has relevance to a state other than a disease state. This state could include exposure to non-disease causing antigens, such as sub-symptomatic allergic reactions to local pollens. Such an embodiment could be used to identify whether an individual had recently traveled to a geography which contained the antigen. The states could include exposure to an antigen related to an industrial process or the manufacture or production of bioterrorism agents.

D. Discovering Correlating and Non-correlating Clonotypes Using a Calibration Test Combined with a Population Study.

In one embodiment of the invention the correlating clonotypes are identified by using a calibration test combined with a population study. In this embodiment the population study does not result in an algorithm that allows clonotypes to be predicted in any sample but rather it allows an algorithm to be developed to predict correlating clonotypes in any sample from a subject for whom a particular calibration clonotype profile has been generated. An example of this could be the development of an algorithm that would predict the correlating clonotypes in a lupus patient based on the clonotype profile measured from a blood sample at any stage of disease after having first having had a blood test taken during a clinical flare state that was used to calibrate the algorithm. Thus, in this embodiment, correlating clonotypes may be identified in steps: (a) generating clonotype profiles from a set of samples from tissues relevant to or affected by a disease to identify a set of clonotypes associated with the disease either by level and/or by function and to identify a relationship between such level and/or function and disease status; (b) measuring a clonotype profile of a sample from a tissue of a first state of the disease; (c) determining a correlating clonotype from the relationship of step (a). In another embodiment, correlating clonotypes may be identified in steps: (a) generating clonotype profiles from a set of samples from tissues relevant to or affected by a disease to identify a set of clonotypes associated with the disease either by level and/or by function and to identify a relationship between such level and/or function and disease status; (b) measuring a calibration clonotype profile in a new subject at a relevant disease stage at a peak stage or from disease affected tissue or at a functionally characterized state; (c) determining a correlating clonotype from the relationship of step (a).

In this embodiment the provided invention encompasses methods for identifying correlating and non-correlating clonotypes by sequencing the immune cell repertoire in a study of samples from patients of disease(s) and optionally healthy controls at different times and, in the case of the patients with a disease, at different (and known) states of the disease course characterized by clinical data. The clonotypes that are found at different frequency (or level) in the first state than in the second state are then used to develop an algorithm that predicts which of the sequences found in the repertoires of each individual at the first disease state will correlate with disease at the later state in each individual as distinct from those that will not correlate with disease in that individual. Unlike the case of the calibration test alone, correlating sequences may be a subset of all the sequences found to be different between disease states. It is also possible that correlating clonotypes are not found in the calibration sample but are predicted based on the algorithm to be correlating if they appear in a future sample. As an example, a clonotype that codes for the same amino acid sequence as a clonotype found in a calibration sample may be predicted to be a correlating clonotype based on the algorithm that results from the population study. Unlike the previous embodiments, the algorithm is developed to predict the correlating clonotypes based on a calibration clonotype profile which is a clonotype profile generated in the individual for whom the correlating clonotypes are to be predicted which at a specific state of disease. In this embodiment the algorithm cannot be used to generate correlating clonotypes in a particular individual until a specific calibration clonotype profile has been measured. After this calibration profile has been measured in a particular subject, all subsequent correlating clonotypes can be predicted based on the measurement of the clonotype profiles in that individual.

In another aspect, a method for discovering one or more correlating clonotypes for an individual is provided, comprising a) inputting a clonotype profile from a sample from the individual into an algorithm, and b) using the algorithm to determine one or more correlating clonotypes for the individual. The algorithms can be ant algorithm developed by: a) generating a plurality of clonotype profiles from a set of samples, wherein the samples are relevant to the disease, b) identifying one or more correlating clonotypes from the set of samples, and c) using sequence parameters and/or functional data from one or more correlating clonotypes identified in b) to develop an algorithm that can predict correlating clonotypes in any sample from a subject with the disease. In one embodiment, the sample is at taken at a peak state of disease. In another embodiment, the sample is taken from disease affected tissue.

In some embodiments, correlating and non-correlating clonotypes using a calibration test combined with a population study is performed for clonotypes present in populations that have been exposed to an antigen which has relevance to a state other than a disease state. This state could include exposure to non-disease causing antigens, such as sub-symptomatic allergic reactions to local pollens. Such an embodiment could be used to identify whether an individual had recently traveled to a geography which contained the antigen. The states could include exposure to an antigen related to an industrial process or the manufacture or production of bioterrorism agents.

E1. Sequence Related Parameters that can be Used to Predict Correlating Clonotypes In order to conduct a population study a training set can be used to understand the characteristics of correlating clonotypes by testing various parameters that can distinguish those correlating clonotypes from those that do not. These parameters include the sequence or the specific V, D, and J segments used. In one embodiment it is shown that specific V segments are more likely to correlate with some diseases as is the case if the clonotypes for a specific disease are likely to recognize related epitopes and hence may have sequence similarity. Other parameters included in further embodiments include the extent of somatic hypermutation identified and the level of a clonotype at the peak of an episode and its level when the disease is relatively inactive. Other parameters that may predict correlating clonotypes include without limitation: 1) sequence motifs including V or J region, a combination VJ, short sequences in DJ region; 2) Sequence length of the clonotype; 3) Level of the clonotype including absolute level (number of clones per million molecules) or rank level; 4) Amino acid and nucleic acid sequence similarity to other clonotypes: the frequency of other highly related clonotypes, including those with silent changes (nucleotide differences that code for same amino acids) or those with conservative amino acid changes; 5) For the BCRs the level of somatic mutations in the clonotype and/or the number of distinct clonotypes that differ by somatic mutations from some germ line clonotypes; 6) clonotypes whose associated proteins have similar 3 dimensional structures.

E2. Databases of Clonotypes Encoding Antibodies Specific for an Antigen

This Correlating clonotypes may encode immunoglobulins or TCRs that are specific for one or more epitopes of one or more antigens. Thus, in one aspect of the invention, correlating clonotypes may be determined by comparing measured clonotypes with entries of a database comprising substantially all possible clonotypes to one or more selected antigens (i.e. an "antigen-specific clonotype database"). Such databases may be constructed by sequencing selected regions of antibody-encoding sequences of lymphocytes that produce antibodies with specificity for the antigens or epitopes of interest, or such databases may be populated by carrying out binding experiments with phage expressing and displaying antibodies or fragments thereof on their surfaces. The latter process is readily carried out as described in Niro et al, Nucleic Acids Research, 38(9): e110 (2010). Briefly, in one aspect, the method comprises the following steps: (a) an antigen of interest, e.g. HCV core protein, is bound to a solid support, (b) a phage-encoded antibody library is exposed to the antigen under antibody-binding conditions so that a fraction of phage-encoded antibodies binds to the bound antigen and another fraction remains free, and (c) collecting and sequencing the phage-encoded antibodies that bind to create entries of a database of correlating clonotypes. The bound phage-encoded antibodies are conveniently sequenced using a high-throughput DNA sequencing technique as described above. In one embodiment, clonotypes of the method encode single chain variable fragments (scFv binding compounds. Antibody-binding conditions of different stringencies may be used. The nucleic acid sequences determined from the bound phage may be tabulated and entered into the appropriate antigen-specific clonotype database.

F. Functional Data to Refine the Determination of Correlating Clonotypes

Further embodiments will make use of functional data to aid in identifying correlating clonotypes. For example, T-cells and/or B-cells containing certain markers that are enriched in cells containing correlating clonotypes can be captured through standard methods like FACS or MACS. In another embodiment the marker is a cell-surface marker. In another embodiment T-cells and/or B-cells reactivity to an antigen relevant to the pathology or to affected tissue would be good evidence of the pathological relevance of a clonotype.

In another embodiment the sequence of the candidate clonotypes can be synthesized and put in the context of the full TCR or BCR and assessed for the relevant reactivity. Alternatively, the amplified fragments of the different sequences can be used as an input to phage, ribosome, or RNA display techniques. These techniques can select for the sequences with the relevant reactivity. The comparison of the sequencing results for those before and after the selection can identify those clones that have the reactivity and hence are likely to be pathological. In another embodiment, the specific display techniques (for example phage, ribosome, or RNA display) can be used in an array format. The individual molecules (or amplifications of these individual molecules) carrying individual sequences from the TCR or BCR (for example CDR3 sequences) can be arrayed either as phages, ribosomes, or RNA. Specific antigens can then be studied to identify the sequence(s) that code for peptides that bind them. Peptides binding antigens relevant to the disease are likely to be pathological.

G. Generating an Immune Load Algorithm

An algorithm can be used to compute an Immune Load, a value or score given by a function of the levels of correlating and non-correlating clonotypes. The Immune Load can be used to make a clinical decision. Using data from an experiment, (e.g., an experiment comprising samples from subjects in a first state of a disease and samples from subjects in a second state of the disease), an algorithm can be developed that combines the information about the levels of the correlating and non-correlating clonotypes into a single score (Immune Load). The parameters of this algorithm can then be adjusted to maximize the correlation between Immune Load and the clinical data. For example, the clinical data can be a clinical measure of disease severity (e.g., the extent of lesions on an MRI for a multiple sclerosis patient). Thus, in one embodiment, an Immune Load may be calculated by the steps: (a) developing an algorithm that uses a set of factors to combine the levels of the correlating clonotypes into a single disease activity score; (b) comparing the score generated in step (a) to the clinical data about disease state; and (c) optimizing the factors in order to maximize the correlation between the clinical data and the disease activity score.

The correlating clonotypes used in generating an Immune Load algorithm can be generated using a calibration test, a population study, or a calibration test and a population study as described above.

Some of the factors that can be considered in combining the correlating clonotypes are the number of correlating clonotypes, their level, their rate of change (velocity), and the rate of change in the velocity (acceleration). Other factors to be assessed include the level of the clonotypes at the episode peak and at the inactive disease state.

In one embodiment, the Immune Load generated relates to an autoimmune disease. Such a Load can be referred to as an AutoImm Load.

In one aspect, a method for generating an algorithm that calculates a disease activity score is provided, comprising: a) developing an algorithm that uses a set of factors to combine levels of correlating clonotypes into a disease activity score, b) comparing the disease activity score to clinical data regarding the disease state, and c) optimizing the factors in order to maximize the correlation between clinical data and the disease activity score.

H. Monitoring Disease Using the Load Algorithm

1. Monitoring Disease without a Calibration Test

In one embodiment of the invention the clonotypes and the Immune Load algorithm are determined using a population study. Immune Load can be used directly without having to first calibrate the individual patient. This test can be done when the patient is in any disease state. This test can be used to generate specific correlating and non-correlating clonotypes based on the algorithm developed above. Immune Load can then be calculated using the second algorithm generated in a population study. This score can then be used clinically. In one embodiment, a monitoring test may be carried out without using a calibration test by the following steps: (a) measuring the clonotypes of a patient at the time at which the patient is to be monitored; and (b) using the correlating clonotypes predicted by the discovery algorithm test and the data from the monitoring test to generate a score reflective of the disease state of the patient using the monitoring algorithm.

In another aspect, a method for monitoring the disease state of an individual is provided comprising: a) determining a clonotype profile from a sample from a subject, b) inputting the clonotype profile information from a) into an algorithm, and c) using the algorithm to generate a score predictive of the disease state of the individual. The algorithm can be an algorithm generated by a) developing an algorithm that uses a set of factors to combine levels of correlating clonotypes into a disease activity score, b) comparing the disease activity score to clinical data regarding the disease state, and c) optimizing the factors in order to maximize the correlation between clinical data and the disease activity score.

2. Monitoring Disease Using a Calibration Test

In one embodiment of the provided invention the correlating clonotypes and the Immune Load algorithm are determined using a calibration test or calibration test and a population study. Immune Load can be used in the clinic by first conducting a calibration test. This test can be done when the patient is in a state which is similar to the first state used in the study that generated the correlating and non-correlating clonotypes that are used in the Immune Load algorithm. For example, this state can be a flare state of an autoimmune disease if this is how the Immune Load algorithm was derived. This calibration test can then be used to generate the specific correlating and non-correlating clonotypes to be used in the subsequent disease monitoring tests. At a later point in the treatment of this patient, another test is done on the patient and Immune Load can be calculated using the algorithm generated in the discovery study, and the list of clonotype levels generated in this patient's specific calibration test. This Immune Load score can then be used clinically. In one embodiment, a monitoring test using a calibration test comprises the following steps: (a) testing a patient in disease state 1 in order to determine a clonotype profile; (b) measuring clonotypes of a patient at a later time (the time at which the patient is to be monitored); (c) using the monitoring algorithm to generate a disease score reflective of a disease state from the clonotype profile from disease state 1 from the calibration test and information from a later time test.

In another aspect, a method for monitoring the disease state of an individual is provided comprising: a) determining a clonotype profile from a sample from a subject, b) inputting the clonotype profile information from a) into an algorithm, and c) using the algorithm to generate a score predictive of the disease state of the individual. The algorithm can be an algorithm generated a) developing an algorithm that uses a set of factors to combine levels of correlating clonotypes into a disease activity score, b) comparing the disease activity score to clinical data regarding the disease state, and c) optimizing the factors in order to maximize the correlation between clinical data and the disease activity score. In another embodiment the method can further comprise determining one or more correlating clonotypes in the individual by any of the methods of the provided invention, and inputting information the one or more correlating clonotypes into the algorithm.

In one embodiment, the disease is an autoimmune disease. In another embodiment, the autoimmune disease is systemic lupus crythematosus, multiple sclerosis, rheumatoid arthritis, or Ankylosing Spondylitis.

3. Other Factors Related to the Use of Immune Load

The same Immune Load may mean different things for different patients. For one, the full clinical picture of a patient needs to be considered. From a testing perspective, one may consider the velocity (rate of change of Immune Load over time) and acceleration (rate of change of velocity over time) in addition to the level of Immune Load in making clinical decisions. For example if the AutoImm Load score is increasing (high velocity) it may be predictive of an incipient flare in an autoimmune disease.

Additional tests that can be integrated in the Load score, for example, an AutoImm Load score, include, for example, erythrocyte sedimentation rate (ESR), C-reactive protein (CRP) levels, Anti-ds DNA, other autoantibody titers, complement levels, urine protein levels. Urine protein/creatinine ratio, creatinine levels, blood urea nitrogen (BUN) levels, platelet levels, WBC counts, hematorcrit (Hct), Hb, urinalysis results. Other tests that are related to SLE that can be integrated include, for example, CD27 level, CD27++ cell level, INF-responsive genes (Baechler, E C et al. (2003) *Proc. Natl. Acad. Sci.* 100: 2610-2615), and chemokine score (Bauer J W et al. (2009) *Arthritis Rheum.* 60:3098-3107). Other tests not related to lupus include, for example, thyroid-stimulating hormone (TSH) test, triiodothyronine (T3) test, thyroxine (T4) test, liver function tests (LFTs), other autoantibodies, calprotectin test, lactoferrin test, and synovial fluid analysis. The additional tests can include imaging test, including, for example, MRI, CT-scan, X-ray, and ultrasound.

I. The Use of Sequencing Technologies in Combination with Partial Cell Enrichments as Pan of a Calibration Step to Find Correlating Clonotypes.

Several technologies exist which can be used to separate cells in blood or tissue based on cell markers. These include solid phase separations such as beads or columns on which specific affinity reagents are immobilized such as antibodies. Liquid phase separation can be achieved using such techniques as flow cytometry in which labeled reagents that specifically bind selected cell markers are used to direct a gated flow device in which specific fluorescent markers can be used to separate cells so labeled. Leukopheresis is another liquid phase separation technique that may be used to enrich leukocyte populations from the blood, e.g. Shelat, Am. J. Med. 123: 777-784 (2010); U.S. Pat. No. 5,846,928; or the like, alter which further enrichment may be carried out by way of cell surface markers.

It will sometimes be advantageous to profile a subset of T and/or B cells when calibrating an algorithm to predict correlating clonotypes and/or to measure the levels of these clonotypes in order to measure a disease load. This can be done using the methods described above for a variety of surface or internal markers. One challenge of using such methods lies in the fact that the selectivity for a given marker is never perfect for a given marker. As a result enrichment is unlikely to lead to a pure population of the selected cells. Another method to achieve enrichment of cell subsets without the separation of cells is to selectively grow the subset of cells of interest. For example, T cells can be activated with antigen in vitro, and the activated cells can be allowed to divide and increase in number leading to their enrichment.

In one embodiment of this invention, clonotype profiles of T and/or B cell populations are generated by sequencing individual, spatially isolated molecules, both before and after enrichment for at least one cell marker. The two profiles are then compared to determine which clonotypes have significantly altered frequencies between the enriched and un-enriched cell populations in order to identify clonotypes that are associated with cells carrying the markers selected for in the enrichment. The advantage of using the sequencing method in accomplishing this identification is that clonotypes can be identified even if the enrichment as relatively poor as clonotype frequencies can be very well measured with sufficient sequencing depth. This in turn will allow a variety of enrichment methodologies to be used routinely and inexpensively as expensive multiple enrichments designed to achieve purity will not be necessary.

In one embodiment, such sequencing of T and B cell receptors before and after cell enrichment could be used as part of a calibration algorithm in order to determine which clonotypes are correlating. In this embodiment, cells are sequenced before and after enrichment for markers that are relevant to disease at a first disease state. Examples of this first disease state could be: blood samples at a peak state of the disease, affected tissue samples, affected tissue samples at a peak state of disease, etc. Clonotypes from the cell fraction that does and does not contain the cell marker are thus obtained and can be used as inputs into an algorithm that is then used to determine correlating clonotypes in that individual.

In another embodiment, the enrichment is not only done on a sample collected during a first disease state but in subsequent samples from the same individual. In this way, the correlating clonotypes are determined within sub fractions of the cells at any one time.

In another embodiment, cell markers are used in conjugation with sequencing to assess not only the frequency of specific relevant clonotypes but also their functional status. In this embodiment the cell markers provide information beyond the identity of the correlating clonotypes as they refine the prediction of disease status obtained by the frequency of the correlating clonotypes. By sequencing before and after enrichment with specific markers, the frequency of a specific clonotype is determined. In addition the frequency and fraction of the cells containing this specific clonotype along with anther cell marker is determined. Consider, two patients with the same frequency of clonotypes relevant to some clinical state but different frequency of particular cell markers (e.g., activation markers) in the cells containing these clonotypes. These patients may have different disease activity in spite of having the same frequency of the relevant clonotypes.

Cell markers can be markers of cell activation. In general markers can be determined by measuring the expression of genes using a population of T and/or B cells that are known to correlate with disease. These markers could be cell surface markers or cells expressed within the cell.

In one embodiment of this invention, the cells that are shown to have affinity for an antigen known to be relevant to a particular disease are enriched. There are several methods for doing this.

In another embodiment, cells of interest are B cells that interact with specific antigen. In this case, B cells will exist that have B-cell receptor sequences that bind this specific antigen. These B cell receptors can thus be used as cell surface markers that can be enriched using antigen specific reagents. In one embodiment, beads or columns on which the antigen is immobilized can be used to enrich for cells expressing B-cell receptors specific to this antigen. In another embodiment, the antigen is rendered multimeric, for example tetrameric, in order to increase the affinity of the cells expressing the appropriate B cell receptors. In another embodiment, these cells can be labeled using a fluorescently labeled antigen reagent. These cells can then be enriched using a flow cytometry method that sorts based on the fluorescent label. This process can be done in combination with other markers of B-cells in the flow cytometry methodology. In another embodiment the fluorescent antigen reagent is rendered multimeric in order to increase the affinity of the cells expressing the appropriate B cell receptor.

One aspect of this invention is that the strength of the interaction of the different clonotypes with the specific antigen can be defined. The degree of enrichment of a clonotype by the antigen interaction provides a measure of the strength of the interaction. As a result instead of the traditional "titer" level of an antibody, more detailed information can be obtained. Specifically, the frequency of different clonotypes with different avidities can be determined. In one embodiment, the antigen so used in enrichment is a single molecular species. In another embodiment, the antigen is a complex mixture of antigens that are relevant to a disease. The antigen may be a cell type or a mixture of cell types.

In another embodiment, the cells of interest are T cells that interact with a specific antigen in the context of an MHC molecule. In one embodiment, the peptide complexed with the MHC molecules is used to capture the relevant cells. Tetramers of MHC-peptide complex have been previously successfully used for this purpose. In another embodiment, blood or relevant tissue containing cells capable of antigen presentation and T cells is incubated with the antigen to allow peptides to be presented to the T cells. The cells that are activated through binding to these antigens can then be enriched by some feature of activation. Potentially any activation feature can be utilized like cell proliferation, leukocyte migration, cytotoxicity, and/or expression of activation markers. For example activated cells proliferate and they can be allowed to divide and become enriched. Similarly, the activated cells can express some markers that can be used to capture them. These markers can be surface markers or some internal marker like cytokines, such as INFγ, IL-2, or IL-17. Cells expressing surface markers can be readily captured using different techniques such as FACS or beads coated with antibodies against the surface marker. Techniques to capture cells expressing intracellular markers, particularly cytokines have also been developed. One technique is called Intracellular Cytokine Staining. In this method, cytokines specific to the immune process in question are trapped within the T cells which are subsequently permeabilized allowing these specific cytokines to be labeled using fluorescent antibodies. These labeled cells can then be enriched using a flow cytometry method. Another method, cytokine capture, uses hybrid antibodies that have dual specificity. One of the specificities is to some generic marker in all T cells (like MHC molecule) and the other is to the cytokine of interest, e.g., INFγ, IL-2, or Il-17. The generic specificity attaches the antibody on the surface of all T cells, and cytokines released from the T cells is then captured by antibodies attached on the same cells. Fluorescent antibodies against the relevant cytokine can then be used allowing for the capture of the relevant cells using FACS.

One aspect of this invention is that the strength of the interaction of the different clonotypes with the specific antigen can be defined. The degree of enrichment of a clonotype by the antigen interaction provides a measure of the strength of the interaction. Therefore the frequency of different clonotypes with different avidities can be determined.

In one embodiment, the antigen so used in enrichment is a single molecular species. In another embodiment, the antigen is a complex mixture of antigens that are relevant to a disease. The complex mixture of antigens can be a cell type or a mixture of cell types.

J. Antigen Enrichment for the Detection of Recurrence of Latent Infection

It is often of use in infectious disease to not only measure the presence or absence of a pathogen but also to measure and monitor immune response to this pathogen. As a result the measurement of antibodies raised by the immune system against specific pathogen antigens is a methodology in routine clinical practice. Such immune responses to specific pathogen antigen as measured by antibodies do not, however, give a comprehensive view of immune response to the antigen. The antibodies measured, may be the product of many different B cell clones each of which is expressing a slightly different antibody each of which may carry slightly different information about the disease state. Furthermore, T-cell responses to these antigens are not being measured at all.

The immune response of a patient to a pathogenic infection could be very comprehensively profiled using the methods disclosed in this invention. In one embodiment, the B cell response can be comprehensively measured in an individual infected with a pathogen using a B cell enrichment at one point in the disease course to ascertain the B cell clonotypes that are relevant to the antibody response to that infection. In order achieve this, B cells that are involved in an immune response to a pathogen would be identified by performing an enrichment using antigens present in the pathogen in question. These antigens could be a single antigen species, a set of distinct antigen species, or a complex mixture of antigens from the pathogen including the entire cells from the pathogen. Such antigens are then immobilized to a solid surface or fluorescently labeled and enrichment is carried out using either a bead based binding protocol, a column based binding protocol, or a flow cytometry method in the case where the antigens are fluorescently labeled. The cells from the patient are profiled before and after enrichment by separating individual DNA or RNA molecules from the B cell receptor in two dimensions and sequencing individual molecules to form a BCR clonotype profile. Clonotype sequences that show a significant frequency shift between the two clonotype profiles are then candidates to be clonotypes that are responsible for an immune response to the antigen(s). Further algorithms can optionally be developed to refine the prediction of which clonotypes are likely to be relevant to this specific immune response. These algorithms can use sequence parameters such as frequency, sequence length, amino acid sequence similarity, similarity to other similar clonotype sequences including those created by somatic hypermutations, etc.

In a preferred embodiment, the antigen capture is done at one calibration point in time to identify the relevant B cells and not done and subsequent profiling time points in which all B cells are profiled without enrichment.

In another embodiment the T cell response is measured. In order achieve this, T cells that are involved in an immune response to a pathogen would be identified by performing an enrichment using antigens present in the pathogen in question. These antigens could be a single antigen species, a set of distinct antigen species, or a complex mixture of antigens from the pathogen including the entire cells from the pathogen. In one embodiment, tetramers of MHC-antigen complex are used to fluorescently label the T cells. In another embodiment, such antigens are added to the blood of a patient at least a first time point and incubated so as to allow antigenic peptides to be presented by antigen presenting cells of this individual. In both of these embodiments, in individual spatially isolated RNA or DNA molecules from blood samples are then profiled before and after the enrichment for these T cells using either tetramers of the MHC-antigen complex, the internal cytokine staining method or the cytokine capture and FACS sorting. T cell clonotype sequences that show a significant frequency shift between the two clonotype profiles are then candidates to be clonotypes that are responsible for an immune response to the antigen(s). Further algorithms can optionally be developed to refine the prediction of which clonotypes are likely to be relevant to this specific immune response. These algorithms can use sequence parameters such as frequency, sequence length, amino acid sequence similarity, similarity to other similar clonotype sequences, etc.

In a preferred embodiment, the antigen capture is done at one calibration point in time to identify the relevant B cells and not done and subsequent profiling time points in which all B cells are profiled without enrichment.

IV. Determining Disease States

Because the immune system is so central to human health, the ability to measure immune responses has wide applications in medicine. This invention teaches the ability to use the immune system to understand underlying disease state when it is mediated by the immune system. This allows a very powerful set of diagnostic and prognostic applications that use the immune profiles to inform the risks of wide variety of clinical outcomes and allow physicians to intervene more effectively.

A. Utility of Immune Profiling in Autoimmune Disease Treatment

The methods of the provided invention can be used to diagnose and treat autoimmune disease in a subject. Autoimmune disease involves adaptive immune cells escaping the usual process conferring autoimmunity and attacking some target(s) on bodily tissue. Autoimmune diseases include, for example, acute disseminated encephalomyelitis, Addison's disease, ankylosing spondylitis, anti-phospholipid antibody syndrome, autoimmune hemolytic anemia, autoimmune hepatitis, autoimmune inner ear disease. Behçet's disease, bullous pemphigoid, Celiac disease, Chagas disease, Chronic obstructive pulmonary disease, dermatomyositis, diabetes mellitus type 1. Goodpasture's syndrome, Graves' disease, Guillain-Barré syndrome, Hashimoto's thyroditis. Hidradenitis suppurativa. Idiopathic thrombocytopenic purpura, Interstitial cystitis, multiple sclerosis, myasthenia gravis, neuromyotonia, pemphigus vulgaris, pernicious anemia, polymyositis, primary biliary cirrhosis, rheumatoid arthritis, scleroderma, systemic lupus erythematosus, Sjögren's syndrome, and vasculitis syndromes. The stages of these autoimmune diseases can be diagnosed using the methods of the provided invention. Treatments can be suggested to a subject based on the stage of the autoimmune disease.

Clinical information regarding a subject with an autoimmune disease, or suspected of having an autoimmune disease, can be used to determine the disease state (or AutoImm load). Clinical information can be used to identify patterns of a clonotype profile that correlate with a disease state. Clinical information can include, for example, height, weight, eye color, age, gender, ethnic group, blood pressure, LDL cholesterol levels, HDL cholesterol levels, family medical history, and molecular marker information.

Clinical information can include symptoms of one or more autoimmune diseases. For autoimmune hepatitis symptoms can include fatigue, hepatomegaly, jaundice, pruritus, skin rash, arthralgia, abdominal discomfort, spider angiomas, nausea, vomiting, anorexia, dark urine, pale or gray stools. For dermatoymyositis (DM), symptoms can include rash (patchy, bluish-purple discolorations on the face, neck, shoulders, upper chest, elbows, knees, knuckles and back) accompanying or preceding muscle weakness, dysphagia, myalgia, fatigue, weight loss and low-grade fever. For Graves' disease, symptoms can include weight loss due to increased energy expenditure, increased appetite, heart rate and blood pressure, and tremors, nervousness and sweating. For Hashimoto's thyroiditis, symptoms can include mental and physical slowing, greater sensitivity to cold, weight gain, coarsening of the skin, goiter. For mixed connective tissue disease (MCTD)), symptoms can include features of systemic lupus erythematosus (SLE), scleroderma and polymyositis. For Pemphigoid, bullous (BP) symptoms can include mildly pruritic welts to severe blisters and infection, oral or esophageal bullae. For pemphigus, symptoms can include blistering of skin and mucous membranes. For pernicious anemia, symptoms can include shortness of breath, fatigue, pallor, tachycardia, inappetence, diarrhea, tingling and numbness of hands and feet, sore mouth and unsteady gait. For polymyositis (PM), symptoms can include muscle weakness, dysphagia and myalgia. For primary biliary cirrhosis (PBC), symptoms can include fatigue and pruritus. For scleroderma (systemic sclerosis), symptoms can include swelling and puffiness of the fingers or hands, skin thickening, skin ulcers on the fingers, joint stiffness in the hands, pain, sore throat and diarrhea. For Sjögren's syndrome, symptoms can include dryness of the eyes and mouth, swollen neck glands, difficulty swallowing or talking, unusual tastes or smells, thirst and tongue ulcers. For systemic lupus erythematosus (SLE)), symptoms can include fever, weight loss, hair loss, mouth and nose sores, malaise, fatigue, seizures and symptoms of mental illness, joint inflammation similar to RA, butterfly rash on nose and cheeks, extreme sensitivity to cold in the hands and feet. For vasculitis syndromes, e.g., Wegener's granulomatosis, idiopathic crescentic glomerulonephritis (ICGN), microscopic polyarteritis (MPA), pulmonary renal syndrome (PRS), symptoms can include fatigue, weakness, fever, arthralgia, abdominal pain, renal problems and neurological problems. The clinical information can be from one or more subjects at one or more points of time.

The clinical information can include information regarding responses of a subject with an autoimmune disease to one or more treatments the subject has received.

The clinical utility of AutoImm Load is discussed for specific autoimmune diseases below. Another embodiment of this invention contemplates the combination of the immune profiling tests with other markers that are already in use for the detection of disease activity in these diseases to allow tests with greater sensitivity and specificity. Other molecular identifiers or markers can be used in computing the AutoImm Load or for determining the disease state. Molecular identifiers can include nucleic acids, proteins, carbohydrates, and lipids, and expression profiles of nucleic acids or proteins. The molecular identifiers can be of human or non-human origin (e.g., bacterial). The identifiers or markers can be determined by techniques that include, for example, comparative genomic hybridization (CGH), chromosomal microarray analysis (CMA), expression profiling. DNA microarray, high-density oligonucleotide microarray, whole-genome RNA expression array, peptide microarray, enzyme-linked immunosorbent assay (ELISA), genome sequencing, copy number (CNV) analysis, small nucleotide polymorphism (SNP) analysis, immunohistochemistry, in-situ hybridization, fluorescent in-situ hybridization (FISH), PCR, Western blotting, Southern blotting, SDS-PAGE, gel electrophoresis, and Northern blotting.

For systemic lupus erythematosus, markers can include levels of erythrocyte sedimentation rate (ESR). C-reactive protein (CRP) levels. Anti-ds DNA, other autoantibody titers, complement levels, urine protein levels, Urine protein/creatinine ratio, creatinine levels, blood urea nitrogen (BUN) levels, platelet levels, WBC counts, hematocrit (Hct), Hb, and urinalysis results. Other tests that are related for instance to SLE that can be integrated include, for example, CD27 level, CD27++ cell level, INF-responsive genes, and chemokine score.

1. Systemic Lupus Erythematosus (SLE)

The methods of the provided invention can be used to determine states or stages of systemic lupus erythematosus (SLE or lupus). SLE is a serious autoimmune condition that often afflicts young adults (mostly females). It is characterized by inflammatory processes that can affect many organs including the skin, joints, kidneys, lungs, heart, and central nervous system leading to frequent disabilities and sometimes death. The disease follows a very unpredictable course marked by flare periods followed by quiescent periods of remission. Nevertheless, patients diagnosed with SLE are seen regularly by a rheumatologist and treated with a variety of serious medications. These medications include steroids such as Prednisone and other immunosuppressants such as Cellcept (mycophenolate mofetil). While these drugs can reduce organ damage they contain significant side effects including risk of infection and infertility. The unreliability for some of the symptoms (e.g., pain and fatigue) and the unpredictable disease course makes tailoring medication doses difficult, resulting in an overtreatment of some patients and under-treatment of others. As a result, the treatment of SLE poses significant therapeutic challenges to the clinician.

There are a number of standard methods a clinician can use to assess the activity of SLE. The status of the disease can be measured by observing the clinical symptoms of the disease. These methods include assessment of signs (e.g., skin rash) and symptoms (e.g., joint pain and fatigue) as well as lab results (e.g., urine protein/creatinine ratio, anti-ds DNA antibody, and blood counts). These clinical markers, however, can be lagging indicators of disease status and as such patients may respond only after weeks or months of therapy. Furthermore, in some cases symptoms can be difficult to assess with precision (e.g., pain and fatigue). Other markers of inflammation, for example anti-ds DNA antibody, complement level (e.g., C3), C reactive protein (CRP), and erythrocyte sedimentation rate (ESR) usually lack specificity and/or sensitivity. Invasive methods such as kidney biopsy are impractical for routine use. As a result clinicians perform quite a frequent testing of their patients without a perfect measure of the disease status. The clinical symptoms and laboratory assessment are integrated in measures such as Systemic Lupus Erythematosus Disease Activity Index (SLEDAI) and Physician Global Assessment (PGA). These measures are not done routinely in clinical practice and often fall short in several clinical situations.

In one embodiment of the invention clonotypes are identified which represent different immune profiles for different disease states. The disease state is then tracked by comparing the identified immune profile to the patient's current immune profile. The disease can be lupus. The disease states can be flare periods and non-flare periods. This immune profile may be used as an early indicator of a flare state. This may drive treatment decisions.

Specific examples of the utility of AutoImm Load in making therapeutic interventions in SLE are discussed in greater detail in the examples section along with specific enabling studies that determine AutoImm Load.

In one aspect, SLE correlated clonotypes are related to antibodies specific for self antigens. Accordingly, a method of determining a likelihood that an individual has systemic lupus erythematosus comprises the following steps: (a) determining a profile of clonotypes from a sample of B cells of the individual, the sample comprising a repertoire of clonotypes thereof; and (b) comparing clonotypes of the profile with clonotypes of an antigen-specific clonotype database to determine a level of clonotype matches, thereby determining a likelihood of systemic lupus erythematosus, the antigen-specific clonotype database including substantially all clonotypes of human immunoglobulin chains specific for the one or more antigens selected from the group consisting of double stranded DNA, malondialdehyde, 4-hydroxynonenal, superoxide dismutase, nitrotyrosine, cardiolipin, ribosomal P protein, phospholipid, core protein of small nuclear ribonuclear-protein (Smith antigen), histone, UI small nuclear ribonuclearprotein, type I topoisomerase, centromeric proteins, SS-A ribonuclearprotein, SS-B ribonuclearprotein, and histidine-tRNA ligase.

2. Multiple Sclerosis (MS)

The methods of the provided invention can also be used to determine states or stages of Multiple Sclerosis (MS). MS is an autoimmune disease that affects the brain and spinal cord (central nervous system). Symptoms vary, because the location and severity of each attack can be different. Episodes can last for days, weeks, or months. These episodes alternate with periods of reduced or no symptoms (remissions). It is common for the disease to return (relapse). However, the disease may continue to get worse without periods of remission.

Because nerves in any pan of the brain or spinal cord may be damaged, patients with multiple sclerosis can have symptoms in many parts of the body. Muscle symptoms include, for example, loss of balance, numbness or abnormal sensation in any area, pain because of muscle spasms, pain in the arms or legs, problems moving arms or legs, problems walking, problems with coordination and making small movements, slurred or difficult-to-understand speech, tremor in one or more arms or legs, uncontrollable spasm of muscle groups (muscle spasticity), and weakness in one or more arms or legs.

Eye symptoms include, for example, double vision, eye discomfort, uncontrollable rapid eye movements, and vision loss (usually affects one eye at a time).

Other brain and nerve symptoms include, for example, decreased attention span, decreased judgment, decreased memory, depression or feelings of sadness, dizziness and balance problems, facial pain, hearing loss, and fatigue.

Bowel and bladder symptoms include, for example, constipation, difficulty beginning urinating, frequent need to urinate, stool leakage, strong urge to urinate, and urine leakage (incontinence).

There is no known cure for multiple sclerosis at this time. However, there are therapies that may slow the disease. The goal of treatment is to control symptoms and help the patient maintain a normal quality of life.

Medications used to slow the progression of multiple sclerosis can include, for example, immune modulators to help control the immune system, including interferons (Avonex, Betaseron, or Rebif), monoclonal antibodies (Tysabri), glatiramer acetate (Copaxone), mitoxantrone (Novantrone), methotrexate, azathioprine (Imuran), cyclophosphamide (Cytoxan), and natalizumab (Tysabri). Steroids can be used to decrease the severity of attacks.

Medications to control symptoms can include, for example, medicines to reduce muscle spasms such as Lioresal (Baclofen), tizanidine (Zanaflex), or a benzodiazepine, cholinergic medications to reduce urinary problems, antidepressants for mood or behavior symptoms, and amantadine for fatigue.

MS affects women more than men. The disorder most commonly begins between ages 20 and 40, but can be seen at any age. MS is a progressive disease, meaning the nerve damage (neurodegeneration) gets worse over time. How quickly MS gets worse varies from person to person. Inflammation occurs when the body's own immune cells attack the nervous system. Repeated episodes of inflammation can occur along any area of the brain and spinal cord. People with a family history of MS and those who live in a geographical area with a higher incidence rate for MS have a higher risk of the disease.

Symptoms of MS may mimic those of many other nervous system disorders. The disease is diagnosed by ruling out other conditions. People who have a form of MS called relapsing-remitting may have a history of at least two attacks, separated by a period of reduced or no symptoms. The health care provider may suspect MS if there are decreases in the function of two different parts of the central nervous system (such as abnormal reflexes) at two different times. A neurological exam may show reduced nerve function in one area of the body, or spread over many parts of the body.

Tests to diagnose multiple sclerosis include, for example, cerebrospinal fluid tests, including CSF oligoclonal banding, head MRI scan, lumbar puncture (spinal tap), nerve function study (evoked potential test), and spine MRI.

Like other autoimmune diseases, MS follows an unpredictable course with acute flares and periods of remission. There are increasing numbers of therapies, each with side effects that range from serious (weight gain and depression) to life threatening (pancytopenia and PML infections), variable effectiveness in different patients, and high costs. At the same time, the lack of highly accurate and specific routine tests of MS disease activity make the challenge of effectively administering therapy complicated. Clinical episodes can be separated by long time periods (up to years in early stage disease) even without treatment. In addition, available medications reduce the likelihood of relapse but do not completely prevent them. Therefore disease activity is difficult to assess and thus, there is an inadequate short term measure of disease activity that could be used to measure whether a specific therapy is showing efficacy in a given patient by measuring the reduction in number or severity of relapses. The only other test available for monitoring disease activity is brain MRI to track the state of lesions as revealed with the aid of contrast enhancing agents such as gadolinium. However, such imaging offers only an integrated view of brain damage and lacks specificity and time resolution. Attempting to use MRI imaging to follow disease course on time scales shorter than a year is impractical given the costs, the lack of specificity and the dangers of excessive contrast exposure. As a result, patients are often treated at great expense for prolonged periods of time without any effective feedback that would allow the physician to modify dosing and/or switch of add therapies.

In one embodiment of the invention clonotypes are identified which represent different immune profiles for different disease states. The disease state is then tracked by comparing the identified immune profile to the patients current immune profile. The disease can be MS. The disease states can be remission periods and active periods. This immune profile may be used as an early indicator of a remission or non-remission period. This may drive treatment decisions.

3. Rheumatoid Arthritis (RA)

The methods can be used to measure disease status for Rheumatoid arthritis patients. Rheumatoid arthritis (RA) is a chronic, systemic inflammatory disorder that can affect many tissues and organs but principally attacks the joints, producing an inflammatory synovitis that often progresses to destruction of the articular cartilage and ankylosis of the joints. Rheumatoid arthritis can also produce diffuse inflammation in the lungs, pericardium, pleura, and sclera, and also nodular lesions, most common in subcutaneous tissue under the skin. Although the cause of rheumatoid arthritis is unknown, autoimmunity plays a pivotal role in its chronicity and progression.

About 1% of the world's population is afflicted by rheumatoid arthritis, women three times more often than men. Onset is most frequent between the ages of 40 and 50, but people of any age can be affected. It can be a disabling and painful condition, which can lead to substantial loss of functioning and mobility. RA is diagnosed chiefly on symptoms and signs, but can also be diagnosed with blood tests (especially a test called rheumatoid factor) and X-rays. Diagnosis and long-term management are typically performed by a rheumatologist, an expert in the diseases of joints and connective tissues.

Various treatments are available. Non-pharmacological treatment includes physical therapy, orthoses, and occupational therapy. Analgesia (painkillers) and anti-inflammatory drugs, including steroids, can be used to suppress the symptoms, while disease-modifying antirheumatic drugs (DMARDs) can be used to inhibit or halt the underlying immune process and prevent long-term damage. In recent times, the newer group of biologics has increased treatment options.

When RA is clinically suspected, immunological studies can be performed, such as testing for the presence of rheumatoid factor (RF, a specific antibody). A negative RF does not rule out RA; rather, the arthritis is called seronegative. This is the case in about 15% of patients. During the first year of illness, rheumatoid factor is more likely to be negative with some individuals converting to seropositive status over time. RF is also seen in other illnesses, for example Sjögren's syndrome, and in approximately 10% of the healthy population, therefore the test is not very specific.

Because of this low specificity, new serological tests have been developed, which test for the presence of so called anti-citrullinated protein antibodies (ACPAs). Like RF, these tests are positive in only a proportion (67%) of all RA cases, but are rarely positive if RA is not present, giving it a specificity of around 95%. As with RF, there is evidence for ACPAs being present in many cases even before onset of clinical disease.

The most common tests for ACPAs are the anti-CCP (cyclic citrullinated peptide) test and the Anti-MCV assay (antibodies against mutated citrullinated Vimentin). Recently, a serological point-of-care test (POCT) for the early detection of RA has been developed. This assay combines the detection of rheumatoid factor and anti-MCV for diagnosis of rheumatoid arthritis and shows a sensitivity of 72% and specificity of 99.7%.

Also, several other blood tests can be done to allow for other causes of arthritis, such as lupus erythematosus. The erythrocyte sedimentation rate (ESR), C-reactive protein, full blood count, renal function, liver enzymes and other immunological tests (e.g., antinuclear antibody/ANA) are all performed at this stage. Elevated ferritin levels can reveal hemochromatosis, a mimic RA, or be a sign of Still's disease, a seronegative, usually juvenile, variant of rheumatoid.

The term Disease modifying anti-rheumatic drug (DMARD) originally meant a drug that affects biological measures such as ESR and hemoglobin and autoantibody levels, but is now usually used to mean a drug that reduces the rate of damage to bone and cartilage. DMARDs have been found both to produce durable symptomatic remissions and to delay or halt progression. This is significant, as such damage is usually irreversible. Anti-inflammatories and analgesics improve pain and stiffness but do not prevent joint damage or slow the disease progression.

There is an increasing recognition among rheumatologists that permanent damage to the joints occurs at a very early stage in the disease. In the past it was common to start therapy with just an anti-inflammatory drug, and assess progression clinically and using X-rays. If there was evidence that joint damage was starting to occur, then a more potent DMARD would be prescribed. Ultrasound and MRI are more sensitive methods of imaging the joints and have demonstrated that joint damage occurs much earlier and in more sufferers than was previously thought. People with normal X-rays will often have erosions detectable by ultrasound that X-ray could not demonstrate. The aim now is to treat before damage occurs.

There may be other reasons why starting DMARDs early is beneficial to preventing structural joint damage. From the earliest stages of the disease, the joints are infiltrated by cells of the immune system that signal to one another in ways that may involve a variety of positive feedback loops (it has long been observed that a single corticosteroid injection may abort synovitis in a particular joint for long periods). Interrupting this process as early as possible with an effective DMARD (such as methotrexate) appears to improve the outcome from the RA for years afterwards. Delaying therapy for as little as a few months after the onset of symptoms can result in worse outcomes in the long term. There is therefore considerable interest in establishing the most effective therapy with early arthritis, when the patient is most responsive to therapy and have the most to gain.

Traditional small molecular mass drugs used to treat arthritis include, for example, chemically synthesized DMARDs: azathioprine, ciclosporin (cyclosporine A), D-penicillamine, gold salts, hydroxychloroquine, leflunomide, methotrexate (MTX), minocycline, and sulfasalazine (SSZ). Cytotoxic drugs include Cyclophosphamide.

The most common adverse events relate to liver and bone marrow toxicity (MTX, SSZ, leflunomide, azathioprine, gold compounds. D-penicillamine), renal toxicity (cyclosporine A, parenteral gold salts. D-penicillamine), pneumonitis (MTX), allergic skin reactions (gold compounds, SSZ), autoimmunity (D-penicillamine, SSZ, minocycline) and infections (azathioprine, cyclosporine A). Hydroxychloroquine may cause ocular toxicity, although this is rare, and because hydroxychloroquine does not affect the bone marrow or liver it is often considered to be the DMARD with the least toxicity. Unfortunately hydroxychloroquine is not very potent, and is usually insufficient to control symptoms on its own.

Biological agents (biologics) can be produced through genetic engineering, and include, for example, tumor necrosis factor alpha (TNFα) blockers—etanercept (Enbrel), infliximab (Remicade), adalimunab (Humira), Interleukin 1 (IL-1) blockers—anakinra (Kineret), monoclonal antibodies against B cells—rituximab (Rituxan). T cell costimulation blocker—abatacept (Orencia), Interleukin 6 (IL-6) blockers—tocilizumab (an anti-IL-6 receptor antibody) (RoActemra, Actemra)

Anti-inflammatory agents include, for example, glucocorticoids. Non-steroidal anti-inflammatory drugs (NSAIDs, most also act as analgesics). Analgesics include, for example, paracetamol (acetaminophen in US and Canada), opiates, diproqualone, and lidocaine topical.

The challenge of treating RA lies in the fact that the disease is a long term chronic illness with that can result in challenging disability for which a large range of treatments exist each of which has significant drawbacks. Many of the DMARDs subject the patients to significant side effects including increased risk for serious infections, cancer, or even autoimmune disease. Furthermore, the biologically derived drugs are very expensive, and the patient can be subjected to frequent injections.

A doctor initiating therapy for a patient faces many possible options. It would be desirable to get rapid feedback once a patient starts therapy to understand whether the patient is responding to the therapy that is chosen before the clinical manifestation presents itself. Imaging is not sensitive and is expensive and many blood markers such as CRP lack sufficient sensitivity. A test that would allow the physician to rapidly determine the state of the disease would allow him or her to adjust the therapy quickly to a more effective therapy, saving the patient from additional joint damage and more effectively using the expensive therapies available.

A patient that has not experienced any acute flares since beginning treatment may in fact still be experiencing ongoing inflammatory damage to the joints that has not manifested itself clinically. A test that would allow the doctor to differentiate this state from the background would allow the therapy to be adjusted to try to bring the patient closer to a state in which no ongoing joint damage is being experienced.

Specific examples of how AutoImm Load can be used in managing RA patients are described in further detail in the examples section of this document.

In one embodiment of the invention clonotypes are identified which represent different immune profiles for different disease states. The disease state is then tracked by comparing the identified immune profile to the patients current immune profile. The disease is RA. The disease states can be, but are not limited to periods of high inflammation and a baseline. These immune profiles are used to drive treatment decisions.

4. Ankylosing Spondylitis

The methods can be used to detect disease activity for Ankylosing spondylitis. Ankylosing spondylitis (AS, from Greek ankylos, bent; spondylos, vertebrae), previously known as Bechterew's disease. Bechterew syndrome, and Marie Strümpell disease, a form of Spondyloarthritis, is a chronic, inflammatory arthritis and autoimmune disease. It mainly affects joints in the spine and the sacroilium in the pelvis, causing eventual fusion of the spine. It is a member of the group of the spondyloarthropathies with a strong genetic predisposition. Complete fusion results in a complete rigidity of the spine, a condition known as bamboo spine.

The typical patient is a young male, aged 18-30, when symptoms of the disease first appear, with chronic pain and stiffness in the lower part of the spine or sometimes the entire spine, often with pain referred to one or other buttock or the back of thigh from the sacroiliac joint. Men are affected more than women by a ratio about of 3:1, with the disease usually taking a more painful course in men than women. In 40% of cases, ankylosing spondylitis is associated with an inflammation of the eye (iridocyclitis and uveitis), causing redness, eye pain, vision loss, floaters and photophobia. Another common symptom is generalized fatigue and sometimes nausea. Less commonly aortitis, apical lung fibrosis and ectasia of the sacral nerve root sheaths may occur. As with all the seronegative spondyloarthropathies, lifting of the nails (onycholysis) may occur There is no direct test to diagnose AS. A clinical examination and X-ray studies of the spine, which show characteristic spinal changes and sacroiliitis, are the major diagnostic tools. A drawback of X-ray diagnosis is that signs and symptoms of AS have usually been established as long as 8-10 years prior to X-ray-evident changes occurring on a plain film X-ray, which means a delay of as long as 10 years before adequate therapies can be introduced. Options for earlier diagnosis are tomography and magnetic resonance imaging of the sacroiliac joints, but the reliability of these tests is still unclear. The Schober's test is a useful clinical measure of flexion of the lumbar spine performed during examination.

During acute inflammatory periods, AS patients will sometimes show an increase in the blood concentration of C-reactive protein (CRP) and an increase in the erythrocyte sedimentation rate (ESR), but there are many with AS whose CRP and ESR rates do not increase so normal CRP and ESR results do not always correspond with the amount of inflammation a person actually has. Sometimes people with AS have normal level results, yet are experiencing a significant amount of inflammation in their bodies.

Ankylosing spondylitis (AS, from Greek ankylos, bent; spondylos, vertebrae), previously known as Bechterew's disease, Bechterew syndrome, and Marie Stümpell disease, a form of Spondyloarthritis, is a chronic, inflammatory arthritis and autoimmune disease. It mainly affects joints in the spine and the sacroilium in the pelvis, causing eventual fusion of the spine.

It is a member of the group of the spondyloarthropathies with a strong genetic predisposition. Complete fusion results in a complete rigidity of the spine, a condition known as bamboo spine.

There are three major types of medications used to treat ankylosing spondylitis: 1) Anti-inflammatory drugs, which include NSAIDs such as ibuprofen, phenylbutazone, indomethacin, naproxen and COX-2 inhibitors, which reduce inflammation and pain Opioid analgesics have also been proven by clinical evidence to be very effective in alleviating the type of chronic pain commonly experienced by those suffering from AS, especially in time-release formulations. 2) DMARDs such as ciclosporin, methotrexate, sulfasalazine, and corticosteroids, used to reduce the immune system response through immunosuppression; 3) TNFα blockers (antagonists) such as etanercept, infliximab and adalimumab (also known as biologics), are indicated for the treatment of and are effective immunosuppressants in as in other autoimmune diseases;

TNFα blockers have been shown to be the most promising treatment, slowing the progress of AS in the majority of clinical cases, helping many patients receive a significant reduction, though not elimination, of their inflammation and pain. They have also been shown to be highly effective in treating not only the arthritis of the joints but also the spinal arthritis associated with AS. A drawback, besides the often high cost, is the fact that these drugs increase the risk of infections. For this reason, the protocol for any of the TNF-α blockers include a test for tuberculosis (like Mantoux or Heal) before starting treatment. In case of recurrent infections, even recurrent sore throats, the therapy may be suspended because of the involved immunosuppression. Patients taking the TNF medications are advised to limit their exposure to others who are or may be carrying a virus (such as a cold or influenza) or who may have a bacterial or fungal infection.

AS affects produces symptoms that are very common in the healthy populations. For example, a patient presenting complaining of severe back pain need not be experiencing an AS flare but rather might just have routine back pain. The physician is forced to make a decision about whether to treat these symptoms with expensive drugs with potentially severe side effects without a very precise view into the state of the disease. CRP and ESR do not provide a very precise view of the disease status. At the same time the course of the untreated disease can result in debilitating long term spinal damage. This state of affairs leads to a difficult clinical challenge and significant overtreatment is used. The availability of an objective measure that reflects disease activity can be of great help in the management of AS patients.

In one embodiment of the invention clonotypes are identified which represent different immune profiles for different disease states. The disease state is then tracked by comparing the identified immune profile to the patients current immune profile. The disease is AS. The disease states can be, but are not limited to periods of high inflammation and a baseline. These immune profiles are used to drive treatment decisions.

B. Utility of Immune Profiling in Cancer Detection

These methods can be used to measure cancer risk. Cancer has become the leading cause of death in the industrialized world. Therefore methods of treatment of cancer are in great need. Many approaches for cancer treatment are being attempted including the development of new small molecule drugs as well as antibodies targeting the tumor.

One set of methods that has been proposed is immunotherapy. Tumor surveillance is one of the functions of cells of the immune system. There are several categories of tumor antigens that are recognized by the immune system. The first category is comprised of antigens that are novel generated by somatic mutation (point mutation or a translocation) in the tumor. Another category consists of antigens from proteins that are only expressed in male germ cells that do not express MHC molecules. The dysregulation of gene expression in many tumors may allow some of these antigens to be expressed. A third category includes antigens from proteins only expressed in particular tissues. The fourth category comprises antigens that are significantly overexpressed in the tumor tissue. Finally the fifth category includes antigens that result from abnormal posttranslational modification.

One of the properties of tumors is their ability to escape effective elimination by the immune system. It is thought that new mutations acquired in the tumor allow it to go from the equilibrium phase (where the tumor is not completely eliminated but its growth is held in check) to the escape phase where the tumor grows without effective control by the immune system. There are many mechanisms that tumors employ to escape the immune system. These mechanisms include the lack of specific antigenic peptides, or the co-stimulatory molecules that can activate T cells. Other mechanisms include the tumor secretion of factor that inhibit T cells and the creation of a tumor-induced privileged site by creating a physical barrier separating the tumor from lymphocytes.

Inducing the immune system to better fight the tumor as a strategy for treating cancer is being studied and tested in multiple ways. One approach is the adoptive T cell therapy. This approach focuses on identifying T cells that are targeting tumor antigens through isolation of cells that are infiltrating the tumor and/or reacting to a specific tumor antigen. These T cells can be grown in vitro in conditions that enhance their effectiveness, like the use of IL-2 and/or antigen-presenting cells. The expanded cells are then infused back to the patient blood. Another approach is to use of retrovirus containing tumor-specific TCR. These retrovirus can be infused in the patient in special cells that later secrete the retrovirus allowing it to infect T cells that then start expressing the tumor-specific TCR. Finally a common approach is the use of vaccination. The premise of this approach of therapy is that immunization of the patient with one or more of the tumor antigens will stimulate the immune system ability to fight the tumor. Immunization is often done with the use of an adjuvant like Bacille Calmette-Guerin (BCG). This approach has been successful in preventing viral-induced cancer as evident by the ability to prevent cervical cancers induced by HPV-16 and HPV-18. However this has been less successful in the treatment of other tumors.

Much of the improvement in mortality because of cancer has come about due to the availability of better early detection methods leading for instance to reduced rates of mortality in breast cancer and cervical cancers. The mutability of tumors makes their early treatment much more effective than when they are detected late. Traditionally, looking for cancer detection biomarkers usually involved looking for markers that are highly expressed in the cancer and are at low level or absent in the normal tissue. This has led to the identification of several tumor markers, like PSA. One problem with early detection of in cancer is that the greatest value in for cancer detection occurs when detection of biomarker is most difficult, i.e., the tumor is very small. Therefore in order to have an effective cancer detection biomarker that can distinguish patients with small tumors from those that do not, there needs to be a tremendous difference in expression between the tumor and the normal tissue due to the large difference in size between the tumor and die normal tissue. Additionally the marker needs to "spill" efficiently to the blood or other body fluid to allow detection using a non-invasive technique.

This invention teaches a novel mechanism for cancer detection using the immune cell response. In this view cancer detection is not achieved by the detection of a marker produced by the tumor itself but by the immune system response to the tumor. Specifically the profile of TCR and/or BCR can provide an insight on whether the body is mounting a response to a tumor or not. This can ameliorate some of the issues with current biomarkers. First the immune response is an amplification signal that can be easier to detect. Second lymphocytes pass through the blood regularly and hence the relevant biomarker may readily present and detectable in peripheral blood than traditional tumor biomarker. Finally the problem of "background" biomarker material generated by the normal tissue is greatly reduced. The great diversity of T and/or B cells provide a way to detect the relevant biomarker with high sensitivity and specificity, particularly with the recent availability of high throughput methods for DNA sequencing. The approach of using the immune system response to cancer to detect it leverages the foundations laid to this field by the promise of immunotherapy. However the risk for the two applications is probably quite different. To use the immune response to cancer for its detection does not require that the specific clonotype be effective in treating the tumor but rather that it is associated with the immune response to the tumor.

Another embodiment of this invention contemplates the combination of the immune profiling tests with other markers that are already in use for the detection of cancer to allow tests with greater sensitivity and specificity. Other molecular identifiers or markers can be used in computing the Load algorithm or for determining the disease state. Molecular identifiers can include nucleic acids, proteins, carbohydrates, and lipids, and expression profiles of nucleic acids or proteins. The molecular identifiers can be of human or non-human origin (e.g., bacterial). The identifiers or markers can be determined by techniques that include, for example, comparative genomic hybridization (CGH), chromosomal microarray analysis (CMA), expression profiling, DNA microarray, high-density oligonucleotide microarray, whole-genome RNA expression array, peptide microarray, enzyme-linked immunosorbent assay (ELISA), genome sequencing, copy number (CNV) analysis, small nucleotide polymorphism (SNP) analysis, immunohistochemistry, in-situ hybridization, fluorescent in-situ hybridization (FISH), PCR. Western blotting, Southern blotting, SDS-PAGE, gel electrophoresis, and Northern blotting.

C. Utility of Immune Profiling in Transplant Medicine

These methods can be used to detect immune rejection of transplanted organs. Transplantation of organs have become an integral part of medicine with over 25,000 solid organ (kidney, liver, heart, pancreas, and lung) transplants and more than 15,000 bone marrow transplants occurring in the US per year. These are generally complicated procedures done at tertiary care centers. To minimize the risk of transplant rejection, patients are often placed on immunosuppression for extended periods of time subjecting them to the risk of cancer and infections. Furthermore many transplants are rejected either acutely or years after the transplantation.

In spite of these issues organ transplant remains an essential treatment modality as patients with organ failures have few other alternatives.

Solid organ transplant rejection primarily occurs due to response of the adaptive immune system to the transplanted organ. This is due to the presence of alloantigens in the graft that are recognized by the host's immune system. The rejection can occur in three different phases. The first is the hyperacute phase within minutes of the transplant where preformed antibodies mount a response to the graft. The second is the acute rejection that occurs in first weeks or months after the transplant. The last is chronic rejection that can occur years after the transplantation. Given these risks care has been taken to minimize the immunogenic differences between the donor and recipient. For example the risk of the hyperacute reaction is greatly reduced when the donor and recipient are matched for their ABO subtypes as well as tested for cross matching (determining whether the recipient has antibodies that react with the leukocytes of the donor). Similarly careful matching for the Major HistoCompatability (MHC) is done to reduce acute rejection. However given that MHC molecules are very polymorphic it is very hard to find to identify a perfect match. Monozygotic twins have a perfect MHC matching. Similarly ¼ siblings are expected to have a perfect MHC match. Unrelated individuals that have the same detected alleles per the clinical test often have differences due to other polymorphic sites that are not tested in routine clinical practice. However even with perfect MHC matching from siblings, there is still a significant risk of rejection due to the existence of minor histocompatibility antigens, and indeed acute rejection is very common occurring to more than half of the grafts.

One might imagine that more aggressive testing of the MHC locus as well as identification and matching the minor histocompatibility antigens would significantly improve the graft rejection and possibly survival rates. While that might be true the limited numbers of available donor organs available makes this task impractical as more aggressive testing may significantly delay the identification of an appropriate graft to be used for each patient. Therefore, much of the progress that has occurred in the transplantation field was in the use of immunosuppressive agents to prevent and treat rejection. Currently many drugs are utilized for this purpose including: Azathioprine, corticosteroids, Cyclosporine, Tacrolimus, Mycophenolate Acid, Sirolimus, Muromonab-CD3, Monoclonal Anti-CD25 Antibody, Monoclonal Anti-CD20 Antibody, and Calcineurin inhibitors.

Bone marrow transplant is most frequently used for leukemia and lymphoma treatment. Typically the recipient undergoes an aggressive regimen of radiation and/or chemotherapy to decrease the load of the tumor before the transplantation. Mature T cells front the donor can attack some of the host tissues in the inverse rejection that is called Graft Versus Host Disease (GVHD). This is often manifested by rash, diarrhea, and liver disease. Careful matching of MHC can ameliorate but not eliminate this problem. One solution is the depletion of the donor bone marrow in vitro of mature T cells that are ultimately responsible for GVHD. One problem with this is that the same phenomenon that causes GVHD may be responsible for some of the therapeutic effect of bone marrow transplant through the graft vs. leukemia effect where donor T cells attack the remaining cancer cells. In addition depletion of donor T cells can expose to patient to the risk of being immunodeficient. Therefore the risk and benefits have to be balanced when considering these approaches. Patients are therefore often treated with immunosuppressants to prevent as well as treat GVHD.

Current management of bone marrow but even more so for solid organ transplantation rely heavily on the treatment with strong immunosuppressive agents. However given that these drugs have significant risks they are used in a manner to balance risk and benefit. However given that the risk for a specific patient at a particular time is not well understood patients are treated with the dose where risk and benefits are balanced for the average patient. Tests that can predict future rejection events may potentially be very helpful in tailoring treatment to the patients at the appropriate times they need them. This may result in reduction in the immunosuppressive doses or some of the patients while improving the rate of rejection and hopefully graft survival.

Another embodiment of this invention contemplates the combination of the immune profiling tests with other markers that are already in use for the detection of transplant rejection to allow tests with greater sensitivity and specificity. Other molecular identifiers or markers can be used in computing the Load algorithm or for determining the disease state. Molecular identifiers can include nucleic acids, proteins, carbohydrates, and lipids, and expression profiles of nucleic acids or proteins. The molecular identifiers can be of human or non-human origin (e.g., bacterial). The identifiers or markers can be determined by techniques that include, for example, comparative genomic hybridization (CGH), chromosomal microarray analysis (CMA), expression profiling. DNA microarray, high-density oligonucleotide microarray, whole-genome RNA expression array, peptide microarray, enzyme-linked immunosorbent assay (ELISA), genome sequencing, copy number (CNV) analysis, small nucleotide polymorphism (SNP) analysis, immunohistochemistry, in-situ hybridization, fluorescent in-situ hybridization (FISH), PCR, Western blotting, Southern blotting, SDS-PAGE, gel electrophoresis, and Northern blotting.

D. Utility of Immune Profiling in the Treatment of Infection

These methods have utility in guiding the treatment of infections particularly when these infections can exist in active and latent states. The advent of antibiotics for the treatment of infectious disease over the past century has made a great impact on life expectancy. Over the past decade molecular diagnostics techniques have taken a rapidly increasing role in the diagnosis and management of infectious disease. The excellent sensitivity and specificity provided by nucleic acid amplification has enabled the application of these techniques to an increasing number of applications. Many of the applications are used for the diagnostic evaluation of the presence or absence of infectious agents. For example the testing of sexually transmitted diseases is often done by a molecular testing employing nucleic acid amplification technique. Another set of application involve the assessment of the "load" of the infection in a patient with an already diagnosed infectious agent. An example of that is the assessment of HIV viral load in patients already diagnosed with AIDS. This test helps the physician in determining whether the state of the patient's disease and hence can provide guidance on the effectiveness of the treatment regimen being used.

It is sometimes helpful not only to consider the level of the infectious agent but also the immune response to the infectious agent. One example where the immune response to the infection is used routinely in clinical practice is in hepatitis B. One aspect of hepatitis B testing relies on detecting the infectious agent through detection of hepatitis B antigens of by a nucleic acid amplification assay. In addition it is common in routine clinical practice to test for the presence of different antibodies that target the hepatitis B virus. The presence of anti-HBc IgM usually occurs in an acute infection setting, the appearance of anti-HBc IgG indicates the infection is chronic. Similarly the emergence of anti-HBs antibody signals clearing of the infection.

In one embodiment of this invention the value of the assessing the immune response to an infection is harnessed along with the sensitivity and specificity of the molecular testing. This can be particularly useful for infectious diseases that are chronic where the infectious agent remains latent in the body. The profile of the TCR and/or BCR can be used to assess the immune response to an infection. Sequencing can be used to obtain a profile of the TCR and/or BCR allowing the detection of particular clonotypes with high sensitivity and specificity. To determine the specific clonotypes that correlate with disease several approaches are conceived.

Another embodiment of this invention contemplates the combination of the immune profiling tests with other markers that are already in use for the detection of infectious agents to allow tests with greater sensitivity and specificity. Other molecular identifiers or markers can be used in computing the Load algorithm or for determining the disease state. Molecular identifiers can include nucleic acids, proteins, carbohydrates, and lipids, and expression profiles of nucleic acids or proteins. The molecular identifiers can be of human or non-human origin (e.g., bacterial). The identifiers or markers can be determined by techniques that include, for example, comparative genomic hybridization (CGH), chromosomal microarray analysis (CMA), expression profiling. DNA microarray, high-density oligonucleotide microarray, whole-genome RNA expression array, peptide microarray, enzyme-linked immunosorbent assay (ELISA), genome sequencing, copy number (CNV) analysis, small nucleotide polymorphism (SNP) analysis, immunohistochemistry, in-situ hybridization, fluorescent in-situ hybridization (FISH), PCR, Western blotting, Southern blotting, SDS-PAGE, gel electrophoresis, and Northern blotting.

E. Utility of Immune Profiling in the Treatment of Aging Patients

These methods have utility in monitoring the state of the immune system in the aged. Older people suffer from a decline in the immune system called immunosenescence that affects their ability to respond to infections and to raise effective responses to vaccines (Weinberger et al. 2008). This is apparent from the high mortality rates due to pneumonia in the elderly (Office for National Statistics, 2005), and their susceptibility to hospital-acquired infections, such as *Clostridium difficile* and methicillin-resistant *Staphylococcus aureus* (Health Protection Agency, 2008). Furthermore the decline in the immune system ability is thought to explain the increased rate of cancers in the elderly. In addition immunosenescence may contribute to other major diseases of the elderly with significant component of inflammatory processes, like Alzheimer and heart disease. An ability to predict which individuals are most at risk for these deadly outcomes would be useful to geriatrics physicians as they make clinical decisions about vaccination, aggressive treatment of infections and hospitalization.

Many aspects of the innate and adaptive immune system are altered in immunosenescence. T cells lose responsiveness, macrophages have a decreased antigen-presenting capacity and altered cytokine secretion, natural killer cells have reduced toxicity, follicular dendritic cells cannot present antigen as efficiently, and neutrophils lose phagocytic ability. There is smaller pool of naïve T and B cells and an increase in the memory and effector pool leading to a reduced diversity of T and B cell repertoires leading to the reduction of the ability of the adaptive immune system to respond to new antigens. In particular T cell repertoires that are associated with cytomegalovirus (CMV) are greatly increased and as much as 45% of the total T cell repertoire may be devoted to it. It has been noted that these expansions are less pronounced in centenarians.

Studies have suggested that immune markers can predict survival in the elderly. The degree of diversity of the B cell repertoire has been shown to predict survival in the elderly at least in one population. Even though these global differences in TCR and BCR diversity were shown to predict clinical outcomes but these markers lack specificity. Deeper analysis of the repertoire data may provide significantly more prediction accuracy. For example, expansions responsive to CMV may have a different significance than other expansions.

In one embodiment of this invention. RNA from the T and B cells found in peripheral blood can be collected from a longitudinal cohort of aging patients whose clinical histories are followed for several years. The TCRα and TCRβ genes and the IgH, IgK and IgL genes can be amplified in each of these cohorts at several time points in their clinical histories. Profiles of patients with long survival is compared to patients with short survival. First, global measure of diversity can be obtained. This will include not only the number of different clonotypes identified but also their diversity. For example, is the V, D, J segment usage the same in the two groups or is one group more restricted in its usage? For example two samples may have the same number of independent clonotype but the clonotypes for one of the two samples do not cover many of the V segments. It is logical to expect that this sample would be less versatile in responding to a new antigen compared with the other sample whose clonotypes are distributed among all the V segments.

In addition to global diversity it is determined whether expanded clonotypes in patients who had a long survival can be distinguished on the basis of some sequence parameter compared to clonotypes in patients who had a short survival. This approach can be supplemented by looking at clonotypes that respond to specific antigens. For example given the available evidence identification of CMV responsive clonotypes can have predictive power. Capturing T cells clonotypes that are CMV reactive in a discovery study can be done from a set of elderly as well as healthy patients. Sequences of these clonotypes can be studied to identify parameters that distinguish them from other clonotypes. Using this predictive algorithm of CMV clonotypes with the longitudinal cohort described above it can be assessed whether adding this information can add to the ability to predict the patient who survive for a long time from that who does not.

Another embodiment of this invention contemplates the combination of the immune profiling tests with other markers that are already in use for the detection of health in the aging population to allow tests with greater sensitivity and specificity. Other molecular identifiers or markers can be used in computing the Load algorithm or for determining the disease state. Molecular identifiers can include nucleic acids, proteins, carbohydrates, and lipids, and expression profiles of nucleic acids or proteins. The molecular identifiers can be of human or non-human origin (e.g., bacterial). The identifiers or markers can be determined by techniques that include, for example, comparative genomic hybridization (CGH), chromosomal microarray analysis (CMA), expression profiling. DNA microarray, high-density oligonucleotide microarray, whole-genome RNA expression array, peptide microarray, enzyme-linked immunosorbent assay (ELISA), genome sequencing, copy number (CNV) analysis, small nucleotide polymorphism (SNP) analysis, immunohistochemistry, in-situ hybridization, fluorescent in-situ hybridization (FISH), PCR, Western blotting, Southern blotting, SDS-PAGE, gel electrophoresis, and Northern blotting.

F. Utility of Immune Profiling in the Administration of Vaccines

These methods have utility in the administration of vaccines. The use of vaccination has led to a great reduction in the rate of infections of multiple organisms. One infectious disease that continues to have a significant health impact with over 30,000 deaths a year in the US is influenza. Influenza vaccination has to be done yearly as the strain mutates rapidly. Most of the severe sequelae of the disease occur in the elderly. Unfortunately the elderly often experience immunosenescence rendering them inadequately responsive to the vaccination.

In order to distinguish patients who are responsive to vaccination from those that are not, a discovery study needs to be performed. In this population pre and (at one or more set time) post vaccination blood samples are available for a cohort of Influenza vaccinated patients with known Influenza outcome (i.e. were they later protected from the infection or not). TCR and/or BCR sequence can be obtained from these samples. Clonotypes that are enriched after vaccination in each patient are determined. Enriched clonotypes in patients who responded to the vaccination are then compared to a control set of clonotypes (e.g., the rest of the clonotypes in the same set of patients) to distinguish the correlating clonotypes from other clonotypes. The algorithm to predict these clonotypes is then used to predict correlating clonotypes among patients who did not respond to the vaccination. Patients who did not respond may generate the same type of clonotypes as those that responded but at lower levels. Alternatively it might be that non-responders generate a distinct class of clonotypes.

The number of correlating clonotypes identified in the non-responder may distinguish these two possibilities.

In another embodiment, an individual's responsiveness to a vaccination is monitored by first obtaining a sample of lymphocytes from the individual after vaccination from which lymphocytes reactive to the vaccine are isolated. Such isolation is readily carried out for B cells using conventional affinity purification with antigenic material from or related to the vaccine as capture moieties attached to a solid support such as magnetic beads. Isolation of T cells may also be carried out with conventional means, e.g. U.S. Pat. Nos. 7,776,562; 7,125,964; 5,635,363; or the like, which are incorporated by reference. A clonotype profile is generated from the isolated sample of lymphocytes to obtain a set of correlating clonotypes. At subsequent time points, peripheral blood samples are obtained from the individual and clonotype profiles are generated. The rate of change of the frequency of correlating clonotypes in the subsequent samples is monitored to determine the responsiveness of the individual to the vaccination. Such method of monitoring responsiveness to a vaccination may be implemented with the following steps: (a) enriching after a vaccination a sample of lymphocytes from peripheral blood of an individual to obtain a sample of vaccine-responsive lymphocytes; (b) determining a clonotype profile from the sample of vaccine-responsive lymphocytes to identify one or more patient-specific clonotypes correlated with vaccine response; and (c) determining a level of each of the one or more patient-specific clonotypes in a clonotype profile from a sample of peripheral blood cells obtained at one or more subsequent times to monitor the responsiveness of the individual to the vaccination. In one embodiment, responsiveness is determined by the increase in amount or frequency of the one or more patient-specific clonotypes in subsequently measured clonotype profiles.

With the correlating clonotypes identified, an algorithm is then built to generate a score for predicting likelihood of immunization. Data from the profiles of the vaccine-responders and those that do not respond are utilized to generate this algorithm. This algorithm can then be used to predict the likelihood of immunization in the next patient using the predicted correlating clonotypes from a sample obtained after immunization. The prediction is done through the application of another algorithm that has also been generated in the discovery study. It can optionally be aided (or substituted) by data from the pre-calibration to limit the search for correlating clonotypes to those that were enriched after immunization.

Another embodiment of this invention contemplates the combination of the immune profiling tests with other markers that are already in use for the detection of response to vaccination to allow tests with greater sensitivity and specificity. Other molecular identifiers or markers can be used in computing the Load algorithm or for determining the disease state. Molecular identifiers can include nucleic acids, proteins, carbohydrates, and lipids, and expression profiles of nucleic acids or proteins. The molecular identifiers can be of human or non-human origin (e.g., bacterial). The identifiers or markers can be determined by techniques that include, for example, comparative genomic hybridization (CGH), chromosomal microarray analysis (CMA), expression profiling, DNA microarray, high-density oligonucleotide microarray, whole-genome RNA expression array, peptide microarray, enzyme-linked immunosorbent assay (ELISA), genome sequencing, copy number (CNV) analysis, small nucleotide polymorphism (SNP) analysis, immunohistochemistry, in-situ hybridization, fluorescent in-situ hybridization (FISH), PCR, Western blotting, Southern blotting, SDS-PAGE, gel electrophoresis, and Northern blotting.

G. Utility of Immune Profiling in the Monitoring of Immune Hypersensitivity (Allergy)

The adaptive immune system has evolved to respond to antigens that are associated with pathogens. As in the case of autoimmune diseases, the immune system can sometimes have the wrong target. Whereas in autoimmune diseases the immune system targets self antigen, in hypersensitivity reactions it mounts a response to harmless stimuli like medications, dust, and food. Hypersensitivity is very common with as many as 50% of the US population having allergy to an environmental stimulus, and it is caused by mechanisms. Hypersensitivity is divided into 4 types. Type I hypersensitivity is the immediate type hypersensitivity and is mediated by IgE. Type II is often due to IgG antibody binding to cell surface-associated antigen. For example a harmless drug that binds to the surface of the cell can make the cell a target for anti-drug IgG in patients who happened to have these antibodies. Type III is caused by deposition of antigen-antibody complexes on tissues. This occurs for example when the amount of antigen is large resulting in small immune complexes that can't be cleared efficiently and are instead deposited on blood vessel walls. Type IV sensitivity is a delayed type hypersensitivity mediated by T cells. Type I and type IV have the highest impact on human health.

In Type I hypersensitivity reaction the patient becomes sensitized to a harmless antigen (allergen) by producing IgE antibody against it. Later exposure to the allergen induces the activation of IgE-binding cells, such as mast cells and basophils. Once activated these cells cause the allergic reaction through inducing an inflammatory process by secreting stored chemicals and synthesizing cytokines, leukotrienes, and prostaglandins. The dose and the route of entry of the allergen determines the magnitude of the allergic reaction that can range from symptoms of allergic rhinitis to the life-threatening circulatory collapse in anaphylaxis. Often the acute Type I reaction is later followed by another late phase that is plays a role in many of the resulting pathological processes. The late phase of recruitment of T helper cells and other inflammatory cells is essentially a Type IV hypersensitivity reaction. Some Type I allergic reactions include seasonal rhinoconjunctivitis (hayfever), food allergy, drug-induced anaphylaxis, atopic dermatitis (eczema), and asthma. These are very common conditions with rising prevalence causing significant costs as well as morbidity and mortality. For example. Asthma is a chronic disease that inflicts ~7% of the US population causing ~4,000 deaths a year. Some of these diseases have some related aspects. For example, patients with atopic dermatitis are at significantly increased risk to have asthma. Food allergy can cause vomiting and diarrhea but can also result in anaphylaxis in a significant number of patients—30,000 cases resulting in ~200 deaths per year in the US. Some of the same allergens that activate submucosal mast cells in the nose causing symptoms of allergic rhinitis can also activate mast cells in the lower airways causing bronchial constriction, a typical symptom of asthma. Some Type IV hypersensitivity reactions are contact dermatitis (e.g., poison ivy), chronic rhinitis, chronic asthma, and celiac disease. Celiac disease is a chronic disease caused by a non-IgE mediated food allergy. It is a disease of the small intestine caused by the allergic response against gluten, a component present in wheat and other foods. Over 95% of patients celiac patients have a specific MHC class II allele, the HLA-DQ2.

Treatment of hypersensitivity reactions differs, but they often had two aspects: the acute treatment and chronic management or prevention. Some of these conditions can be life threatening (anaphylaxis, and acute asthma) and involve immediate medical attention. The chronic management in general it involves trying to avoid the specific allergen. This may be effective when the allergen can be clearly identified (e.g., allergy to nuts), but this can be difficult when the allergen is present widely in the environment, like pollen or dust. Therefore chronic treatment with medications is often utilized for some of these diseases (e.g., asthma and allergic rhinitis). The level of effectiveness of the treatment management is ultimately tested when the patient is re-exposed to the allergen(s). Therefore some patients may be subject to over- or under-treatment. Ideally a test that assesses the disease activity and the degree to which the patient is prone to mount a hypersensitivity response would be available. Such a test would allow the tailoring of treatment to the individual patient needs.

H. Detection of Lymphoid Neoplasms

One aspect of this invention will utilize next generation sequencing technologies to evaluate the level of specific TCR or BCR rearrangements in cancers of the lymphocytes. These sequencing technologies can obtain sequence reads from 1 million or more individually spatially isolated TCR or BCR molecules at a reasonable cost. A sequence present at 1/1,000,000 or lower can still be detected in a specific manner using these technologies thus allowing a cancer cell associated with a particular TCR or BCR rearrangement to be detected at that level. Multiplex amplification to amplify all the different types of sequences for a specific gene can be done from blood or bone marrow DNA. For example to amplify IgH sequences, several primers complementary to all the known V segments and alleles can be used along with several primers complementary to all the J segments and alleles. It is important that little amplification bias occurs among the different sequences. We have shown that we can amplify from RNA the TCRβ and IgH genes with only small differences in the efficiencies of the different V primers, and thereby validating the possibility of doing the same from DNA which will allow the assessment of cancer cells even when the TCR or BCR is not being expressed.

The sensitivity this invention is determined by the counting statistics of the individual spatially isolated molecules taking into account any bias in amplification of different clonotypes. Therefore it is anticipated that this approach will offer more sensitivity and will be less subject to sensitivity differences for different tumor cell TCR or BCR sequences when compared to real time PCR assays developed for the same purpose. Furthermore to obtain more sensitivity one can simply obtain more sequencing reads. Since the sequencing costs continue to drop we anticipate the sensitivity at a given cost will continue to improve. With sufficient sequencing reads the sensitivity becomes limited by the number of lymphocytes in the sample. In contrast, sensitivity for the real time PCR assay is limited by backgrounds caused by nonspecific amplifications and hybridizations of any probes which can be substantial.

In order to use this invention to monitor lymphoid cancers a patient's specific clones can be determined by sequencing a diagnostic leukemia or lymphoma sample; that is, patient-specific clonotypes are determined by generating a clonotype profile from a sample from a disease-related tissue, where disease responsive lymphocytes are found in an enriched state. Once the clonotype profile is determined, levels of disease-related clonotypes can be determined by comparison to a clonotype profile of a sample from a tissue that is not associated with the disease. Afterwards, levels of disease-related clonotypes are determined in clonotype profiles from samples from that patient at subsequent time points in the disease course. Preferably, such subsequent samples are taken from tissues that are conveniently accessed, such as peripheral blood. The cells in the blood sample can be used and alternatively. DNA or RNA from the cell free plasma can be used. There is no requirement for a patient-specific probes or the utilization of patient-specific templates to be run as standards, as is called for in current technology. In this embodiment of the invention patient-specific clonotypes that are identified can be followed by obtaining full sequence repertoires and by informatically measuring the relevant correlating clonotypes based on matching the sequences obtained to stored data regarding the relevant sequences for each patient. Disease-related tissues for lymphomas may include lymphoid tissues, bone marrow, peripheral blood, and the like.

Identification of cancer clonotypes. In order to use the sequencing methods to monitor cancer, it is critical to define the cancer clonotypes in each individual. For secondary testing (recurrence and prognosis application for patients diagnosed with lymphoid neoplasms) identification of the cancer clonotype can often be quite straightforward. For example, blood or bone marrow samples of leukemia patients at diagnosis typically exhibit the cancer clonotype as the most frequent clonotype in the sample. In other cases of secondary testing (for example biopsy from some lymphoma samples) the cancer clone may not be present at very high levels. Other clonotypes that are reactive to a variety of antigens including those that are attacking the cancer may have tumor are found at higher frequency. If the level of the clonotype is not by itself sufficient to determine the cancer clonotype other criteria can be used. Several methods described below can be used to identify the cancer clonotypes.

Cross lineage rearrangement. Some types of otherwise uncommon rearrangements are common in some cancers and thus can be used to associate them with tumor. For example, cross lineage rearrangements, like T cell receptor (α, β, γ, and/or δ) in B cells or B cell receptor (IgH, IgK, and/or IgL) in T cells are common, especially in ALL. The presence of cross lineage rearrangements is likely to support a malignant origin of the clonotype.

Sequencing cross lineage rearrangement using sequencing of specific cell types. Alternatively, cells of one type can be isolated through standard methods (e.g, magnetic beads and FACS) that utilize the presence of certain antigens on the surface of cells. Sequencing can be done to assess for the presence of cross lineage rearrangement. For example, B cells can be isolated and sequencing TRCβ can be performed. The presence of an enriched specific TCRβ sequence would be consistent with cancer. The sequencing can be performed before and after the enrichment allowing for the determination of the level without enrichment and the degree of enrichment.

Inactive immune receptor. Another feature that may be useful to distinguish malignant cells from others is that the non-malignant cells need to have an active immune cell receptor. Lymphocytes proliferate in reaction to antigens and may reach high levels. Therefore reaching high levels for a normal (non-cancer) clonotype is dependent on an active immune receptor. Identification in a biopsy of a high level non-functional sequence is not sufficient to identify cancer since non-functional rearrangements can be found in the same cell as a functional ones due to nonfunctional rearrangements of the second allele within a cell that contains a functional rearrangement. The use of RNA may allow the disambiguation of this point as tumor cells may continue to express nonfunctional rearrangements while this is unlikely to occur in normal cells but in general more definitive methods are useful. There are additional features that may distinguish non-functional sequences in cancer. For example, some of the immature cancers, e.g. ALL, often have only the IgH rearranged but not IgK or IgL. This pattern is not likely to achieve high frequency in the absence of cancer. These nonfunctional rearrangements can be assessed using the following techniques.

Statistical linkage in a series of diluted samples. An alternative to the physical linking is to look for mapping linkage as described above. In this case only one gene (e.g. IgH) is being testing and the question is what are the non-functional sequences linked to i.e. what is the sequence of the other allele of IgH in the same cell. High frequency non-functional alleles linked to a second nonfunctional allele are consistent with achieving high frequency due to cancer.

Sequencing specific cell type. This pattern can also be identified by capturing cells carrying one marker and assessing the sequence of the other. For example, one can use FCM to capture cells that are IgK and IgL negative. Sequencing IgH before and after the FCM enrichment can identify clones that are enriched in this population. Cells that are IgK and IgL negative are not expected to reach high frequency and their presence is consistent with an immature cancer, like ALL.

Inactivating somatic hypermutations. An alternative pattern may be found in B cell lymphomas whose clonotypes have undergone somatic hypermutations. Some of these clones can have inter-clonal variability, in which the cancer cells comprise several clones with different mutations within them. Some of the resulting clones may possibly have inactivating mutations. For a normal antigen-driven somatic hypermutation it is unlikely that a clone with an inactivating somatic hypermutation is selected and expanded. The presence of such clones is consistent with cancer.

Sequencing cell fractions carrying cancer markers. In cases where cancer markers are known, FCM can be performed to enrich for cancer cells using this marker. Sequencing the immune receptor repertoire can be performed before and after the enrichment. Clonotypes that get enriched are likely associated with the cancer clonotype. For example, the lymphoma cells can be enriched using FACS to isolate cells carrying the particular markers (most conveniently surface markers) relevant to the tumor. Sequencing BCR before and after enrichment would readily identify the enriched clonotype and by extension the cancer clonotype.

Alternatively the association of a marker can be assessed at the DNA or RNA level. This can be accomplished by several means including linked PCR or statistical association with serially diluted cells as described above. Quantitating the linkage of these markers will enable better performance of the assay as many markers are overexpressed in cancer cells but still present at some level in normal cells. To account for this the linked PCR can be done using three genes: the immune receptor, the cancer marker, and the control gene. The immune receptor gene can link with either of the other two genes and the fraction of linked molecules that are the result of a linkage between the receptor rearrangement and the cancer marker can indicate the level of expression of this cancer marker.

Detection of translocations. In addition to serving as a marker of cells that have become cancerous IgH is often one of the two pathological translocation partners in lymphoid neoplasms. One example is the t(11:14) that puts the J segment of IgH in close proximity to the cycline D 1(CCND1) gene resulting in its overexpression. This rearrangement which is referred to as BCL1-IgH occurs in as many as 60-70% of mantle cell lymphoma as well as other lymphoid neoplasms (e.g. 20% of multiple myeloma). Another example is t(14:18) that puts the J segment of IgH in close proximity to BCL2 resulting in its over expression. This rearrangement occurs in up to 90% of follicular lymphoma and 20% of large B cell lymphoma. These rearrangements are typically identified by cytogenetics, Southern blotting, or FISH. PCR has the potential to identify rearrangement at very high sensitivity and specificity as shown by BCR-ABL for the detection of Philadelphia chromosome. Different PCR techniques have been used to the assessment of translocations relevant to lymphoma, with the recently introduced real time PCR (e.g. for BCL2-IgH) being probably the most advanced. There are a few features of BCL1-IgH and BCL2-IgH that make their detection less sensitive and specific than that of BCR-ABL. First, in contrast to BCR-ABL, BCL1-IgH and BCL2-IgH do not generate a fusion protein, and there is no splicing event that generates predictable molecular structure. Instead the breakpoints may span a large region. There are common breakpoints that allow the detection of up to 88% of BCL2-IgH using a combination of primers and ~40% of the BCL1-IgH. This results in missing some patients that have the translocation. Second, these rearrangements may be present in normal individuals that would never get cancer. For example, BLC2-IgH translocation has been found at the level of $~10^{-5}$ in a large fraction of the normal individuals with over ~4% carrying BCL2-IgH at a frequency of $>1/25K$. The frequency of BCL2-IgH gets higher with increasing age. It is also hypothesized that different people may have distinct levels of "background" translocation. Presumably the presence of this translocation in normal sample is due to the fact that tumorgenesis is a multi-step process and the BCL2-IgH is not sufficient for tumors to emerge. The presence of this low level background puts a limit on the sensitivity of detection.

Amplification of with a pool of the J primers complementary to all the J segments and primers complementary to the regions upstream of the BCL1 or BCL2 translocation breakpoints can be sequenced. This can generate a method for sensitive detection of these translocations and the cancer cells they appear in. First, deep sequencing of individual isolated molecules (e.g, 100K or 1 million reads) can allow the detection of the appropriate sequences from a small number of cells in a background of amplifications of other loci. In addition, the problem of the background translocations in normal individuals may ameliorate the problem that real time PCR suffer from. There is evidence that, at least in some cases, the background translocations are not clonal but rather appear repeatedly in the same patient. Using sequencing one can distinguish the different translocation events to obtain frequency of the independent translocation events. Since the breakpoint of different translocations is likely to be distinct translocation events can be distinguished from each other. Alternatively or additionally, a linking PCR using the translocation with a B or T cell receptor gene can be done to provide a unique barcode for the translocation. The linking can also be done statistically using a set of dilution samples as described above.

Serial monitoring of the level of the translocation to detect points at which they increase in frequency may be helpful in early cancer detection as well as for detection of recurrence. In that latter case the specific breakpoint relevant to the patient may be identified front the diagnostic biopsy. This concept of distinguishing translocations by their breakpoints through sequencing and therefore distinguishing background from cancer can be extended to other translocation that involve IgH (e.g, t(8:14)) or all other translocations in lymphoid neoplasm or other cancers.

Changing Cancer cell levels and the likelihood of cancer. The mere presence of sequences that point to the existence of remaining tumor cell may not by itself predict a clinical relapse. For example a steady state of tumor level may be achieved by the balancing forces of tumor cell proliferation and immune response to the tumor. It is anticipated that in addition to the absolute level of a clonotype, its rate of change can be informative in predicting the likelihood of relapse. For example consider two patients each with level X of their respective patient-specific cancer clonotypes. If the level on previous tests for one of the patients has been consistently X and the level for the other patient in previous tests has been considerably lower than the likelihood of the second patient developing a relapse might be higher than for the first patient.

Similarly additional data relating to the status of the cell containing the cancer-related clonotype can be used to predict likelihood of recurrence. For example, the presence of certain markers (surface or non-surface) can be an indication of the functional status of the cell and hence the likelihood of recurrence. Sequencing before and after the capture of cells with the relevant markers can determine the fraction of cells with the cancer clonotype that carry the relevant markers. Similarly some markers relevant to the likelihood of recurrence (e.g. expression of some gene relating to cell growth) can be assessed at the RNA level. This can be done by several methods including linking PCR or statistically by cell dilution as described above. Finally, it is possible that the level of immune receptor specific RNA in the tumor cell can have functional consequence and association with the likelihood of recurrence. This level can be assessed by doing linking PCR between a control gene 1 that can link to either the immune receptor rearrangement or control gene 2. The relative fraction of the two products can be indicative of the relative amount of the RNA in the cell. Another method involves comparing the RNA level to the DNA level of the immune receptor rearrangement. The frequency of the cancer-specific clonotype in the DNA identifies the relative level of the cancer-specific clonotype. The frequency of the same clonotype can then be assessed from RNA, and the relative frequency in RNA and in DNA can be followed. A change in this relative frequency can be indicative of a change in the likelihood of recurrence.

Immune reaction to lymphoid cancer. In addition to monitoring the cancer clonotype and its potential progeny, we can also assess the immune response to the tumor. We can identify clonotypes that are likely mounting a response against the tumor. For example B or T cell clonotypes that are enriched in the biopsy of the diagnostic lymph node biopsy may be the result of immune response to the tumor. Additionally functional testing to identify T cells interacting with some tumor antigen can be done. This can be specific antigens or it can be the tumor cells themselves. For example sequencing of the TCR before and after stimulation with antigen or tumor cells can identify the relevant T cells by the virtue of their enrichment after stimulation. The level of these T cells in subsequent blood samples from the patient can be helpful in predicting relapse. For example consider the case mentioned above where a specific level X of the cancer clonotype has been stably detected. This is likely the result of balancing the tumor growth with the immune response to the tumor. If at some point the immune response to the tumor is reduced it is possible to anticipate that the tumor will relapse. The immune response to the tumor can be quantitate through determination of the level of the T cell clonotypes that have been determined to be capable of attacking the tumor.

Integration of sequencing with other cell markers. Detection of the cancer-specific clonotype can be done through sequencing of immune receptor rearrangements as described above. Presence of markers (surface or non-surface) that are relevant to cancer cells can be used to capture cell subpopulations that are later sequenced. The combination of using marker-specific capture and sequencing before and after the capture can provide additional information. First, this can be used to identify the clonotypes that are enriched and hence are likely to be the cancer-specific clonotypes as described above. In addition, sequencing cells that have cancer-specific markers can lead to higher sensitivities. With a perfect marker, only few reads need to be done to detect cancer-specific clonotypes in millions of other cells. Most markers do not perform perfectly and significant background (i.e. non-cancer cells) is generated by their capture. However the enrichment of cancer cells by these markers can lead either to equivalent sensitivity with less sequencing reads or to better sensitivity than doing the same number of sequencing reads without enrichment. For example, with 1 million sequencing reads one can assess ~1 million cells that are captured with a cancer-specific marker. This corresponds to more cells that were present before capture and hence better sensitivity. Finally the use of markers can provide functional aspects that relate to the tumor biology and prognosis. Some level of tumor cells may be present in the blood of different samples, but the functional marker on the cells may distinguish samples that indicate high likelihood of recurrence from those that predict low likelihood of recurrence. For example, samples can be sequenced before and after capture with a relevant marker and the percentage of the clonotype sequences with the specific marker can be assessed. Two samples with the same total level of cancer-specific clonotypes but different fractions of those cells carrying the relevant marker may be predicted to have different likelihood of recurrence.

Clone Evolution and Detection of Phylogenetic Clones (Clans) and other Cancer-Related Mutations As mentioned above, in one aspect, methods of the invention monitor a level of a clan of clonotypes rather than an individual clonotype. This is because of the phenomena of clonal evolution, e.g. Campbell et al, Proc. Natl. Acad. Sci., 105: 13081-13086 (2008); Gerlinger et al, Br. J. Cancer, 103: 1139-1143 (2010). The sequence of a clone that is present in the diagnostic sample may not remain exactly the same as the one in a later sample, such as one taken upon a relapse of disease. Therefore if one is following the exact clonotype sequence that matches the diagnostic sample sequence, the detection of a relapse might fail. Such evolved clone are readily detected and identified by sequencing. For example many of the evolved clones emerge by V region replacement (called VH replacement). These types of evolved clones are missed by real time PCR techniques since the primers target the wrong V segment. However given that the D-J junction stays intact in the evolved clone, it can be detected and identified in this invention using the sequencing of individual spatially isolated molecules. Furthermore, the presence of these related clonotypes at appreciable frequency in the diagnostic sample increases the likelihood of the relevance of the clonotype. Similarly the development of somatic hypermutations in the immune receptor sequence may interfere with the real time PCR probe detection, but appropriate algorithms applied to the sequencing readout (as disclosed above) can still recognize a clonotype as an evolving clonotype. For example, somatic hypermutations in the V or J segments can be recognized. This is done by mapping the clonotypes to the closest germ line V and J sequences. Differences from the germ line sequences can be attributed to somatic hypermutations. Therefore clonotypes that evolve through somatic hypermutations in the V or J segments can be readily detected and identified. Somatic hypermutations in the NDN region can be predicted. When the remaining D segment is long enough to be recognized and mapped, any somatic mutation in it can be readily recognized. Somatic hypermutations in the N+P bases (or in D segment that is not mappable) cannot be recognized for certain as these sequences can be modified in newly recombined cells which may not be progeny of the cancerous clonotype. However algorithms are readily constructed to identify base changes that have a high likelihood of being due to somatic mutation. For example a clonotype with the same V and J segments and 1 base difference in the NDN region from the original clone(s) has a high likelihood of being the result of somatic recombination. This likelihood can be increased if there are other somatic hypermutations in the V and J segments because this identifies this specific clonotype as one that has been the subject of somatic hypermutation. Therefore the likelihood of a clonotype being the result of somatic hypermutation from an original clonotype can be computed using several parameters: the number of differences in the NDN region, the length of NDN region, as well as the presence of other somatic hypermutations in the V and, or J segments.

The clonal evolution data can be informative. For example if the major clone is an evolved clone (one that was absent previously, and therefore, previously unrecorded) then this is an indication of that tumor has acquired new genetic changes with potential selective advantages. This is not to say that the specific changes in the immune cell receptor are the cause of the selective advantage but rather that they may represent a marker for it. Tumors whose clonotypes have evolved can potentially be associated with differential prognosis. In one aspect of the invention, a clonotype or clonotypes being used as a patient-specific biomarker of a disease, such as a lymphoid neoplasm, for example, a leukemia, includes previously unrecorded clonotypes that are somatic mutants of the clonotype or clonotypes being monitored. In another aspect, whenever any previously unrecorded clonotype is at least ninety percent homologous to an existing clonotype or group of clonotypes serving as patient-specific biomarkers, then such homologous clonotype is included with or in the group of clonotypes being monitored going forward. That is, if one or more patient-specific clonotypes are identified in a lymphoid neoplasm and used to periodically monitor the disease (for example, by making measurement on less invasively acquired blood samples) and if in the course of one such measurement a new (previously unrecorded) clonotype is detected that is a somatic mutation of a clonotype of the current set, then it is added to the set of patient-specific clonotypes that are monitored for subsequent measurements. In one embodiment, if such previously unrecorded clonotype is at least ninety percent homologous with a member of the current set, then it is added to the patient-specific set of clonotype biomarkers for the next lest carried out on the patient; that is, the such previously unrecorded clonotype is included in the clan of the member of the current set of clonotypes from which it was derived (based on the above analysis of the clonotype data). In another embodiment, such inclusion is carried out if the previously unrecorded clonotype is at least ninety-five percent homologous with a member of the current set. In another embodiment, such inclusion is carried out if the previously unrecorded clonotype is at least ninety-eight percent homologous with a member of the current set.

It is also possible that a cell evolves through a process that replaces the NDN region but preserves the V and V segment along with their accumulated mutations. Such cells can be identified as previously unrecorded cancer clonotypes by the identification of the common V and J segment provided thereby contain a sufficient number of mutations to render the chance of these mutations being independently derived small. A further constraint may be that the NDN region is of similar size to the previously sequenced clone.

Assessment of Sufficient Number of Cells

The sensitivity of the assay is limited by the number of cells that generate the nucleic acid template that is used in the amplification reaction. Typically ~6 pg of DNA is present in each cell. Therefore to have a sensitivity of 1/1000,000, ~6 µg of DNA need to be used. However is peripheral blood only a fraction of the cells are B cells and hence ~6 µg of DNA from peripheral blood may have only ~100,000 B cells. To obtain higher sensitivity higher amounts of DNA can be used. One problem can be that as more DNA is used the effect of inhibitors purified with the DNA can be more profound and sample to sample variation may be seen. Obtaining purer population of cells may ameliorate this problem. Generating Peripheral Blood Mononuclear Cell (PBMC) is frequently done in clinical settings. ~6 µg of DNA from PBMC can have ~250,000-300,000 B cells. Capturing B cells specifically can be also done to obtain more B cells per µg of DNA used.

More than one immune receptor rearrangements can be followed to maximize sensitivity and ameliorate the problem of clonal evolution. Therefore if 3 rearrangements are being followed then splitting the available cells among them would decrease the sensitivity in the analysis of each rearrangement. Therefore amplification of the DNA (or RNA) in a way where all 3 loci of the rearrangements are amplified before the splitting ameliorates this problem. Whole genome amplification methodologies have been employed previously and can be used here to accomplish the amplification of the three loci prior to the splitting. Alternatively, amplification for the specific loci in one reaction can be employed to achieve the same task. In this case a later split to amplify each rearrangement separately is optional. The whole genome amplification prior to amplification of specific immune receptor rearrangement can also be useful when employed to assess only one immune receptor rearrangement. For example the assessment of IgH is often complicated with somatic hypermutations making the use of multiple primer sets often desirable. In this case whole genome amplification before the splitting of the input nucleic acid between different reactions with different primer sets does not necessarily lead to improved sensitivity to detect the cancer-specific clonotype. In this case the different (e.g 3) reactions assess the full repertoire of available input nucleic acid and hence there would be no advantage of the whole genome amplification (aside from preserving the DNA for other interrogation). However this is not true when somatic hypermutation at the sequence complementary to a primer occurs. For example if there is only one DNA molecule representing the cancer-specific clonotype then it would go to one of the three reactions. A somatic hypermutation prevents this specific clonotype to be amplified. On the other hand whole genome amplification would guard against that since the initial single molecule of cancer-specific sequence is amplified and would therefore be present in all 3 tubes. So even though the frequency of the cancer-specific clonotype does not increase in the input template for the locus amplification, the fact that it is present in all 3 tubes is an advantage. Instead of whole genome amplification locus specific amplification using approaches like long range PCR or using primers from all three primer sets or preliminary amplification can be done.

Screening for lymphoid neoplasms. The above methods apply to the monitoring of patients after initial diagnosis: however, this invention applies also to cancer screening. Screening for primary cancer has been a major force in reducing mortality. Early detection of lymphoid neoplasms may lead to great improvement in the survival rates of these cancers. It has been shown at least in acute and chronic lymphocytic leukemia that the specific cancer clonotypes can be detected years before the ultimate diagnosis. It is possible that lymphoma clonotypes can also be detected earlier than is possible using current diagnostic methodologies. Detection of the cancer clonotypes for screening purposes (i.e., before a primary tumor occurs) can be done using this invention by sequencing immune cell receptors as described above. The cancer clonotype in each patient is likely to be unique, and it is clear that one does not know a priori the sequence to be screened for in each patient. Many of the methods listed above can, however, be used in blood from a patient who has not yet been diagnosed with cancer in order to identify clonotypes that are likely to be associated with cancer and their levels and changes in these levels can be used to assess the risk of a patient developing clinical cancer.

Types of lymphoid neoplasms. The methods of the provided invention can be used to monitor lymphoid neoplasms, e.g., lymphoma or leukemia. Mature B cell neoplasms can include, e.g., chronic lymphocytic leukemia/Small lymphocytic lymphoma. B-cell prolymphocytic leukemia, lymphoplasmacytic lymphoma (such as Waldenström macroglobulinemia), splenic marginal zone lymphoma, plasma cell neoplasms (plasma cell myeloma, plasmacytoma, monoclonal immunoglobulin deposition diseases, and heavy chain diseases), extranodal marginal zone B cell lymphoma (MALT lymphoma), nodal marginal zone B cell lymphoma (NMZL), follicular lymphoma. Mantle cell lymphoma, diffuse large B cell lymphoma, mediastinal (thymic) large B cell lymphoma, intravascular large B cell lymphoma, primary effusion lymphoma, and Burkitt lymphoma/leukemia.

Mature T cell neoplasms can include, e.g., T cell prolymphocytic leukemia. T cell large granular lymphocytic leukemia, adult T cell leukemia/lymphoma, extranodal T cell lymphoma (nasal type), enteropathy-type T cell lymphoma, hepatosplenic T cell lymphoma, mycosis fungoides/Sezary syndrome, primary cutaneous CD30-positive T cell lymphoproliferative disorders, primary cutaneous anaplastic large cell lymphoma, Lymphomatoid papulosis. Angioimmunoblastic T cell lymphoma, Peripheral T cell lymphoma (unspecified), or Anaplastic large cell lymphoma.

The methods of the provided invention can be used to monitor acute leukemia or chronic leukemia. The leukemia can be acute lymphoblastic leukemia (ALL) (e.g., precursor B acute lymphoblastic leukemia, precursor T acute lymphoblastic leukemia, Burkitt's leukemia, and acute biphenotypic leukemia); chronic lymphocytic leukemia (CLL) (e.g., B-cell prolymphocytic leukemia); acute myelogenous leukemia (AML) (e.g., acute promyelocytic leukemia, acute myeloblastic leukemia, and acute megakaryoblastic leukemia); chronic myelogenous leukemia (CML) (e.g., chronic monocyte leukemia); hairy cell leukemia; T-cell prolymphocytic leukemia (T-PLL); or large granular lymphocytic leukemia.

I. Cancer Screening

Another example of a situation in which antigen specific T and/or B cell profiling may be used to inform clinical situations is the use of specific cancer autoantigens in cancer screening. Cancer cells often produce aberrant molecules that are antigenic and provoke an immune response. Such molecules can be screened for directly in blood or bodily fluids in order to assess the likelihood of a patient going on to develop cancer. The sensitivity of these methods has proven to be a limiting factor however in that these antigens are found in very small concentrations in the blood or other bodily fluids when the cancers are at an early stage when they are most likely to be treatable and asymptomatic. These antigenic molecules can, however, provoke an immune response which, though it may be insufficient to control the tumor growth, may be of sufficient strength to be measurable as a way of detecting early cancer. Antibodies against antigens specific to, for example, lung and breast cancer cells have been detected and can be used as a means to screen for these cancers using the antigens themselves to capture and detect the antibodies (M. Nesterova et al. Biochimica et Biophysica Acta 2006: 1762: 398-403). As described above, these assays lack the ability to differentiate amongst different antibody clones and miss any potential T cell immune response to the tumor antigens. The methods described above can be used to enrich for both T cells and/or B cells that express TCR or BCR that bind antigens known to exist in cancer cells. Using the inventions described herein one can generate clonotype frequencies before and after antigen specific T/BCR enrichment in order to identify T or B cells that are likely to be pan of an immune response to these antigens in a particular individual.

There are several ways this invention could be implemented clinically. In the first embodiment, blood from an individual whose risk of developing a dangerous tumor is to be assessed is sampled and profiled for full T and B cell clonotype profiles before and after enrichment for cells that bind to a specific set of cancer antigens. These antigens could be a single antigen species, a set of antigens, or a complex mixture of antigens or could be the entire mix of material from a single tumor of a mix of tumors. These antigens could include p53, c-myc, NY-ESO-1. BRCA1, BRCA2, HER2, MUC1, CAGE, Sox2, GBU4-5, Annexin1, cox-2. Clones that are likely to be associated with an immune response to these antigens could be identified by a significant shift in frequency before and after enrichment, in addition to other parameters including nucleic acid and amino acid sequence parameters, length, segment usage, etc. The risk of developing cancer could be determined based on a single time point measurement of this type or from at least a second time point in which changes in the frequency of these clonotypes are used to calculate a risk of cancer. The enrichment could be done at a first time point to identify the correlating antigen specific clonotypes and these correlating antigen specific clonotypes quantitated in subsequent time points in which enrichment is not carried out in order to calculate a risk score.

A population study could also be used to generate an algorithm to predict correlating clonotypes from the antigen specific enrichment. In this population study more than one individual with known cancer risks are obtained and antigen specific clonotypes are identified using the techniques of this invention. This population is used to generate an algorithm which can be used to predict antigen specific clonotypes that are relevant to the disease in a new individual whose cancer risk is unknown.

J. Adverse Drug Reactions

The benefits of drug treatment are often balanced by their adverse effects. The majority of adverse drug reactions (ADR) is fairly predictable and dose dependent. Other ADRs are idiosyncratic, and many of these are caused by immunological mechanisms. Predisposition to several of these ADRs is associated to specific HLA genotypes. Ideally patients would know ahead of getting the medication that they are predisposed to have an ADR. Recently the FDA added on the label of the HIV medication, Abacavir, a recommendation to test for allele HLA-B*5701 before initiating treatment as patients with this genotype are predisposed to the drug hypersensitivity reaction. In cases where it is not possible to tell a patient they are predisposed to have an ADR, it is desirable to detect evidence the ADR before any symptom appear using blood tests. There are several methods to diagnose immune-related ADR. There are several in vivo methods (Skin testing, intradermal, patch testing, and drug provocation tests) that reproduce the drug allergy by exposing the patient to the drug. The in vitro methods include assessing basophil activation, drug-specific IgE, and drug-specific lymphocyte stimulation test. Different versions of the drug-specific lymphocyte activation tests are used to assess different properties of lymphocyte activation. These include lymphocyte stimulation, lymphocyte migration, lymphocyte toxicity, and lymphocyte transformation tests. Some variants on the tests include the assessment of activation markers like CD69 or the level of cytokine released. Generally all these methods are used to diagnose patients who already had an allergy and not to predict the hypersensitivity reaction. Additional problems plague the different techniques. For example, some of the in vivo tests have some risk of serious allergic response in the patient. The basophil activation lacks the specificity to the relevant antigen and drug-specific IgE are relevant only to those allergy types involving IgE (e.g. hemolytic anemia and anaphylaxis). Therefore there is need for a method that is capable of predicting ADR either before drug administration or before symptoms appear. Assessing the T and/or B cell repertoire can generate such a test. Some of the in vitro methods can be used to identify the clonotypes that interact with the drug. For example the lymphocyte stimulation test can be done with the specific drug to identify clonotypes that interact with the drug.

K. Tissue Damage Detection

The use of molecular markers in blood and bodily fluids and/or tissues has been shown to be able to provide critical information about potentially damaged organs which can point to disease diagnosis and therapeutic interventions. One example of such a marker is the detection of the protein troponin in blood as part of the diagnosis of heart disease. Troponin is a molecule that is highly specific to heart tissues which is largely contained within the cells in heart tissue and is found at very low levels in circulation for individuals with healthy hearts. When heart disease occurs, however, cell death and apoptosis result in the spilling of this and other molecules into the bloodstream where sensitive detection using ELISA assays can reveal elevated levels of troponin that are clearly associated with heart disease.

This paradigm can be readily extended to other tissues that might suffer similar damage but such techniques are limited by the ability of researchers to identify markers that are both sufficiently specific to a given tissue to provide diagnostically relevant information and sufficiently abundant in early phases of tissue damage to provide information at a clinically useful time in the course of a disease that might result in organ damage.

It has been shown that while surface markers present on human cells do not result in immune reactions, internally contained molecules within cells can be immunogenic when they are released into the bloodstream. As in the case of the detection of cancer autoantigens, such organ damage related autoantigens might be more sensitively detected indirectly through detection of immune cells that are reactive to these antigens than would be possible by direct antigen detection of the type that is done in the case of troponin.

This invention thus can be used to provide a diagnostic insight into the levels of organ damage in an individual. In this embodiment, T and/or B cells that are reactive to antigens that are specific to molecules found within a particular type of human tissue are enriched using the methods described above. Shifts in frequency in T and/or B cells clonotypes before and after enrichment can be used to ascertain which clonotypes are likely to be reacting to these antigens. This method can be combined with sequence algorithms that use sequence parameters to ascertain which of these enriched clonotypes are most likely to be reacting to these antigens. Population studies involving more than one individuals with known organ damage whose antigen specific correlating clonotypes have been empirically identified can also be used to inform an algorithm that can be used to reline these predictions by identifying sequence characteristics that are often associated with these correlating clonotypes in subsequent individuals.

Antigen specific clonotype correlation can be done at least at a first time point to identify and predict correlating clonotypes. Blood or bodily fluids sampled at subsequent time points can then be profiled with or without antigen specific enrichment to measure the levels of these correlating clonotypes which can be used to generate an organ damage score that correlates the degree of damage to a specific organ in that individual at that time. Levels of these clonotypes can be used to establish this score as can the shills in these levels over time.

Antigens for specific tissues can be used in this embodiment. Tissues could be: heart, lung, liver, intestine, pancreas, esophagus, stomach, kidney, nerves, testes, ovary, prostate, thymus, placenta, uterus, etc. Antigens for each of these tissues could be a select set of gene products that are known to be specifically expressed in these tissues. These specifically expressed gene products could be the result of looking at differential gene expression between these organs and other organs. The antigens could be a single antigen, a set of antigens, or complex mixtures of materials up to and including material from whole cells from the tissues in question.

L. Identification of Exposure to Local Antigens

In one embodiment of the invention the described methods are used to generate a database of immune profiles related to a particular geographic location based upon local antigens. These antigens could be but are not limited to local pollens. These antigens could have a seasonal component. Once the immune profiles are generated geographic locations a subject will have his or her current immune profile compared to the database. Such a comparison is used to determine whether a subject has recently been exposed to the local antigens. In one embodiment this is method is used to test whether a subject was in a suspected location. In another embodiment this method is used to identify locations where the subject is likely to have been without a preconceived suspicion of where the suspect has been. Accordingly, a method of the invention for determining exposure of an individual to one or more antigens may comprise the steps of (a) determining a profile of clonotypes from a sample of B cells and/or T cells of the individual, such sample comprising a repertoire of clonotypes thereof, and (b) comparing clonotypes of the profile with clonotypes of an antigen-specific clonotype database to determine a level of clonotype matches, thereby determining a level of exposure to the antigen, the antigen-specific clonotype database including substantially all clonotypes of human TCR and/or immunoglobulin chains specific for the one or more antigens. In one embodiment, the one or more antigens consist of antigens of a pathogen. In another embodiment, the pathogen is a virus. In another embodiment, such virus is an influenza virus, a smallpox virus, a hepatitis C virus, a coronavirus, a dengue virus, or a lentivirus. In one embodiment, such antigen-specific clonotype database consists of clonotypes consisting of substantially all CDR3 regions of human TCRβ and IgH chains.

M. Identification of Exposure to Bio-terrorism Related Antigens

In one embodiment of the invention the described methods are used to generate a database of immune profiles related to antigens likely to be related to the production of bioterrorism related compounds. These antigens could be but are not limited to viral vectors capable of being weaponized. Once the immune profiles are generated subject will have his or her current immune profile compared to the database. Such a comparison is used to determine whether a subject has recently been exposed to the bioterrorism related compounds. In one embodiment this is method is used to test whether a subject was exposed to a particular suspected compound. In another embodiment this method is used to identify whether the subject is likely to have been exposed to a list of potential compounds without a preconceived suspicion of which compounds are expected. In one embodiment the immune profile to be tested is generated after a biologic agent has been found. For example, an individual suspected of a bio-terrorism attack is identified by the authorities. A sample is obtained from the suspect and an immune profile is obtained using methods described above. This profile is statistically compared to a database which contains many sample profiles. The sample profiles include immune profiles that represent certain bioterrorism related antigens. The sample profiles include immune profiles that represent certain antigens or combinations of antigens that exist only in particular geographic locations at particular times of the year. The comparison of the suspect's immune profile to this database provides evidence that the suspect was in a particular geographic location during a particular time frame and that the suspect was exposed to certain bioterrorism related antigens. This evidence is used to further direct the investigation and during prosecution.

Kits

In the commercialization of the methods described herein, kits for amplification of specific somatically rearranged regions or portions thereof are particularly useful. Such kits may be for carrying out one or two staged PCRs (as described above) for amplifying a predetermined somatically rearranged region or portion thereof for the purpose of preparing a sample of clonotypes for sequence analysis. A kit typically comprises one or more reagents, such as, without limitation, nucleic acid primers, packaged in a container, such as, without limitation, a vial, tube or bottle, in a package suitable for commercial distribution, such as, without limitation, a box, a sealed pouch, a blister pack or a carton.

The package typically contains a label or packaging insert indicating that the packaged reagents can be used in a method for generating a clonotype profile from a tissue sample of a patient. As used herein, "packaging materials" includes any article used in the packaging for distribution of reagents in a kit, including without limitation containers, vials, tubes, bottles, pouches, blister packaging, labels, tags, instruction sheets and package inserts. One example of such a kit includes reagents necessary for the amplification in one tube of TCRβ sequences from DNA or RNA extracted T cells of a patient or peripheral blood lymphocytes of a patient or bone marrow of a patient, as described above. Another example of such a kit includes reagents necessary for the amplification in a plurality of tubes IgH sequences from DNA or RNA extracted B cells of a patient or peripheral blood lymphocytes of a patient or bone marrow of a patient, as described above.

In the latter example, necessary reagents include a plurality of sets of primers for generating nested sets of templates, as described above. Typically, such plurality is 2 or 3 or 4. For the latter example, in one embodiment, three sets of primers are provided; and more specifically, the following three sets of primers are provided: set 1 comprising forward primers from Table 5 and reverse primers from Table 8; set 2 comprising forward primers from Table 6 and reverse primers from Table 8; set 3 comprising forward primers from Table 7 and reverse primers from Table 8. In another example, the kit would include the above-described reagents, including one or more PCR primer sets and a thermostable DNA polymerase, such as Taq polymerase, and if sequences are amplified from RNA, a reverse transcriptase. The primers may be present in quantities that would yield a balanced amplification of individual clonotype sequences in a patient sample, as described above. In one aspect of the invention, quantities of primers are provided to ensure a balanced amplification of clonotypes. Such balancing of multiplex PCRs is well known by practitioners of ordinary skill in the art and includes, but is not limited to, adjusting the concentrations of primers in the reaction and/or selecting the positions and lengths of primers in a region of interest to increase or decrease the rate of annealing of individual primers. In one embodiment, the quantities of primers are selected so that in the PCR their concentrations are such that the rate at which each primer anneals to its primer binding site is substantially identical. In another embodiment, quantities of primers are selected so that each sequence in a sample is amplified to an amount that is within 2-fold of the average amplification amount of a random sample of clonotypes. In still another embodiment, such random sample contains at least 100 clonotypes.

Thermostable DNA polymerases and transcriptases are commercially available from a variety of manufacturers. Additional materials in the kit may include: suitable reaction tubes or vials, a barrier composition, typically a wax bead, optionally including magnesium; reaction mixtures (often concentrated, for example 2×, 5×, 10× or 20×) for the PCR stages, including necessary buffers and reagents such as dNTPs; nuclease- or RNase-free water, RNase inhibitor; control nucleic acid(s) (i.e. such as internal standards), and/or any additional buffers, compounds, co-factors, ionic constituents, proteins and enzymes, polymers, and the like that may be used in multiplex PCR reactions.

Components of a kit are packaged in any manner that is commercially practicable. For example, PCR primers and/or reverse transcriptase may be packaged individually to facilitate flexibility in configuring the assay, or together to increase ease of use and to reduce contamination. Similarly, buffers, salts and co-factors can be packaged separately or together. The kits also may include reagents and mechanical components suitable for the manual or automated extraction of nucleic acid from a tissue sample. These reagents are known to those skilled in the art and typically are a matter of design choice. For instance, in one embodiment of an automated process, tissue is disrupted ultrasonically in a suitable lysis solution provided in the kit.

EXAMPLE 1

Determining the State of an Autoimmune Disease

A sample of cerebral spinal fluid (CSF) and blood is taken from a patient with an episode peak of multiple sclerosis. CD4+ cells are isolated from the CSF and blood, and the CDR3 of the T cell receptor β gene is amplified by PCR. The amplified fragments are further amplified to add bridge amplification primer binding sites and sequencing primer binding sites for Solexa sequencing. The variable regions of the T cell receptor β gene are sequenced to identify the clonotypes. The sequence information is used to generate a clonotype profile for the patient.

Another blood sample is taken when the patient is at a relatively inactive state of multiple sclerosis. The same procedure as above is repeated to generate a clonotype profile. Pathological clonotypes are identified as those that are high at the peak episode and went down significantly at the inactive state. Another blood sample is taken from the patient at a later state. At this time only a fraction of the T cell receptor β gene CDR3 regions are amplified and then sequenced. This subset contains the pathological clonotypes. The level of the various clonotypes is determined to assess the disease state of the patient.

EXAMPLE 2

TCRβ Repertoire Analysis: Amplification and Sequencing Strategy

In this example, TCRβ chains are analyzed. The analysis includes amplification, sequencing, and analyzing the TCRβ sequences. One primer AGCGACCTCGGGTGGGAACA (SEQ ID NO: 1) is complementary to a common sequence in Cβ1 and Cβ2, and there are 34 V primers (Table 1) capable of amplifying all 48 V segments. Cβ1 or Cβ2 differ from each other at position 10 and 14 from the J/C junction. The primer for Cβ1 and Cβ2 ends at position 16 bp and has no preference for Cβ1 or Cβ2.

The 34 V primers are modified from an original set of primers disclosed in Van Dongen et al, U.S. patent publication 2006/0234234, which is incorporated herein by reference.

TABLE 1

Primer sequences complementary to the different V families.

| V segment family | Primer Sequence | SEQ ID NO |
|---|---|---|
| V20-1 | AACTATGTTTTGGTATCGTCAGT | 2 |
| V29-1 | TTCTGGTACCGTCAGCAAC | 3 |
| V9, 5-1, 5-6, 5-5, 5-8, 5-4A | AGTGTATCCTGGTACCAACAG | 4 |
| V9, 5-1, 5-6, 5-5, 5-8, 5-4B | AGTGTGTACTGGTACCAACAG | 5 |
| V9, 5-1, 5-6, 5-5, 5-8, 5-4C | ACTGTGTCCTGGTACCAACAG | 6 |
| V9, 5-1, 5-6, 5-5, 5-8, 5-4D | AGTGTGTCCTGGTACCAACAG | 7 |
| V9, 5-1, 5-6, 5-5, 5-8, 5-4E | TCTGTGTACTGGTACCAACAG | 8 |
| V7-3, 7-6, 7-9, 7-2, 7-4A | CCCTTTACTGGTACCGACAG | 9 |
| V7-3, 7-6, 7-9, 7-2, 7-4B | GCCTTTACTGGTACCGACAG | 10 |
| V7-3, 7-6, 7-9, 7-2, 7-4C | CCCTTTACTGGTACCGACAAA | 11 |
| V7-8, 16A | TTTTGGTACCAACAGGTCC | 12 |
| V7-8, 16B | TTTTGGTACCAACAGGCCC | 13 |
| V 7-7 | AACCCTTTATTGGTATCAACAG | 14 |
| V4-1, 4-3, 4-2A | CGCTATGTATTGGTACAAGCA | 15 |
| V4-1, 4-3, 4-2B | CGCTATGTATTGGTACAAGCA | 16 |
| V12-3, 12-4, 12-5 | TTTCTGGTACAGACAGACCATGA | 17 |
| V3-1 | TACTATGTATTGGTATAAACAGGACTC | 18 |
| V25-1 | CAAAATGTACTGGTATCAACAA | 19 |
| V28, 10-3, 6-2, 6-3, 6-1, 6-6, 24-1A | CAAAATGTACTGGTATCAACAA | 20 |
| V28, 10-3, 6-2, 6-3, 6-1, 6-6, 24-1B | ATGTACTGGTATCGACAAGACC | 21 |
| V6-4, 6-9A | TGCCATGTACTGGTATAGACAAG | 22 |
| V6-4, 6-9B | ATACTTGTCCTGGTATCGACAAG | 23 |
| V10-1, 10-2, 6-5, 6-9, 6-8, 27A | ATATGTTCTGGTATCGACAAGA | 24 |
| V10-1, 10-2, 6-5, 6-9, 6-8, 27B | ATATGTCCTGGTATCGACAAGA | 25 |
| V10-1, 10-2, 6-5, 6-9, 6-8, 27C | ACATGTCCTGGTATCGACAAGA | 26 |
| V14 | TAATCTTTATTGGTATCGACGTGT | 27 |
| V19 | GCCATGTACTGGTACCGACA | 28 |

TABLE 1-continued

Primer sequences complementary to the different V families.

| V segment family | Primer Sequence | SEQ ID NO |
|---|---|---|
| V18 | TCATGTTTACTGGTATCGGCAG | 29 |
| V30 | CAACCTATACTGGTACCGACA | 30 |
| V11-1, 11-3, 11-2A | CATGCTACCCTTTACTGGTACC | 31 |
| V11-1, 11-3, 11-2B | CACAATACCCTTTACTGGTACC | 32 |
| V2 | ATACTTCTATTGGTACAGACAAATCT | 33 |
| V13 | CACTGTCTACTGGTACCAGCA | 34 |
| V15 | CGTCATGTACTGGTACCAGCA | 35 |

The Illumina Genome Analyzer is used to sequence the amplicon produced by the above primers. A two-stage amplification is performed on messenger RNA transcripts (200), as illustrated in FIGS. 2A-2B, the first stage employing the above primers and a second stage to add common primers for bridge amplification and sequencing. As shown in FIG. 2A, a primary PCR is performed using on one side a 20 bp primer (202) whose 3' end is 16 bases from the J/C junction (204) and which is perfectly complementary to Cβ1 (203) and the two alleles of Cβ2. In the V region (206) of RNA transcripts (200), primer set (212) is provided which contains primer sequences complementary to the different V region sequences (34 in one embodiment). Primers of set (212) also contain a non-complementary tail (214) that produces amplicon (216) having primer binding site (218) specific for P7 primers (220). After a conventional multiplex PCR, amplicon (216) is formed that contains the highly diverse portion of the J(D)V region (206, 208, and 210) of the mRNA transcripts and common primer binding sites (203 and 218) for a secondary amplification to add a sample tag (221) and primers (220 and 222) for cluster formation by bridge PCR. In the secondary PCR, on the same side of the template, a primer (222 in FIG. 2B and referred to herein as "C10C-17-P5") is used that has at its 3' and the sequence of the bases closest to the J/C junction, followed by 17 bp with the sequence of positions 15-31 from the J/C junction, followed by the P5 sequence (224), which plays a role in cluster formation by bridge PCR in Solexa sequencing. (When the C10-17-P5 primer (222) anneals to the template generated from the first PCR, a 4 bp loop (position 11-14) is created in the template, as the primer hybridizes to the sequence of the 10 bases closest to the J/C junction and bases at positions 15-31 from the J/C junction. The looping of positions 11-14 eliminates differential amplification of templates carrying Cβ1 or Cβ2. Sequencing is then done with a primer complementary to the sequence of the 10 bases closest to the J/C junction and bases at positions 15-31 from the J/C junction (this primer is called C'). C10-17-P5 primer can be HPLC purified in order to ensure that all the amplified material has intact ends that can be efficiently utilized in the cluster formation.)

In FIG. 2A, the length of the overhang on the V primers (212) is preferably 14 bp. The primary PCR is helped with a shorter overhang (214). Alternatively, for the sake of the secondary PCR, the overhang in the V primer is used in the primary PCR as long as possible because the secondary PCR is priming from this sequence. A minimum size of overhang (214) that supports an efficient secondary PCR was investigated. Two series of V primers (for two different V segments) with overhang sizes from 10 to 30 with 2 bp steps were made.

Using the appropriate synthetic sequences, the first PCR was performed with each of the primers in the series and gel electrophoresis was performed to show that all amplified. In order to measure the efficiency of the second PCR amplification SYBR green real time PCR was performed using as a template the PCR products from the different first PCR reactions and as primers Read2-tag1-P7 and Read2-tag2-P7. A consistent picture emerged using all 4 series of real time data (2 primary PCRs with two different V segments and two secondary PCR with different primers containing two different tags). There was an improvement in efficiency between overhang sizes 10 and 14 bp. However there was little or no improvement in efficiency with an overhang over 14 bp. The efficiency remained high as the overhang became as small as 14 bp because of the high concentration of primers allowing the 14 bp to be sufficient priming template at a temperature much higher than their melting temperature. At the same time the specificity was maintained because the template was not all the cDNA but rather a low complexity PCR product where all the molecules had the 14 bp overhang.

As illustrated in FIG. 2A, the primary PCR uses 34 different V primers (212) that anneal to V region (206) of RNA templates (200) and contain a common 14 bp overhang on the 5' tail. The 14 bp is the partial sequence of one of the Illumina sequencing primers (termed the Read 2 primer). The secondary amplification printer (220) on the same side includes P7 sequence, a tag (221), and Read 2 primer sequence (223) (this primer is called Read2_tagX_P7). The P7 sequence is used for cluster formation. Read 2 primer and its complement are used for sequencing the V segment and the tag respectively. A set of 96 of these primers with tags numbered 1 through 96 are created (see below). These primers are HPLC purified in order to ensure that all the amplified material has intact ends that can be efficiently utilized in the cluster formation.

As mentioned above, the second stage primer, C-10-17-P5 (222, FIG. 2B) has interrupted homology to the template generated in the first stage PCR. The efficiency of amplification using this primer has been validated. An alternative primer to C-10-17-P5, termed CsegP5, has perfect homology to the first stage C primer and a 5' tail carrying P5. The efficiency of using C-10-17-P5 and CsegP5 in amplifying first stage PCR templates was compared by performing real time PCR. In several replicates, it was found that PCR using the C-10-17-P5 primer had little or no difference in efficiency compared with PCR using the CsegP5 primer.

Amplicon (300) resulting from the 2-stage amplification illustrated in FIGS. 2A-2B has the structure typically used with die Illumina sequencer as shown in FIG. 3A. Two primers that anneal to the outmost part of the molecule, Illumina primers P5 (AATGATACGGCGACCCACCGAG) (SEQ ID NO: 36) and P7 (CAAGCAGAAGACGGCATACGAGAT) (SEQ ID NO: 37) are used for solid phase amplification of the molecule (cluster formation). Three sequence reads are done per molecule. The first read of 100 bp is done with the C' primer, which has a melting temperature that is appropriate for the Illumina sequencing process. The second read is 6 bp long only and is solely for the purpose of identifying the sample tag. It is generated using the Illumina Tag primer (AGATCGGAAGAGCACACGTCTGAACTCCAGTCAC) (SEQ ID NO: 38). The final read is the Read 2 primer, an Illumina primer with the sequence GTGACTGGAGTTCAGACGTGTGCTCTTCCGATCT (SEQ ID NO: 39). Using this primer, a 100 bp read in the V segment is generated starting with the 1st PCR V primer sequence.

A set of 6 bp sequence tags to distinguish different samples run in the same sequencing lane was designed, where each tag is different from all the other tags in the set by at least 2 differences. The 2 differences prevent misassignment of a read to the wrong sample if there is a sequencing error. The alignment done to compare the tags allowed gaps and hence one deletion or insertion error by sequencing will also not assign the read to the wrong sample. Additional features in selecting the tags was to limit single base runs (4 A or T and 3 G or C) as well as no similarity to the Illumina primers. In total 143 tags were generated, 96 of them are used.

Sequencing TCRβ. Six multiplexed amplifications with the pooled oligos and one cDNA sample as a template were used. Three of each of the amplifications were done with Accuprime and another three with high fidelity Taq. Two amplifications with each enzyme used cDNA that correspond to 500 ng initial RNA, and one amplification with each enzyme used 10 times less cDNA. For each of the six reactions a primary and secondary PCR was performed and the amplified material was sequenced using the Illumina platform and the scheme described above. 100 bp sequence from each side was obtained. The primary analysis of the data was done using the same concepts described below.

To assess reproducibility of the assay it was determined whether clonotype levels are consistent in the duplicate experiments. As shown in FIGS. 5A-5C, high correlation is obtained when the same enzyme and starting input cDNA amount was used (each of the 2 comparisons had r2=0.944). When different enzymes were used the correlation gets worse (median correlation for the 4 possible combinations r2=0.931), and it is only modestly reduced (R2=0.924) when the 2 enzymes were used to amplify smaller input cDNA (corresponding to only 50 ng RNA).

Figure 7C:
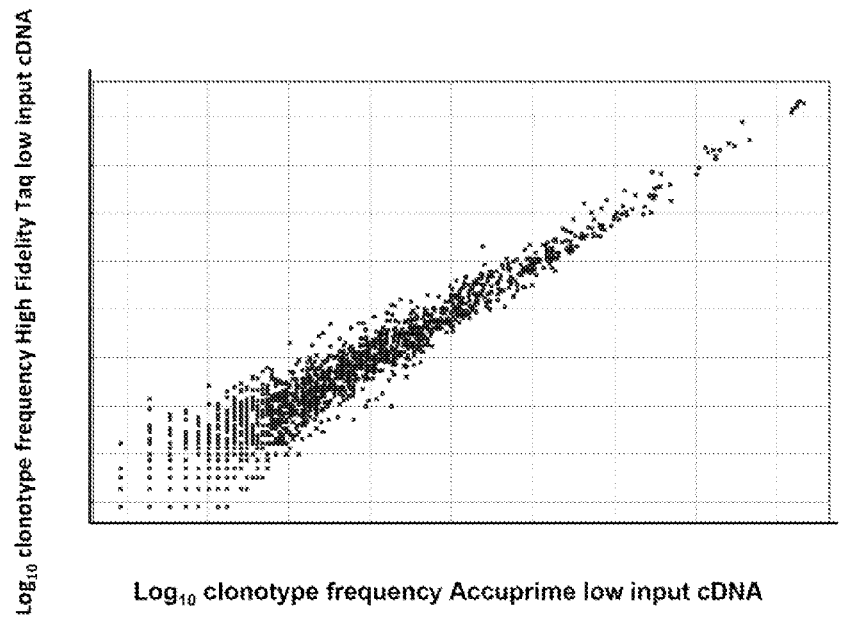
FIG. 7C shows the log10 of the frequency of each clonotype using cDNA corresponding to 50 ng of RNA as input template and Accuprime (X axis) or High fidelity Taq (Y axis).
Figure 7A:
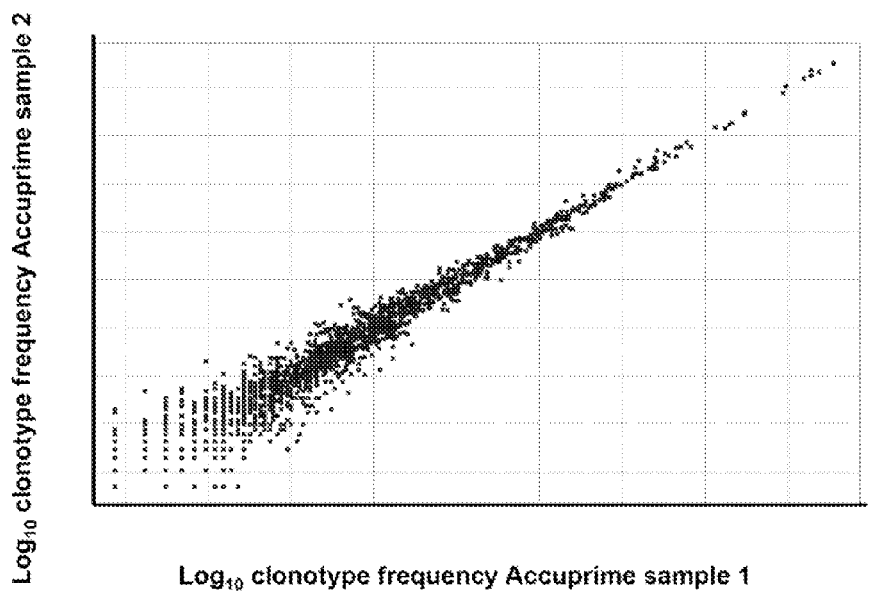
FIG. 7A shows the log10 of the frequency of each clonotype in the two duplicate samples using Accuprime and cDNA corresponding to 500 ng of RNA as input template.
Figure 7B:
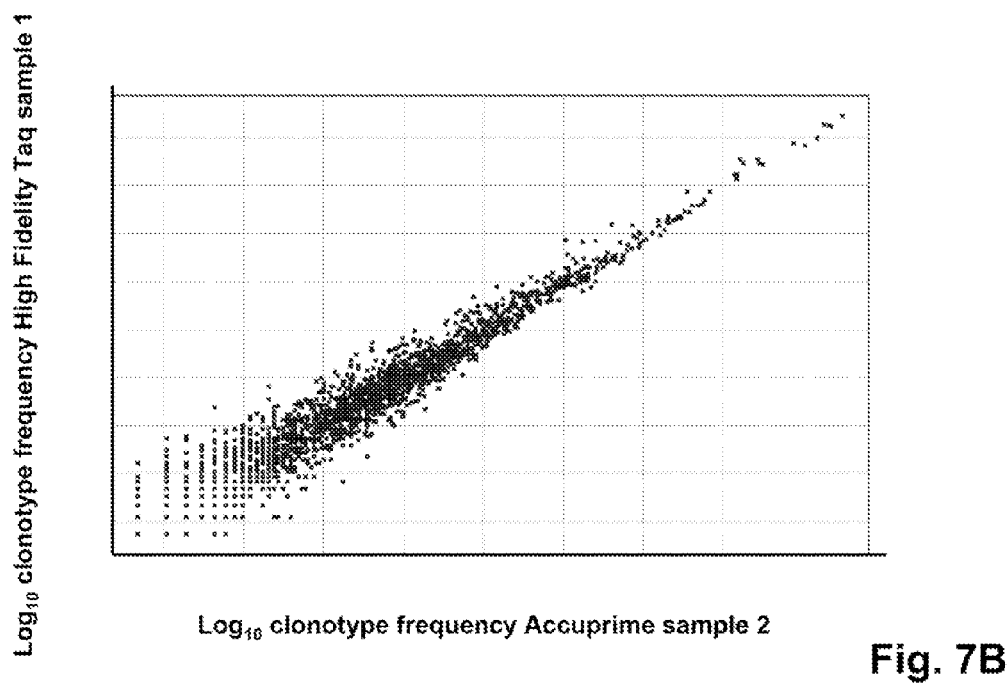
FIG. 7B depicts the log10 of the frequency of each clonotype using cDNA corresponding to 500 ng of RNA as input template and Accuprime (X axis) or High fidelity Taq (Y axis).

In FIGS. 5A-5C, identical sequences in each sample were identified. Then to deal with sequencing errors some clonotypes were coalesced to form larger clonotypes using the general approaches described in the section of primary analysis of sequence. The counts of clonotypes were then computed in each sample. A fraction of the clonotypes (not shown in the figure) were present in one sample but not another, likely due to the algorithm coalescing them with another clonotype in one sample but not the other. The frequency of clonotypes in a sample is then computed as its number of counts divided by the total number of reads obtained for that sample. For example if 1,000 counts are observed for a clonotype in a sample with 1,000,000 reads, its frequency is computed as 0.1%. FIG. 7A shows the $\log_{10}$ of the frequency of each clonotype in the two duplicate samples using Accuprime and cDNA corresponding to 500 ng of RNA as input template. The correlation ($r^2$) between these duplicates is 0.944. FIG. 7B depicts the $\log_{10}$ of the frequency of each clonotype using cDNA corresponding to 500 ng of RNA as input template and Accuprime (X axis) or High fidelity Taq (Y axis). There are 4 comparisons with this combination with a median correlation $r^2$=0.931. The one shown in the figure has $r^2$=0.929. FIG. 7C shows the $\log_{10}$ of the frequency of each clonotype using cDNA corresponding to 50 ng of RNA as input template and Accuprime (X axis) or High fidelity Taq (Y axis). The observed correlation r2=0.924.

EXAMPLE 3

IgH repertoire Analysis: Amplification and Sequencing Strategy

In this example, three primers are used to amplify V regions of IgH molecules. Preferably, the primers are in regions avoiding the CDRs, which have the highest frequency of somatic mutations. Three different amplification reactions are performed. In each reaction, each of the V segments is amplified by one of the three primers and all will use the same C segment primers. The primers in each of the separate reactions are approximately the same distance from the V-D joint and different distances with respect to the primers in different reactions, so that the primers of the three reactions are spaced apart along the V segment. Assuming the last position of the V segment as 0, then the first set of primers (frame A) have the 3' end at approximately −255, the second set (frame B) have the 3' end at approximately −160, and the third set (frame C) have the 3' end at approximately −30. Given the homology between several V segments, to amplify all the 48V segments and the many known alleles (as defined by the international ImMunoGeneTics information system <<http://imgt-.cines.fr/>>) 23, 33, and 32 primers in the A, B, and C frames respectively, is needed. The list of primers are shown in Tables 2, 3, and 4.

TABLE 2

Frame A Primers

| Segment | Sequence | SEQ ID NO |
|---|---|---|
| IGHV1_1 | CCTCAGTGAAGGTCTCCTGCAAGG | 40 |
| IGHV1_2 | CCTCGGTGAAGGTCTCCTGCAAGG | 41 |
| IGHV1_3 | CCTCAGTGAAGGTTTCCTGCAAGG | 42 |
| IGHV1_4 | GGGCTACAGTGAAAATCTCCTGCAAGG | 43 |
| IGHV2_1 | AAACCCACACAGACCCTCACGCTGAC | 44 |
| IGHV2_2 | AAACCCACAGAGACCCTCACGCTGAC | 45 |
| IGHV2_3 | AAACCCACACAGACCCTCACACTGAC | 46 |
| IGHV3_1 | CTGGGGGGTCCCTGAGACTCTCCTG | 47 |
| IGHV3_2 | CTGGGGGGTCCCTTAGACTCTCCTG | 48 |
| IGHV3_3 | CAGGGCGGTCCCTGAGACTCTCCTG | 49 |
| IGHV3_4 | CAGGGCCGTCCCTGAGACTCTCCTG | 50 |
| IGHV3_5 | CTGGGGGGTCCCTGAAACTCTCCTG | 51 |
| IGHV3_6 | CTGGCAGGTCCCTGAGACTCTCCTG | 52 |
| IGHV3_7 | CTGGAGGGTCCCTGAGACTCTCCTG | 53 |
| IGHV3_8 | CTGGGAGGTCCCTGAGACTCTCCTG | 54 |
| IGHV3_9 | TGGGGGGGCCCTGAGACTCTCCT | 55 |

TABLE 2-continued

Frame A Primers

| Segment | Sequence | SEQ ID NO |
|---|---|---|
| IGHV4_1 | CTTCGGAGACCCTGTCCCTCACCTG | 56 |
| IGHV4_2 | CTTCGGACACCCTGTCCCTCACCTG | 57 |
| IGHV4_3 | CTTCACAGACCCTGTCCCTCACCTG | 58 |
| IGHV4_4 | CTTCGGAGACCCCGTCCCTCACCTG | 59 |
| IGHV4_5 | CGGGGACCCTGTCCCTCACCTG | 60 |
| IGHV5_1 | GATCTCCTGTAAGGGTTCTGGATACAGCT | 61 |
| IGHV6 | TCGCAGACCCTCTCACTCACCTGTG | 62 |

TABLE 3

Frame B Primers

| Segment | Sequence | SEQ ID NO |
|---|---|---|
| IGHV6 | TGGATCAGGCAGTCcCCATCGAGAG | 63 |
| IGHV5_1 | GCTGGGTGCGCCAGATGCCC | 64 |
| IGHV2_1 | TGGATCCGTCAGCCCCCAGG | 65 |
| IGHV2_2 | TGGATCCGTCAGCCCCCGGG | 66 |
| IGHV1_1 | GTGCGACAGGCCCCTGGACAA | 67 |
| IGHV1_2 | GGGTGCGACAGGCCACTGGACAA | 68 |
| IGHV2_3 | GTGCGCCAGGCCCCCGGACAA | 69 |
| IGHV1_4 | GGGTGCGACAGGCTCGTGGACAA | 70 |
| IGHV1_5 | GGGTGCAACAGGCCCCTGGAAAA | 71 |
| IGHV1_6 | GGGTGCGACAGGCTCCTGGAAAA | 72 |
| IGHV1_7 | GTGCGACAGGCCCCCGGACAA | 73 |
| IGHV1_8 | GTGCGACAGGCCCCCAGACAA | 74 |
| IGHV4_1 | TCCGCCAGCCCCCAGGGAAGG | 75 |
| IGHV4_2 | TCCGGCAGCCCCCAGGGAAGG | 76 |
| IGHV4_3 | TCCGGCAGCCACCAGGGAAGG | 77 |
| IGHV4_4 | TCCGCCAGCACCCAGGGAAGG | 78 |
| IGHV4_5 | TCCGGCAGCCCGCCGGGAA | 79 |
| IGHV4_6 | TCCGGCAGCCGCCGGGAA | 80 |
| IGHV4_7 | TCCGGCAGCCCGCTGGGAAGG | 81 |
| IGHV4_8 | TCCGCCAGCCCCTAGGGAAGG | 82 |
| IGHV3_1 | GGTCCGCCAGGCTCCAGGGAA | 83 |
| IGHV3_2 | GTTCCGCCAGGCTCCAGGGAA | 84 |
| IGHV3_3 | GGTCCGCCAGGCTTCCGGGAA | 85 |
| IGHV3_4 | GGTCCGTCAAGCTCCGGGAA | 86 |
| IGHV3_5 | GATCCGCCAGGCTCCAGGGAA | 87 |
| IGHV3_6 | GGTCCGCCAAGCTCCAGGGAA | 88 |
| IGHV3_7 | GGTCCGCCAGGCTCCAGGCAA | 89 |

TABLE 3-continued

Frame B Primers

| Segment | Sequence | SEQ ID NO |
|---|---|---|
| IGHV3_8 | GGTCCGCCAGGCTCCAGGCAA | 90 |
| IGHV3_9 | GGTCCGCCAGGCTCCGGGCAA | 91 |
| IGHV3_10 | GGGTCCGTCAAGCTCCAGGGAAGG | 92 |
| IGHV3_11 | CTGGGTCCGCCAAGCTACAGGAAA | 93 |
| IGHV3_12 | GGTCCGCCAGCCTCCAGGGAA | 94 |
| IGHV3_13 | GGTCCGGCAAGCTCCAGGGAA | 95 |

TABLE 4

Frame C Primers

| Segment | Sequence | SEQ ID NO |
|---|---|---|
| GHV7 | CTAAAGGCTGAGGACACTGCCGTGT | 96 |
| GHV6 | CTCTGTGACTCCCGAGGACACGGCT | 97 |
| IGHV5_1 | AGTGGAGCAGCCTGAAGGCCTC | 98 |
| IGHV2_1 | TGACCAACATGGACCCTGTGGACAC | 99 |
| IGHV1_1 | ACATGGAGCTGAGCAGCCTGAGATC | 100 |
| IGHV1_2 | ACATGGAGCTGAGCAGGCTGAGATC | 101 |
| IGHV1_3 | ACATGGAGCTGAGGAGCCTGAGATC | 102 |
| IGHV1_4 | ACATGGAGCTGAGGAGCCTAAGATCTGA | 103 |
| IGHV4_1 | GAGCTCTGTGACCGCCGCGGAC | 104 |
| IGHV4_2 | GAGCTCTGTGACCGCCGTGGACA | 105 |
| IGHV4_3 | GAGCTCTGTGACCGCTGCAGACACG | 106 |
| IGHV4_4 | GAGCTCTGTGACCGCTGCGGACA | 107 |
| IGHV4_5 | GAGCTCTGTGACTGCCGCAGACACG | 108 |
| IGHV4_6 | GAGCTCTGTGACTGCAGCAGACACG | 109 |
| IGHV4_7 | GAGCTCTGTGACTGCCGCGGACA | 110 |
| IGHV4_8 | GAGCTCTGTGACCGCGGACGCG | 111 |
| IGHV4_9 | GGCTCTGTGACCGCCGCGGAC | 112 |
| IGHV4_10 | GAGCTCTGTGACCGCCGCAGACA | 113 |
| IGHv4_11 | GAGCTCTGTGACCGCTGACACGG | 114 |
| IGHV3_1 | CAAATGAACAGCCTGAGAGCCGAGGACA | 115 |
| IGHV3_2 | CAAATGAACAGCCTGAAAACCGAGGACA | 116 |
| IGHV3_3 | CAAATGAACAGTCTGAAAACCGAGGACA | 117 |
| IGHV3_4 | CAAATGATCAGCCTGAAAACCGAGGACA | 118 |
| IGHV3_5 | CAAATGAACAGTCTGAGAACTGAGGACACC | 119 |
| IGHV3_6 | CAAATGAACAGTCTGAGAGCCGAGGACA | 120 |
| IGHV3_7 | CAAATGAACAGCCTGAGAGCTGAGGACA | 121 |
| IGHV3_8 | CAAATGAGCAGCCTGAGAGCTGAGGACA | 122 |

TABLE 4-continued

Frame C Primers

| Segment | Sequence | SEQ ID NO |
|---|---|---|
| IGHV3_9 | CAAATGAACAGCCTGAGAGACGAGGACA | 123 |
| IGHV3_10 | CAAATGGGCAGCCTGAGAGCTGAGGACA | 124 |
| IGHV3_11 | CAAATGAACAGCCTGAGAGCCGGGGA | 125 |
| IGHV3_12 | CAAATGAACAGTCTGAGAGCTGAGGACA | 126 |
| IGHV3_13 | CAAATGAGCAGTCTGAGAGCTGAGGACA | 127 |

On the C segment side, two sequences with one base difference between them (GCCAGGGGGAAGACCGATGG (SEQ ID NO: 128), and GCCAGGGGGAAGACGGATGG) (SEQ ID NO: 129) cover the four segments and the multiple known alleles of IgG. A scheme similar to the two stages of PCR for TCRβ genes is used.

On the V side, the same 5' 14 bp overhang on each of the V primers is used. In the secondary PCR, the same Read2-tagX-P7 primer on the V side is employed. On the C side a strategy similar to that used with TCRβ amplification is used to avoid variants among the different IgG segments and their known alleles. The primer sequence (AATGATACGGCGACCAC-CGAGATCTGGGAAGACGATGGGCCCTTGGTGGA) (SEQ ID NO: 130) comprises the sequence of the C segment from positions 3-19 and 21-28 and it skips position 20 that has a different base in at least one of the different IgG alleles and the sequence for P5 that is can be used for formation of the clusters as shown in FIG. 4A.

A multiplexed PCR using three pools of primers corresponding to the three frames was carried out using cDNA as a template. After primary and secondary PCRs, the products were run on an agarose gel. Single bands with the appropriate relative sires were obtained from the three pools.

In one embodiment, three different reactions from a single sample are mixed at equimolar ratio and subjected to sequencing. Sequencing is done from both directions using the two Illumina primers, such as described above. 100 bp is sequenced from each side. The maximal germ line sequences encompassing the D-J segments are ~30 bp longer for BCR than TCR. Therefore if the net result of nucleotide removal and addition at the joints (N and P nucleotides) generate a similar distribution for IgH and TCRβ, on average 90 bp and maximally 120 bp of sequence after the C segment is sufficient to reach the 3' of the V segment. Therefore, in most cases, the sequence from the C primer is sufficient to reach the V segment. Sequencing from one of the Illumina adapters identifies the V segment used as well as somatic hypermutations in the V segments. Different pieces of the V segments are sequenced depending on which of the three amplification reactions the sequence originated from. The full sequence of the BCR, can be aligned from different reads that originated from different amplification reactions. The sequencing reaction from the one end showing the full CDR3 sequence greatly facilitates the accurate alignment of different reads.

EXAMPLE 4

TCR and IgH Repertoire Analysis in SLE Patient Samples

It will first be tested whether there are clonotypes that correlate with disease activity in patients.

Second, a set of sequence characteristics and/or cell surface markers that distinguish clonotypes that correlate with disease from those that do not is defined. Third, the degree to which clonotype analysis provides clinically useful information is measured, such as the correlation with short term (e.g. 3 month) outcome.

1. Presence of Clonotypes Correlating with Disease

There is two main tasks: identifying correlating clonotypes and measuring disease activity from their level. These tasks can be done in a clinical setting in two steps for each patient:

1) A Calibration test can be done to determine the identity of the correlating clonotypes for the specific patient. This can be done by sequencing IgH and TCRβ RNA (or linked TCRα-TCRβ sequence from a single cell) for each patient at a time of a peak of an episode, at which time the correlating clonotype level can reach their highest levels.

2) A Monitoring test can be done to determine the level of the correlating clonotypes at a time point subsequent to the calibration test. This can be done by sequencing IgH and TCRβ RNA and determining the level of the specific correlating clonotypes that had been identified in the calibration sample of the same patient. The level of the correlating clonotypes is used to compute the disease activity at these points.

Amplification, sequencing, and primary analysis development as described above is used to assess patient samples. Specifically, a set of systemic lupus erythematosus (SLE) patients is assessed that have a one year follow up period and serial blood samples during this period. These patients were seen By Dr. Michele Petri at Johns Hopkins Medical School every three months for one year, and clinical measures of disease activity including Systemic Lupus Erythematosus Disease Activity Index (SLEDAI). Physician Global Assessment (PGA), as well as multiple lab tests including C3 (Complement 3) and anti-ds DNA levels are available for all visits of all patients. Drugs being administered to the patients, include prednisone, plaquenil. NSAID, NSAIDType, acetylsalicylic acid (ASA) dose, plavix, diuretic. ACE-Inhibitors or angiotensin receptor blockers (ARBs), Ca channel blocker, Triam and, solumedrol. Patients who had at least at one time during the follow up a significant change in disease activity as defined by a 3 points change on the SLEDAI or a 1 point change in PGA is studied. Overall there are 181 patients (with a total of 815 blood samples) who fit these criteria. RNA from all these blood samples is subjected to multiplex PCR using primers described above to amplify the sequences that encompass CDR3 in IgH and TCRβ. All the amplified materials is sequenced (to a million reads) and the abundance of different clonotypes is determined.

Using the clinical data, sequencing, characteristics that distinguish clonotypes whose level correlate with disease activity from those that do not is identified. Second, an algorithm to determine disease activity using the blood IgH and TCRβ profile is developed.

2. Identification of Characteristics of Correlating Clonotypes

It is anticipated that clonotypes that are relevant to the disease is increased at the time of high disease activity. However, not all enriched clonotypes at a point of high disease activity necessarily correlate with disease. For example, in a particular patient there might be 10 enriched clonotypes at the point of high disease activity, but only 5 correlate with the disease. In order to identify these relevant clonotypes, a subset of clonotypes that are clearly correlating with disease and another set that clearly do not correlate with disease is studied. Characteristics that distinguish those two classes of clonotypes is investigated.

All patients will have at least one significant change in disease activity during the one year follow up in this experimental design. The IgH and TCR clonotypes obtained at the peak of disease activity in each patient is analyzed. Sets of correlating and not correlating clonotypes among those with the highest level clonotypes is selected. Hence the first step is to define clonotypes that are at a high level. The specific criteria to choose the clonotypes that will enter the analysis will include a combination of frequency rank of the clonotype and the level of clonotype (number of clonotype reads per million), as well as evidence the clonotype does not belong to the distribution of low frequency clonotypes.

This set of clonotypes from each patient sample, termed High Prevalent Clonotypes (HPC) is further analyzed. The correlation of the level of each of these clonotypes with clinical measures is evaluated. The correlation of SLEDAI score with the clonotype level is computed. For each patient there is 4-5 study points that can be used to assess the correlation of SLEDAI with the level of each HPC. The distribution of these obtained correlations is investigated. It is anticipated that most of the HPCs will have low correlation with SLEDAI. It is investigated whether at the high correlation end there is an excess to what is expected to be generated randomly. For example with 4 and 5 data points it is expected that ~2.5% and ~0.6% of the correlation levels ($r^2$) is >0.9 by chance. A higher proportions of HPCs with $r^2$>0.9 indicates the presence of a clonotypes that correlate with disease. In addition to comparing the number of correlating clonotypes with random expectation, a permutation analysis is performed where the correlation of SLEDAI scores from one patient and the level of individual HPCs from another is calculated. The distribution of correlations generated from this permutation can be used as the "background" correlation. (To ensure its validity, it is confirmed that there is little correlation between SLEDAI between different patients). Excess correlation at the high correlation end, e.g., $r^2$>0.9 will indicate the presence of clonotypes that correlate with disease. The highest correlating clonotypes as the set of correlating clonotypes is picked. Because the number of HPCs that has a by chance correlation higher than a set threshold is known (from calculation using random assumption or through the permutation analysis described above), the threshold to define the correlating clonotype can be set in such a way as to have 10% false discovery rate, i.e. 10% of the correlating clonotypes set is correlating by chance. A set of HPCs that have very little correlation with SLEDAI score is picked. Those will serve as the set of non-correlating clonotypes. These 2 sets of clonotypes can be further analyzed to identify characteristics that may distinguish them. These characteristics can then be looked for in new samples to identify the clonotypes likely to be correlating with disease activity in these samples. The blood levels of these clonotypes can then be followed to determine disease activity.

One complication arises from the premise that clonotype level may change before disease activity does. Hence it is possible that by attempting to study only HPCs that highly correlate with SLEDAI, clinically useful clonotypes that change earlier than SLEDAI may be eliminated. Another set of clonotypes is picked that correlate with a Modified SLEDAI (MSLEDAI) score. MSLEDAI is the same as SLEDAI in all the study points except those just before a significant change. For those data points the MSLEDAI score is the average between the SLEDAI score at that point and the next study point. Clonotypes that change before SLEDAI are likely to show better correlation to MSLEDAI than SLEDAI. It is informative to compute the excess number of HPCs that have high correlation with MSLEDAI than expected by random or permutation generated expectations.

Characteristics that distinguish correlating clonotypes from those that do not correlate will then be identified. The analysis is done in the exact manner for those clonotypes that correlate with SLEDAI or MSLEDAI. In either case the goal would be for these set of characteristics to correctly recapitulate this classification enabling the identification of correlating clonotypes in the next set of samples. It is expected that each patient will have a unique set of correlating clonotypes, but the training study is designed to generate the rules that predict the correlating clonotypes from a calibration sample (at high disease activity). Two general types of parameters can be tested: those that are obtained from the sequencing data itself, and those that can use extra experimentation. Extra experimentation can include the assessment of different cells with different cell surface or other markers. Here are a few types of parameters that is investigated: 1) Sequence motif: The motif can be a specific V or J region, a combination VJ, or short sequences in DJ region that is associated with a clonotype being correlating. 2) Size of the clonotype. 3) Level: Absolute level (number of reads per million) or rank level. 4) Similarity to other clonotypes: The presence of other highly related clonotypes, like those with silent changes (nucleotide differences that code for same amino acids) or those with conservative amino acid changes. 5) For the BCRs the level of somatic mutations in the clonotype and/or the number of distinct clonotypes that differ by somatic mutations from some germ line clonotypes.

Each of these parameters is individually studied for association with correlating clonotypes. A threshold of 0.05 (uncorrected for multiple testing) is set to eliminate factors that are not likely to contribute to prediction of correlating clonotypes. Given the multiple parameters, many tests is performed to generate multiple positive results by chance. However the main goal of this step is to filter the parameters to a smaller set. The set of positive parameters will then be used to create an algorithm to classify the two sets of clonotypes. A machine learning algorithm is employed that uses the different parameters to classify the two sets of clonotypes. In order to minimize the risk of overfitting, the cross validation technique is used. Using this algorithm each clonotype will get a score that corresponds to the likelihood it is a correlating clonotype. A threshold will then be placed to classify clonotypes above it as correlating and those below it as non-correlating. The accuracy of the classification can be estimated by the cross validation technique; for example, the clonotypes are put in equal groups and the algorithm using all clonotypes except one group. Clonotypes in the last group (test group) are then classified using the algorithm that was obtained using the rest of the clonotypes. This is iterated as many times as the number of groups, and in each iteration all the groups except one are used for training and one group is classified. The accuracy of the algorithm can be estimated from the average accuracy of the different classifications in the different iterations. It is of note that in all these iterations the exact algorithm would be slightly different. The accuracy of classification is then an estimate as it is not on the final algorithm but rather on a set of related algorithms generated with training data from all clonotypes except one.

Ultimately, two algorithms is generated trained on two different correlating clonotypes sets: one correlating with SLEDAI and the other correlating with MSLEDAI. Even if the clonotypes in the training set are different the resulting algorithm may or may not be very different, depending on whether these clonotypes indeed come from two distinct populations. The algorithms is compared. Additionally these algorithms is used to identify correlating clonotypes that were not initially in the training set. The clonotypes identified in the two algorithms is compared, and if the initial clonotypes in the two training sets were from the same population, the identified clonotypes are likely to be very similar. Unless the results of the algorithm were quite similar, both algorithms is carried to identify correlating clonotypes in order to measure lupus disease activity.

Other experimental approaches can add to the power of sequencing in identifying clonotypes that correlate with diseases. Correlating clonotypes may be enriched in cells with some surface or other markers. For example B cells with high levels of CD27 are known in active lupus patients, and hence it might be that correlating clonotypes might be enriched in the CD27 population of cells. If that is borne out to be true, prediction of correlating clonotypes can be improved by doing an enrichment for cells with high levels of CD27. Specifically, a sequencing reaction can be performed on the IgH sequences from all B cells in the blood sample as well as from those B cells with high CD27. Correlating clonotypes are expected to be present at higher frequency in the high CD27 population than in the all blood sample.

3. Using IgH and TCRβ Profiles to Determine Lupus Disease Activity

The section above described clonotype-based analysis to identify features of correlating clonotypes. In addition, for that analysis only a fraction of all the HPCs were used to clearly designate clonotypes as correlating or non-correlating. This section describes analysis that is at the patient level aiming to compute a measure of disease activity, to be called AutoImm (AI) score. The algorithm developed per the above section is applied to identify correlating clonotypes among all the HPCs. The level of these correlating HPCs is determined. The level of the correlating clonotypes can be normalized to the total number of TCR clonotypes as well as to HPCs predicted not to correlate with disease. The level of these correlating clonotypes at different time points is used to compute AI score at these different points.

In patients with more than one correlating clonotypes, the information regarding the level of these different clonotypes is combined. In addition data from IgH and TCRβ clonotypes is integrated. Different algorithms for making the combination is attempted. For example, the average, median, sum, and highest correlating clonotype level is studied. The clonotype level can be its simple linear read counts, the logarithm of that or some other conversion. It can potentially be the difference between correlating and non-correlating clonotypes. Furthermore methods for weighted average can be utilized. The weighting can be based on the likelihood of a clonotype to be correlating.

In order to evaluate which of the models is optimal, all the models is assessed to identify the one that generates the highest correlation between the AI score and the SLEDAI score. For this analysis the correlation of SLEDAI and AI scores is done across all the data obtained from all the study points from all patients. In order to estimate and ameliorate the degree of overfitting, the cross validation technique is used. The level of correlation measured reflects the "cross sectional" relationship between the AI and SLEDAI scores. In addition to SLEDAI, the correlation with other clinical measures like C3 and anti-ds DNA antibody levels as well as urine protein/serum creatinine for patients with kidney manifestation and blood counts for patients with hematological involvement is studied. The correlation may be due to the classification of patients into high and low disease activity, and is not necessarily a reflection of AI correlating with SLEDAI score within a patient. To demonstrate that, "longitudinal" assessment is done.

4. Longitudinal Analysis

In the longitudinal analysis, two general questions is assessed: does AI score at one study point predict disease activity at the same point, and does AI score at one study point predict disease activity at a later point, e.g., the next study point 3 months later.

The relationship between AI and SLEDAI scores at the same study point is assessed in two ways. First the correlation of the AI and SLEDAI in each patient is calculated, and then the average and median patient correlation level is computed. If the correlation seen in cross sectional analysis above is due to classification of high and low disease activity patients and not changing disease activity within individual patients, then the longitudinal correlation in individual patients is likely to be low. A high median patient correlation level suggests that AI does reflect the SLEDAI score at an individual patient level. In addition to the correlation of AI and SLEDAI scores, the correlation of AI with other relevant measures like C3 and anti-ds DNA antibody is assessed as well as urine protein/serum creatinine for patients with kidney manifestation and blood counts for patients with hematological involvement.

Another way to demonstrate the ability of AI score to measure disease activity changes in individual patients is by determining its accuracy in distinguishing states of high from low disease activity in the same patients. For each of the 181 patients, the two study points when the SLEDAI where at the highest (to be called HDAP for high disease activity point) and lowest levels (to be called LDAP for low disease activity point) is selected. The distribution of the AI of all the HDAPs with that of the AI of all the LDAPs is compared, and the p-value that they are different is computed. In addition, the frequency that the AI at HDAP is higher than LDAP in each patient is assessed. If AI does not change with disease activity in an individual patient then it is expected that AI at HDAP is higher than that at LDAP only 50% of times. Another analysis is done where the fraction of times that AI at HDAP is higher than that at LDAP by a meaningful difference (i.e., above the likely AI variation) is determined. To measure the fluctuation of AI, all the study points from all the patients is used, and the standard deviation (and relative standard deviation) of AI in the different bins of SLEDAI values can be computed. This will generate relative standard deviation across all patients (AI-RSDall) and this value may or may not be dependent on SLEDAI (i.e. the AI-RSDall may be different at different SLEDAI values). The proportion of patients where AI at HDAP is higher than AI at LDAP by a specific number (e.g., 2) of AI-RSDall can be computed. There can be some systematic bias where the computed AI in some patients is consistently higher (or lower) than what is expected from the SLEDA score. Therefore AI-RSDall is a combination of the intrinsic fluctuation of AI within a patient as well as the systematic difference of AI for patients with similar SLEDAI. The intrinsic fluctuation of AI can be computed within a patient by calculating the standard deviation (and relative standard deviation) of AI scores among study points with similar SLEDAI values (<2 points difference) within a patient. The median among all the patients of the relative standard deviation can be computed (AI-RSDpt-med). The proportion of patients where AI at HDAP is higher than AI at LDAP by a specific number (e.g., 2) of AI-RSDpt-med can then be evaluated.

After demonstration that AI does indeed fluctuate with SLEDAI within individual patients it is evaluated whether AI can predict SLEDAI at the next study point, 3 months later. To assess that correlation level between the AI score at time 0 and the SLEDAI score at time +3 months can be quantitated. The correlation can be computed on a patient level and then the median patient correlation can be obtained. Another way to demonstrate the ability of AI to predict near future disease activity is to evaluate the sensitivity and specificity of AI in predicting disease activity 3 months in the future. Clinically, those patients who are doing well on their current management can be distinguished from those that do not. A patient state at a particular time is classified into one of two classes: Poor Control (PC) and include patients who in 3 months will have high disease activity (SLEDAI>6 points) and/or a flare (SLEDAI increase by 3 points), and Good Control (GC) and include patients who in 3 months will have low or moderate with disease activity (SLEDAI <6) and/or a significant reduction in disease activity (SLEDAI decrease by 3 points). The classification sensitivity can then be evaluated and specificity obtained using different thresholds of AI. A ROC curve that describes the performance of AI in predicting the state of the patient (PC or GC) can be generated 3 months ahead of time. The performance obtained by this test is compared with that of standard clinical measures including SLEDAI, anti-ds DNA and C3 levels.

An analysis to evaluate the ability of AI to predict changes in SLEDAI scores 3 months later will also conducted. Using data from all study points of all patients, the relationship between AI and SLEDAI scores can be plotted to identify the "cross sectional" correlation level as discussed above. This determines the relationship between SLEDAI and AI at the same study point. This relationship is fit with an equation allowing the prediction of the SLEDAI score given an AI score (or vice versa). If AI predicts flares then changes in SLEDAI at some study point 1 is preceded by changes in AI at point 0. Therefore, if a flare occurs between point 0 and 1, the AI score at point 0 (to be called AImeas) is higher than what is expected (to be called AIexp) given the SLEDAI at study point 0. On the other hand with no change in disease activity between the study point 0 and study point 1, the AI score at point 0 is very similar to what is expected given the SLEDAI at study point 0. The relative AI change (Rel-AI-diff) can be computed by dividing the difference of AImeas and AIexp by AImeas. The sensitivity and specificity of AI in predicting a significant change in SLEDAI 3 months later can be evaluated by using different thresholds of Rel-AI-diff. The thresholds can be bidirectional so if the Rel-AI-diff at a specific study point is higher than a specific threshold a flare is predicted, and similarly if it is lower than the negative of the specific threshold a significant reduction in SLEDAI is expected. On the other hand when the Rel-AI-diff at a study point is between the threshold and its negative, no significant changes in disease activity is expected. A ROC curve showing the trade of sensitivity and false positives can be generated using many different thresholds of Rel-AI-diff. Similar ROC curves can be generated using standard clinical measures including SLEDAI, anti-ds DNA and C3 levels.

If the fluctuation of AI varies at different SLEDAI values, the above analysis is refined. A section above described the computation of AI-RSDall and AI-RSDpt-med and mentioned evaluating whether they change at different SLEDAI values. If they do then the ROC analysis can be done as described above but instead of using different thresholds of Rel-AI-diff, different thresholds of AI-RSDall and AI-RSDpt-med is used. The performance obtained by the test with that of standard clinical measures including SLEDAI, anti-ds DNA and C3 levels is compared.

In the above analysis, attempts are made to predict the SLEDAI at point 1 from the AI score at point 0. It is likely that in addition to the absolute level at point 0, the change of AI from point −1 to 0 is informative in predicting SLEDAI at point 1. For example consider a patient who has at study point −1 an AI score of X-I, and at point 0 the AI score is increased to a new value X0 that is appreciably higher than X-I. This patient may have higher likelihood of a flare at point 1 than a patient whose AI has been stable at X0 at study points −1 and 0. This concept of AI change or velocity is incorporated to generate a Modified AI (MAI) score. To generate a MAI at point 0 the AI score at point −1 and at point 0 is needed, and hence one data point per patient will not have an MAI associated with it. The specific formula to incorporate the velocity into AI calculation to obtain MAI is optimized. This optimization may be done through maximization of the correlation of MAI and SLEDAI three months later. The cross validation design is used to evaluate and control the degree of overfitting. Correlation can be done for data points of all samples, but also can be done at a patient level and the median correlation among all patients can be assessed. The latter approach ameliorates the issue of some patients having a systematic bias of too low or too high AI score. Using MAI, the same type of ROC analysis that was mentioned for AI can be performed to assess its ability to predict SLEDAI 3 months later. First, analogously to what is described for AI, an analysis can be done to show the ability of MAI at point 0 to distinguish PC and GC states at point 1. Additionally, an analysis similar to what was described for AI to assess the ability of MAI at point 0 can be performed to predict significant disease activity change (3 points change on SLEDAI) between points 0 and 1. For this latter analysis different thresholds of Rel-AI-diff. AI-RSDall or AI-RSDpt-med can be used. The performance of MAI is compared with that of AI to determine whether the addition of the velocity factor is useful.

One complication of the described study is that treatment changes are done for different patient during the follow up period of the study. This is likely to complicate the prediction of disease activity. For example, consider two patients with the same AI score at point 0 and one of those patients had a reduction in medication at the same time. The likelihood of this patient to have a rise in disease activity at point 1 is then likely to be higher than for the patient who did not change medications at point 0. This is likely to lead to underestimation of the performance of AI. One way to alleviate that is to eliminate all the points with significant medication changes from the study. Another is to modify the AI score to include whether a patient has a medication change and create a medication-modified AI. So in the example above with the two patients, the one with the medication change will have a higher medication-modified AI.

5. Integration with other Predictive Markers

The predictive ability of the disease activity marker can be maximized. Therefore the predictive ability of the TCR/BCR repertoire information integrated with other markers is tested. These markers include standard markers used in the clinic like anti-ds DNA and C3 levels. It will also include other markers that are published. For example a panel of chemokines has already been shown to have some predictive ability using the same set of patients as is used. Whether this panel will increase the predictive ability of the TCR and BCR repertoire is evaluated. The first step is to integrate the AI score with the additional measure to generate an Expanded AI (EAI) score. Different ways to do the integration can be assessed, and this can be optimized through maximization of the correlation of EAT and SLEDAI three months later. The cross validation design is used to evaluate and control the degree of overfitting. Using EAI the ability to predict disease activity 3 months later is assessed by its ability to distinguish GC from PC and to predict changes in disease activity. The performance in measuring disease activity and change in disease activity can be described through ROC analysis as described above.

6. Validation

The number of variables being tested is high compared with the number of samples. This can lend itself to overfitting, with initially promising results not being able to be validated in later studies. A cross validation approach is used in the training to get a measure of the extent of overfitting. However, a validation on an independent set of samples is involved in later work. This is not part of this proposal, but this marker can be clinically applicable. Using the data obtained above, it can be determined whether AI, MAI, or EAI, should be validated and the specific way to compute the measure of interest. One specific algorithm is taken for validation. In addition one or more specific endpoints is specified. The sensitivity and specificity of AI can be assessed in the ability to distinguish GC from PC 3 months later to evaluate the ability of AI to predict disease activity. In another example the sensitivity and specificity of AI to predict significant disease activity change in 3 month using a specific Rel-AI-diff threshold can be assessed.

EXAMPLE 5

Measuring Response of an SLE patient to Drug Therapy

The methods of the provided invention is used to measure the response of an SLE patient to drug therapy. Determination of whether an SLE patient being given an expensive drug with serious side effects is responding to the drug plays a role in both patient care and also for making the administration of such care cost effective. Many clinical indicators of disease activity respond to treatment imprecisely and after a time lag of up to several months. During this time, disease may progress and side effects may add complications to therapy. A prompt understanding of the drug response would allow patients to be switched to more effective therapies more rapidly.

In this Example, a 35 year old African American female with a prior diagnosis of lupus presents to her regular rheumatologist. The patient's disease status is assessed on a quarterly basis through a comprehensive clinical assessment in addition to laboratory testing including measurement of C3, anti-ds DNA antibody levels, blood counts, and urinalysis. During one visit the patient complains of skin lesions and fatigue, and urinalysis shows evidence of proteinuria and/or cell casts. The rheumatologist refers the patient to a nephrologist for a kidney biopsy to assess inflammatory status of the kidney and orders serum creatinine and 24 hour urine protein to creatinine ratio to assess the degree of the impairment of the kidney function. A kidney biopsy shows evidence of diffuse lupus nephritis, while the urine protein to creatinine test reveals evidence of nephrotic syndrome (urine protein to creatinine ratio of 3.6). Based on this information a diagnosis of acute lupus nephritis is given and the patient is begun on a course of drug therapy. There are several possible drugs that can be chosen at this point. Immunomodulators such as mycophenolate mofetil (Cellcept) are often used although sometimes in severe cases drugs such as Methotrexate, Azathiopurine (Imuran) Cyclophosphamide (cytoxan), are prescribed. Rituximab (Rituxan) is also sometime used as a second or third choice. One of these drugs is often used in combination with a systemic steroid such as Prednisone or methylprednisolone in order to suppress the acute symptoms. Here, mycophenolate mofetil is prescribed at 150 mg per day alongside 60 mg of prednisone. Given the many side effects of steroids, including the risk of osteoporosis, hyperglycemia, weight gain, and other Cushingoid symptoms in the long term, the patient's prednisone dose is tapered over ~6 weeks if the clinical picture allows that.

The first question that is determined is whether the patient is responding to therapy, and as a result, can the dose of steroid can be appropriately decreased. Therefore, during this period the patient's serum creatinine as well as urine protein and creatinine are followed to ensure the patient is responding to the medications. Frequent kidney biopsy can be done to detect whether the inflammatory damage is being reversed; however, routine use of kidney biopsy carries too great a risk and is too invasive to be practical. Current blood based markers that are being used to assess inflammatory status are of limited use in making this decision in that they are not sufficiently well correlated with underlying disease to be relied upon to risk the increased side effects that accompany high doses of steroids. Scrum and urine function markers may have some delay in detecting improvement in inflammatory status and hence steroids may be tapered before these markers show a definitive change and hence extending the period of the renal flare. A slower taper, informed by more sensitive markers, in these cases could have shortened the flare period preventing further damage to kidney tissue. After the reduction of steroid to a maintenance dose of approximately 10 mg the patient may show persistently elevated levels of protein in the urine and the high urine protein to creatinine ratio of 2, and the physician must now decide whether to switch from Cellcept to another medication. Arguing in favor of this is the continued evidence of loss of kidney function but without an accurate measure of inflammatory kidney status, it can be difficult to know whether the disease itself is in remission having nevertheless done some level of irreversible kidney damage that is resulting in these persistent levels of proteinuria. Here again the existing blood based markers are imperfectly informative and a further kidney biopsies are not practical. This decision would be greatly aided by an accurate blood based measure of disease status.

AutoImm Load would be very helpful in this situation to assess the response to therapy by measuring disease activity either alone or in combination with other markers of disease activity. An algorithm for AutoImm Load is developed using the study described above. The correlating clonotypes that is used to calculate AutoImm Load is measured using a calibration test. This calibration test is done using blood from a patient at a time of peak disease activity, for example at the start of therapy. The calibration test is performed using blood or alternatively using the tissue that is affected (e.g. kidney biopsy or skin biopsy). At a later time at which the response to therapy is to be assessed, a blood sample is taken and used along with the calibration test to measure AutoImm Load. This is used to make a treatment decision. If the correlating clonotypes are derived from a populations study, there is no need for the calibration test and a blood test at the time at which the response to therapy is to be assessed is sufficient to measure AutoImm Load in order to inform the treatment decision.

EXAMPLE 6

Determination of Appropriate Time to Taper or Stop Therapy for an SLE Patient

The methods of the provided invention can be used to determine the appropriate time to taper or stop therapy for an SLE patient. In addition to the time lag that can be exhibited by the clinical measures of disease activity, a further difficulty lies in the lack of sensitivity of these measurements. Subclinical disease can nonetheless result in a re-flaring of the disease if therapy is tapered too early. As a result of this, courses of immunosuppressant therapy are typically administered for a time period that is much longer than is necessary for the average patient to ensure that the risk of re-flaring is low for the average patient yet may still be long enough for the tail end of distribution. Therefore significant over-treatment, causing side effects and costs are occurring in most patients, while under-treatment of some patients occurs causing potentially preventable re-flares. A method that could measure subclinical activity that was predictive of the risk of re-flaring would allow therapy to be tapered based on such measures instead of relying on overtreatment by design.

In this example, the patient from Example 7 is on prednisone and mycophenolate mofetil for a period of 6 months and urine protein to creatinine ratio returns to a level of 0.5. This level remains above the baseline level expected in healthy individuals but it is not clear that this level is not due to some kidney damage that is not reversible. Other clinical measures of inflammation are normal and the patient does not report any other symptoms. At the same time the patient is experiencing moderate levels of nausea and weight gain as possible side effects to the medications that additionally have serious long term side effects. The doctor is faced with a difficult decision: balancing the fear of tapering the Cellcept and/or steroid too quickly, which could result in renewed kidney inflammation and likely further long term irreversible kidney damage and the adverse reactions that can occur due to the medications. Here again an unambiguous assessment of the disease status without having to perform a kidney biopsy would play a role in making this decision. Attempt of reducing steroids is recommended through repeated trials of steroids leading to the recurrence of the same clinical dilemma. In fact this question arises at every time the patient is in remission and the patient is on steroids or immunomodulators.

AutoImm Load would be very helpful in this situation to assess whether or not to taper therapy by measuring disease activity either alone or in combination with other markers of disease activity. An algorithm for AutoImm Load is developed using the study described above. The correlating clonotypes that is used to calculate AutoImm Load is measured using a calibration test. This calibration test is done using blood from a patient at a time of peak disease activity, for example at the start of therapy. The calibration test could be performed using blood or alternatively using the tissue that is affected (e.g. kidney biopsy or skin biopsy). At a later time at which the level of disease activity is to be assessed, a blood sample can be taken and used along with the calibration test to measure AutoImm Load. This is used to make a treatment decision and to evaluate whether the patient has any detectable disease activity. If the correlating clonotypes are derived from a populations study, there is no need for the calibration test and a blood test at the time at which the response to therapy is to be assessed is sufficient to measure AutoImm Load in order to inform the treatment decision.

EXAMPLE 7

Prediction of Flares in an SLE Patient

One challenge in treating SLE patients is that represented by the fact that flares arise without warning, thus thwarting the physicians' efforts to treat the disease preventively. Waiting for flares to occur before beginning treatment subjects patients to potentially destructive clinical symptoms, can involve expensive and inconvenient hospitalization, and may cause long term organ damage to be done while also necessitating aggressive therapeutic interventions that are themselves fraught with side effects. A much more desirable paradigm would be a therapeutic paradigm in which flares are detected at a subclinical phase at which time therapy could be administered proactively saving significant suffering to the patient, resulting in less expensive hospitalizations and ultimately enabling better long term prognosis for the patients.

The patient from Example 7 is recovering from the acute flare described above, and the patient is tapered off of all therapies except Plaquinil and a low dose of 5 mg of Prednisone. Nevertheless this patient remains at a high risk of having another inflammatory episode. As a result, this patient will remain in the care of a rheumatologist who will continue following patient's clinical symptoms and laboratory tests. Unfortunately these symptoms and tests do not provide early warning for an imminent flare until patients actually have exhibited clinical symptoms of a flare and the sequence repeats itself. A highly specific marker of increasing subclinical activity could be included in the routine clinical assessment of the patient in order to detect unambiguous signs of a flare which may reach a clinically detectable stage within the subsequent 1-3 months. Beginning therapies earlier might make the flare less severe and may allow treatment to be accomplished with less long term organ damage or less steroids used than what is currently the case.

AutoImm Load would be very helpful in this situation to assess the likelihood of an incipient flare by measuring disease activity either alone or in combination with other markers of disease activity. This score either by itself or the rate of increase (velocity) or acceleration of this score can be used to assess the likelihood of progression to a flare. An algorithm for AutoImm Load could be developed using the study described above. The correlating clonotypes that is used to calculate AutoImm Load could be measured using a calibration test. This calibration test could be done using blood from a patient at a time of peak disease activity, for example at the start of therapy. The calibration test could be performed using blood or alternatively using the tissue that is affected (e.g. kidney biopsy or skin biopsy). At a later time at which the response to therapy is to be assessed, a blood sample can be taken and used along with the calibration test to measure AutoImm Load. This can be used to make a treatment decision. If the correlating clonotypes are derived from a populations study, there is no need for the calibration test and a blood test at the time at which the flare risk is to be assessed is sufficient to measure AutoImm Load in order to inform the treatment decision.

EXAMPLE 8

Objective Measure to Assess Subjective Symptoms of SLE Patients

SLE affects many organs and produces many potential symptoms including ones that are very common in the healthy populations. For example, if an SLE patient complains of a headache, the headache may be a sign of CNS lupus or can be due to the common headache. Similarly, if SLE patients complain of worsening fatigue over a period of time, the worsening fatigue may be due to deterioration of their disease or can be due to depression or other causes. The availability of an objective measure that reflects disease activity can be of great help in the management of SLE patients.

The patient in Example 7 presents to the rheumatologist with chief complaints of headache, fatigue, and difficulty with concentration. Patient's headache is recurrent and only transiently gets better with Motrin treatment. The patient's SLE is otherwise in good control. Relevant psychosocial stressors in the patient's life include that she is going through divorce. Physicians are in a dilemma when they face SLE patients with symptoms that are non-specific to SLE and are common in the general population. Is the patient suffering from CNS lupus? Or could she suffering from other common causes of her symptoms, like depression? Current laboratory tests currently lack the sensitivity and specificity to be relied on to distinguish these possibilities. A reliable test to measure SLE disease activity can be utilized routinely to help in distinguishing the two possibilities.

AutoImm Load would be very helpful in this situation to objectively assess the disease activity either alone or in combination with other markers of disease activity. An algorithm for AutoImm Load is developed using the study described above. The correlating clonotypes that is used to calculate AutoImm Load will be measured using a calibration test. This calibration test is done using blood from a patient at a time of peak disease activity, for example at the start of therapy. The calibration test is performed using blood or alternatively using the tissue that is affected (e.g. kidney biopsy or skin biopsy). At a later time at which the objective disease activity is to be assessed, a blood sample can be taken and used along with the calibration test to measure AutoImm Load. This is used to make a treatment decision. If the correlating clonotypes are derived from a populations study, there is no need for the calibration test and a blood test at the time at which the objective disease activity is to be assessed is sufficient to measure AutoImm Load in order to inform the treatment decision.

EXAMPLE 9

Measuring Response to Drug Therapy of an MS Patient

As stated above, one of the principle challenges in MS therapy is measuring how well and whether a patient is responding to a drug therapy. During progressive and late stage disease there are clinical assessments such as the Expanded Disability Status Score (EDSS) which measure the degree of physical impairment that has resulted from the disease. However, these assessments are not useful in early stage or relapsing/remitting disease. Clinical parameters around relapses can be used to assess disease progression, but these are coarse and lagging indicators, as patients can go several years between relapses, during which little evidence can be gleaned from clinical assessments. Lastly, brain imaging such as gadolinium enhanced MRI can be used to examine brain lesions. MS patients are typically given such an MRI on a yearly basis. However, such images lack specificity. Furthermore, as a measure on integrated brain damage, they are not good measures of current disease activity but rather reflect the history of the disease and its impact on the brain.

While it is true that the current clinical treatment paradigm for MS is that patients diagnosed with relapsing remitting disease should be under continuous therapy in order to delay the onset of progressive disease, the increasing repertoire of approved drugs to treat MS makes the lack of biological feedback increasingly problematic. The list shown above of approved drugs to treat MS continues to get longer as the substantial investment in MS therapies begins to bear fruit. Each of these drugs has serious side effects and is very expensive to administer, with costs from $30,000-$100,000 per year of treatment. Patients that are not well managed will sooner transition to progressive disease which is debilitating and causes expensive health care interventions including hospitalizations and long term care. Hence, the patient can be allowed to receive optimal therapy early in treatment.

Clinical Utility Example

Patient profile: A 30 year old female comes to the hospital with monocular visual impairment with pain. She is given a neurological assessment and a lumbar puncture to obtain cerebral spinal fluid which is used to assess whether clonal T cells are present. She also is referred for a brain MRI. Based on these tests, a diagnosis of MS is made. She is prescribed Betaseron 250 mcg per injection to be self-administered subcutaneously every other day. At a follow-up visit six months later, the patient is complaining of depression and weight gain. No further neurological events have been reported to the physician. The doctor is now faced with a clinical dilemma. Should the doctor maintain the therapy as it is been administered? Should a new therapy be used? Should the doctor order an MRI incurring cost and subjecting the patient to additional contrast exposure? Should the doctor wait until the next scheduled MRI shows new lesions? Should the doctor wait to see if flares recur? All of these decisions would benefit from an unambiguous measure of whether the disease is active or not.

AutoImm Load would be very helpful in this situation to assess the response to therapy by measuring disease activity either alone or in combination with other markers of disease activity. An algorithm for AutoImm Load is developed using the studies described herein. The correlating clonotypes that is used to calculate AutoImm Load is measured using a calibration test. This calibration test is done using blood from a patient at a time of peak disease activity, for example at the start of therapy. The calibration test could be performed using blood or alternatively using the tissue that is affected (e.g. CSF). At a later time at which the response to therapy is to be assessed, a blood sample can be taken and used along with the calibration test to measure AutoImm Load. This can be used to make a treatment decision. If the correlating clonotypes are derived from a population study, there is no need for the calibration test and a blood test at the time at which the response to therapy is to be assessed is sufficient to measure AutoImm Load in order to inform the treatment decision.

EXAMPLE 10

Prediction of MS Flares

As in all autoimmune diseases, the amelioration of flares is a principle goal of therapy. Not only are flares debilitating for the patient and expensive to treat, but it is increasingly believed that each flare contributes to longer term non reversible disease progression. Several therapies can be used to control incipient flares such as IV methylprednisolone or oral prednisone. Such medications have significant side effects and as such are not prescribed without evidence of an active flare. A measure of increasing subclinical activity that was correlated with subsequent clinical flares could be used to inform this sort of proactive flare treatment which could result in shorter and less damaging flares. In addition there are therapies that demonstrate high clinical efficacy for reduction of flares that carry risks of very significant and lethal of side effects. One such drug is Tysabri, a drug that has been shown to result both in improved clinical outcomes and to increase the risk of deadly brain infections such as PML. These risks have reduced the value of such drugs to last line therapy when other drugs are proving to no longer control progression and limited the value of these drugs as chronic treatments. A test that could predict when the flare state is incipient could increase the utility of such drugs as they could be used in a manner similar to steroids to control acute flare periods while minimizing the risks of lethal side effects.

Clinical Utility Example

The patient from Example 11 is on Betaseron for 3 years and reports a clinical flare that lasts a week. The patient's MRI at the end of the year shows significant new lesions (multiple discrete variable sized ovoid perpendicularly directed T2W and FLAIR hyperintense lesions (plaques), appearing isohypointense on T1W images and hyperintense on T2W images involving bilateral periventricular and subcortical white matter regions, including the calloso-sepal interface). The doctor is concerned that the patient is at high risk of flares over the course of the next 12 months. A clinical dilemma presents itself. Does the doctor wait for further clinical symptoms to intervene with additional therapy? Should the doctor switch therapies? If so, should another class of injectable be used such as copaxone or should a new class of therapy be used such as Tysabri? Should steroids be prescribed? A test that could monitor sub clinical disease activity and show when the disease is increasing and when a flare is likely to result could be used to help make these clinical decisions.

AutoImm Load would be very helpful in this situation to assess the risk of flare by measuring disease activity either alone or in combination with other markers of disease activity. An algorithm for AutoImm Load could be developed using the studies described in this invention. The correlating clonotypes that is used to calculate AutoImm Load could be measured using a calibration test. This calibration test could be done using blood from a patient at a time of peak disease activity, for example at the start of therapy. The calibration test could be performed using blood or alternatively using the tissue that is affected (e.g. CSF). At a later lime at which the risk of flare is to be assessed, a blood sample can be taken and used along with the calibration test to measure AutoImm Load. This can be used to make a treatment decision. If the correlating clonotypes are derived from a population study, there is no need for the calibration test and a blood test at the time at which the flare risk is to be assessed is sufficient to measure AutoImm Load in order to inform the treatment decision.

EXAMPLE 11

Monitoring Therapy Compliance for MS

Because of the relative infrequency of clinical symptoms in the early stages of the disease, the interactions between a patient and his or her physician are not very frequent. At the same time, the therapies that are being prescribed are both expensive and inconvenient for the patient, involving self injections that can cause painful reaction and side effects. There is as a result a significant degree of noncompliance with therapeutic regimes which are hard for a physician to monitor as the interactions between the patient and doctor is not routine. A test that could measure the state of the sub clinical disease would allow both doctor and patient to see on a routine basis how well controlled the underlying disease is. Such methods have proved very effective in HIV patients in motivating them to pursue therapy effectively. A test blood test that was performed quarterly would allow the physician to see the patient and measure the state of the disease.

AutoImm Load would be very helpful in this situation to assess the compliance with therapy by measuring disease activity either alone or in combination with other markers of disease activity. An algorithm for AutoImm Load is developed using the studies described herein. The correlating clonotypes that is used to calculate AutoImm Load is measured using a calibration test. This calibration test is done using blood from a patient at a time of peak disease activity, for example at the start of therapy. The calibration test could be performed using blood or alternatively using the tissue that is affected (e.g. CSF). At a later time at which the compliance with therapy is to be assessed, a blood sample is taken and used along with the calibration test to measure AutoImm Load. This is used to make a treatment decision and to better guide the patient toward better compliance. If the correlating clonotypes are derived from a population study, there is no need for the calibration test and a blood test at the time at which the compliance with therapy is to be assessed is sufficient to measure AutoImm Load in order to inform the treatment decision.

EXAMPLE 12

Amplification of Mouse TCRβ and IgH Sequences

An amplification and sequencing scheme for mouse TCRβ and IgH is developed that is similar to that developed for humans. Similar methods to minimize the differences in amplification efficiency of different sequences and similar validation techniques using spikes and the 5' RACE technique described above is applied. The minimum input amount of cDNA is determined in a similar methodology as described for human samples. One difference in the amplification scheme between mouse and humans is that the two C segments for TCRβ in mouse do not have any polymorphisms in the 50 bp closest to the J/C junction. Therefore, in the scheme the primer for the first stage amplification is placed at positions 25-50 and for the second stage amplification the primer is placed at positions 1-25, and the primer will have a 5' tail for the latter primer containing the P5 sequence. The different sequences will improve specificity and is similar to the strategy used in humans except there is no need to "loop out" any bases for polymorphisms.

EXAMPLE 13

Primary Analysis of Mouse Sequence Data

The analysis framework that is used for analysis of mouse data is similar to that described above for the human data. One difference is that the mouse samples is sequenced to less depth than the human samples. It is anticipated that the blood samples from the mouse is 100 µl. In 100 µl of blood there are ~100K lymphocytes and hence sequencing to a depth much higher than 100K does not significantly improve the precision. Therefore, only 100K reads for each mouse sample is obtained. Even though the number of reads is smaller for mouse than humans, a larger fraction of mouse total and blood lymphocytes is sampled. The number of total mouse lymphocytes is expected to be more than 3 orders of magnitude smaller than that of humans. Similarly 100 µl of blood will provide a better sampling (~10%) of the lymphocytes in the mouse blood at the time when compared to sampling obtained using 10 ml of human blood (0.2%).

EXAMPLE 14

IgH and TCR Repertoire Analysis in Mouse SLE Model

A mouse model of SLE is used to study the relationship between TCR/BCR repertoire and disease activity. The mouse model is the B6 with the sle1 and sle3 loci from NZM2410. These B6.sle1.sle3 (BSS) mice develop SLE-like nephritis in a spontaneous fashion. Three types of cohorts is studied. For all study points, blood BUN, creatinine, and anti-nuclear autoantibodies, urine protein, and creatinine level is obtained. It is determined whether a score generated from blood TCR/BCR repertoire correlates well with these measured indices of kidney disease. The first cohort is similar to the human cohort described where longitudinal blood samples is collected along with kidney function assessment. Specifically, 7 BSS mice is followed on a monthly basis till month 8. At the end, these mice is sacrificed and in addition to blood, spleen and kidney tissue are analyzed. As a control, 5 B6 mice is assessed in a similar manner. The second cohorts is cross sectional where different cohorts of animals is sacrificed at specific times and spleen, kidney, and blood samples is analyzed at that time. Specifically, 5 BSS mice is sacrificed each month and blood, spleen, and kidney is analyzed. As a control, two B6 control mice is assessed in the same fashion. Finally a third cohort is treated with steroids after disease onset and nephritis assessment and blood samples obtained on a regular basis after that. Specifically at 4 months of age, 20 mice that have the disease is treated with steroids and then on a biweekly basis for the next 4 months blood is taken for TCR/BCR repertoire analysis and kidney function assessment. As a control 5 BSS mice is treated with placebo and followed in a similar fashion. TCR and BCR repertoire analysis is performed from all the study points (i.e. different time points and different tissues for the same time point). The analysis will involve 2 stage PCR, sequencing processing, and primary data analysis as described above.

EXAMPLE 15

Identification and Dynamics of Clonotypes that Correlate with Mouse SLE

First, a set of clonotypes that correlate with renal function is identified. As a measure of renal function, urine protein/creatinine ratio, scrum creatinine, or BUN levels can be used. In the first and third cohorts, the correlation of the blood level of each HPC clonotype with each of the three measures can be assessed. In a similar manner to what is described in humans, it can be assessed whether there is a great increase in the number of clonotypes with high correlation to 1, 2, or all 3 of the renal function measures over random expectation (or permutation testing). Given that random expectation, the correlation threshold is picked where only 10% of the clonotypes with a correlation level above that threshold are expected to have the observed correlation level by chance (10% false discovery). These clonotypes is focused on, and this set is defined as "correlating clonotypes".

In addition to this statistical method to identify correlating clonotypes, clonotypes might be identified relevant to disease by a "functional" method of enrichment of specific clonotypes in kidney tissue. By the functional method a set of clonotypes may be identified in cohort 2 that may be relevant to disease, and these is called functionally-identified correlating clonotypes. The extent of overlap between the "statistical" definition and the "functional" definition of correlating clonotypes can be assessed. Cohorts 1 and 3 have kidney samples collected at the last time point. It can be assessed whether clonotypes enriched in these kidney samples are present in the blood and are among the clonotypes with higher correlation with renal function.

The dynamics of correlating clonotypes (statistically and functionally identified) can then be evaluated. For example, using data from cohort 2, the time course of the rise and fall (if any) of their levels is evaluated in the three compartments: kidney, blood, and spleen.

In the statistically identified correlating clonotypes, a subset of the correlating clonotypes would be identified by virtue of their correlation with renal function. The correlating clonotypes can be identified without knowing the renal function data. In other words, the characteristics that distinguish the correlating clonotypes from those that are irrelevant to disease can be understood. In order to do that a set of clonotypes with low correlation to renal function is identified as control non correlating clonotypes.

Characteristics of clonotypes that correlate with disease. After identification of the two sets of clonotypes, correlating and not correlating, characteristics that distinguish these two sets is searched for. Separate and combined analysis using the correlating clonotypes identified statistically and functionally is performed. The same type of characteristics studied in humans is assessed, for example the level of the clonotype, the presence of particular sequence motifs, and the sequence of other related clonotypes. As described for the human study, there is a significant risk of overfitting and hence cross validation technique or separate training and testing sets need to be employed.

One utility for the mouse experiment is the availability of cells allowing for assessment of whether correlating clonotypes are enriched in a specific subtype of cells. It is studied whether correlating clonotypes are enriched in some cell subtypes; sequencing from the full set of lymphocytes and from the specific subtype where correlating clonotypes are enriched can be done, and this criteria of enrichment can be used as an extra characteristic to distinguish correlating clonotypes from other disease-irrelevant clonotypes. In order to know what cell subtypes clonotypes are enriched a couple approaches is taken: hypothesis driven and hypothesis free. The first is to try a dozen candidate surface markers on T or B cells in a set of samples. For example, one candidate is CD69 on T cells to select activated T cells. For B cells studies have shown the increase of CD27high cells in active SLE, and therefore that is a good candidate for a marker of cells that may have enrichment of the correlating clonotypes. In each of these experiments, the specific cell subtypes is purified through FACS. Then a sequencing reaction is done for cDNA from the full complement of the lymphocytes as well as for cDNA from the lymphocytes that were purified by FACS from a collection of different samples. It is assessed whether the two sets of correlating and non-correlating clonotypes are present in different proportions in the full complement of lymphocyte compared to the FACS purified subset. Markers that have a large difference can be useful in identifying correlating clonotypes. Enrichment of clonotypes in subtypes of cells with these markers is used in addition to the sequence parameters to detect correlating clonotypes.

In the hypothesis free approach, markers is searched for which are differentially expressed in cells with a correlating clonotype from other cells. A few cases is chosen where a specific TCR clonotype is clearly correlating with disease, and cases is picked where that clonotype is highly enriched that it represents the majority of the clonotypes with the same V segment. FACS is done using antibody to the specific V segment (antibodies against all V segments are commercially available) to select a population that is highly enriched for cells carrying the correlating clonotype. The RNA can be prepared from these cells and the expression of all the genes can be studied by performing an array experiment. As a control, total RNA from lymphocytes can be used and/or RNA from FACS purified cells carrying another irrelevant V segment. Markers that maximally distinguish the sample obtained from the FACS purified V segment with the correlating clonotype from the controls can be searched for. Markers, including surface markers (since it is much easier to do FACS with surface proteins) that distinguish the two populations can be found. If a consistent RNA marker from samples of several mice is observed it is validated at the protein level. Using the same samples, antibodies against the marker protein is used in a FACS assay to purify cells carrying the matter protein. More than one marker may be tested to increase the chance of validating one of them. The TCR and/or BCR from the purified cells is sequenced. If the RNA results hold at the protein level then the correlating clonotypes should be enriched in the purified subset of cells. After validating that RNA results still hold at the protein level, the results is validated in other samples. Samples that were not subject to the array analysis is subjected to FACS analysis using the antibody to the marker protein(s). The TCR and/or BCR of the purified cells is sequenced. It is evaluated whether the correlating clonotypes are enriched in the cells purified using antibody to the specific marker(s). This will validate the utility of the marker(s) in the identification of correlating clonotypes.

EXAMPLE 16

Use of IgH and TCRβ Repertoire to Measure Disease Activity

The algorithm for correlating clonotypes from above can be applied to identify in all samples of cohorts 1 and 3 correlating clonotypes by virtue of their sequence and/or markers. Using the level of the correlating clonotypes in each patient, an AI score can be generated that correlates with a measure of renal function. As described above, there is an overfitting risk and the cross validation technique and/or separate training and testing set need to be employed. The correlation of AI and renal function measures can be evaluated in a cross sectional manner (all study points of all mice). The question of whether the AI score changes in an individual mouse can also be evaluated when renal function changes. This can be evaluated by comparing the AI from high and low renal function in the same animal in a similar manner to what is described in humans.

EXAMPLE 17

Monitoring for Metastatic Recurrence in Colon Cancer Patients

Many cancers that are detected at a treatable stage still carry an ongoing risk to the patient of metastatic tumor recurrence. Such recurrences are often detected late and at untreatable stages an can be fatal to the patients. One example of such a situation is that of recurrent colon cancer. Despite increasingly aggressive colon cancer screening programs, colon cancer represents one of the most common malignancies in the US. Approximately 150,000 patients per year are diagnosed with colon cancer at serious but treatable stages (Stage II and Stage III). These patients are treated by tumor resection followed by a course of chemotherapy. While these treatments are generally effective, there is nonetheless a significant chance that these patients will have metastatic recurrences of the primary tumor in the years following treatment. 50% of Stage III patients for instance will have a recurrence within 5 years of surgery. These recurrences can be either isolated (e.g. in the colon or liver) or multifocal. In either case but particularly if they are isolated, detecting them at an early stage can play a role in maximizing the chances of successful therapy (surgery and/or chemotherapy).

There are currently two tests used in post treatment surveillance. CT scan of the abdomen and chest is used to identify tumors visible on these images. Typically these scans are done at intervals of 6-12 months for the first 5 years post therapy. While these scans can reveal early stage malignancies, there clinical effectiveness is in debate. Drawbacks of these scans include the fact that they subject the patients to significant amounts of radiation which can itself cause further tumors and the significant expense. Another blood based test has been shown to have some value: CEA testing. This antibody test measures the level of a protein in serum that is specific to some colon tumors. The drawback to CEA testing is its lack of sensitivity (<60% of patients with positive CT scans have a positive CEA test).

In this embodiment of the invention, lymphocytes obtained from the resected primary tumor are used to develop an immune profile that can be used to add sensitivity to a blood based test for early cancer recurrence TCRs (and/or BCRs) of the lymphocytes found in the resected tumor can be amplified and sequenced. Clonotypes that are enriched in the tumor sample are likely relevant to the immune response to the tumor. Subsequent blood draws from the patient can be used to assess the level of these clonotypes. A rise in the level of these clonotypes can signal an immune response to a tumor recurrence. In this case the detection of the immune response may be more sensitive than the detection of the tumor marker itself.

Discovery study for the detection of cancer recurrence using a calibration test. A discovery study is performed to determine the likelihood of detection of recurrence given the profile of blood TCR (and/or BCR). Samples of resected tumor samples as well as follow up blood samples of patients with known outcome are used for this study. TCR (and/or BCR) from all these samples is sequenced. Candidates for the correlating clonotypes are those that are present in the TCR (and/or BCR) data from the tumor samples Given the known outcomes in this training study one using the standard cross validation techniques, a model that generates a score (Recurrence Risk) given the level of the different clonotypes is devised. This Recurrence score is thus be calculated in a new patient by measuring the clonotypes in the resected tumor (calibration point) and the data from the clonotypes found in the same patient's blood at a later time during the surveillance for recurrence. The use of the tumor data allows great reduction in the number of clonotypes present in blood that are considered in this analysis.

Discovery study for the detection of cancer recurrence using a calibration test and a population study. It is likely that not all clonotypes that are enriched in the tumor specimen are relevant to the immune response to the tumor. There might be some lymphocyte that expanded locally due to a favorable inflammatory condition. In another embodiment of this invention the discovery study is done using the same samples but the study is used to identify parameters that distinguish "correlating" from "non-correlating" clonotypes. These parameters can include 1) Sequence motif: The motif can be a specific V or J region, a combination VJ, or short sequences in DJ region that is associated with a clonotype being correlating; 2) Size of the clonotype; 3) Level: Absolute level (number of reads per million) or rank level; 4) Similarity to other clonotypes: the presence of other highly related clonotypes, like those with silent changes (nucleotide differences that code for same amino acids) or those with conservative amino acid changes; 5) For the BCRs the level of somatic mutations in the clonotype and/or the number of distinct clonotypes that differ by somatic mutations from some germ line clonotype. 6) Presence in a cell carrying a specific marker. This study then results in an algorithm that can predict which clonotypes are likely to be correlating with cancer recurrence in blood given a specific set clonotypes present in a given tumor sample. These clonotypes are then be used to develop a score of Recurrence Risk in the same manner as described above.

Discovery study for the detection of cancer recurrence using a population study. In another embodiment of this invention, the clonotypes measured in the resected tumor are used to generate a model that predicts correlating clonotypes in as yet unseen samples. This model can also be used to generate a Recurrence Risk score in a manner analogous to that described above. In this model there would be no need to measure the clonotypes in the resected cancer tissue in a new patient undergoing recurrence surveillance but rather the Recurrence Risk could be assessed by simply measuring the clonotypes in a given blood sample.

Discovery study for the detection of primary colon cancer using a population study. As an extension the detection of primary cancers is achieved using the same methodology. With the primary cancers there is no tumor resected that can be used to enrich for relevant clonotypes. However, even in the presence of tumor resection data the additional sequence and other parameters need used to identify relevant clonotypes and generate a score for likelihood of cancer detection. Therefore by extension if the algorithm is predictive enough one can detect the cancer from blood (or other bodily fluid) without the data from the resected tumor. In this embodiment of the invention, a discovery study with blood samples from patients preceding their diagnosis of primary cancer need to be available. In an analogous fashion to the one described above, parameters (sequence and other) can be identified to predict the clonotypes that are correlated to the immune system response to the tumor. A model can then be used to generate a Cancer Risk score that predicts the progression risk to colon cancer. This algorithm can then be applied to new patient's blood sample to measure the risk of primary colon cancer.

EXAMPLE 18

Monitoring for Rejection in Heart Transplant Patients

Heart transplants are a relatively uncommon procedure as the supply of organs is very limited. 3,500 heart transplants performed every year worldwide. Each procedure is very expensive and the organs that are used are priceless. As a result the patients that receive these organs are treated extremely proactively. In order to measure the state of the immune reaction to the donated organ at a time at which interventions with immunosuppressants can be effective, patients are given periodic heart biopsies to measure inflammation of the organ. Based on these tests, aggressive courses of immunosuppressants may be given. These procedures have several limitations. As invasive surgical procedures they have risks to the patient. Furthermore they are expensive and can only be done at infrequent intervals. A blood based tests based on profiling the expression of a panel of 11 test genes (Allomap) have been shown to be quite sensitive in detecting organ rejection but lacks sufficient sensitivity to be used as a replacement for biopsy and is instead used to decide when to do a biopsy. In one embodiment of this invention TCR (and/or BCR) profiles are used to assess the state of "rejection" and generate a Rejection Risk score that predicts the likelihood of rejection in a specific time frame. It is conceived that a discovery study can be performed to determine the likelihood of rejection given the profile of blood TCR (and/or BCR). This can be used in the clinic to inform the immunosuppressive therapies that are being used.

Discovery of correlating clonotypes using a population study. In this embodiment of the invention a population of post-transplant patients with blood samples with known clinical outcome is used. TCR (and/or BCR) from all these samples is sequenced and correlation of individual clonotypes with rejection outcome used to distinguish correlating from non-correlating clonotypes. Subsequently, parameters are derived that distinguish those two classes of clonotypes. These parameters can include 1) Sequence motif: The motif can be a specific V or J region, a combination VJ, or short sequences in DJ region that is associated with a clonotype being correlating; 2) Size of the clonotype; 3) Level: Absolute level (number of reads per million) or rank level; 4) Similarity to other clonotypes: the presence of other highly related clonotypes, like those with silent changes (nucleotide differences that code for same amino acids) or those with conservative amino acid changes; 5) For the BCRs the level of somatic mutations in the clonotype and/or the number of distinct clonotypes that differ by somatic mutations from some germ line clonotype. 6) Presence in a cell carrying a specific marker. An alternative or supplemental method to define the correlating and non-correlating clonotype would come if the study samples have biopsy samples of the graft, particularly if it was in active rejection. It is expected that at that time there is great enrichment of the correlating clonotypes. Parameters to distinguish these from the other clonotypes are identified as discussed above.

The profile data from the blood samples is then used to predict the likelihood of rejection. Given the known outcomes in this training study one can devise, a model using the standard cross validation techniques that generates a Rejection Risk score given the level of the different clonotypes. Given the profile in a new blood sample of TCR (and/or BCR) at a specific point a Rejection Risk score relating to the likelihood of rejection can be generated Discovery of correlating clonotypes using a calibration test. In another embodiment a method of identifying correlating clonotypes are implemented using a calibration test for each patient. This method involves a first biopsy sample be taken post transplant. The presence of biopsy material of the graft post transplant offers the possibility of analyzing TCRs from the biopsy sample to identify the correlating clonotypes as defined by those that are prevalent in this sample. This set of clonotypes sis then followed in blood and a score is generated for the likelihood of rejection. The algorithm to generate the Rejection Risk score is derived through a discovery study that is similar to the one described above that utilizes the available clinical data and the levels of the correlating clonotypes to generate a Rejection Risk score that approximates the likelihood of rejection.

In this embodiment a specific calibration test is done using material from a first biopsy post transplant but further biopsies could be replaced by the use of blood samples whose clonotypes could be used along with this calibration test to measure a Rejection Risk score.

In addition to the graft biopsy, the blood samples before transplant serve as another calibration point. Clonotypes that are prevalent in this sample are unlikely to be related to the rejection representing rather the history of prior antigens the patient has seen. Therefore when considering the blood samples after transplant one can subtract the clonotypes that were present before the transplant in determining the correlating clonotypes.

These clonotypes are then used to generate a model of Rejection Risk. In this embodiment, two calibration tests would be can be used: one prior to transplant and one from a biopsy after transplant. These calibrations could then be used along with clonotypes derived from a blood test to measure Rejection Risk.

Discovery of correlating clonotypes using a calibration test and a population study. In another embodiment, the identification of the correlating clonotypes can be achieved through a combination of the above approaches. Specifically this can be achieved by using the population study to generate an algorithm to predict correlating clonotypes. In addition it can be achieved through calibration data from the same patient using graft biopsy and/or blood samples pre-transplant. A more preferred embodiment will employ both approaches: population-built algorithm and individual calibration to most accurately identify the correlating clonotypes. A Rejection Risk score is then generated using the level of these clonotypes to predict the likelihood of rejection through the use of the population study as a training set.

In this embodiment, two calibration tests can be used: one prior to transplant and one from a biopsy after transplant. These calibrations could then be used along with clonotypes derived from a blood test to measure Rejection Risk.

The prediction of GVHD can be done in a very similar manner with the same concept of the population study to generate an algorithm to predict correlating clonotypes. Also the "negative" calibration can be generated from the donor sample pre-transplantation. An approach using both the algorithm and calibration is likely to be more predictive of the correlating clonotypes. An algorithm to compute a score of the likelihood of GVHD given the level of the correlating clonotypes can be generated using a population study in a manner as described above. This algorithm can then be used for the prediction of the likelihood of GVHD in the next set of patients.

EXAMPLE 19

Monitoring for PML Infection in MS Patients Treated with Natalizumab

One embodiment of the invention uses TCR and/or BCR profile to detect subclinical Progressive Multifocal Leukoencephalopathy (PML) in MS patients. PML is a serious and often fatal disease that causes often rapidly progressive demyelinating disease through killing oligodendrocytes that synthesize myelin. It is caused by JC virus that is present in a latent phase in the majority of the population. In a fraction of the immunosuppressed population (e.g. AIDS) the virus is reactivated leading to the development of this serious disease. In addition some patients who are being immunosuppressed through the use of medication like post transplant patients can also develop PML. Some specific medication has been linked to the risk of PML in specific patient populations. For example natalizumab (Tysabri) was associated with the development of more than 10 cases of PML among patients with multiple sclerosis (MS) leading to its withdrawal of the market for a period of time. Natalizumab is well accepted to be more effective than the other FDA approved medications for multiple sclerosis, but its use has been limited by the fear of PML development. Once PML is suspected, plasmapheresis can be performed to reduce the concentration of the drug in the patient. The overlap between symptoms of MS and PML can sometimes delay the detection of PML. Early detection of subclinical PML is urgently needed.

These clonotypes may be discerned from blood samples from a population where some patients developed PML. This population can be used to identify clonotypes that correlate with the later development of PML. With the availability of these clonotypes an algorithm to identify parameters that distinguish these from other clonotypes can be generated.

Discovery of correlating clonotypes using a population study. In this case an algorithm is generated to predict the clonotypes that are relevant to the emergence of PML. The algorithm can be trained on a set of clonotypes deemed to be correlating with the disease. In this embodiment of the invention blood (or other body fluid) samples in a discovery study from a population of patients with a latent infection with JC virus some of whom go on to develop PML can be used. TCR (and/or BCR) from all these samples can be sequenced and correlation of individual clonotypes with infectious agent reactivation outcome can be used to distinguish correlating from non-correlating clonotypes. Parameters that distinguish those two classes of clonotypes can be identified. These parameters can include 1) Sequence motif: The motif can be a specific V or J region, a combination VJ, or short sequences in DJ region that is associated with a clonotype being correlating; 2) Size of the clonotype; 3) Level: Absolute level (number of reads per million) or rank level; 4) Similarity to other clonotypes: the presence of other highly related clonotypes, like those with silent changes (nucleotide differences that code for same amino acids) or those with conservative amino acid changes; 5) For the BCRs the level of somatic mutations in the clonotype and/or the number of distinct clonotypes that differ by somatic mutations from some germ line clonotype. 6) Presence in a cell carrying a specific marker. An alternative or supplemental method to define the correlating and non-correlating clonotype would come from a set of patients who are mounting an immune response to the same infectious agent. Enriched clonotypes (particularly those that are at a significantly higher level than before the immune response) in these patients can be considered correlating and parameters that distinguish them from other clonotypes can be identified.

Similarly the correlating clonotypes can be identified from samples of patients with active PML or from in vitro studies to identify clonotypes that respond to JC virus antigen. The responding clonotypes may originate from one or a plurality of subjects that may be healthy or infected with the infectious agent. These clonotypes can be considered correlating and parameters that distinguish then from other clonotypes can be identified.

The profile data from the samples in the discovery study is then used to predict the likelihood of reactivation. Given the known outcomes in this training study one can devise using the standard cross validation techniques, a model that generates a PML Risk score given the level of the different clonotypes. So given the profile in a blood sample of TCR (and/or BCR) at a specific point a score relating to the likelihood of reactivation can be generated. This algorithm can now be used with data from a novel patient to predict the patient's correlating clonotypes as well as to generate a PML Risk score for the likelihood of reactivation.

In a very similar manner other infection-related outcomes can be studied. For example in addition to reactivation of latent infection, one can assess clearance of infection. Furthermore given the TCR and/or BCR repertoire one may be able to evaluate likelihood of having immunity for a specific infectious agent

EXAMPLE 20

Monitoring for Reactivation of Latent Infections

In another embodiment TCR and BCR profiling can be used to monitor infections that have periods of acute infection followed by latency and reactivation. Examples of such diseases include Hepatitis B and C as well as Herpes viruses. Predicting infections at early stage would be desirable.

Discovery of correlating clonotypes using a calibration test. In another embodiment a method of identifying correlating clonotypes can be implemented using a calibration test for each patient. The presence of a biological sample from the same patient at a previous time point when the patient was mounting an immune response to the infectious agent can serve to identify the correlating clonotypes. This set of clonotypes can then be followed in blood and a Reactivation Risk score is generated for the likelihood of reactivation. The algorithm to generate the score is derived through a discovery study that is similar to the one described above that utilizes the available clinical data and the counts of the correlating clonotypes to generate a Reactivation Risk score that approximates the likelihood of reactivation. To use this score a sample taken from a new patient in clinical practice during a period of acute infection. This data would be used along with a subsequent sample taken during the latent period to measure the Reactivation Risk for clinical purposes.

Discovery of correlating clonotypes using a calibration test and a population study. In another embodiment, the identification of the correlating clonotypes can be achieved through a combination of the above approaches. Specifically this can be achieved by using the population study to generate an algorithm to predict correlating clonotypes. The correlating clonotypes can be obtained from a population study of patients with known outcome of the infection and/or a set of patients with active immune response to the infectious agent, and/or from in vitro experiments to identify clonotypes reactive with the infectious agent. In addition it can be achieved through calibration data from the same patient using older data points at the time of an active immune response against the relevant infectious agent. A more preferred embodiment will employ both approaches: population-built algorithm and individual calibration to most accurately identify the correlating clonotypes. A Reactivation Risk score is then generated using the level of these clonotypes to predict the likelihood of reactivation through the use of the population study as a training set. To use this score a sample taken from a new patient in the clinic during a period of acute infection is profiled. This data would be used along with a subsequent sample taken during the latent period to measure the Reactivation Risk for clinical purposes. A similar structure can be employed to study infectious agent clearance and or immunity to it.

EXAMPLE 21

Monitoring for Allergic Response during Immunotherapy

Allergic rhinitis is a common condition afflicting ~11% of the US population. This is typically an allergy to pollen or dust. Eliminating the exposure is difficult and it involves vigilant effort. The most common treatments used in chronic rhinitis are decongestants, antihistamines, and nasal steroids. In severe cases immunotherapy is done. The goal of the immunotherapy is to de-sensitize the patient. First a challenge with many potential allergens is done to identify the specific allergen the patient is reacting to. Then the patient is injected with increasing amount of allergen over a period of months to years until a maintenance dose is achieved, and the treatment is then continued for several years. Typically the patient can feel an improvement in symptoms within 3-6 months, but that can also be as late as 12-18 months, but a large fraction of the patients do not benefit from the treatment or have relapses. One reason for the slow dose escalation is the risk of anaphylaxis if the patient is given a high dose of allergen before s/he sufficiently de-sensitized.

In one embodiment of this invention TCR (and/or BCR) profiles are used to assess the state of disease in allergic rhinitis and generate an Allergy Score that predicts how prone the patient to mount an allergic response should s/he be exposed to the relevant allergen. It is conceived that a discovery study can be performed to determine the likelihood of allergy response given the profile of blood TCR (and/or BCR). This can be used in tailoring the immunotherapy treatment. Possible clinical decision can be to discontinue the treatment if it is deemed ineffective, continue the injection regimen, or accelerate the treatment to reach the maintenance dose faster.

Discovery of correlating clonotypes using a population study. In this embodiment of the invention a population of allergic rhinitis patients on immunotherapy with blood samples with known clinical outcome can be used. TCR (and/or BCR) from all these samples can be sequenced and correlation of individual clonotypes with allergy outcome can be used to distinguish correlating from non-correlating clonotypes. Subsequently, parameters can be derived that distinguish those two classes of clonotypes. These parameters can include 1) Sequence motif: The motif can be a specific V or J region, a combination VJ, or short sequences in DJ region that is associated with a clonotype being correlating; 2) Size of the clonotype; 3) Level: Absolute level (number of reads per million) or rank level; 4) Similarity to other clonotypes: the presence of other highly related clonotypes, like those with silent changes (nucleotide differences that code for same amino acids) or those with conservative amino acid changes; 5) For the BCRs the level of somatic mutations in the clonotype and/or the number of distinct clonotypes that differ by somatic mutations from some germ line clonotype. 6) Presence in a cell carrying a specific marker. An alternative or supplemental method to define the correlating and non-correlating clonotype would use biopsy of positive allergy test material from patients positive for a specific allergen. At the site of injection of the allergen it is expected that there is great enrichment of the correlating clonotypes. Parameters to distinguish these from the other clonotypes can be identified as discussed previously.

The profile data from the blood samples is then used to predict the allergy state. Given the known outcomes in this training study one can devise, a model using the standard cross validation techniques that generates an Allergy Score given the level of the different clonotypes. Given the profile in a new blood sample of TCR (and/or BCR) at a specific point, an Allergy Score can be generated to estimate the degree to which this patient is prone to mount an allergic response.

Discovery of correlating clonotypes using a calibration test. In another embodiment a method of identifying correlating clonotypes can be implemented using a calibration test for each patient. This method involves a biopsy sample from a site with a positive allergen response be taken from the patient. This can be from the initial allergy test that was performed to determine the specific allergen the patient is responding to or sample from the site of any further treatment injections. This can be done more than once to ensure that the appropriate clonotypes are being followed in case there is some epitope spreading. TCR and/or BCR from these biopsy samples can be used to identify the correlating clonotypes as defined by those that are prevalent in this sample. This set of clonotypes can then be followed in blood and a score is generated for the likelihood of allergy response. The algorithm to generate the Allergy Score is derived through a discovery study that is similar to the one described above that utilizes the available clinical data and the levels of the correlating clonotypes to generate an Allergy Score that estimates the allergy state.

Discovery of correlating clonotypes using a calibration test and a population study. In another embodiment, the identification of the correlating clonotypes can be achieved through a combination of the above approaches. Specifically this can be achieved by using the population study to generate an algorithm to predict correlating clonotypes. In addition it can be achieved through calibration data from the same patient using biopsy from a site with a positive allergen response. A more preferred embodiment will employ both approaches: population-built algorithm and individual calibration to most accurately identify the correlating clonotypes. An Allergy Score is then generated using the level of these clonotypes to predict the state of allergy through the use of the population study as a training set.

EXAMPLE 22

Amplification of IgH Sequences from Genomic DNA

In this example, amplification of IgH sequences from genomic DNA is described. Such amplification is advantageous because (1) the level of a clonotype in genomic DNA can be readily convened to number of cells, and (2) in some lymphoid neoplasms, RNA may not be expressed for the relevant immune receptor rearrangement.

Amplification of immune receptor rearrangement is important for the detection of lymphoid neoplasms. B cell neoplasms are more common than T cell tumors and IgH is the most common rearranged immune receptor in B cell neoplasms. Because of somatic hypermutation, reliability of amplifying of IgH from genomic DNA may be increase by amplifying with multiple primers for each V segment, although there is a risk of differential amplification. In amplification from genomic DNA, the same V primers were used that were used in amplification from cDNA. Each V segment is amplified by 3 primers (in 3 distinct regions of the V segment: A, B, and C) in three different reactions (Tables 5-7, respectively) (see FIG. 4A).

TABLE 5

Human IgH V. Segment Primers for Reaction A
(All the primers have a common 14 bp
(AGATCGGAAGAGCA) (SEQ ID NO 165)
appended to their 5' end)

| Sequence | SEQ ID NO |
|---|---|
| TCGCAGACCCTCTCACTCACCTGTG | 62 |
| GATCTCCTGTAAGGGTTCTGGATACAGCT | 61 |
| AAACCCACACAGACCCTCACGCTGAC | 44 |
| AAACCCACAGAGACCCTCACGCTGAC | 45 |
| AAACCCACACAGACCCTCACACTGAC | 46 |

TABLE 5-continued

Human IgH V. Segment Primers for Reaction A
(All the primers have a common 14 bp
(AGATCGGAAGAGCA) (SEQ ID NO 165)
appended to their 5' end)

| Sequence | SEQ ID NO |
|---|---|
| CCTCAGTGAAGGTCTCCTGCAAGG | 40 |
| CCTCGGTGAAGGTCTCCTGCAAGG | 41 |
| CCTCAGTGAAGGTTTCCTGCAAGG | 42 |
| GGGCTACAGTGAAAATCTCCTGCAAGG | 43 |
| CTTCGGAGACCCTGTCCCTCACCTG | 55 |
| CTTCGGACACCCTGTCCCTCACCTG | 57 |
| CTTCACAGACCCTGTCCCTCACCTG | 58 |
| CTTCGGAGACCCCGTCCCTCACCTG | 59 |
| CGGGGACCCTGTCCCTCACCTG | 60 |
| CTGGGGGGTCCCTGAGACTCTCCTG | 47 |
| CTGGGGGGTCCCTTAGACTCTCCTG | 48 |
| CAGGGCGGTCCCTGAGACTCTCCTG | 49 |
| CAGGGCCGTCCCTGAGACTCTCCTG | 50 |
| CTGGGGGGTCCCTGAAACTCTCCTG | 51 |
| CTGGCAGGTCCCTGAGACTCTCCTG | 52 |
| CTGGAGGGTCCCTGAGACTCTCCTG | 53 |
| CTGGGAGGTCCCTGAGACTCTCCTG | 54 |
| TGGGGGGGCCCTGAGACTCTCCT | 55 |

TABLE 6

Human IgH V Segment Primers for Reaction B
(All the primers have a common 14 bp
(AGATCGGAAGAGCA) (SEQ ID NO 165)
appended to their 5' end)

| Sequence | SEQ. ID NO |
|---|---|
| TGGATCAGGCAGTCCCCATCGAGAG | 63 |
| GCTGGGTGCGCCAGATGCCC | 64 |
| GTGTGAGCTGGATCCGTCAGCC | 131 |
| GTGTGGGCTGGATCCGTCAGCC | 132 |
| GTGCGACAGGCCCTGGACAA | 67 |
| GGGTGCGACAGGCCACTGGACAA | 68 |
| GTGCGCCAGGCCCCCGGACAA | 69 |
| GGGTGCGACAGGCTCGTGGACAA | 70 |
| GGGTGCAACAGGCCCCTGGAAAA | 71 |
| GGGTGCGACAGGCTCCTGGAAAA | 72 |
| GTGCGACAGGCCCCCGGACAA | 73 |
| GTGCGACAGGCCCCCAGACAA | 74 |

TABLE 6-continued

Human IgH V Segment Primers for Reaction B
(All the primers have a common 14 bp
(AGATCGGAAGAGCA) (SEQ ID NO 165)
appended to their 5' end)

| Sequence | SEQ. ID NO |
|---|---|
| TCCGCCAGCCCCCAGGGAAGG | 75 |
| TCCGGCAGCCCCCAGGGAAGG | 76 |
| TCCGGCAGCCACCAGGGAAGG | 77 |
| TCCGCCAGCACCCAGGGAAGG | 78 |
| TCCGGCAGCCCGCCGGGAA | 79 |
| TCCGGCAGCCGCCGGGAA | 80 |
| TCCGGCAGCCCGCTGGGAAGG | 81 |
| TCCGCCAGCCCCTAGGGAAGG | 82 |
| GGTCCGCCAGGCTCCAGGGAA | 83 |
| GTTCCGCCAGGCTCCAGGGAA | 84 |
| GGTCCGCCAGGCTTCCGGGAA | 85 |
| GGTCCGTCAAGCTCCGGGAA | 86 |
| GATCCGCCAGGCTCCAGGGAA | 87 |
| GGTCCGCCAAGCTCCAGGGAA | 88 |
| GGTCCGCCAGGCTCCAGGCAA | 89 |
| GGTCCGCCAGGCCCCAGGCAA | 90 |
| GGTGCCGCCAGGCTCCGGGCA | 91 |
| GGGTCCGTCAAGCTCCAGGGAAGG | 92 |
| CTGGGTCCGCCAAGCTACAGGAAA | 93 |
| GGTCCGCCAGCCTCCAGGGAA | 94 |
| GGTCCGGCAAGCTCCAGGGAA | 95 |
| GTGCGAGCTGGATCCGTCAGCC | 133 |

TABLE 7

Human IgH V Segment Primers for Reaction C
(All the primers have a common 14 bp
(AGATCGGAAGAGCA) (SEQ ID NO 165)
appended to their 5' end

| Sequence | SEQ ID NO |
|---|---|
| GCAGCCTAAAGGCTGAGGACACTG | 134 |
| CTCTGTGACTCCCGAGGACACGGCT | 97 |
| AGTGGAGCAGCCTGAAGGCCTC | 98 |
| TGACCAACATGGACCCTGTGGACAC | 99 |
| ACATGGAGCTGAGCAGCCTGAGATC | 100 |
| ACATGGAGCTGAGCAGGCTGAGATC | 101 |
| ACATGGAGCTGAGCAGGCTGAGATC | 102 |
| ACATGGAGCTGAGGAGCCTAAGATCTGA | 103 |
| GAGCTCTGTGACCGCCGCGGAC | 104 |

TABLE 7-continued

Human IgH V Segment Primers for Reaction C
(All the primers have a common 14 bp
(AGATCGGAAGAGCA) (SEQ ID NO 165)
appended to their 5' end

| Sequence | SEQ ID NO |
|---|---|
| GAGCTCTGTGACCGCCGTGGACA | 105 |
| GAGCTCTGTGACCGCTGCAGACACG | 106 |
| GAGCTCTGTGACCGCTGCGGACA | 107 |
| GAGCTCTGTGACTGCCGCAGACACG | 108 |
| GAGCTCTGTGACTGCAGCAGACACG | 109 |
| GAGCTCTGTGACTGCCGCGGACA | 110 |
| GAGCTCTGTGACCGCGGACGCG | 111 |
| GGCTCTGTGACCGCCGCGGAC | 112 |
| GAGCTCTGTGACCGCCGCAGACA | 113 |
| GAGCTCTGTGACCGCTGACACGG | 114 |
| CAAATGAACAGCCTGAGAGCCGAGGACA | 115 |
| CAAATGAACAGCCTGAAAACCGAGGACA | 116 |
| CAAATGAACAGTCTGAAAACCGAGGACA | 117 |
| CAAATGATCAGCCTGAAAACCGAGGACA | 118 |
| CAAATGAACAGTCTGAGAACTGAGGACACC | 119 |
| CAAATGAACAGTCTGAGAGCCGAGGACA | 120 |
| CAAATGAACAGCCTGAGAGCTGAGGACA | 121 |
| CAAATGAGCAGCCTGAGAGCTGAGGACA | 122 |
| CAAATGAACAGCCTGAGAGACGAGGACA | 123 |
| CAAATGGGCAGCCTGAGAGCTGAGGACA | 124 |
| CAAATGAACAGCCTGAGAGCGGGGA | 125 |
| CAAATGAACAGTCTGAGAGCTGAGGACA | 126 |
| CAAATGAGCAGTCTGAGAGCTGAGGACA | 127 |
| GCACGCTAAAGGCTGAGGACACTG | 135 |

Amplification of IgH from genomic DNA has several differences from its amplification from cDNA. The C segment gets attached to the VDJ region through splicing and hence sequences of the C segment can be used for amplification from cDNA but not genomic DNA. The use of C segment allows the use of two distinct primers in the $1^{st}$ and $2^{nd}$ amplifications increasing the specificity. For the amplification from genomic DNA we have opted to use primers that are complementary to the J sequences (Table 8).

TABLE 8

Human IgH J Segment Primers*

| J Segment Primer | SEQ ID NO |
|---|---|
| ACGAGCCTCATGCGTAGANctcacCTGAGGAGACGGTGACC | 136 |
| ACGAGCCTCATGCGTAGANctcacCTGAGGAGACAGTGACC | 137 |

TABLE 8-continued

Human IgH J Segment Primers*

| J Segment Primer | SEQ ID NO |
|---|---|
| ACGAGCCTCATGCGTAGANcttacCTGAAGAGACGGTGACC | 138 |
| ACGAGCCTCATGCGTAGANcttacCTGAGGAGACGGTGACC | 139 |

*The J segment primers used. The 18 bp on the 5' are common sequences that are appended to the sequence complementary to the J segment in order to allow the second stage amplification. The position N signifies one random position in order to obtain diversity in the sequenced clusters. The small letter sequence are in the intron, and the capital letter sequences in the 3' of the sequence are in the exon. The letters in italics emphasize the bases that differ among the primers.

These primers span the exon-intron boundaries, and the four primers utilized amplify the different J segments and alleles described in the IMGT database. Primers of the second stage do not have any sequences complementary to genomic sequences.

Using the J primers over constant region primers complementary to the IgG constant region allows the assessment of the other classes (IgM, IgD, IgA, and IgE).

In the case of cDNA there is a choice of whether to use the J primer or the constant region primers. Several constant region primers can be used to amplify all the classes and sequence some of the constant region before entering into the J sequence in order to link the information on the clonotype and its specific class. The sequencing reads for many of the sequencing technologies are short and would be difficult to accomplish this. One of the current platforms on the market (454 Roche) does have a longer read but it has lower throughput than other platforms. As these technologies develop further this option become possible. With the current short reads (<100 bp) our work on the genomic DNA assay suggests that for amplification from cDNA can be done using both the J and the C priming approach. We can implement amplification using J primers from cDNA. However given that the exonic segment of these primers may be too short for specific amplification from cDNA, potentially the first stage PCR can be done using a set of constant region primers encompassing all the different classes (and the V segment primers on the other side as we have demonstrated). Then the second stage PCR can be done with the J primers which are long enough to have high specificity for second stage PCR which is utilizing a low complexity template. The products are then be sequenced. As stated above, the disadvantage compared with the scheme demonstrated for IgG is that somatic mutations in the J sequence may inhibit the amplification. The advantage is that all the different classes are assessed, even though the information on the class of each clonotype is not fully determined. Potentially one can do class specific amplification IgG, IgM, IgD, IgA, or IgE and compare with the overall picture obtained from using all the primers followed by J primer. For example one can compare clonotype profile obtained from IgG amplification to that using all the primers followed by J primer. The difference presumably would be due to somatic mutation in the J primer (which can be readily identified in the reaction using the IgG primer) and clonotypes of the other classes, which can then be quantified.

The use of J primers in cDNA also allows the direct comparison between the cDNA and genomic DNA results. This would provide expression level information at a clonotype level and can indeed have functional relevance. One aspect of this invention is that comparing the clonotype profile of cDNA and genomic DNA from the same blood or other biological sample identifies clonotypes that have different frequencies indicating unusually high or low expression per cell. This functional information can be utilized to predict whether a clonotype is likely to be correlating with disease or not. In addition the level of expression per cell of a clonotype correlating with a disease can be used to determine the disease activity or the likelihood of a disease outcome. For example obtaining the same level in the cDNA assay for a correlating clonotype in two individuals may still indicate the patients have different disease activities if the clonotypes level of expression per cell (as determined by comparison with the genomic DNA clonotype profiling) is different.

The second stage PCR is to attach the sequences necessary for the amplification. The primers used in the second stage are listed in Table 9.

TABLE 9

Common primers*

| Primer Sequence | Utilization | SEQ ID NO |
|---|---|---|
| AATGATACGGCGACCACCGAGATCT | Third stage PCR | 140 |
| CAAGCAGAAGACGGCATACGAGAT | Third stage PCR | 37 |
| CAAGCAGAAGACGGCATACGAGATNNNNNNNGTGACTGGAGTTCAGACGTGTGCTCTTCCGATCT | Common second stage PCR | 141 |
| TGATGGCTCAAACAAGGAGACCT | First stage PCR for mouse TCRβ | 142 |
| AATGATACGGCGACCACCGAGATCTGACCTTGGGTGGAGTCACATTTCTCCAGATCCT | Second stage PCR for mouse TCRβ | 143 |
| AATGATACGGCGACCACCGAGATCTACACTCTTTCCCTACACGAGCCTCATGCGTAGA | Second stage for human IgH from genomic DNA | 144 |

*Third stage is an optional amplification stage for all the assays (e.g. mouse TCRβ and human IgH). It is done to ensure the integrity of the end sequences that hybridize to the oligonucleotides attached to the flow cell. The common second stage primer is used in all the assays (e.g. mouse TCRβ and human IgH). Note that use of N in the common second stage primer is to denote the fact that each of these primers contains a unique 6 base pair tag to allow samples to be later identified.

Amplification is possible using the above primers and other sequences that are substantially similar. FIGS. 8A-8B show examples of such amplifications, which were successful at least in the range of genomic DNA 50-2,000 μg in 20 μl of input genomic DNA.

The assay needs to accommodate a large dynamic range of DNA. Biopsy samples may not have large amount of material, but given that the tumor is likely to be greatly enriched there is no need for a large amount of starting material. On the other hand, one million cells will have ~6 µg of genomic DNA. PBMC containing 1 million B cells will likely have ~20 µg of genomic DNA. To be able to assess 1 million B cells, ~6.6 µg of genomic DNA is used in each of the 3 PCR reactions. Of note is that if there is a somatic mutation in the sequence complementary to one of the primers then in this example only ~660K B cells are being interrogated. It is useful if the assay works over the range of 50 to 10,000 ng. The assay has been demonstrated to work in the range of 50-2,000 ng of DNA in 20 µl. By scaling up the reaction to 100 µl, 10 µg of DNA can be used.

EXAMPLE 23

Monitoring Acute Lymphoblastic Leukemia (ALL)

Minimal Residual Disease (MRD) is an important prognostic factor for the stratification of childhood ALL. MRD is typically tested in the bone marrow in the few weeks after induction therapy. More sensitive detection of leukemic cells can allow the monitoring for cancer recurrence in the blood.

Clonotype profiling to assess the level of the tumor clonotype in the blood is used to detect the leukemic cells sensitively.

The calibration is identified through the interrogation of a sample with high leukemic load. Leukemic cells typically are present at high frequency in diagnostic samples (blood or bone marrow). The diagnostic sample is often sequenced for several rearrangements.

If the tumor is B cell, the fully rearranged IgH, the partial D-J rearranged IgH, IgK including the Kde rearrangements can be assessed.

Cross lineage rearrangements frequently occur, and the most frequent is the partially rearranged (V-D) or (D-D) TCRβ. For T cells frequent rearrangement occur for TCRα and TCRβ, and at lower frequency TCRα.

Sequencing the clonotype repertoire for these different rearrangements identifies the particular tumor the rearrangement present in the tumor. The blood level of the specific sequence can then be monitored.

The monitoring test may involve the relevant rearrangements types only. For example if the tumor rearrangements identified in the diagnostic sample are IgH and IgK, then IgH and IgK would be amplified and sequenced in later blood samples. DNA from up to about 1 million B cells from these samples can be used to amplify IgH and IgK and up to about 1 million or more sequencing reads can be obtained, which gives an assay sensitivity of 1 in a million B cell is~to a sensitivity of 1 in 10 million white blood cells. With this great sensitivity, leukemic cells are likely to be detected significantly before a frank relapse.

Clonal evolution has been described in ALL. This can occur through V replacement or other mechanisms. To detect evolution, we will identify clonotypes that are related to those present in the diagnostic sample. For example, clonotypes with the same D-J junction, but with a different V will be identified. The presence of these related clonotypes at appreciable frequency in the diagnostic sample increases the likelihood of the relevance of the clonotype. Following more than one rearrangement (for this example tumor IgH and IgK) can also ameliorate this problem.

The mere presence of leukemic cells may not necessarily be sufficient for predicting relapse. A discovery study is performed with longitudinal blood samples for patients with known outcome. We will assess in these samples whether the mere presence of leukemic clonotype is sufficient to predict a relapse some time later. In addition we will assess the change in the frequency of these clonotypes as a predictor of relapse. In addition to the clonotype frequency, markers on the leukemic cells may be indicative of relapse. Sequencing can be performed before and after the enrichment of cells with the relevant marker. Therefore the total frequency of the clonotype is determined. In addition the fraction of these cells with the relevant marker is determined allowing a more precise estimation of the risk of relapse.

In accordance with the above, in one aspect the invention provides assays for MRD based on clonotype profile measurements. Such assays include using clonotype profiles to (i) monitor the presence and abundance of patient-specific clonotypes associated with the disease, including evolved clones, (ii) provide counts of lymphocytes from which the clonotypes are derived, and (iii) provide a measure of clonality (that is, a measure of how "skewed" a profile is to one or a few clonotypes). In one aspect, an assay is provided that gives values for (i) and (ii) simultaneously; and in another aspect, an assay is provided that gives all three quantities simultaneously from a single measurement of a patient's clonotype profile.

EXAMPLE 24

Monitoring of Transplant Rejection of a Solid Organ

Rejection of a solid organ transplant can occur through two distinct pathways: direct and indirect presentation. The direct pathway uses the donor antigen presenting cells that are transferred with the transplant. T cell receptors are recognizing in this case the donor HLA. The indirect pathway on the other hand, occurs some time later. In this case the donor peptides are presented by the recipient HLA to T cells.

Samples from biopsy of the transplanted organ can be used to identify relevant sequences for calibration of the relevant T (or B) cell receptors in transplant rejection. Clonotypes enriched in a biopsy of the transplanted organ can be compared to the blood at the time of rejection to identify clonotypes that are relevant to the rejection. The level of these clonotypes in the blood are then monitored to predict the state of the rejection.

Antigen specific calibration is also performed. To identify clonotypes relevant to rejection by the direct pathway, donor lymphocytes are irradiated and mixed with recipient PBMC. Recipient PBMC able to recognize donor lymphocytes are activated. Isolation of these activated cells is done by any of several techniques. For example these cells are isolated by virtue of cytokine release by intracellular cytokine staining or cytokine capture techniques. Instead (or in addition) to isolation the cells are allowed to replicate in vitro. Comparing sequences of the isolated (and/or the replicated cells) with the pre-activation sequences identifies clonotypes that interact with the donor PBMC. The same procedures of T cell activation without the addition of antigen followed by sequencing in order to subtract potential background of antigen-independent activation is also performed. The blood level of the transplant rejection relevant clonotypes is then monitored to assess the rejection activity of the direct pathway. A measure of the overall diversity is then used to monitor the level of rejection by the direct pathway.

To identify clonotypes relevant to rejection by the indirect pathway, donor antigens need to be presented in the context of the recipient HLA. Since the donor HLA is often an important antigen, the donor HLA is incubated with recipient antigen presenting cells that are able to present peptides from the donor HLA in the context of the recipient HLA to recipient T cells. In a manner similar to what is described above, these cells are isolated and replicated to identify clonotypes that are interacting with the donor HLA in the indirect pathway. Alternatively the same procedures of T cell activation without the addition of antigen followed by sequencing in order to subtract potential background of antigen-independent activation is performed. Alternatively donor cells and not just HLA are used as a source of antigen. The donor cells are prepared in a manner that makes it easy for recipient antigen presenting cells to present donor antigen in the context of recipient HLA. This is done by several alternative methods including lysing using several cycles of freezing and thawing or by sonication before addition to the antigen recipient presenting cells. The clonotypes that are activated by these antigens in the context of recipient HLA, are then identified by sequencing the isolated and/or replicated cells as described above The same procedures of T cell activation without the addition of antigen followed by sequencing in order to subtract potential background of antigen-independent activation is alternatively performed. Once these clonotypes are identified their blood level is monitored to assess the rejection activity of the indirect pathway.

EXAMPLE 25

Cancer Recurrence

Cancer recurrence is detected by the detection of the immune response to the tumor. The level of T and B cell clonotypes that are relevant to the tumor are used to detect cancer recurrence. The increase in the blood level of the relevant T and B cells (or the frequency of the relevant clonotypes cDNA obtained in blood) is detected and indicates recognition by the immune system of tumor recurrence.

The reduction of these levels is also detected and indicates the success of the tumor in evading the immune system and hence the development of cancer recurrence.

Cell markers change on the cells containing relevant clonotypes are detected and indicate tumor recurrence in the absence of a change in the frequency of the relevant clonotypes. These latter cases can be a reflection of tumor effect on the immune cells to make them ineffective or anergic.

In order to determine the relevant clonotypes in an individual, samples of the original tumor as well as algorithms developed in population studies are used. Alternatively, tumor-specific antigen are used to define clonotypes that interact with the tumor cells. For example B or T cells that interact with some tumor-specific antigens are captured and sequenced before and after this enrichment to determine the specific clonotypes that interact with the specific antigens.

In vitro experimentation are performed using techniques like the ones discussed above (e.g, tetramer binding, intracellular cytokine staining, or cytokine capture) to determine in a patient's sample the specific clonotypes interacting with the particular tumor-specific antigens. Once these clonotypes are defined, their level is monitored in other blood samples. Change in the level of these clonotypes indicates a tumor recurrence.

Cancer relevant clonotypes in an individual are identified using an in vitro assay to determine clonotypes interacting with the tumor. Tumor cells are lysed using repeated cycles of freezing and thawing or sonication. This preparation is added to autologous antigen presenting cells (or to autologous PBMC containing antigen presenting cells and T cells). The mixture is added to autologous T cells and clonotypes that are activated by antigen are identified by sequencing isolated and/or replicated T cells and comparing to the sequence of the unenriched material as described above. The same procedure of T cell activation is performed without the addition of antigen followed by sequencing in order to optionally subtract potential background of antigen-independent activation. Once the relevant clonotypes are determined their level in the blood is monitored in order to assess the likelihood of recurrence.

Where the cancer is of cells that are capable of antigen presentation, the tumor cells may optionally not be lysed as they may serve as the antigen presenting cells. Lymphoma, a B cell tumor that may be able to present antigens in some cases, serves as an antigen presenting cell. The tumor cells are optionally activated in vitro to improve its antigen presenting capability. These tumors are then mixed with autologous T cells (or PBMC). Sequencing of the T cell clonotypes before and after enrichment identifies the cancer-relevant clonotypes. The level of these clonotypes is then monitored in the blood to determine the risk of recurrence.

The level of the clonotype in a specific type of cells, e.g., those with specific surface markers is monitored to detect cancer cells which may evade the immune system. So for two patients with the same level of the relevant clonotype, then depending on the markers contained in the cell containing the clonotypes, one patient may have a higher likelihood of recurrence compared to another. In order to obtain the information, sequencing can be done before and after enrichment of cells by the particular marker. Therefore the total as well as the fraction and number of clonotype cells with the particular marker can be measured.

EXAMPLE 26

Monitoring of Hepatitis C Infection

The acute infection of hepatitis C is often accompanied by an immune response that is capable of clearing the infection in ~15% of cases. The ability to clear the infection has been shown to be associated with certain HLA genotypes. In the majority of cases the virus is not cleared and a chronic infection occurs. During this chronic infection the virus is able to evade the immune response which is probably responsible to the much of the resulting liver damage. The most effective treatment for the disease is interferon. This treatment kills the virus at least partly through activation of the immune response. Monitoring of the immune response can therefore be helpful in different states during the course of the disease. During the acute phase assessing the extent of the immune reaction may be helpful in predicting who is likely to clear the virus. During the chronic phase measurement of the level of the immune response can provide an indication of the degree of the liver inflammation. Finally, the evaluation of the immune reaction during interferon treatment can provide an early indication of whether treatment is being effective. The assessment of the immune response can be done by measurement of the T and B cell repertoire by sequencing as described above.

The identification of the clonotypes relevant to hepatitis C in each individual is done by several methods. Hepatitis C antigens are used as individual peptides, a mixture of peptides, proteins, or the full virus. T cell and/or B cells interacting with antigen are identified by evidence of enrichment of the clonotypes in cells activated by antigens compared to their level in the rest of the cells. In addition liver biopsy is optionally done for these patients during the course of treatment.

That provides additional or alternative means to identify hepatitis C relevant clonotypes. Clonotypes significantly more enriched in the liver compared to the blood are likely to be relevant at least regarding the inflammatory process in the liver. Therefore their levels in the blood in later points are monitored to assess the liver inflammatory activity. Finally discovery studies in a population of patients may indicate a set of sequences or motifs that are relevant to hepatitis C. In this population study relevant clonotypes are identified by the virtue of their correlation with disease or enrichment in liver biopsy and algorithms to distinguish these clonotypes from others is discovered. Some of criteria include clonotype frequency, rank, sequence similarity of multiple clonotypes, or sequence motif as well as the presence of some cell marker.

HLA typing is used as a stratification method. Specific motifs are predictive only in the context of specific HLA types.

Virus infected cells can sometimes evade the immune system. Therefore monitoring of the level of the clonotype in a specific type of cells, e.g., those with specific surface markers, is performed. So for two patients with the same level of the relevant clonotype, then depending on the markers contained in the cell containing the clonotypes, one patient is mounting a more rigorous response than the other. For example, the effect of interferon treatment may be in the qualitative as well as quantitative change in the clonotype cells. Therefore it is important to obtain the level of the clonotype and define whether they have specific cell markers. In order to obtain the information, sequencing is done before and after enrichment of cells by the particular marker. Therefore the total as well as the fraction and number of clonotype cells with the particular marker can be measured.

EXAMPLE 27

Drug Hypersensitivity

The identification of clonotypes that are relevant to a specific drug hypersensitivity is done using population studies. In these studies clonotypes that correlate with the ADR are identified and characteristics that distinguish them from the other clonotypes are identified by different criteria like frequency, rank, relative change before and after treatment, sequence similarity of multiple clonotypes, sequence motif, as well as the presence of cell marker. Sequence motif can be HLA-dependent where different motifs are determined to be relevant to different corresponding HLA sequences.

Another method for identification of drug-hypersensitivity relevant clonotypes is by interaction with antigen. Drugs and/or its metabolite(s) is used to capture B cells that interact with it. Similarly the drug or its metabolites are incubated with autologous antigen presenting cells optimally before or at the same time of addition of T cells. Activated T cells are isolated or replicated using some of the methods discussed above to obtain an antigen-enriched cells. These antigen-enriched cells are then sequenced and clonotypes enriched in these cells compared with the un-enriched cells are identified as relevant to the drug interaction.

The same procedures of T cell activation without the addition of antigen is also performed followed by sequencing in order to subtract potential background of drug antigen independent activation.

This calibration test is done before or after taking the drug. Blood samples before and after taking the drug and the in vivo increase in the level of the clonotype are used as an additional criteria to define the relevant clonotypes. Once these clonotypes are identified they are monitored to predict the likelihood of a drug hypersensitivity. This invention utilizes the lymphocyte activation with drugs merely to define the relevant clonotypes and the blood level of these clonotypes can be monitored in subsequent samples by sequencing generating a sensitive and specific method to predict ADRs. The drugs that are used are small molecules or biological, like antibodies. Similarly, a drug metabolite or a combination of metabolites is used to identify T cells that interact with it as described above. The metabolite is generated by chemical synthesis or purified from a biological sample. For example the drug is introduced into an organism and the drug metabolites are purified for use in the assay. The metabolites are also obtained by processing the drug by cells in vitro.

The level of the clonotype in a specific type of cells, e.g., those with specific surface markers is monitored The increase in a clonotype level in cells carrying activation markers after the introduction of drug is more indicative of drug hypersensitivity than if the activation marker is not present. In order to obtain the information, sequencing is done before and after enrichment of cells by the particular marker. Therefore the total as well as the fraction and number of clonotype cells with the particular marker is measured.

An ADR is predicted without taking the drug. A high level of clonotypes that interact with the drug or the presence of sequence motif likely to mount a strong response to the drug is detected to predict the ADR without administering the medication to the patient.

Similar immune response characteristics of drugs with idiosyncratic immune-related ADRs are identified. These drugs may have high frequency clonotypes that interact with the drugs or their metabolites. Drugs that are likely to have immune-related ADRs are identified after administration in only a small number of patients.

The subclinical response of an ADR causing drug is detected by the determination of an increase in the clonotypes specific to drug (and/or its metabolite) after the administration of the medication.

Drugs that are likely to have an immune related ADR are identified by tracking the increase in the clonotypes corresponding to ARDs after administration in a small number of patients.

EXAMPLE 28

Methods for Risk Stratification in Carotid Vascular Disease

Inflammation involved in the formation as and stability of the plaques is detected in a patient. The immune response specific to vascular inflammation is used to indicate the risk of plaque destabilization. Specific antigens relevant in the immune reaction in the ICA (including modified or oxidized LDL and heat shock protein) are utilized to identify the specific clonotypes relevant to immune reaction in ICA. Using similar procedures as described above T or B cell clonotypes that interact with the specific antigens are identified. The levels of the identified, clonotypes are monitored to assess the risk of ICA plaque destabilization.

Clonotypes that are relevant to ICA plaque destabilization are also identified using an algorithm that is generated from a population study that identifies characteristics that distinguish the relevant clonotypes from others. These relevant clonotypes are identified in the population study by the virtue of their correlation with plaque destabilization or by their significant enrichment in the ICA plaque (for example as obtained from carotid endarterectomy) compared with blood. The sequence motifs can be specific to distinct corresponding HLA genotypes. The developed algorithm are then be used to predict ICA plaque destabilization relevant clonotypes in other patients.

EXAMPLE 29

TCR Repertoire Analysis in EAE Mice 10 mice of SJL strain were treated with the peptide 139-151 along with complete Freund's adjuvant (CFA) using a commercially available protocol, e.g. Hooke Laboratories (Lawrence, Mass.). Eight of these mice developed Experimental Autoimmune Encephalitis (EAE), a mouse model of multiple sclerosis, and the other two did not. In addition 2 mice of the same strain were treated with CFA only. For each mouse disease scores were obtained daily for 61 days after injection. The score range was from 0 to 5. Blood samples were obtained before injection and specific days afterwards. Overall, 11 blood samples were obtained from each mouse and the mice were sacrificed at day 62 or 63 and spleen, lymph nodes, and spinal cord was obtained. Blood and the tissue were immediately stored in animal blood protect RNA reagent and RNA later, respectively. RNA was extracted from the blood samples using Qiagen animal protect blood extraction kit and the tissue samples were mechanically homogenized, and RNA prepared using RNA Qiagen Plus minikit, cDNA was produced from each sample using Vilo cDNA synthesis kit (Life technologies). The TCRβ repertoire from each of the samples was amplified using the primers in Table 10.

TABLE 10

Mouse V Segment Primers*

| V Segment Primers | SEQ ID NO |
|---|---|
| CAAAGAGGTCAAATCTCTTCCCG | 145 |
| CTTATGGACAATCAGACTGCCTCA | 146 |
| GTCATGGAGAAGTCTAAACTGTTTAAGG | 147 |
| GTAAACGAAACAGTTCCAAGGCG | 148 |
| GGTGCCCAGTCGTTTTATACCTGAAT | 149 |
| CCCAGCAGATTCTCAGTCCAACAGT | 150 |
| AGATATCCCTGATGGATACAAGGC | 151 |
| AGATATCCCTGATGGGTACAAGGC | 152 |
| AGATGTCCCTGATGGGTACAAGGC | 153 |
| GATAATTCACAGTTGCCCTCGGAT | 154 |
| GATGGTGGGGCTTTCAAGGATC | 155 |
| CAAGCTCCTATAGATGATTCAGGG | 156 |
| CTATGATAAGATTTTGAACAGGGAAGC | 157 |
| GATCTACTATTCAATAACTGAAAACGATCTTC | 158 |
| TAGCACTTTCTACTGTGAACTCAGCA | 159 |
| CTTGATCAAATAGACATGGTCAAGG | 160 |
| AGAGATTCTCAGCTAAGTGTTCCTCG | 161 |
| GTTCTTCAGCAAATAGACATGACTG | 162 |

TABLE 10-continued

Mouse V Segment Primers*

| V Segment Primers | SEQ ID NO |
|---|---|
| AGCGAAGGAGACATCCCTAAAGGAT | 163 |
| CGAGAGTGGATTCACCAAGGACAAG | 164 |

*Each of the primers have a common 14 bp (AGATCGGAAGAGCA) (SEQ ID NO 165) appended to its 5' end.

A second PCR was performed on each of the samples using primers in Table 7. Each sample was amplified with one pair of primers that amplified the complete set of first stage PCR amplicons but which also included an individual sequence tag that could later allow individual samples to be identified in a mixture of sequence data. A third PCR is done using one pair of primers for all samples (table 7). The purpose of the third PCR was to ensure the integrity of the terminal sequences. The structure of the PCR product is shown in FIGS. 2A-2B and FIG. 3A. These PCR reactions were pooled in sets of 64 such that each sample with the pool was indexed by one of the unique tags incorporated in the second stage PCR. The molecules from these pools were then denatured and separated in two dimensions on a solid surface through hybridization with a flow cell containing oligonucleotides that hybridize with the terminal sequences of the amplified products. The hybridized molecules were then amplified by a bridging amplification to form clusters on the two dimensional surface such that each cluster contained approximately 1,000 molecules each the result of an amplification of a single molecule from the PCR pool. A method was then used to cleave and release one of the two strands of each of these molecules leaving a single stranded template. A sequencing primer was then hybridized to the clusters. Iterative rounds of sequencing were then carried out involving: the introduction of 4 fluorescently labeled chemically terminated nucleotides of each nucleic acid base and a polymerase and buffers such that an incorporation of a single nucleotide would occur for the active position of the extension product that was complementary to each nucleotide; a washing step, a fluorescence scan of the surface to measure which clusters incorporated which fluorescent dye, the introduction of a cleavage chemical that released the termination molecules from the incorporated bases along with the fluorescent label to allow for subsequent cycles; a wash step. These steps were iterated ~100 times to reveal the sequence of each cluster (read 1). The synthesized strand was then removed by denaturation. A second primer was then introduced and the sequencing process re-iterated to read a 6 base tag. This synthesized strand was then removed by denaturation. The original template strand was then allowed to hybridize back to the immobilized surface primers which were extended to re-form the double stranded clusters. At this point the original strand was cleaved resulting in clusters formed from the complements of the original single stranded clusters. A third sequencing primer was introduced and it hybridized to this strand and the sequencing was iterated ~60 cycles to obtain sequences from the reverse strand of the amplicons (read 2). The resulting sequences contributed ~100,000-200,000 reads per sample after having been sorted based on the tag sequences.

The obtained sequences were first mapped to specific regions of the V and J segments. Specifically the first 27 bp of read 1 were mapped to the last 27 bp of the different mouse J segments. Similarly the initial sequences of read2 were mapped to the sequences of the used primers. When a sequence is mapped to one of the primers then the sequence of the read2 following the primer is mapped to the different mouse V segments. Since Read1 is expected to reach the V segment, we also attempted to map it in order to determine the frame and the amino acid sequence. Positions 81-95 of read 1 were mapped to the most 3' 60 bp of the specific V segment that read2 maps to. If a sequence does not have substantial identity to any of the J and V sequences it would be eliminated. Additionally the J and V mapping s are extended in read1. Since the specific J and V are mapped for each cluster we can assess whether the bases outside the originally mapped sequence are consistent with the sequence of the mapped V and J. These sequences will cease to be consistent when the bases that result from the non-templated replication (N bases) or D segment are reached. Differences between read sequences and the V or J sequence in the originally mapped or the extended regions are then considered to be due to error and are "corrected".

Reads that have identical sequences for positions 28-80 are then considered a clonotype. Clonotypes that are very similar in sequence are then assessed to whether they are likely to be independent clonotypes or one clonotypes that separated due to PCR and/or sequencing error. We have devised an algorithm that incorporates the frequency of the two clonotypes under consideration the number of differences between them and the likelihood of error at that position to determine whether the two clonotypes are to be coalesced into one clonotype or not. When one of the two clonotypes is at a very high frequency and the other is rare and there is only one base difference towards the end of the read (that generally has more errors) then the two clonotypes are likely a result of error and they are then coalesced. On the other hand the presence of two clonotypes at similar frequency and with three differences between them indicates that these two clonotypes are genuinely independent and are not coalesced. The frequency of each TCR□ clonotype is then computed.

A public clonotype was present in all 12 mice. This clonotype had the signature of a clonotype reactive to CFA. It was undetectable in any of the mice before the injection or at day 5, but it dramatically increases to high frequency at later time points. Multiple nucleotide sequences across mice and within a single mouse coded for the same amino acid sequence of this clonotype. Overall and after eliminating clonotypes seen in less than 3/10 time points for a mouse (time point number 8 was eliminated from all the mice as there was unusual characteristics in a few of the mice), there are 23 observations of clonotypes with this amino acid sequence (19 of which present at mean frequency >10-4) with 10 distinct nucleotide sequences in the 12 mice (8 distinct sequences for the 19 high frequency clonotypes) were obtained (see table 10). In addition there are additional related clonotypes (with only one amino acid difference) that also have the same pattern of being low before injection and high after 10 days of the injection. This provides an overwhelming evidence of a clonotype that is responsive to CFA.

TABLE 11

Mouse TCRβ public clonotype in response to CFA*

| Mouse ID | Log10 clone mean frequency | Nucleotide Sequence | SEQ ID NO | Protein Sequence | SEQ ID NO |
|---|---|---|---|---|---|
| 62 | -2.73861 | CAAAATACAGCGTTTCTGCACTACCCCAAGCTATACTGCTGGCACAGAGAAAA | 171 | FLCASSIAWGSAETLYF | 193 |
| 62 | -3.78089 | CAAAATACAGCGTTTCTGCACTCCCCCAGGCTATACTGCTGGCACAGAGAAAA | 172 | FLCASSIAWGSAETLYF | 193 |
| 34 | -3.75307 | CAAAATACAGCGTTTCTGCACTCCCCCAGGCTATACTGCTGGCACAGAGAAAA | 172 | FLCASSIAWGSAETLYF | 193 |
| 34 | -3.2046 | CAAAATACAGCGTTTCTGCACTACCCCAGGCTATACTGCTGGCACAGAGAAAA | 173 | FLCASSIAWGSAETLYF | 193 |
| 64 | -2.95504 | CAAAATACAGCGTTTCTGCACTCCCCCAAGCTATACTGCTGGCACAGAGAAAA | 174 | FLCASSIAWGSAETLYF | 193 |
| 14 | -3.10634 | CAAAATACAGCGTTTCTGCACTCCCCCAGGCTATACTGCTGGCACAGAGAAAA | 172 | FLCASSIAWGSAETLYF | 193 |
| 61 | -3.07614 | CAAAATACAGCGTTTCTGCACTACCCCAAGCTATACTGCTGGCACAGAGAAAA | 171 | FLCASSIAWGSAETLYF | 193 |
| 61 | -4.62344 | CAAAATACAGCGTTTCTGCACTACCCCAGGCTATACTGCTGGCACAGAGAAAA | 173 | FLCASSIAWGSAETLYF | 193 |
| 61 | -4.6644 | CAAAATACAGCGTTTCTGCACTTCCCCAGGCTATACTGCTGGCACAGAGAAAA | 175 | FLCASSIAWGSAETLYF | 193 |

TABLE 11-continued

Mouse TCRβ public clonotype in response to CFA*

| Mouse ID | Log10 clone mean frequency | Nucleotide Sequence | SEQ ID NO | Protein Sequence | SEQ ID NO |
|---|---|---|---|---|---|
| 55 | -2.70719 | CAAAATACAGCGTTTCTGCACTC CCCCAGGCTATACTGCTGGCACA GAGAAAA | 172 | FLCASSIAWGSAETLYF | 193 |
| 55 | -3.05281 | CAAAATACAGCGTTTCTGCACTA CCCCAGGCAATACTGCTGGCAC AGAGAAAA | 176 | FLCASSIAWGSAETLYF | 193 |
| 55 | -3.44137 | CAAAATACAGCGTTTCTGCACTC CCCCAGGCAATACTGCTGGCAC AGAGAAAA | 177 | FLCASSIAWGSAETLYF | 193 |
| 65 | -3.73.155 | CAAAATACAGCGTTTCTGCACTG CCCCAAGCTATACTGCTGGCACA GAGAAAA | 178 | FLCASSIAWGSAETLYF | 193 |
| 65 | -3.42266 | CAAAATACAGCGTTTCTGCACTA CCCCAGGCTATACTGCTGGCACA GAGAAAA | 173 | FLCASSIAWGSAETLYF | 193 |
| 35 | -4.35749 | CAAAATACAGCGTTTCTGCACTG CCCCAGGCTATACTGCTGGCACA GAGAAAA | 179 | FLCASSIAWGSAETLYF | 193 |
| 35 | -2.97796 | CAAAATACAGCGTTTCTGCACTC CCCCAGGCTATACTGCTGGCACA GAGAAAA | 172 | FLCASSIAWGSAETLYF | 193 |
| 23 | -3.20311 | CAAAATACAGCGTTTCTGCACTC CCCCAGGCTATACTGCTGGCACA GAGAAAA | 172 | FLCASSIAWGSAETLYF | 193 |
| 23 | -4.70989 | CAAAATACAGCGTTTCTGCACTA CCCCAGGCTATACTGCTGGCACA GAGAAAA | 173 | FLCASSIAWGSAETLYF | 193 |
| 11 | -2.8685 | CAAAATACAGCGTTTCTGCACTC CCCCAGGCTATACTGCTGGCACA GAGAAAA | 172 | FLCASSIAWGSAETLYF | 193 |
| 63 | -3.38278 | CAAAATACAGCGTTTCTGCACTA CCCCAGGCTATACTGCTGGCACA GAGAAAA | 173 | FLCASSIAWGSAETLYF | 193 |
| 63 | 3.21617 | CAAAATACAGCGTTTCTGCACTC CCCCAAGCTATACTGCTGGCACA GAGAAAA | 174 | FLCASSIAWGSAETLYF | 193 |
| 45 | -3.79581 | CAAAATACAGCGTTTCTGCACTC CCCCAGGCTATACTGCTGGCACA GAGAAAA | 172 | FLCASSIAWGSAETLYF | 193 |
| 45 | -3.55157 | CAAAATACAGCGTTTCTGCGCTC CCCCATGCTATACTGCTGGCACA GAGAAAA | 180 | FLCASSIAWGSAETLYF | 193 |

*The log10 mean frequency describes the mean frequency among all 10 time points for the specific mouse.

While preferred embodiments of the present invention have been shown and described herein, it is obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The public clonotype described in the above example was validated by looking at TCR repertoires of additional mice. Specifically, the presence of the clonotype in 11 PLP treated and 3 sham treated mice were assessed. The clonotype was present in 12/14 mice. In addition the related clonotype mentioned in the above example (with one amino acid difference) was also seen repeatedly. There were 15 observations (different nucleotide sequences in the same animal or in different animals) for the clone with one amino acid difference. The clonotype was not seen in any of the animals before vaccination. The pattern of frequency was also quite similar to what was seen in the first set of animals. This validates that the identified public clonotype is indeed common to the majority of mice who were treated with the Freund's adjuvant.

The use of affected tissue to help determine clonotypes relevant to disease. Clonotypes correlating with disease activity in the above EAE model were found. However, it is not readily obvious whether the clonotypes were specific to the adjuvant aspect of the vaccination or the PLP peptide. The presence or absence of the clonotypes in the sham treated samples was a method to distinguish the two possibilities. As was disclosed previously, affected tissue can be used to determine clonotypes relevant to the disease. In this case, spinal cord tissue was available. Clonotypes were filtered from the data which had a frequency that is at least 3 larger in spinal cord than each of the three other samples obtained at the sane time (spleen, lymph node, and blood). Clonotypes were then examined that were correlated with the disease score. A clonotype was identified that appeared more than once. The sequence of the clonotype was LYCTCSALGGSSYEQYF (sequence A) (SEQ ID NO: 194). This sequence was looked for and identified it in all 8 mice with the disease. Two mice that were treated with PLP but did not develop disease and it was not detected in the two sham-treated mice. The pattern of frequency of the clonotype in the serial blood samples differed between mice. However, in all mice the clonotype was absent before vaccination. In addition the pattern of higher frequency in the spinal cord than the other tissue at the same time point was demonstrated in all except one mouse.

Given the risk of overfitting, an independent set of mice was examined to validate these finding. The presence of sequence A in additional mice was examined. Specifically, the presence of sequence A was tested in the following circumstances: in eight additional PLP treated mice that developed EAE, three PLP treated mice that did not develop EAE, and three sham treated mice. Among the 11 PLP-treated mice, the clonotype was present in eight mice. Two out of the three that did not have the clonotype did not develop disease. The clonotype was not found in the three sham treated mice nor was it found in any of the PLP-treated mice at the point before vaccination. In addition, the pattern of higher frequency in the spinal cord than the other tissues of the same time point was demonstrated in all the animals. In all the samples (the initial discovery and later validation) among 21 animals treated with PLP, 18 have the clones, but none before vaccination. In addition none of the five sham treated mice have sequence A. This provides strong evidence for a public EAE clonotype that is specific to the disease.

Additional clonotypes that correlate with disease and are enriched in the spinal cord appear to have very similar sequences to each other. These semi-private clonotypes are additional disease-specific clonotypes. These can be more comprehensively identified through a the utilization of a motif finding algorithm to determine shared sequences among clonotypes enriched in spinal cord and correlate with disease.

EXAMPLE 30

Somatic Hypermutations Identified in IgH Clonotype Profiling

Three sets of amplifications were performed using IgH V segment primers listed in table 5 and the primers complementary to the IgG constant sequence that are also disclosed above. cDNA from 7 normal samples, 7 samples from patients with multiple sclerosis, and 4 samples with SLE were used as templates for amplification. After second stage PCR that introduced a unique tag for each sample, the products were spatially isolated and subjected to sequencing.

The sequences were then mapped to individual V and J segments and assembled into clonotypes using methodologies disclosed above. We sought evidence of frequent highly related clonotypes that may be the result of somatic hypermutation in these samples. Data in table 11 shows a striking example in one of the multiple sclerosis patients. In this example, 12 distinct clonotypes were identified. These 12 nucleotide clonotypes code for 3 highly related amino acid sequences. Two of the amino acid sequences are at very high frequency (>1%) and differ by one conserved amino acid (Lysine vs. Arginine).

TABLE 12

List of related clonotypes in a multiple sclerosis patient*

| Frequency (%) | Consensus Sequence | SEQ ID NO | Protein Sequence | SEQ ID NO |
|---|---|---|---|---|
| 0.095834689 | CTGGCCCCAATTCCATCTGCCTGTAAAGCATGTACAGTAATACACAGCCGTGT | 181 | TAVYYCTCFTGRWNWGQ | 195 |
| 2.098569825 | CTGGCCCCAGTTCCATTTGGTAGTAAAACATGTACAGTAATACACAGCCGTGT | 182 | TAVYYCTCFTTKWNWGQ | 196 |
| 0.856216488 | CTGGCCCCAATTCCACTTGGTAGTAAAACATGTACAGTAATACACAGCCGTGT | 183 | TAVYYCTCFTTKWNWGQ | 196 |
| 0785914399 | CTGGCCCCAATTCCACTTGGTGGTAAAACATGTACAATAATAGACAGCCGTGT | 184 | TAVYYCTCFTTKWNWGQ | 196 |
| 0.395930174 | CTGGCCCCAGTTCCATTTGGTAGTAAAACATGTACAGTAATATACAGCAGTGT | 185 | TAVYYCTCFTTKWNWGQ | 196 |
| 0.128712283 | CTGGCCCCAGTTCCATTTGGTAGTAAAACATGTACAGTAATATACAGCTGTGT | 186 | TAVYYCTCFTTKWNWGQ | 196 |

TABLE 12-continued

List of related clonotypes in a multiple sclerosis patient*

| Frequency (%) | Consensus Sequence | SEQ ID NO | Protein Sequence | SEQ ID NO |
|---|---|---|---|---|
| 0.094435642 | CTGGCCCCAGTTCCATTTGGTAG TAAAACATGTACAGTAATATACA GCGGTGT | 187 | TAVYYCTCFTTKWNWGQ | 196 |
| 0.053513531 | CTGGCCCCAATTCCACTTGGTAG TAAAACATGTACAGTAATAGAC AGCAGTGT | 188 | TAVYYCTCFTTKWNWGQ | 196 |
| 0.019936413 | CTGGCCCCAGTTCCATTTGGTAG TAAAACATGTACAGTAATATACG GCCGTGT | 189 | TAVYYCTCFTTKWNWGQ | 196 |
| 0.014340227 | CTGGCCCCAGTTCCATTTGGTAG TAAAACATGTACAGTAATATACA GCCGTTG | 190 | TAVYYCTCFTTKWNWGQ | 196 |
| 1.305310431 | CTGGCCCCAGTTCCATCTCGTAG TAAAACATGTACAATAATACACA GCCGTGT | 191 | TAVYYCTCFTTRWNWGQ | 197 |
| 0.199364133 | CTGGCCCCAGTTCCATCTGGTAG TAAAACACGTACAATAATACACA GCCGTGT | 192 | TAVYYCTCFTTRWNWGQ | 197 |

*The sequence of positions 28-80 is shown with the amino acid sequence. The frequency column notes the frequency of the clonotype in the sample. For example the second clonotypes represent over 2% of all the sequences in this sample.

EXAMPLE 31

Forensic Use of Immune Profiling

Figure 10:
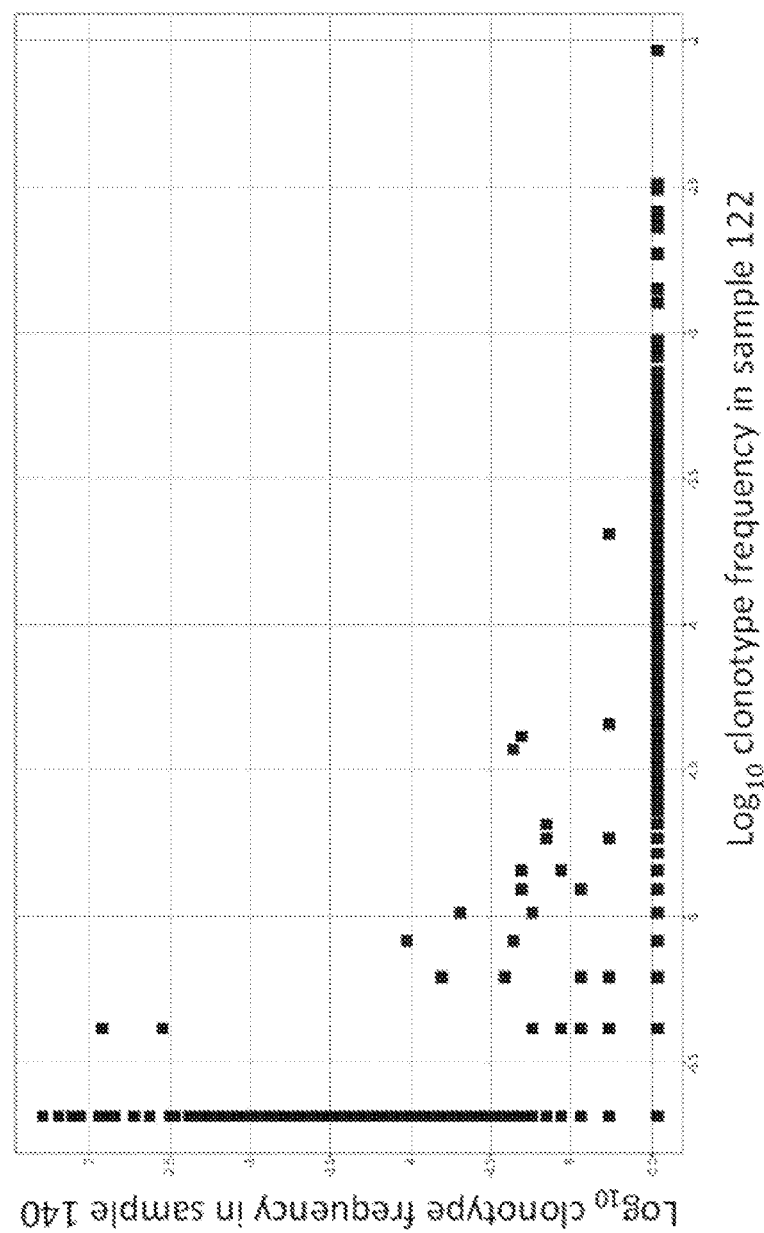
FIG. 10 shows data comparing clonotypes of two individuals.

Clonotype profiles for T and/or B cell receptors may be employed for human and animal identification. The tremendous diversity of these of clonotype profiles provides a very unique signature of the individual. This is exemplified by profiles of FIG. 10. In this example TCRβ sequences were amplified by reverse transcriptase PCR from mRNA extracted from the blood of two different individuals. The primers complementary to the V regions are listed in Table 13. The second stage amplification primers are the same as those of Example 2. The products were sequenced and the frequency of each clonotype frequency determined. As can be seen in FIG. 10, the vast majority of clonotypes from the individuals are different, clonotypes of one individual (sample 122) positioned almost exclusively along the X axis and clonotypes of the other individual (sample 140) positioned almost exclusively along the Y axis. Only about 25 clonotypes appear to be shared, as indicated by off-axis data points. This disparity of clonotype usage between individuals has been corroborated by Warren et al. Genome Research, Epub (24 Feb. 2011). In one aspect of the invention, this disparity in clonotype usage provides a method for distinguishing individuals comprising the steps: (a) obtaining a clonotype profile of a first sample, (b) obtaining a clonotype profile of a second sample, and (c) determining whether the first sample and the second sample are from the same individual by measuring the degree to which usage of clonotypes overlaps.

TABLE 13

Human TCRβ V sement primers

| V Segment Primer | SEQ ID NO |
|---|---|
| AACTATGTTTTGGTATCGTCAGT | 2 |
| TTCTGGTACCGTCAGCAAC | 3 |
| AGTGTATCCTGGTACCAACAG | 4 |
| AGTGTGTACTGGTACCAACAG | 5 |
| ACTGTGTCCTGGTACCAACAG | 6 |
| AGTGTGTCCTGGTACCAACAG | 7 |
| TCTGTGTACTGGTACCAACAG | 8 |
| CCCTTTACTGGTACCGACAG | 9 |
| GCCTTTATTGGTACCGACAG | 166 |
| CCCTTTACTGGTACCGACAAA | 11 |
| CCCTTTATTGGTACCGACAG | 167 |
| TTTTGGTACCAACAGGTCC | 12 |
| TTTTGGTACCAACAGGCCC | 13 |
| AACCCTTTATTGGTATCAACAG | 14 |
| CGCTATGTATTGGTACAAGCA | 15 |
| GGCAATGTATTGGTACAAGCA | 16 |
| GGCTATGTATTGGTACAAGCA | 168 |
| TTTCTGGTACAGACAGACCATGA | 17 |
| TACTATGTATTGGTATAAACAGGACTC | 18 |
| CAAAATGTACTGGTATCAACAA | 19 |
| ATGTTCTGGTATCGACAAGACC | 20 |
| ATGTACTGGTATCGACAAGACC | 21 |

TABLE 13-continued

Human TCRβ V sement primers

| V Segment Primer | SEQ ID NO |
|---|---|
| TGCCATGTACTGGTATAGACAAG | 22 |
| GTATCGACAAGACCCAGGCA | 169 |
| ATGTCCTGGTATCGACAAGACC | 170 |
| TAATCTTTATTGGTATCGACGTGT | 27 |
| GCCATGTACTGGTACCGACA | 28 |
| TCATGTTTACTGGTATCGGCAG | 29 |
| CAACCTATACTGGTACCGACA | 30 |
| CATGCTACCCTTTACTGGTACC | 31 |
| CACAATACCCTTTACTGGTACC | 32 |
| ATACTTCTATTGGTACAGACAAATCT | 33 |
| CACTGTCTACTGGTACCAGCA | 34 |
| CGTCATGTACTGGTACCAGCA | 35 |

*All the primers have a common 14 bp (AGATCGGAAGAGCA) (SEQ ID NO 165) appended to their 5' end.

Of 342 clonotypes in blood from the first sample (sample 122) at a frequency >$10^{-4}$ only one is detected in the second individual (sample 140). Reciprocally, out of 505 clonotypes present at frequency >10-4 in the sample 144, 3 are detected in the sample 122. As a control for random fluctuation of the measurement, out of the same 505 clonotypes, 504 clonotypes were present in a replicate amplification sample. This demonstrates the potential for a complete clonotype profile of being a potentially extremely specific identifier. Of course, the nature of these profiles is that they are not stable in time as new immune reactions will add new clonotypes to the spectrum. These processes however do not alter these profiles very rapidly. It can be seen that while the precise frequency of individual clonotypes shift in time, the set of clonotypes present at a measurable frequency is likely much greater than what would be found in a second individual. Algorithms can be developed to define the fraction and number of identical clonotypes that would be necessary to determine that two specimens are from the same individual. Furthermore, because this diversity is found in a gene with a great deal of active function in contrast to microsatellite diversity, it is possible to extract potentially relevant identification information without needing to haw a matched sample from an identified donor sample. Information about the health of this individual, his or her vaccination history, etc. is measurable from the clonotype information.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

DEFINITIONS

Unless otherwise specifically defined herein, terms and symbols of nucleic acid chemistry, biochemistry, genetics, and molecular biology used herein follow those of standard treatises and texts in the field, e.g. Kornberg and Baker, DNA Replication. Second Edition (W.H. Freeman, New York, 1992); Lehninger, Biochemistry. Second Edition (Worth Publishers. New York, 1975): Strachan and Read, Human Molecular Genetics, Second Edition (Wiley-Liss, New York, 1999); Abbas et al, Cellular and Molecular Immunology, $6^{th}$ edition (Saunders, 2007).

"Amplicon" means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to polymerase chain reactions (PCRs), linear polymerase reactions, nucleic acid sequence-based amplification (NASBAs), rolling circle amplifications, and the like, disclosed in the following references that are incorporated herein by reference: Mullis et al. U.S. Pat. Nos. 4,683,195; 4,965,188; 4.683.202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al. Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Clonality" as used herein means a measure of the degree to which the distribution of clonotype abundances among clonotypes of a repertoire is skewed to a single or a few clonotypes. Roughly, clonality is an inverse measure of clonotype diversity. Many measures or statistics are available from ecology describing species-abundance relationships that may be used for clonality measures in accordance with the invention, e.g. Chapters 17 & 18, in Pielou, An Introduction to Mathematical Ecology, (Wiley-Interscience, 1969). In one aspect, a clonality measure used with the invention is a function of a clonotype profile (that is, the number of distinct clonotypes detected and their abundances), so that after a clonotype profile is measured, clonality may be computed from it to give a single number. One clonality measure is Simpson's measure, which is simply the probability that two randomly drawn clonotypes will be the same. Other clonality measures include information-based measures and McIntosh's diversity index, disclosed in Pielou (cited above).

"Clonotype" means a recombined nucleotide sequence of a T cell or B cell encoding a T cell receptor (TCR) or B cell receptor (BCR), or a portion thereof. In one aspect, a collection of all the distinct clonotypes of a population of lymphocytes of an individual is a repertoire of such population, e.g. Arstila et al. Science, 286: 958-961 (1999); Yassai et al. Immunogenetics, 61: 493-502 (2009); Kedzierska et al, Mol. Immunol., 45(3): 607-618 (2008); and the like. As used herein, "clonotype profile." or "repertoire profile," is a tabulation of clonotypes of a sample of T cells and/or B cells (such as a peripheral blood sample containing such cells) that includes substantially all of the repertoire's clonotypes and their relative abundances. "Clonotype profile," "repertoire profile," and "repertoire" are used herein interchangeably. (That is, the term "repertoire," as discussed more fully below, means a repertoire measured from a sample of lymphocytes). In one aspect of the invention, clonotypes comprise portions of an immunoglobulin heavy chain (IgH) or a TCR β chain. In other aspects of the invention, clonotypes may be based on other recombined molecules, such as immunoglobulin light chains or TCRα chains, or portions thereof.

"Complementarity determining regions" (CDRs) mean regions of an immunoglobulin (i.e., antibody) or T cell receptor where the molecule complements an antigen's conformation, thereby determining the molecule's specificity and contact with a specific antigen. T cell receptors and immunoglobulins each have three CDRs: CDR1 and CDR2 are found in the variable (V) domain, and CDR3 includes some of V, all of diverse (D) (heavy chains only) and joint (J), and some of the constant (C) domains.

"Internal standard" means a nucleic acid sequence that is amplified in the same amplification reaction as one or more target polynucleotides in order to permit absolute or relative quantification of the target polynucleotides in a sample. An internal standard may be endogenous or exogenous. That is, an internal standard may occur naturally in the sample, or it may be added to the sample prior to amplification. In one aspect, multiple exogenous internal standard sequences may be added to a reaction mixture in a series of predetermined concentrations to provide a calibration to which a target amplicon may be compared to determine the quantity of its corresponding target polynucleotide in a sample. Selection of the number, sequences, lengths, and other characteristics of exogenous internal standards is a routine design choice for one of ordinary skill in the art. Preferably, endogenous internal standards, also referred to herein as "reference sequences," are sequences natural to a sample that correspond to minimally regulated genes that exhibit a constant and cell cycle-independent level of transcription, e.g. Selvey et al. Mol. Cell Probes, 15: 307-311 (2001). Exemplary reference sequences include, but are not limited to, sequences from the following genes: GAPDH, $\beta_2$-microglobulin, 18S ribosomal RNA, and β-actin (although see Selvey et al, cited above).

"Kit" refers to any delivery system for delivering materials or reagents for carrying out a method of the invention. In the context of reaction assays, such delivery systems include systems that allow for the storage, transport, or delivery of reaction reagents (e.g., primers, enzymes, etc. in the appropriate containers) and/or supporting materials (e.g. buffers, written instructions for performing the assay etc.) from one location to another. For example, kits include one or more enclosures (e.g. boxes) containing the relevant reaction reagents and/or supporting materials. Such contents may be delivered to the intended recipient together or separately. For example, a first container may contain an enzyme for use in an assay, while a second container contains primers.

"Lymphoid neoplasm" means an abnormal proliferation of lymphocytes that may be malignant or non-malignant. A lymphoid cancer is a malignant lymphoid neoplasm. Lymphoid neoplasms are the result of, or are associated with, lymphoproliferative disorders, including but not limited to, follicular lymphoma, chronic lymphocytic leukemia (CLL), acute lymphocytic leukemia (ALL), hairy cell leukemia, lymphomas, multiple myeloma, post-transplant lymphoproliferative disorder, mantle cell lymphoma (MCL), diffuse large B cell lymphoma (DLBCL), T cell lymphoma, or the like, e.g. Jaffe et al, Blood, 112: 4384-4399 (2008); Swerdlow et al, WHO Classification of Tumours of Haematopoietic and Lymphoid Tissues (e. $4^{th}$) (IARC Press, 2008).

"Minimal residual disease" means remaining cancer cells after treatment. The term is most frequently used in connection with treatment of lymphomas and leukemias.

"Pecent homologous." "percent identical," or like terms used in reference to the comparison of a reference sequence and another sequence ("comparison sequence") mean that in an optimal alignment between the two sequences, the comparison sequence is identical to the reference sequence in a number of subunit positions equivalent to the indicated percentage, the subunits being nucleotides for polynucleotide comparisons or amino acids for polypeptide comparisons. As used herein, an "optimal alignment" of sequences being compared is one that maximizes matches between subunits and minimizes the number of gaps employed in constructing an alignment Percent identities may be determined with commercially available implementations of algorithms, such as that described by Needleman and Wunsch, J. Mol. Biol., 48: 443-453 (1970)("GAP" program of Wisconsin Sequence Analysis Package. Genetics Computer Group, Madison. WI), or the like. Other software packages in the art for constructing alignments and calculating percentage identity or other measures of similarity include the "BestFit" program, based on the algorithm of Smith and Waterman. Advances in Applied Mathematics, 2: 482-489 (1981) (Wisconsin Sequence Analysis Package, Genetics Computer Group. Madison, Wis.). In other words, for example, to obtain a polynucleotide having a nucleotide sequence at least 95 percent identical to a reference nucleotide sequence, up to five percent of the nucleotides in the reference sequence may be deleted or substituted with another nucleotide, or a number of nucleotides up to five percent of the total number of nucleotides in the reference sequence may be inserted into the reference sequence.

"Polymerase chain reaction," or "PCR," means a reaction for the in vitro amplification of specific DNA sequences by the simultaneous primer extension of complementary strands of DNA. In other words. PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al. editors. PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al. U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes): Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified. Typically, the number of target sequences in a multiplex PCR is in the range of from 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin. GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996): Diviacco et al. Gene, 122: 3013-3020 (1992); Becker-Andre et al, Nucleic Acids Research, 17: 9437-9446 (1989); and the like.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, $2^{nd}$ Edition (Cold Spring Harbor Press. New York, 2003).

"Quality score" means a measure of the probability that a base assignment at a particular sequence location is correct. A variety methods are well known to those of ordinary skill for calculating quality scores for particular circumstances, such as, for bases called as a result of different sequencing chemistries, detection systems, base-calling algorithms, and so on. Generally, quality score values are monotonically related to probabilities of correct base calling. For example, a quality score, or Q, of 10 may mean that there is a 90 percent chance that a base is called correctly, a Q of 20 may mean that that is a 99 percent chance that a base is called correctly, and so on. For some sequencing platforms, particularly those using sequencing-by-synthesis chemistries, average quality scores decrease as a function of sequence read length, so that quality scores at the beginning of a sequence read are higher than those at the end of a sequence read, such declines being due to phenomena such as incomplete extensions, carry forward extensions, loss of template, loss of polymerase, capping failures, deprotection failures, and the like.

"Repertoire", or "immune repertoire", means a set of distinct recombined nucleotide sequences that encode T cell receptors (TCRs) or B cell receptors (BCRs), or fragments thereof, respectively, in a population of lymphocytes of an individual, wherein the nucleotide sequences of the set have a one-to-one correspondence with distinct lymphocytes or their clonal subpopulations for substantially all of the lymphocytes of the population. In one aspect, a population of lymphocytes from which a repertoire is determined is taken front one or more tissue samples, such as one or more blood samples. A member nucleotide sequence of a repertoire is referred to herein as a "clonotype." In one aspect, clonotypes of a repertoire comprises any segment of nucleic acid common to a T cell or a B cell population which has undergone somatic recombination during the development of TCRs or BCRs, including normal or aberrant (e.g. associated with cancers) precursor molecules thereof, including, but not limited to any of the following: an immunoglobulin heavy chain (IgH) or subsets thereof (e.g. an IgH variable region, CDR3 region, or the like), incomplete IgH molecules, an immunoglobulin light chain or subsets thereof (e.g. a variable region, CDR region, or the like), T cell receptor α chain or subsets thereof, T cell receptor β chain or subsets thereof (e.g. variable region, CDR3, V(D)J region, or the like), a CDR (including CDR1, CDR2 or CDR3, of either TCRs or BCRs, or combinations of such CDRs). V(D)J regions of either TCRs or BCRs, hypermutated regions of IgH variable regions, or the like. In one aspect, nucleic acid segments defining clonotypes of a repertoire are selected so that their diversity (i.e. the number of distinct nucleic acid sequences in the set) is large enough so that substantially every T cell or B cell or clone thereof in an individual carries a unique nucleic acid sequence of such repertoire. That is, in accordance with the invention, a practitioner may select for defining clonotypes a particular segment or region of recombined nucleic acids that encode TCRs or BCRs that do not reflect the full diversity of a population of T cells or B cells; however, preferably, clonotypes are defined so that they do reflect the diversity of the population of T cells and/or B cells from which they are derived. That is, preferably each different clone of a sample has different clonotype. (Of course, in some applications, there will be multiple copies of one or more particular clonotypes within a profile, such as in the case of samples from leukemia or lymphoma patients). In other aspects of the invention, the population of lymphocytes corresponding to a repertoire may be circulating B cells, or may be circulating T cells, or may be subpopulations of either of the foregoing populations, including but not limited to, CD4+ T cells, or CD8+ T cells, or other subpopulations defined by cell surface markers, or the like. Such subpopulations may be acquired by taking samples from particular tissues, e.g. bone marrow, or lymph nodes, or the like, or by sorting or enriching cells from a sample (such as peripheral blood) based on one or more cell surface markers, size, morphology, or the like. In still other aspects, the population of lymphocytes corresponding to a repertoire may be derived from disease tissues, such as a tumor tissue, an infected tissue, or the like. In one embodiment, a repertoire comprising human TCR β chains or fragments thereof comprises a number of distinct nucleotide sequences in the range of from $0.1 \times 10^6$ to $1.8 \times 10^6$, or in the range of from $0.5 \times 10^6$ to $1.5 \times 10^6$, or in the range of from $0.8 \times 10^6$ to $1.2 \times 10^6$. In another embodiment, a repertoire comprising human IgH chains or fragments thereof comprises a number of distinct nucleotide sequences in the range of from $0.1 \times 10^6$ to $1.8 \times 10^6$, or in the range of from $0.5 \times 10^6$ to $1.5 \times 10^6$, or in the range of from $0.8 \times 10^6$ to $1.2 \times 10^6$. In a particular embodiment a repertoire of the invention comprises a set of nucleotide sequences encoding substantially all segments of the V(D)J region of an IgH chain. In one aspect, "substantially all" as used herein means every segment having a relative abundance of 0.001 percent or higher; or in another aspect, "substantially all" as used herein means every segment having a relative abundance of 0.0001 percent or higher. In another particular embodiment, a repertoire of the invention comprises a set of nucleotide sequences that encodes substantially all segments of the V(D)J region of a TCR β chain. In another embodiment, a repertoire of the invention comprises a set of nucleotide sequences having lengths in the range of from 25-200 nucleotides and including segments of the V, D, and J regions of a TCR β chain. In another embodiment, a repertoire of the invention comprises a set of nucleotide sequences having lengths in the range of from 25-200 nucleotides and including segments of the V, D, and J regions of an IgH chain. In another embodiment, a repertoire of the invention comprises a number of distinct nucleotide sequences that is substantially equivalent to the number of lymphocytes expressing a distinct IgH chain. In another embodiment, a repertoire of the invention comprises a number of distinct nucleotide sequences that is substantially equivalent to the number of lymphocytes expressing a distinct TCR β chain. In still another embodiment, "substantially equivalent" means that with ninety-nine percent probability a repertoire of nucleotide sequences will include a nucleotide sequence encoding an IgH or TCR β or portion thereof carried or expressed by every lymphocyte of a population of an individual at a frequency of 0.001 percent or greater. In still another embodiment, "substantially equivalent" means that with ninety-nine percent probability a repertoire of nucleotide sequences will include a nucleotide sequence encoding an IgH or TCR β or portion thereof carried or expressed by every lymphocyte present at a frequency of 0.0001 percent or greater. The sets of clonotypes described in the foregoing two sentences are sometimes referred to herein as representing the "full repertoire" of IgH and/or TCRβ sequences. As mentioned above, when measuring or generating a clonotype profile (or repertoire profile), a sufficiently large sample of lymphocytes is obtained so that such profile provides a reasonably accurate representation of a repertoire for a particular application. In one aspect, samples comprising from $10^5$ to $10^7$ lymphocytes are employed, especially when obtained from peripheral blood samples of from 1-10 mL.

"Sequence tag" (or "tag") means an oligonucleotide that is attached to a polynucleotide or template and is used to identify and/or track the polynucleotide or template in a reaction. An oligonucleotide tag may be attached to the 3'- or 5'-end of a polynucleotide or template or it may be inserted into the interior of such polynucleotide template to form a linear conjugate, sometime referred to herein as a "tagged polynucleotide," or "tagged template." or "tag-polynucleotide conjugate." or the like. Oligonucleotide tags may vary widely in size and compositions: the following references provide guidance for selecting sets of oligonucleotide tags appropriate for particular embodiments: Brenner, U.S. Pat. No. 5,635, 400; Brenner et al, Proc. Natl. Acad. Sci., 97: 1665-1670) (2000); Church et al, European patent publication 0 303 459: Shoemaker et al, Nature Genetics, 14: 450-456 (1996); Morris et al, European patent publication 0799897A1; Wallace, U.S. Pat. No. 5,981,179; and the like. Lengths and compositions of oligonucleotide tags can vary widely, and the selection of particular lengths and/or compositions depends on several factors including, without limitation, how tags are used to generate a readout, e.g. via a hybridization reaction or via an enzymatic reaction, such as sequencing; whether they are labeled, e.g. with a fluorescent dye or the like; the number of distinguishable oligonucleotide tags required to unambiguously identify a set of polynucleotides, and the like, and how different must tags of a set be in order to ensure reliable identification, e.g. freedom from cross hybridization or misidentification from sequencing errors. In one aspect, oligonucleotide tags can each have a length within a range of from 2 to 36 nucleotides, or from 4 to 30 nucleotides, or from 8 to 20 nucleotides, or from 6 to 10 nucleotides, respectively. In one aspect, sets of tags are used wherein each oligonucleotide tag of a set has a unique nucleotide sequence that differs from that of every other tag of the same set by at least two bases; in another aspect, sets of tags are used wherein the sequence of each tag of a set differs from that of every other tag of the same set by at least three bases.

What is claimed is:

1. A method of monitoring a lymphoid proliferative disorder in a patient, the method comprising the steps of:
   (a) obtaining from the patient a sample comprising T-cells and/or B-cells;
   (b) amplifying molecules of nucleic acid from the T-cells and/or B-cells of the sample, the molecules of nucleic acid comprising recombed DNA sequences from T-cell receptor genes and/or immunoglobulin genes;
   (c) sequencing the amplified molecules of nucleic acid to form a clonotype profile, wherein the sequencing comprises at least 10,000 reads per run; and
   (d) determining from the clonotype profile a presence, absence and/or level of one or more patient-specific clonotypes correlated with the lymphoid proliferative disorder and phylogenic clonotypes thereof wherein such phylogenic clonotypes comprise: (i) clonotypes that are at least ninety percent identical to any of the one or more patient-specific clonotypes; (ii) clonotypes that are related to the one or more patient-specific clonotypes by somatic hypermutation; or (iii) clonotypes that are related to the one or more patient-specific clonotypes by somatic rearrangement.

2. The method of claim 1 further including a step of repeating said steps (a) through (d) on a successive sample from said patient to monitor said lymphoid proliferative disorder in the patient.

3. The method of claim 1 wherein the clonotype profile includes every clonotype present in the sample at a frequency of 0.01 percent or greater with a probability of ninety-nine percent.

4. The method of claim 1 wherein the clonotype profile includes at least $10^4$ clonotypes.

5. The method of claim 1 wherein said phylogenic clonotypes include clonotypes that are at least ninety percent identical to any of said one or more patient-specific clonotypes.

6. The method of claim 1 wherein said molecules of nucleic acid comprise recombed sequences from immunoglobulin heavy chain genes and wherein said phylogenic clonotypes include clonotypes that are related to said one or more patient-specific clonotypes by somatic hypermutation.

7. The method of claim 1 wherein said phylogenic clonotypes include clonotypes that are related to said one or more patient-specific clonotypes by somatic rearrangement.

8. The method of claim 7 wherein said somatic rearrangement comprises a VH replacement.

9. The method of claim 7 wherein said phylogenic clonotypes comprising somatic rearrangement comprise an identically mutated V region and J region as any of said one or more patient-specific clonotypes but comprise a different NDN region as such one or more patient-specific clonotypes.

10. The method of claim 1 wherein said lymphoid proliferative disorder is a malignant lymphoid neoplasm.

11. The method of claim 10 wherein said one or more patient-specific clonotypes correlated with said malignant lymphoid neoplasm are determined by comparing a clonotype profile from a sample of lymphocytes in a non-disease-related tissue in the same patient to a clonotype profile from a sample of lymphocytes in a disease-related tissue.

12. The method of claim 11 wherein said malignant lymphoid neoplasm is a lymphoma and said disease-related tissue is bone marrow or a lymphoid tissue or wherein said malignant lymphoid neoplasm is a leukemia and said disease-related tissue is bone marrow or peripheral blood.

13. The method of claim 1 wherein said recombed sequences comprise a genomic rearrangement selected from the group consisting of a VDJ rearrangement of IgH, a DJ rearrangement of IgH, a VJ rearrangement of IgK, a VJ rearrangement of IgL, a VDJ rearrangement of TCR β, a DJ rearrangement of TCR β, a VJ rearrangement of TCR α, a VJ rearrangement of TCR γ, a VDJ rearrangement of TCR δ, and a VD rearrangement of TCR δ.

14. The method of claim 13 wherein said step of sequencing includes generating sequence reads in a range of from 20 to 400 nucleotides for determining clonotypes and wherein the clonotype profile includes at least $10^4$ clonotypes.

15. The method of claim 1 wherein said recombed sequences comprise an incomplete somatically recombined region of an IgH or a TCR.

16. The method of claim 15 wherein said incomplete somatically recombined region comprises an incomplete IgH molecule, an incomplete TCR δ molecule, or an inactive IgK molecule.

17. The method of claim 1 further including a step of treating said patient by transplanting bone marrow based on said level of said one or more patient-specific clonotypes.

18. The method of claim 2 wherein said lymphoid proliferative disorder is a lymphoma or a leukemia.

19. A method of monitoring a lymphoma or a leukemia in a patient, the method comprising the steps of:
   (a) obtaining a sample from the patient comprising T-cells and/or B-cells;
   (b) amplifying in a polymerase chain reaction molecules of nucleic acid from the T-cells and/or B-cells of the sample, the molecules of nucleic acid comprising or derived from recombed DNA sequences from T-cell receptor genes or immunoglobulin genes selected from the group consisting of a VDJ rearrangement of IgH, a DJ rearrangement of IgH, a VJ rearrangement of IgK, a VJ rearrangement of IgL, a VDJ rearrangement of TCR β, a DJ rearrangement of TCR β, a VJ rearrangement of TCR α, a VJ rearrangement of TCR γ, a VDJ rearrangement of TCR δ, and a VD rearrangement of TCR δ;
   (c) sequencing the amplified molecules of nucleic acid to form a clonotype profile, wherein the sequencing comprises at least 10,000 reads per run; and
   (d) determining from the clonotype profile a level of one or more patient-specific clonotypes correlated with the lymphoma or the leukemia, wherein such level includes phylogenic clonotypes of each of such one or more patient-specific clonotypes, wherein such phylogenic clonotypes comprise: (i) clonotypes that are at least ninety percent identical to any of the one or more patient-specific clonotypes; (ii) clonotypes that are related to the one or more patient-specific clonotypes by somatic hypermutation; and (iii) clonotypes that are related to the one or more patient-specific clonotypes by somatic rearrangement.

20. The method of claim 19 wherein said phylogenic clonotypes comprising somatic rearrangement include clonotypes that are related to said one or more patient-specific clonotypes by a VH replacement or clonotypes having an identically mutated V region and J region as those of any of said one or more patient-specific clonotypes but having a different NDN region as such one or more patient-specific clonotypes.

21. The method of claim 19 wherein said phylogenic clonotypes include clonotypes that are identical to any of said one or more patient-specific clonotypes except for one or more insertions and/or deletions of from 1 to 10 nucleotides.

22. The method of claim 19 further including a step of repeating said steps (a) through (d) on a successive sample from said patient, wherein each of said clonotype profiles has at least $10^4$ clonotypes.

23. The method of claim 22 wherein said successive sample is a peripheral blood sample.

24. The method of claim 19 wherein said step of sequencing includes generating sequence reads in a range of from 20 to 400 nucleotides for determining a sequence of each clonotype and wherein said clonotype profile has at least $10^4$ clonotypes.

25. The method of claim 19 wherein said phylogenic clonotypes include clonotypes that are at least ninety percent identical to any of said one or more patient-specific clonotypes.

26. The method of claim 19 wherein said molecules of nucleic acid comprise recombined sequences from immunoglobulin heavy chain genes and wherein said phylogenic clonotypes include clonotypes that are related to said one or more patient-specific clonotypes by somatic hypermutation.

27. The method of claim 19 further including a step of treating said patient by transplanting bone marrow based on said level of said one or more patient-specific clonotypes.

28. The method of claim 2 further comprising determining if a fraction of said patient-specific clonotypes correlated with said lymphoid proliferative disorder and phylogenic clonotypes thereof in a clonotype profile from the successive sample has increased or decreased with respect to a fraction in an immediately previous sample.

29. The method of claim 22 further comprising determining if a fraction of said patient-specific clonotypes correlated with said lymphoid proliferative disorder and phylogenic clonotypes thereof in a clonotype profile from the successive sample has increased or decreased with respect to a fraction in an immediately previous sample.

* * * * *